(12) United States Patent
Weinberger

(10) Patent No.: US 8,871,443 B2
(45) Date of Patent: Oct. 28, 2014

(54) SCHIZOPHRENIA-RELATED ISOFORM OF KCNH2 AND DEVELOPMENT OF ANTIPSYCHOTIC DRUGS

(75) Inventor: Daniel R. Weinberger, Washington, DC (US)

(73) Assignee: The United States of America, as represented by the Secretary, Department of Health and Human Services, Washington, DC (US)

( * ) Notice: Subject to any disclaimer, the term of this patent is extended or adjusted under 35 U.S.C. 154(b) by 111 days.

(21) Appl. No.: 13/357,416

(22) Filed: Jan. 24, 2012

(65) Prior Publication Data

US 2012/0190558 A1 Jul. 26, 2012

Related U.S. Application Data

(63) Continuation-in-part of application No. 12/593,159, filed as application No. PCT/US2008/057913 on Mar. 21, 2008, now Pat. No. 8,101,980.

(60) Provisional application No. 60/920,220, filed on Mar. 26, 2007.

(51) Int. Cl.
  *C12Q 1/68* (2006.01)
  *C12P 19/34* (2006.01)
  *G01N 33/68* (2006.01)

(52) U.S. Cl.
  CPC ........ *C12Q 1/6883* (2013.01); *C12Q 2600/136* (2013.01); *C12Q 2600/172* (2013.01); *G01N 33/6896* (2013.01); *C12Q 2600/156* (2013.01); *G01N 2800/302* (2013.01); *C12Q 2600/158* (2013.01); *G01N 33/6872* (2013.01); *C12Q 2600/106* (2013.01); *G01N 2800/52* (2013.01)
  USPC .......................................... 435/6.1; 435/91.2

(58) Field of Classification Search
  CPC ................. C12Q 2600/106; G01N 2800/302; G01N 2800/52; G01N 33/6896
  See application file for complete search history.

(56) References Cited

U.S. PATENT DOCUMENTS 5,986,081 A 11/1999 Ganetzky et al.
6,518,398 B1 2/2003 Curtis

FOREIGN PATENT DOCUMENTS

WO WO 2005042732 5/2005

OTHER PUBLICATIONS dbSNP Reference SNP (refSNP) Cluster Report: rs1036145, from www.ncbi.nlm.nih.gov, pp. 1-5, printed Dec. 10, 2013.*
Huffaker S.J. et al. Nat Med. May 2009;15(5):509-518.*
GeneCard output for the KCNH2 gene, from http://www.genecards.org, printed on Dec. 10, 2013, pp. 1-14.*
Langford E. et al. The American Statistician (2001) vol. 55, Issue 4, pp. 322-325.*
Chen G. et al. Molecular & Cellular Proteomics (2002) pp. 304-313.*
Hoshikawa Y. et al. Physiol Genomics 12: 209-219, 2003.*
Cobb J. P. et al. Crit Care Med 2002 vol. 30, No. 12, pp. 2711-2721.*
Cheung V.G. et al. Nature Genetics, vol. 33 (Mar. 2003), pp. 422-425.*
Juppner H. Bone vol. 17, No. 2, Supplement, Aug. 1995:39S-42S.*
Lucentini J. The Scientist, Dec. 20, 2004, p. 20.*
Hegele R.A. Arterioscler Thromb Vasc Biol. 2002;22:1058-1061.*
Pennisi E. et al. Science (Sep. 18, 1988) vol. 281, No. 5384, pp. 1787-1789.*
Aydin Atakan et al: "Single nucleotide polymorphism map of five long-QT genes," Journal of Molecular Medicine (Berlin), vol. 83, No. 2, Feb. 2005, pp. 159-165, XP002500747.
Huffaker Stephen J et al., "Identification of a novel genetic locus at 7q36.1 in strong LD with schizophrenia and the differential expression of the flanking genes, NOS3 and KCNH2," Neuropsychopharmacology, vol. 30, No. Suppl. 1, Dec. 2005, p. S191, XP009107512 & 44th Annual Meeting of the American-College-Neuropsychopharmacology; Waikoloa, HI, USA; Dec. 11-15, 2005.
Examiner's First Report for Australian Patent Application No. 2008231012, dated Mar. 19, 2012.
International Search Report issued by the European Patent Office on Dec. 10, 2008, for International Application No. PCT/US2008/057913.
Written Opinion issued by the European Patent Office on Dec. 10, 2008, for International Application No. PCT/US2008/057913.

* cited by examiner

*Primary Examiner* — Stephen Kapushoc
(74) *Attorney, Agent, or Firm* — Sheridan Ross P.C.

(57) ABSTRACT

The invention is related to a novel primate specific brain isoform of the potassium channel KCNH2 and genetic association with risk for schizophrenia and response to therapy.

5 Claims, 41 Drawing Sheets

KCNH2-1A Protein Sequence
SEQUENCE   1159 AA;  126,670 MW

```
    MPVRRGHVAP QNTFLDTIIR KFEGQSRKFI IANARVENCA VIYCNDGFCE LCGYSRAEVM
    QRPCTCDFLH GPRTQRRAAA QIAQALLGAE ERKVEIAFYR KDGSCFLCLV DVVPVKNEDG
    AVIMFILNFE VVMEKDMVGS PAHDTNHRGP PTSWLAPGRA KTFRLKLPAL LALTARESSV
    RSGGAGGAGA PGAVVVDVDL TPAAPSSESL ALDEVTAMDN HVAGLGPAEE RRALVGPGSP
    PRSAPGQLPS PRAHSLNPDA SGSSCSLART RSRESCASVR RASSADDIEA MRAGVLPPPP
    RHASTGAMHP LRSGLLNSTS DSDLVRYRTI SKIPQITLNF VDLKGDPFLA SPTSDREIIA
    PKIKERTHNV TEKVTQVLSL GADVLPEYKL QAPRIHRWTI LHYSPFKAVW DWLILLLVIY
    TAVFTPYSAA FLLKETEEGP PATECGYACQ PLAVVDLIVD IMFIVDILIN FRTTYVNANE
    EVVSHPGRIA VHYFKGWFLI DMVAAIPFDL LIFGSGSEEL IGLLKTARLL RLVRVARKLD
    RYSEYGAAVL FLLMCTFALI AHWLACIWYA IGNMEQPHMD SRIGWLHNLG DQIGKPYNSS
    GLGGPSIKDK YVTALYFTFS SLTSVGFGNV SPNTNSEKIF SICVMLIGSL MYASIFGNVS
    AIIQRLYSGT ARYHTQMLRV REFIRFHQIP NPLRQRLEEY FQHAWSYTNG IDMNAVLKGF
    PECLQADICL HLNRSLLQHC KPFRGATKGC LRALAMKFKT THAPPGDTLV HAGDLLTALY
    FISRGSIEIL RGDVVVAILG KNDIFGEPLN LYARPGKSNG DVRALTYCDL HKIHRDDLLE
    VLDMYPEFSD HFWSSLEITF NLRDTNMIPG SPGSTELEGG FSRQRKRKLS FRRRTDKDTE
    QPGEVSALGP GRAGAGPSSR GRPGGPWGES PSSGPSSPES SEDEGPGRSS SPLRLVPFSS
    PRPPGEPPGG EPLMEDCEKS SDTCNPLSGA FSGVSNIFSF WGDSRGRQYQ ELPRCPAPTP
    SLLNIPLSSP GRRPRGDVES RLDALQRQLN RLETRLSADM ATVLQLLQRQ MTLVPPAYSA
    VTTPGPGPTS TSPLLPVSPL PTLTLDSLSQ VSQFMACEEL PPGAPELPQE GPTRRLSLPG
    QLGALTSQPL HRHGSDPGS
```

Isoform 3.1 Protein sequence
SEQUENCE   1063 AA;  115,650 MW

```
               MSSH SAGSCFLCLV DVVPVKNEDG AVIMFILNFE VVMEKDMVGS PAHDTNHRGP
    PTSWLAPGRA KTFRLKLPAL LALTARESSV RSGGAGGAGA PGAVVVDVDL TPAAPSSESL
    ALDEVTAMDN HVAGLGPAEE RRALVGPGSP PRSAPGQLPS PRAHSLNPDA SGSSCSLART
    RSRESCASVR RASSADDIEA MRAGVLPPPP RHASTGAMHP LRSGLLNSTS DSDLVRYRTI
    SKIPQITLNF VDLKGDPFLA SPTSDREIIA PKIKERTHNV TEKVTQVLSL GADVLPEYKL
    QAPRIHRWTI LHYSPFKAVW DWLILLLVIY TAVFTPYSAA FLLKETEEGP PATECGYACQ
    PLAVVDLIVD IMFIVDILIN FRTTYVNANE EVVSHPGRIA VHYFKGWFLI DMVAAIPFDL
    LIFGSGSEEL IGLLKTARLL RLVRVARKLD RYSEYGAAVL FLLMCTFALI AHWLACIWYA
    IGNMEQPHMD SRIGWLHNLG DQIGKPYNSS GLGGPSIKDK YVTALYFTFS SLTSVGFGNV
    SPNTNSEKIF SICVMLIGSL MYASIFGNVS AIIQRLYSGT ARYHTQMLRV REFIRFHQIP
    NPLRQRLEEY FQHAWSYTNG IDMNAVLKGF PECLQADICL HLNRSLLQHC KPFRGATKGC
    LRALAMKFKT THAPPGDTLV HAGDLLTALY FISRGSIEIL RGDVVVAILG KNDIFGEPLN
    LYARPGKSNG DVRALTYCDL HKIHRDDLLE VLDMYPEFSD HFWSSLEITF NLRDTNMIPG
    SPGSTELEGG FSRQRKRKLS FRRRTDKDTE QPGEVSALGP GRAGAGPSSR GRPGGPWGES
    PSSGPSSPES SEDEGPGRSS SPLRLVPFSS PRPPGEPPGG EPLMEDCEKS SDTCNPLSGA
    FSGVSNIFSF WGDSRGRQYQ ELPRCPAPTP SLLNIPLSSP GRRPRGDVES RLDALQRQLN
    RLETRLSADM ATVLQLLQRQ MTLVPPAYSA VTTPGPGPTS TSPLLPVSPL PTLTLDSLSQ
    VSQFMACEEL PPGAPELPQE GPTRRLSLPG QLGALTSQPL HRHGSDPGS
```

FIG. 3-1

KCNH2-1A cDNA Sequence
(3,897 bps)

```
CCATGGGCTC AGGATGCCGG TGCGGAGGGG CCACGTCGCG CCGCAGAACA   50
CCTTCCTGGA CACCATCATC CGCAAGTTTG AGGGCCAGAG CCGTAAGTTC  100
ATCATCGCCA ACGCTCGGGT GGAGAACTGC GCCGTCATCT ACTGCAACGA  150
CGGCTTCTGC GAGCTGTGCG GCTACTCGCG GGCCGAGGTG ATGCAGCGAC  200
CCTGCACCTG CGACTTCCTG CACGGGCCGC GCACGCAGCG CCGCGCTGCC  250
GCGCAGATCG CGCAGGCACT GCTGGGCGCC GAGGAGCGCA AAGTGGAAAT  300
CGCCTTCTAC CGGAAAGATG GGAGCTGCTT CCTATGTCTG GTGGATGTGG  350
TGCCCGTGAA GAACGAGGAT GGGGCTGTCA TCATGTTCAT CCTCAATTTC  400
GAGGTGGTGA TGGAGAAGGA CATGGTGGGG TCCCCGGCTC ATGACACCAA  450
CCACCGGGGC CCCCCCACCA GCTGGCTGGC CCCAGGCCGC GCCAAGACCT  500
TCCGCCTGAA GCTGCCCGCG CTGCTGGCGC TGACGGCCCG GGAGTCGTCG  550
GTGCGGTCGG GCGGCGCGGG CGGCGCGGGC GCCCGGGGG CCGTGGTGGT  600
GGACGTGGAC CTGACGCCCG CGGCACCCAG CAGCGAGTCG CTGGCCCTGG  650
ACGAAGTGAC AGCCATGGAC AACCACGTGG CAGGGCTCGG GCCCGCGGAG  700
GAGCGGCGTG CGCTGGTGGG TCCCGGCTCT CCGCCCCGCA GCGCGCCCGG  750
CCAGCTCCCA TCGCCCCGGG CGCACAGCCT CAACCCCGAC GCCTCGGGCT  800
CCAGCTGCAG CCTGGCCCGG ACGCGCTCCC GAGAAAGCTG CGCCAGCGTG  850
CGCCGCGCCT CGTCGGCCGA CGACATCGAG GCCATGCGCG CCGGGGTGCT  900
GCCCCCGCCA CCGCGCCACG CCAGCACCGG GGCCATGCAC CCACTGCGCA  950
GCGGCTTGCT CAACTCCACC TCGGACTCCG ACCTCGTGCG CTACCGCACC 1000
ATTAGCAAGA TTCCCCAAAT CACCCTCAAC TTTGTGGACC TCAAGGGCGA 1050
CCCCTTCTTG GCTTCGCCCA CCAGTGACCG TGAGATCATA GCACCTAAGA 1100
TAAAGGAGCG AACCCACAAT GTCACTGAGA AGGTCACCCA GGTCCTGTCC 1150
CTGGGCGCCG ACGTGCTGCC TGAGTACAAG CTGCAGGCAC CGCGCATCCA 1200
CCGCTGGACC ATCCTGCATT ACAGCCCCTT CAAGGCCGTG TGGGACTGGC 1250
TCATCCTGCT GCTGGTCATC TACACGGCTG TCTTCACACC CTACTCGGCT 1300
GCCTTCCTGC TGAAGGAGAC GGAAGAAGGC CCGCCTGCTA CCGAGTGTGG 1350
CTACGCCTGC CAGCCGCTGG CTGTGGTGGA CCTCATCGTG GACATCATGT 1400
TCATTGTGGA CATCCTCATC AACTTCCGCA CCACCTACGT CAATGCCAAC 1450
GAGGAGGTGG TCAGCCACCC CGGCCGCATC GCCGTCCACT ACTTCAAGGG 1500
CTGGTTCCTC ATCGACATGG TGGCCGCCAT CCCCTTCGAC CTGCTCATCT 1550
TCGGCTCTGG CTCTGAGGAG CTGATCGGGC TGCTGAAGAC TGCGCGGCTG 1600
CTGCGGCTGG TGCGCGTGGC GCGGAAGCTG GATCGCTACT CAGAGTACGG 1650
CGCGGCCGTG CTGTTCTTGC TCATGTGCAC CTTTGCGCTC ATCGCGCACT 1700
GGCTAGCCTG CATCTGGTAC GCCATCGGCA ACATGGAGCA GCCACACATG 1750
GACTCACGCA TCGGCTGGCT GCACAACCTG GGCGACCAGA TAGGCAAACC 1800
CTACAACAGC AGCGGCCTGG GCGGCCCCTC CATCAAGGAC AAGTATGTGA 1850
CGGCGCTCTA CTTCACCTTC AGCAGCCTCA CCAGTGTGGG CTTCGGCAAC 1900
GTCTCTCCCA ACACCAACTC AGAGAAGATC TTCTCCATCT GCGTCATGCT 1950
CATTGGCTCC CTCATGTATG CTAGCATCTT CGGCAACGTG TCGGCCATCA 2000
TCCAGCGGCT GTACTCGGGC ACAGCCCGCT ACCACACACA GATGCTGCGG 2050
GTGCGGGAGT TCATCCGCTT CCACCAGATC CCCAATCCCC TGCGCCAGCG 2100
CCTCGAGGAG TACTTCCAGC ACGCCTGGTC CTACACCAAC GGCATCGACA 2150
```

FIG. 3-2

```
TGAACGCGGT GCTGAAGGGC TTCCCTGAGT GCCTGCAGGC TGACATCTGC  2200
CTGCACCTGA ACCGCTCACT GCTGCAGCAC TGCAAACCCT TCCGAGGGGC  2250
CACCAAGGGC TGCCTTCGGG CCCTGGCCAT GAAGTTCAAG ACCACACATG  2300
CACCGCCAGG GGACACACTG GTGCATGCTG GGGACCTGCT CACCGCCCTG  2350
TACTTCATCT CCCGGGGCTC CATCGAGATC CTGCGGGGCG ACGTCGTCGT  2400
GGCCATCCTG GGGAAGAATG ACATCTTTGG GGAGCCTCTG AACCTGTATG  2450
CAAGGCCTGG CAAGTCGAAC GGGGATGTGC GGGCCCTCAC CTACTGTGAC  2500
CTACACAAGA TCCATCGGGA CGACCTGCTG GAGGTGCTGG ACATGTACCC  2550
TGAGTTCTCC GACCACTTCT GGTCCAGCCT GGAGATCACC TTCAACCTGC  2600
GAGATACCAA CATGATCCCG GGCTCCCCCG GCAGTACGGA GTTAGAGGGT  2650
GGCTTCAGTC GGCAACGCAA GCGCAAGTTG TCCTTCCGCA GGCGCACGGA  2700
CAAGGACACG GAGCAGCCAG GGGAGGTGTC GGCCTTGGGG CCGGGCCGGG  2750
CGGGGGCAGG GCCGAGTAGC CGGGGCCGGC CGGGGGGGCC GTGGGGGGAG  2800
AGCCCGTCCA GTGGCCCCTC CAGCCCTGAG AGCAGTGAGG ATGAGGGCCC  2850
AGGCCGCAGC TCCAGCCCCC TCCGCCTGGT GCCCTTCTCC AGCCCCAGGC  2900
CCCCCGGAGA GCCGCCGGGT GGGGAGCCCC TGATGGAGGA CTGCGAGAAG  2950
AGCAGCGACA CTTGCAACCC CCTGTCAGGC GCCTTCTCAG GAGTGTCCAA  3000
CATTTTCAGC TTCTGGGGGG ACAGTCGGGG CCGCCAGTAC CAGGAGCTCC  3050
CTCGATGCCC CGCCCCCACC CCCAGCCTCC TCAACATCCC CCTCTCCAGC  3100
CCGGGTCGGC GGCCCCGGGG CGACGTGGAG AGCAGGCTGG ATGCCCTCCA  3150
GCGCCAGCTC AACAGGCTGG AGACCCGGCT GAGTGCAGAC ATGGCCACTG  3200
TCCTGCAGCT GCTACAGAGG CAGATGACGC TGGTCCCGCC CGCCTACAGT  3250
GCTGTGACCA CCCCGGGGCC TGGCCCCACT TCCACATCCC CGCTGTTGCC  3300
CGTCAGCCCC CTCCCCACCC TCACCTTGGA CTCGCTTTCT CAGGTTTCCC  3350
AGTTCATGGC GTGTGAGGAG CTGCCCCCGG GGGCCCCAGA GCTTCCCCAA  3400
GAAGGCCCCA CACGACGCCT CTCCCTACCG GGCCAGCTGG GGCCCTCAC   3450
CTCCCAGCCC CTGCACAGAC ACGGCTCGGA CCCGGGCAGT TAGTGGGGCT  3500
GCCCAGTGTG GACACGTGGC TCACCCAGGG ATCAAGGCGC TGCTGGGCCG  3550
CTCCCCTTGG AGGCCCTGCT CAGGAGGCCC TGACCGTGGA AGGGGAGAGG  3600
AACTCGAAAG CACAGCTCCT CCCCCAGCCC TTGGGACCAT CTTCTCCTGC  3650
AGTCCCCTGG GCCCCAGTGA GAGGGGCAGG GGCAGGGCCG GCAGTAGGTG  3700
GGGCCTGTGG TCCCCCCACT GCCCTGAGGG CATTAGCTGG TCTAACTGCC  3750
CGGAGGCACC CGGCCCTGGG CCTTAGGCAC CTCAAGGACT TTTCTGCTAT  3800
TTACTGCTCT TATTGTTAAG GATAATAATT AAGGATCATA TGAATAATTA  3850
ATGAAGATGC TGATGACTAT GAATAATAAA TAATTATCCT GAGGAGA     3897
```

Isoform 3.1 cDNA Sequence
(4,717 bps)

```
GGGGCGGGGG GCGGTGGGGC AGCAGGGGGC CCATGTGCTC AACAGGGAGC  50
TGAGGGAGAC CAGGGGTGCT TGGCTTAGGG GACTGACCTC ATCTGGTACA  100
GGGCCTTTGG TGGACAGAGA GAGACTGGAA AAGAAAAAGT CAAGGATCGA  150
GGGGAACGCG AGGCGAGGTG AAGATGAAAG ATCTAGAAGC AGTGCTTCTT  200
AGACTCTTTG GTGAAGGATC AGTGTTTTTT AATGCTAATA TGTTATAGGC  250
TGGTACATCT GTGAAATACA AGAGCACATG CGTGGATTTT GTGGTGATGC  300
CAAATTGCTG TAAAGTTTTT GAATTCTTG CTCTCAACGT CTGTCCTTAT   350
```

FIG. 3-3

```
CTTGTGTGCT GACACAACGG CTGGTGCTAA TCTAGAGAGA ACAGAGAGAC    400
AGATAGTAAC AGCTAACCGT CTGTAGTGTG CGGCATACGC CAGGCATTGC    450
CTAAGCGCTC AGCATGTGCT GACTTGGTTA ATCTTTATAA CTCATGAGAA    500
AAGAATTATA TACATTATGT GTATCACAAC ATCACTGTGT ACCCCATAAA    550
TATGTACAAT TATTGTGTCA ATTAAAAAGT TAAAAAATTT TAAAAGAAA     600
AAATTATTAT TCTTCCCATT TTATAGATGG AAAAAATGAG GCACAAGGAT    650
GTTAAATAAT TTAGGAAAAA AGCATAAGTG ATTAAGCAGC AGATCCGGGC    700
TATGAACCCA GAGATCGTAG GCCTAAAGTC TGTGGGCTTA AGCACTGTGC    750
TACAGCGCCT CGCTTGAGGG AAAGGCAGAG GTGCTGGGAG GATATGAGGA    800
AATGAGATAG GGAGGAAATG AGATCAAAGA TGGCAGAAGA AAGGATCATA    850
GCCAGCGTGA GAAAAAGTGC AGCCGGGAAA GAGCTAGATA AATCATATAG    900
GCAGAGAGAG GGGTAGGGGA GCCTGGCAGC AACAAGCTGG GGTAGACAGA    950
TTGAGGGGAG CCATAAGGGC GGCAGGCACA TGGCCGGGTG CGGGATCAGG    1000
ACGGGAGATC CCGGAGAGGA AGGGCCATAC GGGGAGGCAG AAGTGGACGG    1050
GCCCACTTGG GTTCCAGGGT CCATCCTGCG TGGCTTTCTG CTCTGCCCAC    1100
TGAGTGGGTG CCAAGGGGGC TATGTCCTCC CACTCTGCAG GGAGCTGCTT    1150
CCTATGTCTG GTGGATGTGG TGCCCGTGAA GAACGAGGAT GGGGCTGTCA    1200
TCATGTTCAT CCTCAATTTC GAGGTGGTGA TGGAGAAGGA CATGGTGGGG    1250
TCCCCGGCTC ATGACACCAA CCACCGGGGC CCCCCCACCA GCTGGCTGGC    1300
CCCAGGCCGC GCCAAGACCT TCCGCCTGAA GCTGCCCGCG CTGCTGGCGC    1350
TGACGGCCCG GGAGTCGTCG GTGCGGTCGG GCGGCGCGGG CGGCGCGGGC    1400
GCCCCGGGGG CCGTGGTGGT GGACGTGGAC CTGACGCCCG CGGCACCCAG    1450
CAGCGAGTCG CTGGCCCTGG ACGAAGTGAC AGCCATGGAC AACCACGTGG    1500
CAGGGCTCGG GCCCGCGGAG GAGCGGCGTG CGCTGGTGGG TCCCGGCTCT    1550
CCGCCCCGCA GCGCGCCCGG CCAGCTCCCA TCGCCCCGGG CGCACAGCCT    1600
CAACCCCGAC GCCTCGGGCT CCAGCTGCAG CCTGGCCCGG ACGCGCTCCC    1650
GAGAAAGCTG CGCCAGCGTG CGCCGCGCCT CGTCGGCCGA CGACATCGAG    1700
GCCATGCGCG CCGGGGTGCT GCCCCCGCCA CCGCGCCACG CCAGCACCGG    1750
GGCCATGCAC CCACTGCGCA GCGGCTTGCT CAACTCCACC TCGGACTCCG    1800
ACCTCGTGCG CTACCGCACC ATTAGCAAGA TTCCCCAAAT CACCCTCAAC    1850
TTTGTGGACC TCAAGGGCGA CCCCTTCTTG GCTTCGCCCA CCAGTGACCG    1900
TGAGATCATA GCACCTAAGA TAAAGGAGCG AACCCACAAT GTCACTGAGA    1950
AGGTCACCCA GGTCCTGTCC CTGGGCGCCG ACGTGCTGCC TGAGTACAAG    2000
CTGCAGGCAC CGCGCATCCA CCGCTGGACC ATCCTGCATT ACAGCCCCTT    2050
CAAGGCCGTG TGGGACTGGC TCATCCTGCT GCTGGTCATC TACACGGCTG    2100
TCTTCACACC CTACTCGGCT GCCTTCCTGC TGAAGGAGAC GGAAGAAGGC    2150
CCGCCTGCTA CCGAGTGTGG CTACGCCTGC CAGCCGCTGG CTGTGGTGGA    2200
CCTCATCGTG GACATCATGT TCATTGTGGA CATCCTCATC AACTTCCGCA    2250
CCACCTACGT CAATGCCAAC GAGGAGGTGG TCAGCCACCC CGGCCGCATC    2300
GCCGTCCACT ACTTCAAGGG CTGGTTCCTC ATCGACATGG TGGCCGCCAT    2350
CCCCTTCGAC CTGCTCATCT TCGGCTCTGG CTCTGAGGAG CTGATCGGGC    2400
TGCTGAAGAC TGCGCGGCTG CTGCGGCTGG TGCGCGTGGC GCGGAAGCTG    2450
GATCGCTACT CAGAGTACGG CGCGGCCGTG CTGTTCTTGC TCATGTGCAC    2500
CTTTGCGCTC ATCGCGCACT GGCTAGCCTG CATCTGGTAC GCCATCGGCA    2550
ACATGGAGCA GCCACACATG GACTCACGCA TCGGCTGGCT GCACAACCTG    2600
```

FIG. 3-4

```
GGCGACCAGA TAGGCAAACC CTACAACAGC AGCGGCCTGG GCGGCCCCTC 2650
CATCAAGGAC AAGTATGTGA CGGCGCTCTA CTTCACCTTC AGCAGCCTCA 2700
CCAGTGTGGG CTTCGGCAAC GTCTCTCCCA ACACCAACTC AGAGAAGATC 2750
TTCTCCATCT GCGTCATGCT CATTGGCTCC CTCATGTATG CTAGCATCTT 2800
CGGCAACGTG TCGGCCATCA TCCAGCGGCT GTACTCGGGC ACAGCCCGCT 2850
ACCACACACA GATGCTGCGG GTGCGGGAGT TCATCCGCTT CCACCAGATC 2900
CCCAATCCCC TGCGCCAGCG CCTCGAGGAG TACTTCCAGC ACGCCTGGTC 2950
CTACACCAAC GGCATCGACA TGAACGCGGT GCTGAAGGGC TTCCCTGAGT 3000
GCCTGCAGGC TGACATCTGC CTGCACCTGA ACCGCTCACT GCTGCAGCAC 3050
TGCAAACCCT TCCGAGGGGC CACCAAGGGC TGCCTTCGGG CCCTGGCCAT 3100
GAAGTTCAAG ACCACACATG CACCGCCAGG GGACACACTG GTGCATGCTG 3150
GGGACCTGCT CACCGCCCTG TACTTCATCT CCCGGGGCTC CATCGAGATC 3200
CTGCGGGGCG ACGTCGTCGT GGCCATCCTG GGGAAGAATG ACATCTTTGG 3250
GGAGCCTCTG AACCTGTATG CAAGGCCTGG CAAGTCGAAC GGGGATGTGC 3300
GGGCCCTCAC CTACTGTGAC CTACACAAGA TCCATCGGGA CGACCTGCTG 3350
GAGGTGCTGG ACATGTACCC TGAGTTCTCC GACCACTTCT GGTCCAGCCT 3400
GGAGATCACC TTCAACCTGC GAGATACCAA CATGATCCCG GGCTCCCCCG 3450
GCAGTACGGA GTTAGAGGGT GGCTTCAGTC GGCAACGCAA GCGCAAGTTG 3500
TCCTTCCGCA GGCGCACGGA CAAGGACACG GAGCAGCCAG GGGAGGTGTC 3550
GGCCTTGGGG CCGGGCCGGG CGGGGCAGG GCCGAGTAGC CGGGGCCGGC 3600
CGGGGGGGCC GTGGGGGGAG AGCCCGTCCA GTGGCCCCTC CAGCCCTGAG 3650
AGCAGTGAGG ATGAGGGCCC AGGCCGCAGC TCCAGCCCCC TCCGCCTGGT 3700
GCCCTTCTCC AGCCCCAGGC CCCCCGGAGA GCCGCCGGGT GGGGAGCCCC 3750
TGATGGAGGA CTGCGAGAAG AGCAGCGACA CTTGCAACCC CCTGTCAGGC 3800
GCCTTCTCAG GAGTGTCCAA CATTTTCAGC TTCTGGGGGG ACAGTCGGGG 3850
CCGCCAGTAC CAGGAGCTCC CTCGATGCCC CGCCCCCACC CCCAGCCTCC 3900
TCAACATCCC CCTCTCCAGC CCGGGTCGGC GGCCCCGGGG CGACGTGGAG 3950
AGCAGGCTGG ATGCCCTCCA GCGCCAGCTC AACAGGCTGG AGACCCGGCT 4000
GAGTGCAGAC ATGGCCACTG TCCTGCAGCT GCTACAGAGG CAGATGACGC 4050
TGGTCCCGCC CGCCTACAGT GCTGTGACCA CCCCGGGGCC TGGCCCCACT 4100
TCCACATCCC CGCTGTTGCC CGTCAGCCCC CTCCCCACCC TCACCTTGGA 4150
CTCGCTTTCT CAGGTTTCCC AGTTCATGGC GTGTGAGGAG CTGCCCCGG 4200
GGGCCCCAGA GCTTCCCCAA GAAGGCCCCA CACGACGCCT CTCCCTACCG 4250
GGCCAGCTGG GGGCCCTCAC CTCCCAGCCC CTGCACAGAC ACGGCTCGGA 4300
CCCGGGCAGT TAGTGGGGCT GCCCAGTGTG GACACGTGGC TCACCCAGGG 4350
ATCAAGGCGC TGCTGGGCCG CTCCCCTTGG AGGCCTGCT CAGGAGGCCC 4400
TGACCGTGGA AGGGGAGAGG AACTCGAAAG CACAGCTCCT CCCCCAGCCC 4450
TTGGGACCAT CTTCTCCTGC AGTCCCCTGG GCCCCAGTGA GAGGGGCAGG 4500
GGCAGGGCCG GCAGTAGGTG GGGCCTGTGG TCCCCCCACT GCCCTGAGGG 4550
CATTAGCTGG TCTAACTGCC CGGAGGCACC CGGCCCTGGG CCTTAGGCAC 4600
CTCAAGGACT TTTCTGCTAT TTACTGCTCT TATTGTTAAG GATAATAATT 4650
AAGGATCATA TGAATAATTA ATGAAGATGC TGATGACTAT GAATAATAAA 4700
TAATTATCCT GAGGAGA                                    4717
```

FIG. 3-5

Genotype vs. Cognitive Performance

| Cognitive Trait | Model | M30 1/2 | 2/2 |
|---|---|---|---|
| Factor 1 (n = 231): Verbal Memory | 0.81 | 0.77 (0.025) | 0.52 (0.087) |
| Factor 2 (n = 289): Nback | 0.66 | 0.45 (-0.079) | 0.46 (-0.12) |
| Factor 3 (n = 230): Visual Memory | 0.55 | 0.44 (0.078) | 0.33 (0.15) |
| Factor 4 (n = 320): Processing Speed | 0.044 | 0.94 (0.0040) | 0.02 (-0.196) |
| Factor 5 (n = 295): Card Sorting | 0.630 | 0.54 (0.061) | 0.62 (-0.078) |
| Factor 6 (n = 304): Attention | 0.21 | 0.091 (-0.132) | 0.28 (-0.127) |
| Factor 7 (n = 231): Digit Span | 0.71 | 0.45 (0.085) | 0.94 (-0.013) |

Genotype vs. Structural Volumes

G/G > G/T > T/T

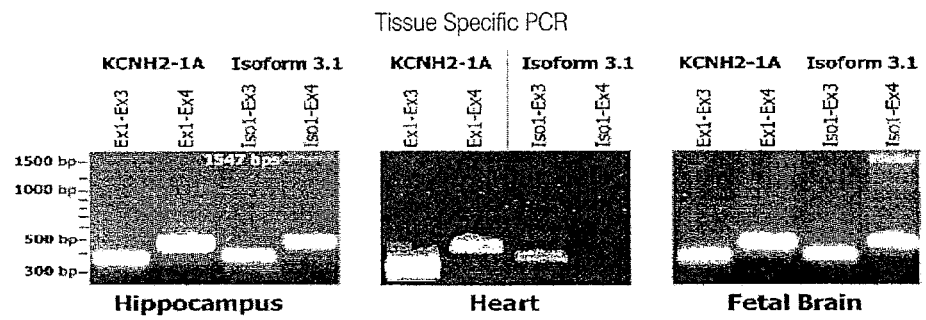
FIG. 8A
Tissue Specific QPCR
|  | Hippocampus | PFC | Heart | Skeletal Muscle |
|---|---|---|---|---|
| Isofrom 3.1 vs. KCNH2-1A Expression | -188.7 % (± 19.7) | -3.8 % (± 0.9) | -1297.2 % (± 91.6) | Undetectable |
FIG. 8B
Protein Expression
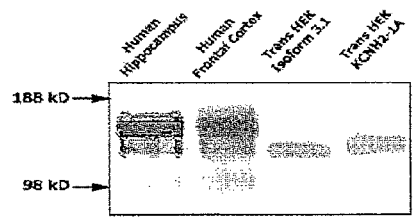
FIG. 8C
Transfection and Cellular Localization
(Rat Primary Neurons: 1000X)
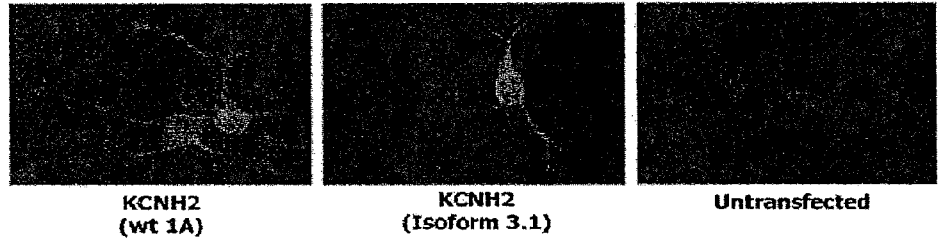
KCNH2 (wt 1A)    KCNH2 (Isoform 3.1)    Untransfected
FIG. 8D

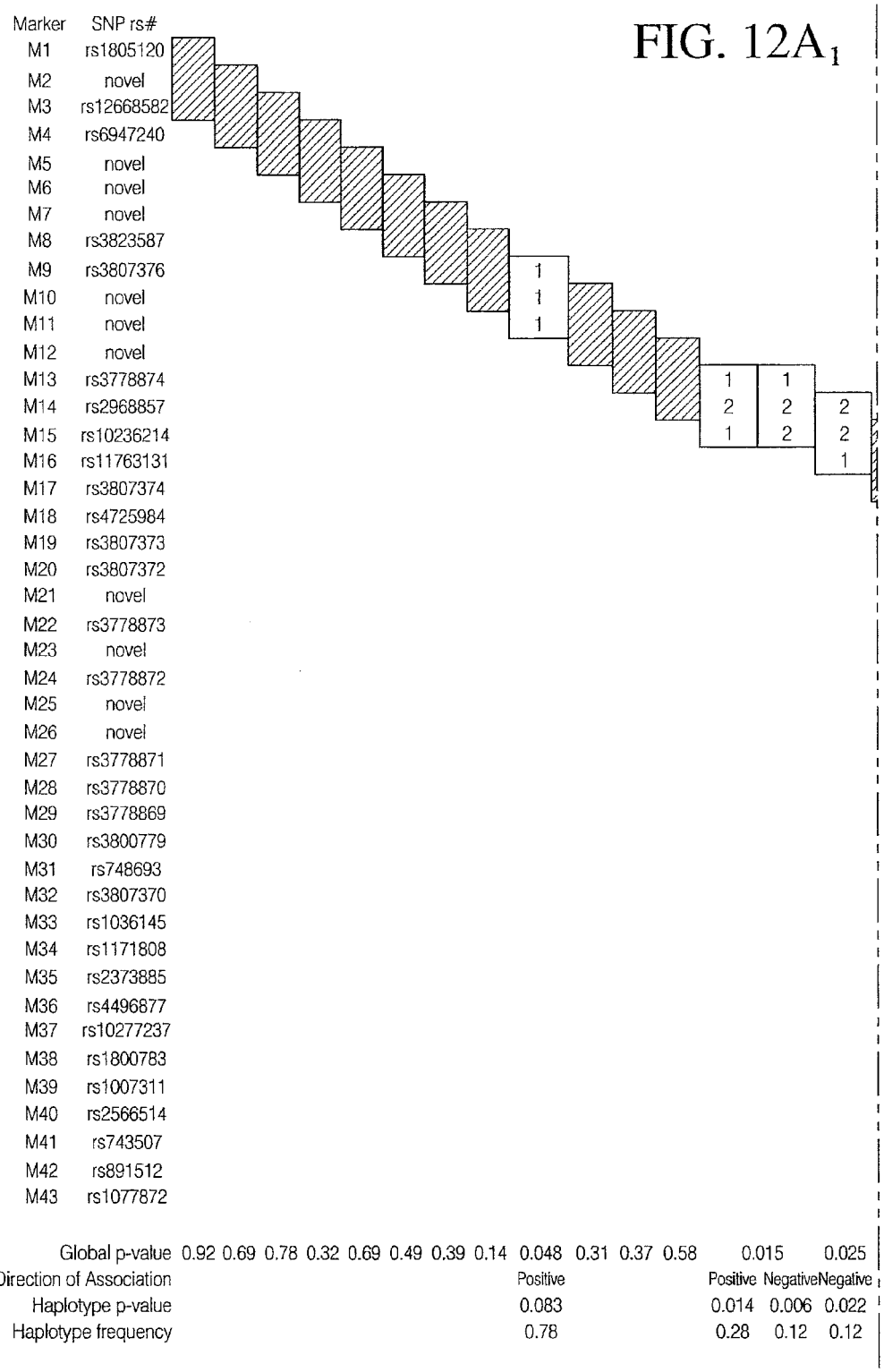
FIG. 12A₁

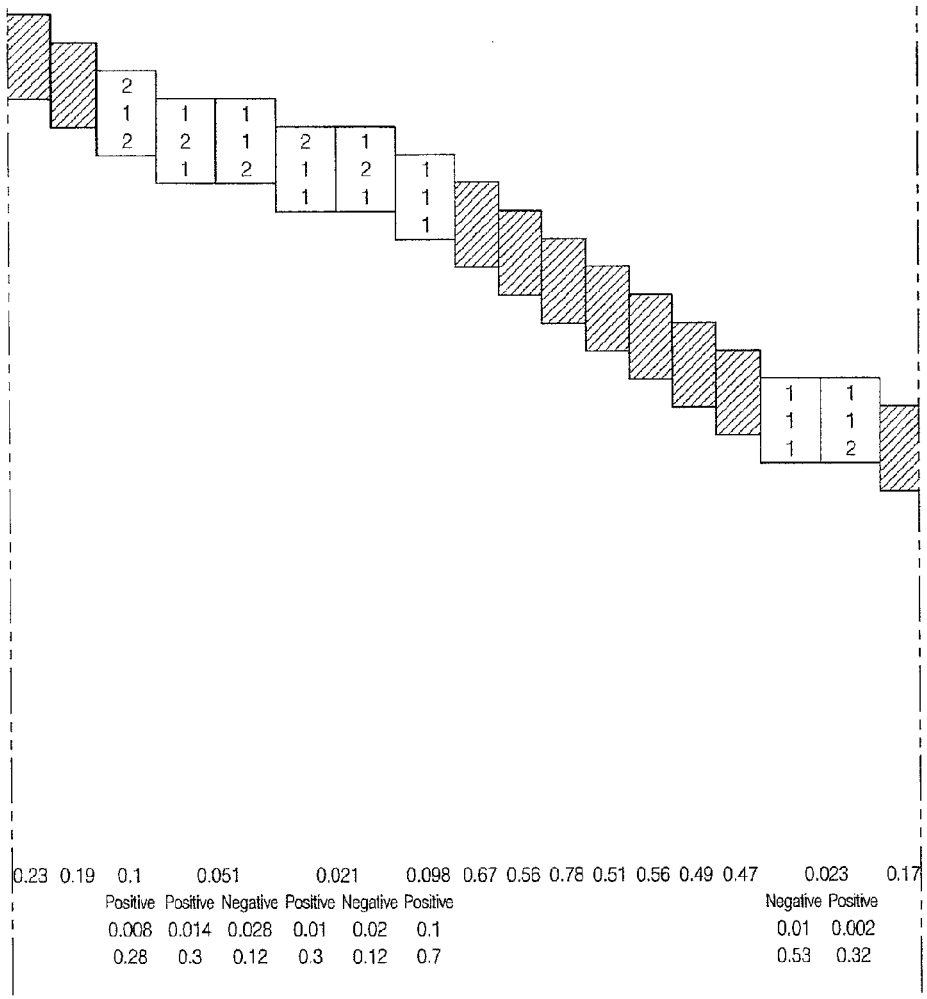

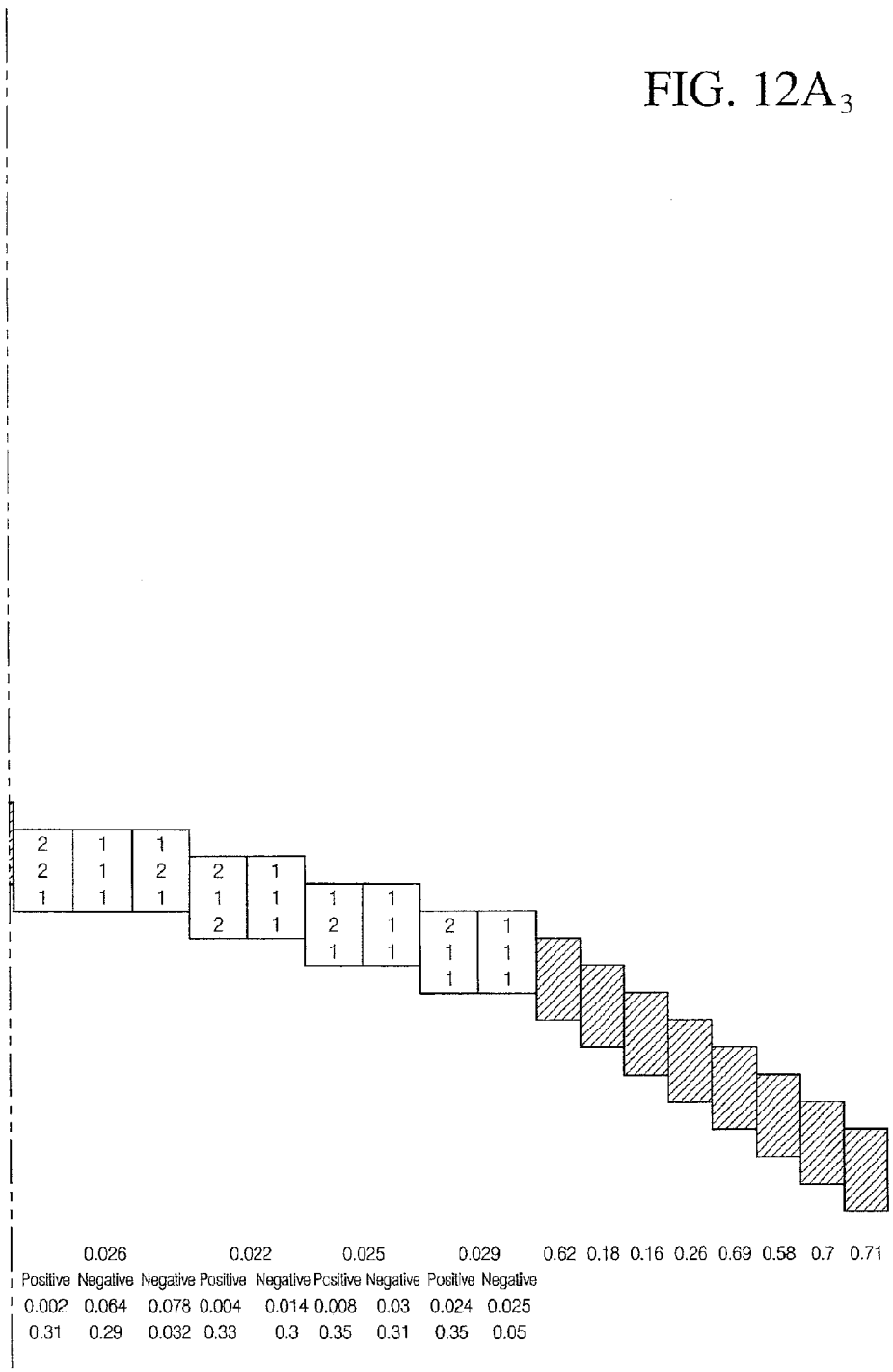

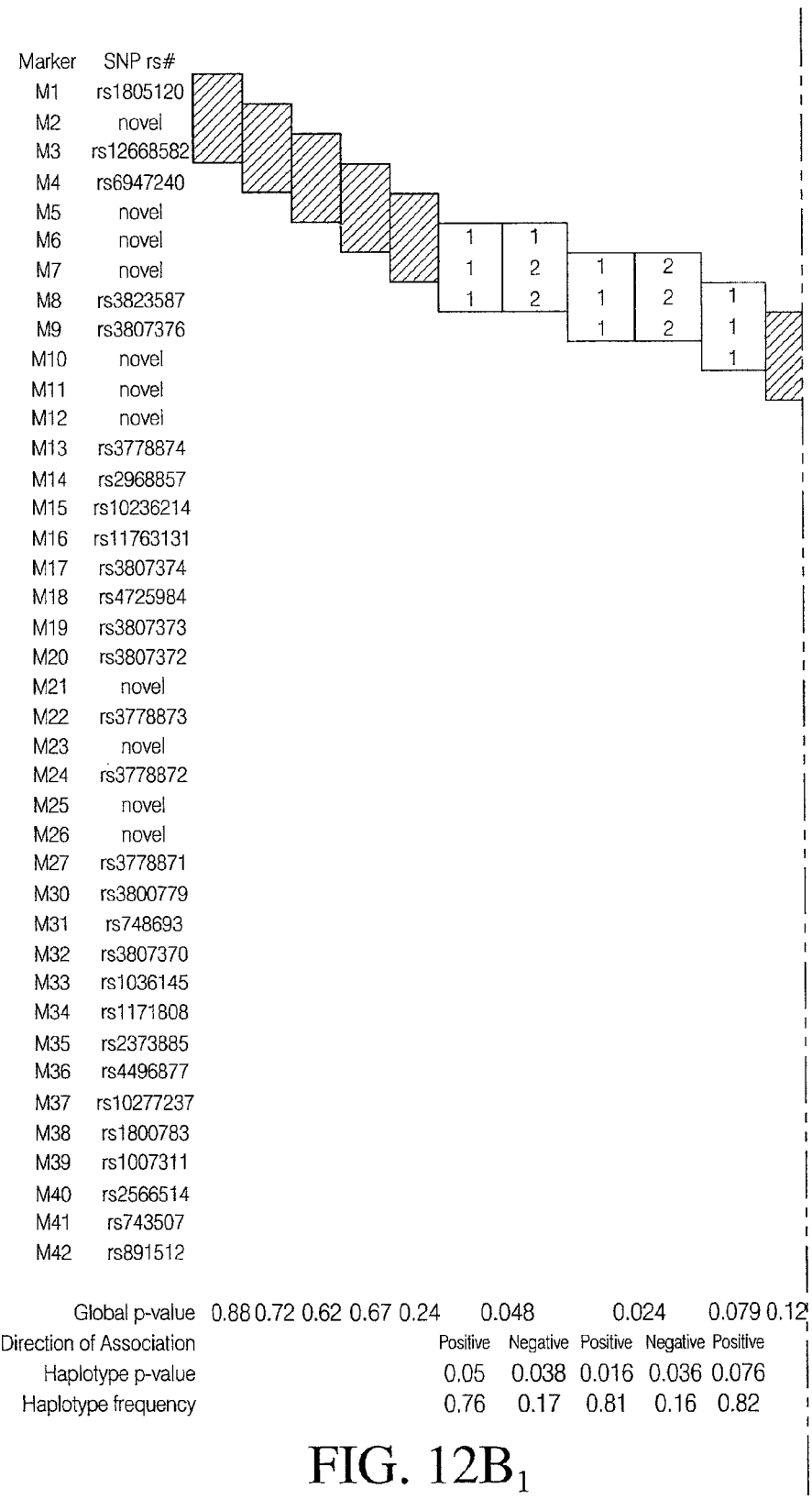
FIG. 12B₁

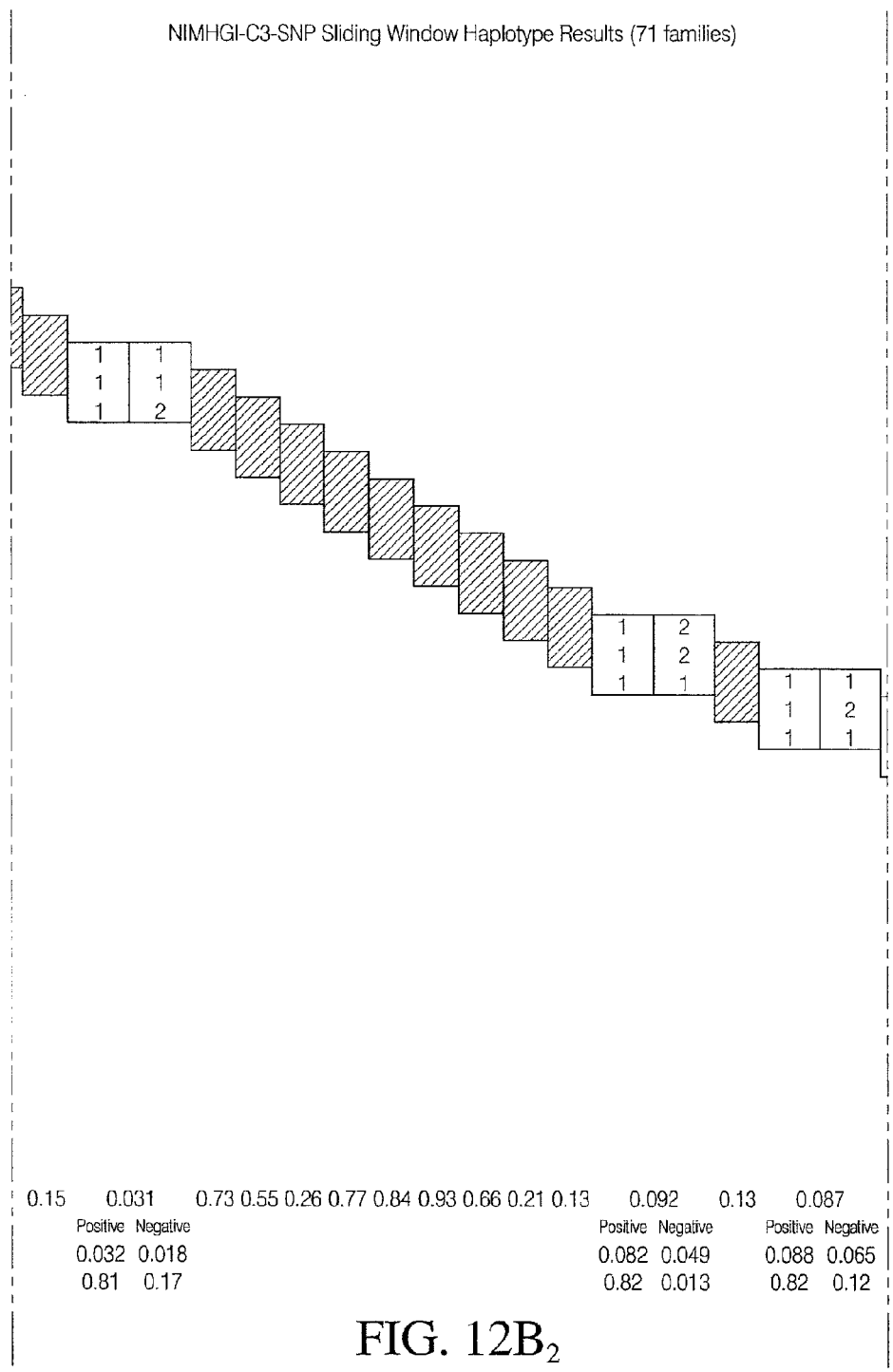
FIG. 12B$_2$

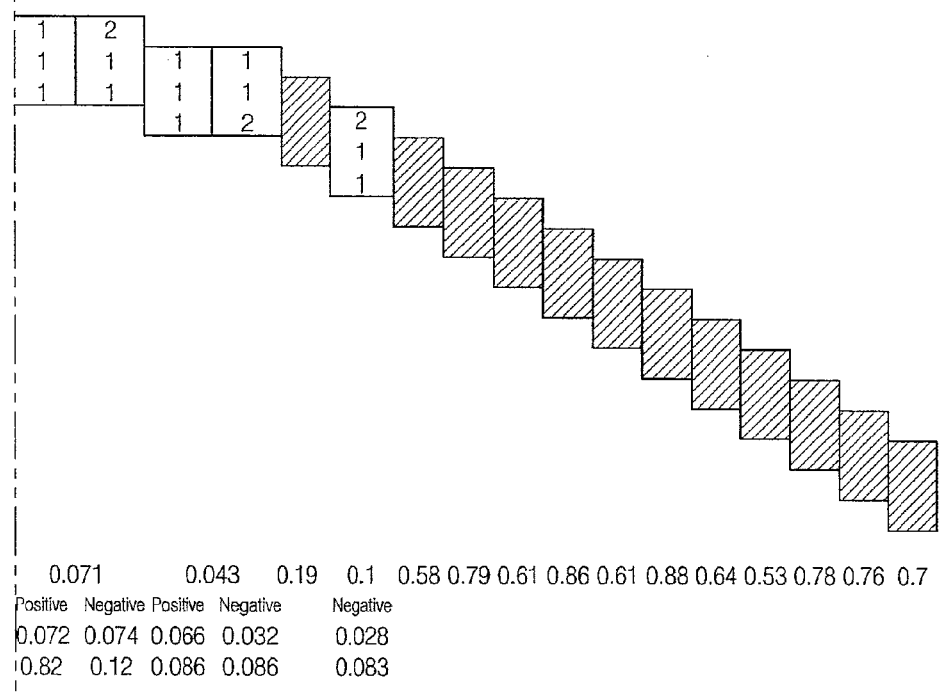
FIG. 12B₃

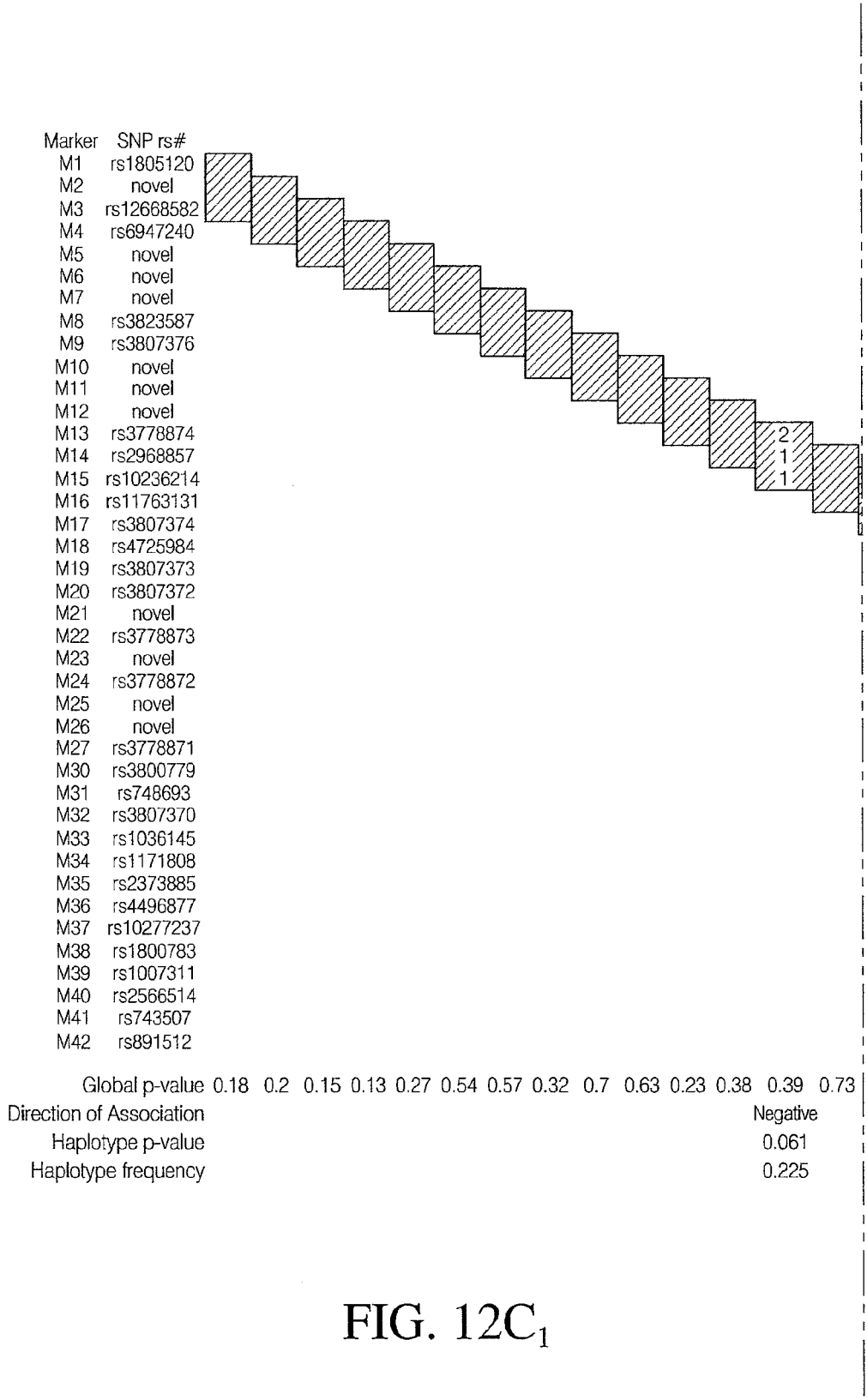
FIG. 12C$_1$

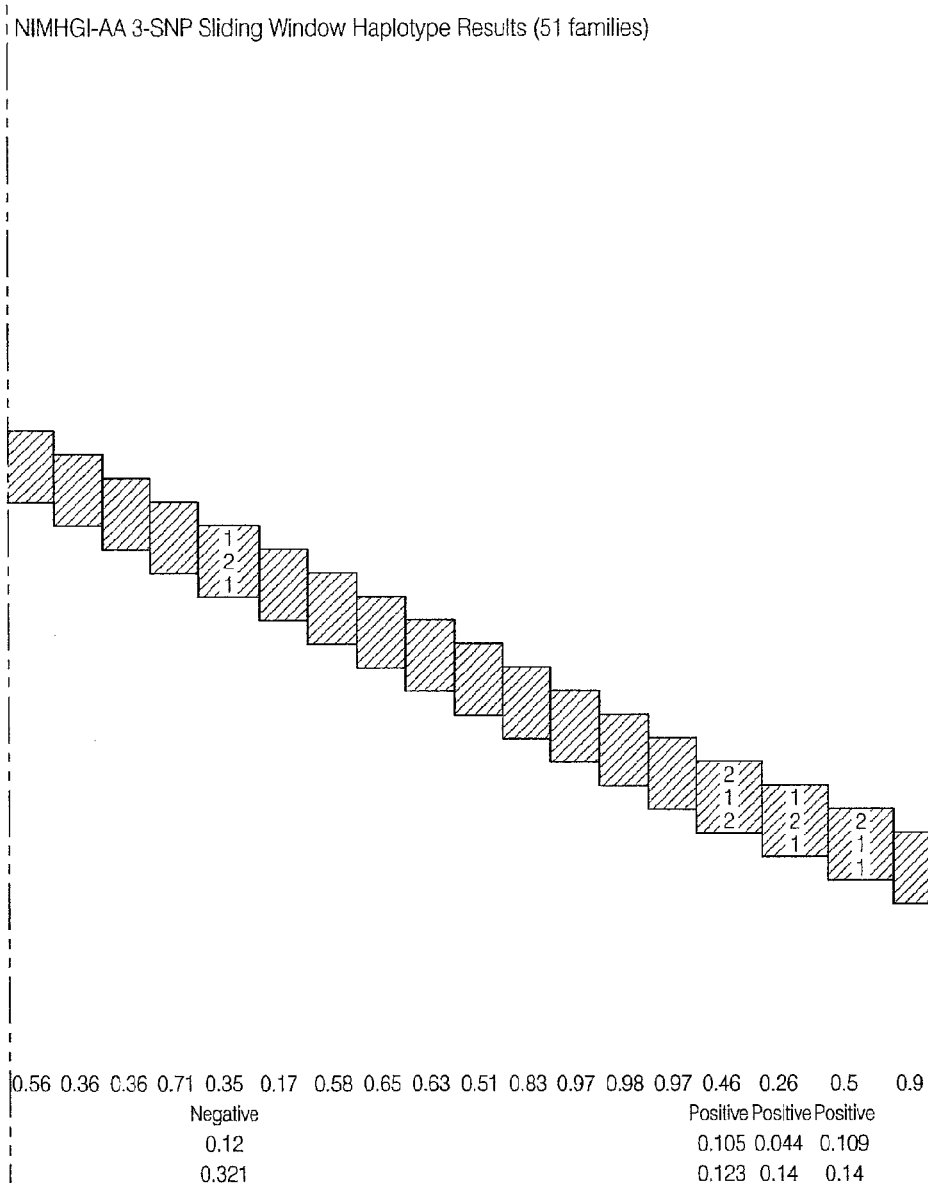
FIG. 12C$_2$

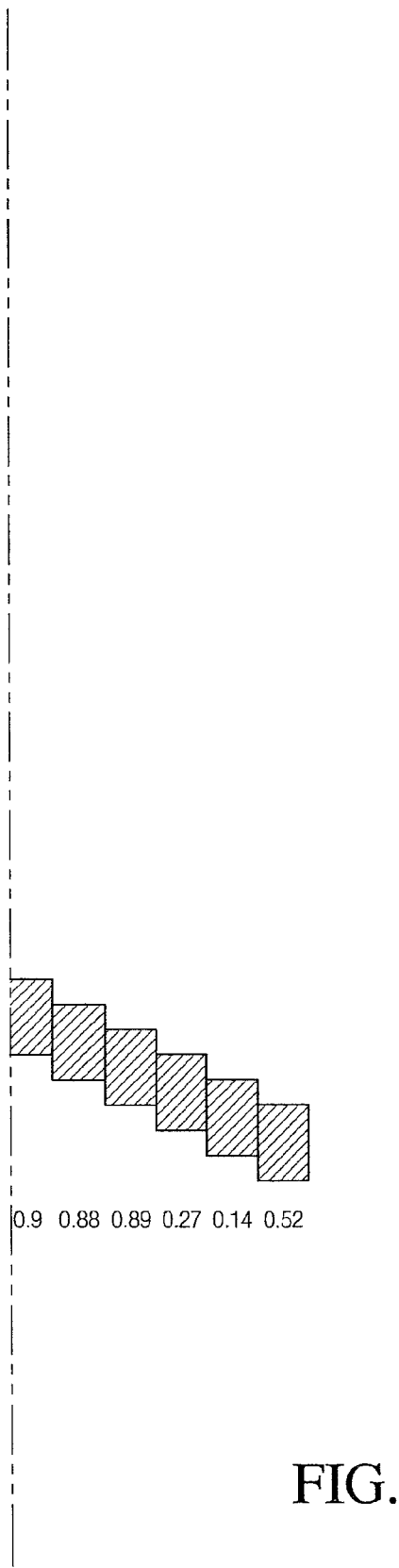
FIG. 12C$_3$

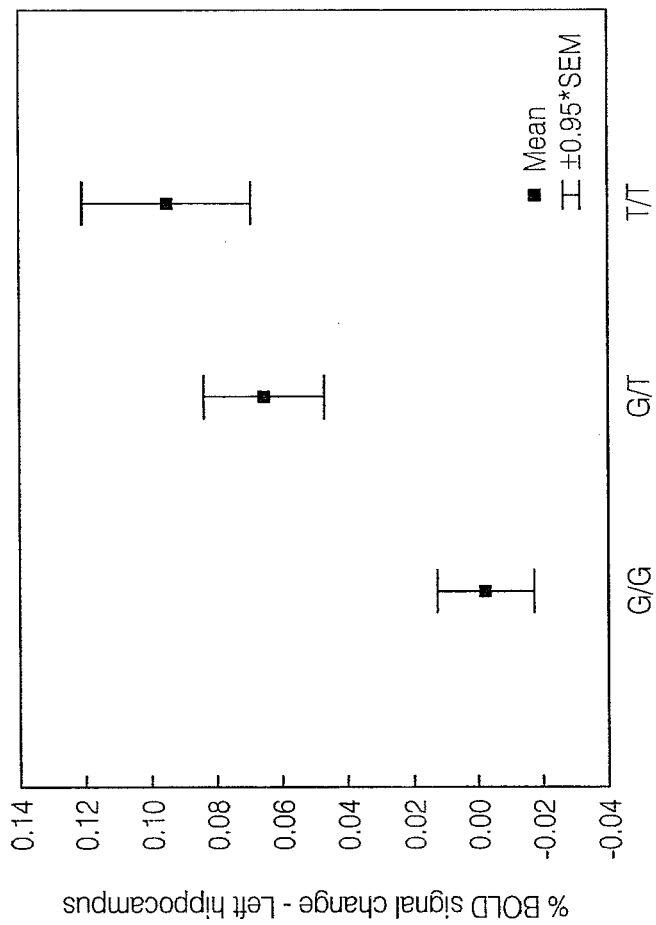
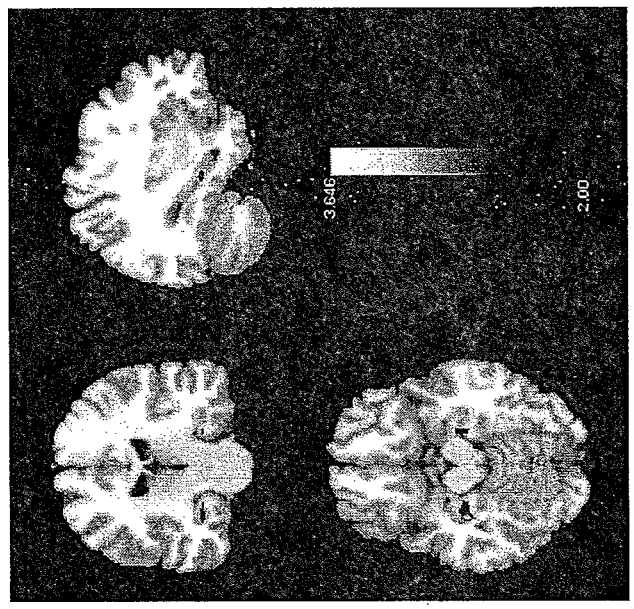
FIG. 17A
FIG. 17B

(A) DNA Sequence alignment of upstream region of exon 3
Conserved splice acceptor site
Herg-1a exon 3 sequence conservation and 250 bps upstream

```
CLUSTAL W (1.83) multiple sequence alignment of DNAseq upstream of Exon3
Human    --------GGGGAGCCTGGCAGCAACAAGCTGGGGTAGACAGATTGAGGGGAGCCATAA-  51
Rhesus   -------------------TAGCAACAAGCTGGGGCAGACAGATTGAGGGGAGCCATAA-  40
Mouse    CAGGAGAAACAGGGAAAGAAGGCTGAGAGATGAGATGAGCAGTGAGGGAGGAAGTGTGGA  60
Rat      -AGGAGAAACTGGGAAAGAAGGCTGAGGGATGAGATGGGTGGTGAGGGAGGAAGTGTGGA  59
                          **     * **  *          *   *  *  ***      *

Human    --GGGCGGCAGGC--ACATGGCCGGGTGGGGGA-TCAGGACGGG---AGATCCCGGAGAG  103
Rhesus   --GGGTGGCAGGC--ACATGGCCGGGTGGGGGA-TCAGGATGGG---AGATCCTGGAGAG   92
Mouse    CTGGCTGGCAGTCTGGCACAGCCAGCTGCAGGG-TTAGAGCAGGGTCAGGAGTTGCAGAT  119
Rat      CTGGCTG-CAGTCTGGCCTAGCCAGGTGCAGGGGTCAGAGCAGGGCTGGGAATTGTAGAT  118
           **  *  **** *       *    *** *  **   * **    **    *  ***

Human    GAAGGGCCATACGGGGAGGCAGAAGTGGACGGGCCCACTTGGGTTCCAGGGTCCATCCTG  163
Rhesus   GAAGGGCCATATGGGGAGGCAGAACTGGAAGGGTCGCTTGGGCTCCAGG----------  142
Mouse    GTGGGCTATTGGGCTGTCGGTAGAGGCTGATGGGCCCCTTTTGGGTTTAGAGGTCCTTCCTG  179
Rat      GTGGGCTGTTGGGGTGTCGGTAGAAGTTGATGGGCCCCTTCTGGGTTCAGAGGTCCTTCCTG  178
          * **     *   *   *  * ***  *  ** ***  **     **** *   *

Human    CGTGGCTTTCTGCTCTGCCCACT----GAGTGGGTGCCAAGGGGGCTATG--------TC  211
Rhesus   -----CTTTCTGCTCTGCCCACT----GAGAGGGTGCCAAGGGGACTATG--------TT  185
Mouse    --GCCATTTTGTGTCATGCACACTTGGGGAGGAGAATCTGGGGTCACCATGGCAATGCCT  238
Rat      -GTCACTTTGTGTCCTGCCCACTTGGGGAGAAGGATCTGGTGTCACCATGGCCCATGCCT  237
              ***  **   *** ****        ***    *     *    * ***

Human    CTCCCACTCTGCAGGGAGCTGCTTCCTATGTCTGGTGGATGTGGTGCCCGTGAAGAACGA  271
Rhesus   CTCCCACTCCACAGGGAGCTGCTTCCTATGTCTGGTGGATGTGGTGCCCGTGAAGAACGA  245
Mouse    TTCCTACTCTGCAGGGAGCTGCTTCCTGTGTCTGGTGGATGTGGTACCCGTGAAGAATGA  298
Rat      TTCCC---TTGCAGGGAGCTGCTTCCTGTGTTTGGTGGATGTGGTGCCCGTGAAGAATGA  294
         ***       ***************** *** ************ *********** **

Human    GGATGGGGCTGTCATCATGTTCATCCTCAATTTCGAGGTGGTGATGGAGAAGGACATGGT  331
Rhesus   GGATGGGGCTGTCATCATGTTCATCCTCAATTTCGAGGTGGTGATGGAGAAGGACATGGT  305
Mouse    AGATGGGGCTGTGATCATGTTCATCCTCAACTTTGAAGTAGTGATGGAGAAGGACATGGT  358
Rat      GGATGGGGCTGTCATCATGTTTATCCTCAACTTTGAAGTGGTGATGGAGAAGGACATGGT  354
          *********** ******** ********  ** **  * *******************

Human    GGGGTCCCCGGCTCATGACACCAACCACCGGGGCCCCCCCACCAGCTGGCTGGCCCCAGG  391
Rhesus   GGGGTCCCCGGCTCATGACACCAATCACCGGGGCCCCCCCACCAGCTGGCTGGCCTCAGG  365
Mouse    AGGGTCCCCGGCTCATGACACCAACCACAGGGGCCCCTCTACCAGCTGGCTAGCTTCTGG  418
Rat      AGGGTCGCCAGCTCATGACACCAATCACAGGGGGCCCTCTACCAGCTGGCTAGCTTCTGG  414
          **** ** * ************* *** **** *** * *********** **  * **

Human    TAAGTGTACTTG  402
Rhesus   TAAGTGTACTTG  377
Mouse    TAAGTGCAGCCA  425
Rat      TAAGTGCAGTCA  420
         ****** *
```

FIG. 21A

Predicted longest ORF upstream of hERG-1a Exon 3

```
              10         20         30       *  40             50         60
              |          |          |          |          |          |
Human    ............................................MSSHS......AGSCFLCLVDVV
Rhesus   ............................................MFSHS......TGSCFLCLVDVV
Mouse    ...................LAILCHAHLGRRIWGHHGQCLSYSAGSCFLCLVDVV
Rat      LGIVDVGCWGVVEVDGPFWQRSFLVTLCPAHLGRRIWCHHGPCLSL.AGSCFLCLVDVV 70         80         90         100
              |          |          |          |
Human    PVKNEDGAVIMFILNFEVVMEKDMVGSPAHDTNHRGPPTSWLASGKCT
Rhesus   PVKNEDGAVIMFILNFEVVMEKDMVGSPAHDTNHRGPPTSWLASGKCT
Mouse    PVKNEDGAVIMFILNFEVVMEKDMVGSPAHDTNHRGPSTSWLASGKCS
Rat      PVKNEDGAVIMFILNFEVVMEKDMVGSPAHDTNHRGPSTSWLASGKCS
```

Exon 3 Coding Sequence

SCHIZOPHRENIA-RELATED ISOFORM OF KCNH2 AND DEVELOPMENT OF ANTIPSYCHOTIC DRUGS

RELATED APPLICATIONS

This application is a continuation-in-part of U.S. patent application Ser. No. 12/593,159, filed Sep. 25, 2009, and issued as U.S. Pat. No. 8,101,380; which is a 371 filing of PCT/US08/57913, filed Mar. 21, 2008; which claims the benefit of U.S. Provisional Application No. 60/920,220 filed Mar. 26, 2007. All of the foregoing applications are hereby expressly incorporated by reference in their entirety.

FIELD OF THE INVENTION

The invention is related to a novel primate specific brain isoform of the potassium channel KCNH2 and genetic association with risk for schizophrenia.

DESCRIPTION OF THE RELATED ART

A major challenge in modern medicine is to understand cellular and molecular mechanisms underlying common mental illnesses such as schizophrenia, which involve complex genetic and environmental determinants. Recent evidence indicates that multiple genes, each accounting for relatively small effects across populations, contribute to risk for schizophrenia (P. J. Harrison and D. R. Weinberger 2005 Mol Psychiatry 10:40). Prevailing etiological hypotheses maintain that the interaction of such genetic factors with each other and the environment results in neurodevelopmental abnormalities predisposing to the illness later in life (D. A. Lewis and P. Levitt 2002 Annu Rev Neurosci 25:409). Given this complexity, together with likely genetic and allelic heterogeneity, epistatic effects, undetected population stratification, and imprecise and differing definitions of phenotype, it is not surprising that statistical association studies to identify putative risk genes for schizophrenia have not enjoyed unanimous replication. In light of these difficulties in the statistical evidence for causative genes, it has been argued that the end game in gene identification for complex polygenic disorders, such as schizophrenia, will require demonstration that risk variants impact on the biology of the gene in a manner that converges on important aspects of the biology of the illness (K. M. Weiss and J. D. Terwilliger 2000 Nat Genet. 26:151). This has led to efforts to study the effects of potential schizophrenia susceptibility genes on intermediate biologic phenotypes relevant to schizophrenia (A. Meyer-Lindenberg and D. R. Weinberger 2006 Nat Rev Neurosci 7:818; M. F. Egan et al. 2004 Proc Natl Acad Sci USA 101:12604).

Among the most promising intermediate phenotypes are prefrontal cortex (PFC) mediated executive functions, and hippocampal formation (HF) mediated memory functions, both of which are impaired in patients with schizophrenia and in their healthy relatives (D. R. Weinberger 1999 Biol Psychiatry 45:395). Biological abnormalities in hippocampal and prefrontal cortices also are frequently reported in patients with schizophrenia and are also found with increased frequency in their healthy relatives, suggesting that they are heritable traits related to susceptibility genes. For example, schizophrenia patients and their healthy relatives show reductions in HF volumes (L. J. Seidman et al. 2003 Schizophr Bull 29:803; M. D. Nelson et al. 1998 Arch Gen Psychiatry 55:433), and in levels of N-acetylaspartate (NAA) (R. G. Steen et al. 2005 Neuropsychopharmacology 30:1949), a measure of neuronal activity and synaptic abundance, possibly related to diminished neuropil observed on postmortem examination (P. J. Harrison 1999 Brain 122:593). Various physiologic investigations of cortical activity in patients with schizophrenia and in their healthy relatives reveal disorganized activation in HF and PFC (J. H. Callicott et al. 2003 Am J Psychiatry 160:709; C. S. Carter 2006 Biol Psychiatry 60:1169; G. Winterer et al. 2004 Am J Psychiatry 161:490; E. Bramon et al. 2004 Schizophr Res 70:315; S. Frangou et al. 1997 Schizophr Res 23:45; R. Freedman et al. 1991 Schizophr Res 4:233; S. Heckers et al. 1998 Nat Neurosci 1:318; A. M. Achim and M. Lepage 2005 Br J Psychiatry 187:500; D. Ongur et al. 2006 Arch Gen Psychiatry 63:356). Studies in non-human primates and in other animal models indicate that abnormal activation and disorganized, high-frequency discharges in cortical networks may underlie impaired memory performance (P. S. Goldman-Rakic 1995 Neuron 14:477). However, the molecular and genetic factors that contribute to abnormal neuronal activity associated with schizophrenia have so far not been identified.

SUMMARY OF THE INVENTION

The invention is related to a novel primate specific brain isoform of the voltage-gated potassium channel KCNH2 and genetic association with risk for schizophrenia, and to related nucleic acid molecules, polypeptides, antibodies, screening assays, and diagnostics.

Some embodiments concern an isolated nucleic acid molecule comprising a polynucleotide sequence that is at least 85%, 90%, 95%, 96%, 97%, 98%, or 99% identical to a nucleotide sequence encoding a polypeptide comprising the amino acid sequence of SEQ ID NO:5. More embodiments concern the isolated nucleic acid molecule above, wherein the first amino acid of said polypeptide is replaced with M S S H S A (SEQ ID NO: 16) or M F S H S T (SEQ ID NO: 17). Still more embodiments concern the nucleic acid molecule above comprising a polynucleotide sequence that is at least 85%, 90%, 95%, 96%, 97%, 98%, or 99% identical to the cDNA having SEQ ID NO:3.

In desirable embodiments, the isolated nucleic acid molecule above is a nucleic acid that encodes the amino acid sequence of SEQ ID NO: 5. In some embodiments, the isolated nucleic acid molecule above is a nucleic acid that encodes the polypeptide of SEQ ID NO: 5, wherein the first amino acid of said polypeptide is replaced with M S S H S A (SEQ ID NO: 16) or M F S H S T (SEQ ID NO: 17). Still more embodiments concern an isolated nucleic acid molecule that hybridizes under stringent hybridization conditions to the nucleic acid molecule above, wherein said nucleic acid molecule that hybridizes does not hybridize under stringent hybridization conditions to a nucleic acid molecule having a nucleotide sequence consisting of only A residues or of only T residues.

More embodiments concern an isolated polypeptide comprising an amino acid sequence that is at least 85%, 90%, 95%, 96%, 97%, 98%, or 99% identical to a polypeptide comprising the amino acid sequence of SEQ ID NO: 5. In some aspects, the isolated polypeptide above is modified in that the first amino acid of said polypeptide is replaced with M S S H S A (SEQ ID NO: 16) or M F S H S T (SEQ ID NO: 17). In more embodiments, said polypeptide comprises the amino acid sequence of SEQ ID NO: 5 and, in yet more embodiments, the isolated polypeptide above is modified such that the first amino acid of said polypeptide is replaced with M S S H S A (SEQ ID NO: 16) or M F S H S T (SEQ ID NO: 17).

Some aspects of the invention also concern a method of making a recombinant vector comprising inserting any of the isolated nucleic acid molecules described above into a vector. Recombinant vectors produced by the method above and methods of making a recombinant host cell comprising introducing this vector into a host cell are also contemplated embodiments. Recombinant host cells produced by these methods are also embodiments. Additionally, some aspects of the invention concern a method of making a recombinant polypeptide comprising culturing the host cell above under conditions such that said recombinant polypeptide is expressed. An isolated antibody capable of specifically binding to any one of the polypeptides described above is also a contemplated embodiment.

More embodiments concern a method of screening for therapeutic agents useful in the treatment of a neurological disease in a human comprising contacting a test compound with any one of the polypeptides described above; and detecting binding of said test compound to said polypeptide.

Still more embodiments concern a method of screening for therapeutic agents useful in the treatment of a neurological disease in a human comprising (a) determining the activity of any one of the polypeptides described above, at a first concentration of a test compound or in the absence of said test compound, (b) determining the activity of said polypeptide at a second concentration of said test compound, and comparing the activity of said polypeptide under conditions (a) and (b) to the activity of the polypeptide in the presence of a known regulator. In some embodiments, the activity is current. Additional embodiments concern a method of screening for therapeutic agents useful in the treatment of a neurological disease in a human comprising contacting a test compound with a nucleic acid molecule comprising a polynucleotide sequence that encodes any one of the polypeptides described above, and detecting binding of said test compound to said polynucleotide.

Further, some aspects of the invention concern a method for the preparation of a pharmaceutical composition useful for the treatment of a neurological disease in a human comprising identifying a regulator of any one of the polypeptides described above, determining whether said regulator ameliorates the symptoms of said neurological disease in a human, and combining said regulator with an acceptable pharmaceutical carrier. In some embodiments, the method above is practised, wherein said regulator is a small molecule, an RNA molecule, an antisense oligonucleotide, a polypeptide, an antibody, or a ribozyme.

Still further embodiments concern a method for predicting the likelihood that an individual will have schizophrenia or will have increased symptomology associated with schizophrenia comprising obtaining a DNA sample from an individual to be assessed, and determining the nucleotide present at a single nucleotide polymorphism (SNP) selected from Marker M1, M2, M3, M4, M5, M6, M7, M8, M9, M10, M11, M12, M13, M14, M15, M16, M17, M18, M19, M20, M21, M22, M23, M24, M25, M26, M27, M28, M29, M30, M31, M32, M33, M34, M35, M36, M37, M38, M39, M40, M41, M42, or M43, wherein the presence of a nucleotide from the risk allele at the SNP indicates that the individual has a greater likelihood of having schizophrenia, or a likelihood of having increased symptomology associated with schizophrenia, than an individual having a nucleotide from the protective allele at that SNP.

BRIEF DESCRIPTION OF THE DRAWINGS

FIG. 3. Protein and cDNA sequences for KCNH2-1A and Isoform 3.1 in human. KCNH2-1A protein (SEQ ID NO: 2), KCNH2-1A cDNA (SEQ ID NO: 1); Isoform 3.1 protein (SEQ ID NO: 4), Isoform 3.1 cDNA (SEQ ID NO: 3). HERG Δ2-102 is defined as a protein lacking amino acids 2-102 of HERG (SEQ ID NO: 2), thus making it SEQ ID NO: 5.

FIG. 8: Detection and quantification of Isoform 3.1 mRNA and protein. (A) Tissue-specific PCR; (B) Tissue-specific QPCR; (C) Protein Expression; and (D) Transfection and Cellular localization.

FIG. 17. Genotype based differences in hippocampal engagement during a declarative memory task for SNP M31. A) Percent blood oxygen level-dependent (BOLD) signal change during the encoding condition of the task in the left posterior hippocampus. B) Thresholded statistical t-maps.

FIG. 21. Alignment and conservation of Isoform 3.1 5'-UTR sequence in primate and non-primate species. (A) DNA Sequence alignment of upstream region of exon 3. Human, (SEQ ID NO: 8); Rhesus, (SEQ ID NO: 9); Mouse, (SEQ ID NO: 10); Rat, (SEQ ID NO: 11). (B) Predicted longest ORF upstream of hERG-1a Exon 3. Human, (SEQ ID NO: 12); Rhesus, (SEQ ID NO: 13); Mouse, (SEQ ID NO: 14); Rat, (SEQ ID NO: 15).

DETAILED DESCRIPTION OF THE PREFERRED EMBODIMENT

Definitions

Figure 1:
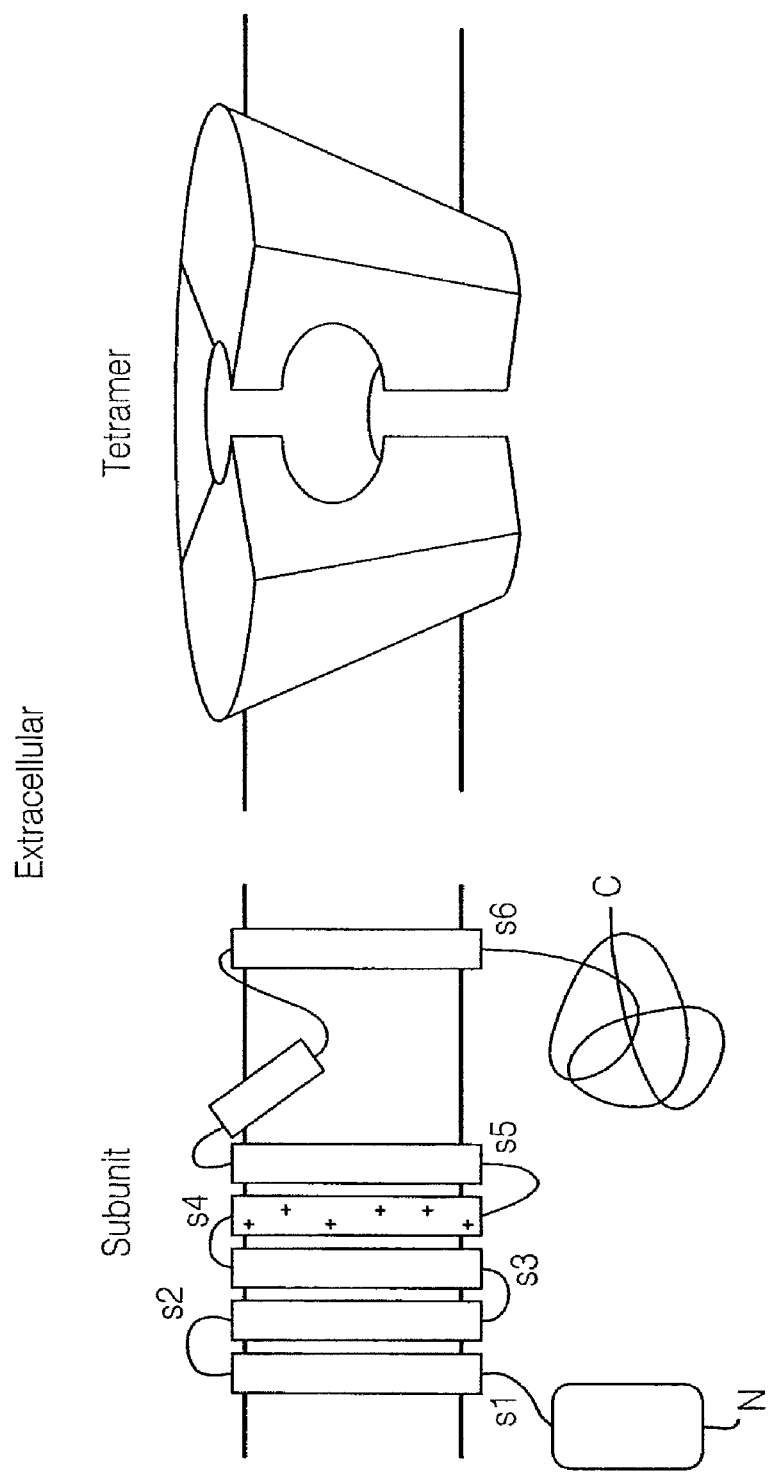
FIG. 1. Membrane-spanning topology of HERG K⁺ Channels.

Unless defined otherwise, technical and scientific terms used herein have the same meaning as commonly understood by one of ordinary skill in the art to which this invention belongs. See, e.g., Singleton P and Sainsbury D., in Dictionary of Microbiology and Molecular Biology 3rd ed., J. Wiley & Sons, Chichester, N.Y., 2001.

The transitional term "comprising" is synonymous with "including," "containing," or "characterized by," is inclusive or open-ended and does not exclude additional, unrecited elements or method steps.

The transitional phrase "consisting of excludes any element, step, or ingredient not specified in the claim, but does not exclude additional components or steps that are unrelated to the invention such as impurities ordinarily associated therewith.

The transitional phrase "consisting essentially of limits the scope of a claim to the specified materials or steps and those that do not materially affect the basic and novel characteristic(s) of the claimed invention.

Overview

As described herein, we report an extensive series of basic and clinical experiments leading to the discovery and characterization of a novel isoform of the voltage-gated potassium channel KCNH2, whose expression in human brain is markedly increased in schizophrenia, significantly correlated with schizophrenia-risk single nucleotide polymorphisms (SNPs), and whose expression in cell culture dramatically alters neuronal excitability.

An ultimate goal of modern medicine is to understand the basic mechanisms underlying common and complex human diseases, such as diabetes and mental illness. Conventional genetic linkage and association studies have been less than conclusive because these diseases involve multiple genes, and each gene elicits relatively small effects across populations. Moreover, because of the complexity of genetic factors and their interaction with the environment, it is often difficult to link genetic findings to important biological or mechanistic aspects of the illness. To overcome these obstacles, we have taken a powerful translational approach that dissects the complex phenomenology of schizophrenia into neural system and molecular components and maps genetic association onto these multiple levels of analysis. Using this approach in the present study, we identify a new class of schizophrenia susceptibility gene, the KCNH2 potassium channel, but more importantly, a novel isoform of this type of voltage-gated potassium channel that is primate and brain specific and increased 2.5 fold in schizophrenia. In addition, we characterize the electrophysiological properties of this novel isoform of KCNH2 and reveal that elevated expression in neurons leads to disorganized neuronal activation patterns, a physiological correlate of schizophrenia. These convergent findings provide dramatic new insights into the molecular mechanisms underlying schizophrenia and related disorders.

The main findings and the potential impact of the study are as follows. First, based on differential gene expression data from schizophrenic brain tissues, we identified a region on 7q36 containing KCNH2, where SNPs within a 3 kb intronic region are significantly associated with schizophrenia. More importantly, we were able to replicate this genetic association in four independent clinical samples, including one of African-American origin, which suggests that this gene impacts on risk for schizophrenia throughout the world, albeit to varying degrees. The consistency of our genetic association study strongly implicates KCNH2 as a risk gene for schizophrenia.

Second, we have shown, in an independent set of healthy control individuals, significant association of the risk SNPs with schizophrenia-like shifts in several of the most consistently reported intermediate biologic phenotypes: impairments in memory and IQ/cognitive processing speed, reduced hippocampal volumes as measured by MRI, and inefficient physiological engagement of the hippocampus during memory tasks as measured by fMRI. These independent associations with variations in brain structure and function provide further links between the gene and well-established cognitive functions and neurobiological phenomena relevant to schizophrenia.

Third, we have extended the study beyond the clinic to elucidate the basic mechanisms that may underlie the genetic associations with KCNH2. We started with characterizing the expression of KCNH2 mRNA in postmortem human brain. Unexpectedly, we identified a novel isoform (3.1) of KCNH2 that is primate specific and highly abundant within the brain. Unlike the classic KCNH2-1A form, this novel Isoform 3.1 shows trace expression in heart. Remarkably, expression of this isoform is significantly increased within the hippocampus of patients with schizophrenia (2.5 fold increase relative to the full length form) and even in normal individuals who carry risk alleles. Thus, genetic association appears to relate to this novel isoform specifically, relating largely to regulation of its expression. In addition, structural analysis reveals that the novel isoform lacks the major part of the PAS domain, which is known to be critical for the characteristic slow deactivation of KCNH2. We then overexpressed this novel isoform in rodent pyramidal neurons and found that it produced a rapidly deactivating K+ current and a high-frequency, non-adapting firing pattern. These results have important implications for normal higher order cognition and also for disordered cognition seen in schizophrenia. As a sustained, non-adapting discharge pattern has been considered to be important for cortical information processing underlying higher-order cognitive and memory tasks in primates, normal physiological levels of the 3.1 Isoform may be an important evolutional development in primates to support this pattern of neuronal activity. However, elevated expression of this isoform, as is found in schizophrenia, might cause uncontrolled and desynchronized firings in cortical circuits, thus leading to anomalies in performance in complex cognitive functions seen in schizophrenia patients and even in normal subjects carrying risk alleles and abnormal patterns of cortical physiological activity. Indeed, disorganized physiologic activity is a hallmark of recent neurophysiologic studies of patients with schizophrenia.

Taken together, these convergent findings provide compelling evidence to implicate a novel KCNH2 isoform as playing a role in the etiology and pathophysiology of schizophrenia. Given that many available antipsychotic drugs also bind to KCNH2-1A (reference Kongsamut et al., Eur J Pharmacol. 2002 Aug. 16; 450(1):37-41), accounting for their cardiac side effects, and that Isoform 3.1 is relatively brain specific and plays a major role in controlling neuronal firing, our results also point to a promising new therapeutic target that could spare the cardiac side effects typically associated with other antipsychotic agents.

Description of HERG and PAS Domain

HERG (human eag-related gene) is a member of the eag (ether-a-go.go) K+ channel family (Warmke, J. W. et al. 1991 Science 252:1560-1562; Warmke, J. W. and Ganetzky, B 1994 Proc Natl Acad Sci USA 91:3438-3442). These channels, found in human heart and nervous system, underlie one form of the long QT syndrome, LQT2 (Curran, M. E. et al. 1995 Cell 80:795-803), a genetic condition causing familial cardiac arrhythmia and sudden death. In common with other voltage-dependent K+ channels, HERG has a subunit topology of six membrane-spanning stretches (FIG. 1). Four of these subunits form a tetramer with a central ion conduction pore. Voltage-dependent gating, or opening and closing of the pore, is conferred by the S4 "voltage sensor" (the arginine-rich fourth membrane-spanning stretch) present in all members of the voltage-dependent cation channel family (Sigworth, F J. 1994 Rev Biophys 27:1-40).

Referring to FIG. 1, the HERG channel monomer has six transmembrane segments labeled S1 to S6; S4 is the voltage sensor, and it contains six positively charged amino acids as indicated by the + symbols. The channel has a large C terminus and the characteristic N-terminal eag domain, both cytosolic; the pore region is situated between S5 and S6. The functional channel is a tetramer with a central ion conduction pathway.

HERG exhibits two distinct and physiologically significant gating characteristics: rapid inactivation and slow deactivation (Trudeau, M. C. et al. 1995 Science 269:92-95; Smith, et al. 1996 Nature 379:833-836; Spector, P. S. et al. 1996 J Gen Physiol 107:611-619). The presence of rapid inactivation means that when the channel is opened with cell membrane depolarization it very quickly enters a nonconducting (inactivated) state, passing very little current in the outward direction. When the membrane is returned to its normal resting potential near −80 mV, the channel apparently retraces its conformational steps and passes through the open state on the way back to its closed configuration. The return to the closed state, referred to as the process of deactivation, is very slow in the HERG channel, and consequently a large inward "tail" K+ current is observed during a voltage clamp experiment. This slow rate of HERG channel deactivation plays an important role in cardiac electrical excitability by governing the length of the action potential (Sanguinetti. M. C. et al. 1995 Cell 81:299-307).

Figure 2:
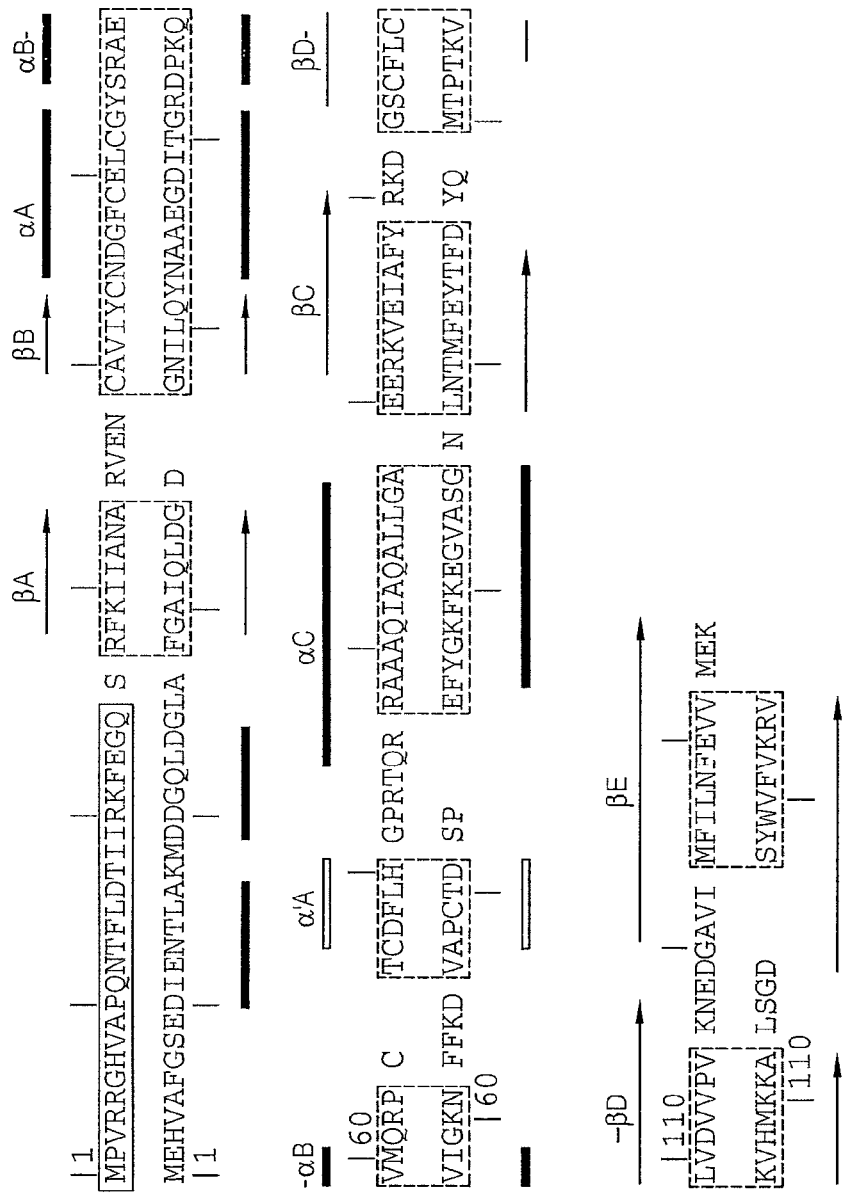
FIG. 2. Sequence alignment of the eag domains of KCNH2 (top, SEQ ID NO: 6) and Photoactive Yellow Protein (bottom, SEQ ID NO: 7).

Deletion of the HERG cytoplasmic amino terminus has been shown to profoundly affect the rate of deactivation (Schönherr, R. and Heinemann, S. H. 1996 J Physiol 493:635-642; Spector, P. S. et al., 1996 J Gen Physiol 107:611-619; Terlau et al. 1997 J Physiol 502:537-543). This finding is very interesting because the amino terminus of HERG contains a sequence of about 135 amino acids, which is not only highly conserved, but is sufficiently unique to be considered a defining feature of the eag K+ channel family (Warmke, J. W. and Ganetzky, B. 1994 Proc Natl Acad Sci USA 91:3438-3442). The eag domain controls deactivation by tightly associating with the body of the K+ channel, presumably through a hydrophobic patch on its surface. Its three-dimensional structure defines the first eukaryotic member of the PAS domain family. PAS (acronym for the gene products of Per, Arnt, and Sim) (Reppert, S. M. 1998 Cell 21:1-4; Sassone-Corsi, P. 1998 Nature 392:871-874) domains are found in proteins involved in the circadian rhythm, the cyclic patterns of hormone secretion, breeding, and locomotor activity in mammals and the oscillation of photosynthesis in plants. In prokaryotic cells, PAS domains regulate a variety of biochemical processes by serving as light and chemical sensors. Referring to FIG. 2, the eag domains of KCNH2 (top) and Photoactive Yellow Protein (PYP) (bottom) are aligned according to superimposed structural models. It is clear that the eag domain and PYP have highly similar three-dimensional structures. The dashed boxes mark stretches of sequence where aligned residues occupy the same position in secondary structural elements that are common to both structures. Secondary structural elements are marked above and below the corresponding sequences: α helices as arrows, β strands as filled rectangles, 3io helix as open rectangle. The structural elements of the eag domain structure are labeled. The solid box marks residues that are disordered in the eag domain structure. Residue numbering is shown above and below the respective sequences. The eag domain is an α+β protein with a five-stranded antiparallel β sheet (βA to βE) packed against a long ordered "vine" composed of coil and a single turn of 3io helix (α'A). The sheet is decorated on two sides by α helices (αA to αC). The structure has its N and C termini positioned side by side forming two central strands of the β sheet.

The major difference between the two proteins occurs in the way the αC helix and associated "vine" pack against the β sheet. A structure-based sequence alignment of the eag domain and PYP shows that there is no significant sequence conservation. The relatedness of these proteins is apparent only through comparison of their three-dimensional structures. HERG and other members of the eag K+ channel family contain a PAS domain on their cytoplasmic N terminus. Cabral et al. 1998 (Cabral et al. 1998 Cell 95:649-655) artificially created an N-terminally truncated protein (HERG Δ2-135) lacking amino acids 2-135 of HERG.

The investigators determined that removal of the PAS domain alters a physiologically important gating transition in HERG, and addition of isolated domain to the cytoplasm of cells expressing truncated HERG reconstitutes wild-type gating. In summary, Cabral et al. 1998 concluded that the eag domain is a member of the PAS domain family and its role is to modify K+ channel gating.

Nucleic Acid Molecules

Figure 4:
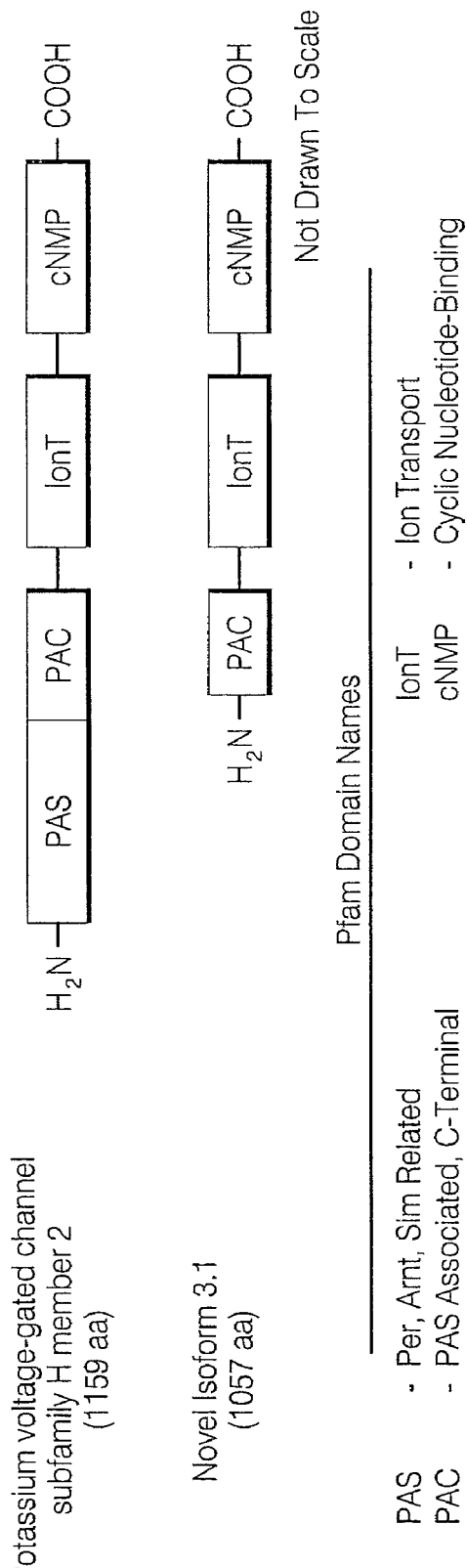
FIG. 4. General Domain Layouts of KCNH2 and Novel Isoform 3.1.

The cDNA sequence (SEQ ID NO:1) and deduced amino acid sequence (SEQ ID NO:2) of KCNH2 are shown in FIG. 3; the general domain layouts are illustrated in FIG. 4. The cDNA sequence (SEQ ID NO:3) and deduced amino acid sequence (SEQ ID NO:4) of Isoform 3.1 are shown in FIG. 3; the general domain layouts are illustrated in FIG. 4.

The present invention provides isolated nucleic acid molecules comprising polynucleotide sequences that have been identified as encoding isoform 3.1, here defined as HERG Δ2-102. HERG Δ2-102 means an N-terminally truncated polypeptide lacking amino acids 2-102 of HERG (SEQ ID NO: 2) thus missing much of the PAS domain but retaining secondary structural elements βD and βE sheets and making it SEQ ID NO: 5, and, in some embodiments, replacing the first amino acid with 6 amino acids unique to the isoform in humans (M S S H S A; SEQ ID NO: 16), in monkeys (M F S H S T; SEQ ID NO: 17), or in other species. The invention further provides a nucleotide sequence determined from a mRNA molecule encoding isoform 3.1, which comprises the cDNA encoding isoform 3.1, including the 1.1 Kb 5' untranslated region unique to isoform 3.1 (SEQ ID NO:3).

SEQ ID NO: 5

```
MGSCFLCLVDVVPVKNEDGAVIMFILNFEVVMEKDMVGSPAHD

TNHRGPPTSWLAPGRAKTFRLKLPALLALTAPVESSVRSGGAGGAGAPG

AVVVDVDLTPAAPSSESLALDEVTAMDNHVAGLGPAEERRALVGPGSPP

RSAPGQLPSPRAHSLNPDASGSSCSLARTRSRESCASVRRASSADDIEA

MRAGVLPPPPRHASTGAMHPLRSGLLNSTSDSDLVRYRTISKIPQITLN

FVDLKGDPFLASPTSDREIIAPKIKERTHNVTEKVTQVLSLGADVLPEY

KLQAPRIHRWTILHYSPFKAVWDWLILLLVIYTAVFTPYSAAFLLKETE

EGPPATECGYACQPLAVVDLIVDIMFIVDILINFRTTYVN ANEEVVSH

PGRIAVHYFKGWFLIDMVAAIPFDLLIFGSGSEELIGLLKTARLLRLVR

VARKLDRYSEYGAAVLFLLMCTFALIAHWLACIWYAIGNMEQPHMDSRI

GWLHNLGDQIGKP YNSSGLGGPSIKDKYVTAL YFTFSSLTSVGFGNV

SPNTNSEKIFSICVMLIGSLMYASIFGNVSAIIQRLYSGTARYHTQMLR

VREFIRFHQIPNPLRQRLEEYFQHAWSYTNGIDMNAVLKGFPECLQADI

CLHLNRSLLQHCKPFRGATKGCLRALAMKFKTTHAPPGDTLVHAGDLLT

ALYFISRGSIEILRGDVVVAILGKNDIFGEPLNLYARPGKSNGDVRALT

YCDLHKIHRDDLLEVLDMYPEFSDHFWSSLEITFNLRDTNMIPGSPGST

ELEGGFSRQRKRKLSFRRRTDKDTEQPGEVSALGPGRAGAGPSSRGRPG

GPWGESPSSGPSSPESSEDEGPGRSSSPLRLVPFSSPRPPGEPPGGEPL

MEDCEKSSDTCNPLSGAFSGVSNIFSFWGDSRGRQYQELPRCPAPTPSL

LNIPLSSPGRRPRGDVESRLDALQRQLNRLETRLSADMATVLQLLQRQM

TLVPPAYSAVTTPGPGPTSTSPLLPVSPLPTLTLDSLSQVSQFMACEEL

PPGAPELPQEGPTRRLSLPGQLGALTSQPLHRHGSDPGS
```

The term "isolated" means that the material is removed from its original environment (e.g., the natural environment if it is naturally occurring). For example, a naturally-occurring nucleic acid molecule or polynucleotide present in a living organism is not isolated, but the same nucleic acid molecule or polynucleotide, separated from some or all of the coexisting materials in the natural environment, is isolated. Such nucleic acid molecule could be part of a vector and/or such polynucleotide could be part of a composition, and still be isolated in that such vector or composition is not part of the natural environment of the nucleic acid molecule or polynucleotide.

By "nucleotide sequence" of a nucleic acid molecule or polynucleotide is intended, for a DNA molecule or polynucleotide, a sequence of deoxyribonucleotides, and for an RNA molecule or polynucleotide, the corresponding sequence of ribonucleotides (A, G, C and U), where each thymidine deoxyribonucleotide (T) in the specified deoxyribonucleotide sequence is replaced by the ribonucleotide uridine (U).

Using the information provided herein, such as a nucleotide sequence shown in the sequence listing, a nucleic acid molecule of the present invention encoding a polypeptide may be obtained using standard cloning and screening procedures, such as those for cloning cDNAs using mRNA as starting material. See, for example, Molecular Cloning: a Laboratory Manual, 3rd edition, Sambrook et al. 2001 Cold Spring Harbor Laboratory Press, New York and Current Protocols in Molecular Biology, Ausubel et al. eds., John Wiley & Sons, 1994.

Nucleic acid molecules of the present invention may be in the form of RNA, such as mRNA, or in the form of DNA, including, for instance, cDNA and genomic DNA obtained by cloning or produced synthetically. The DNA may be double-stranded or single-stranded. Single-stranded DNA or RNA may be the coding strand, also known as the sense strand, or it may be the non-coding strand, also referred to as the anti-sense strand.

In addition to nucleic acid molecules encoding isoform 3.1, isolated nucleic acid molecules of the invention include DNA molecules that comprise a sequence substantially different from those described above but that, due to the degeneracy of the genetic code, still encode the proteins shown in the sequence listing. Of course, the genetic code and species-specific codon preferences are well known in the art. Thus, it would be routine for one skilled in the art to generate the degenerate variants described above, for instance, to optimize codon expression for a particular host (e.g., change codons in the human mRNA to those preferred by a bacterial host such as E. coli).

The invention further provides a nucleic acid molecule having a sequence complementary to one of the above sequences. Such isolated molecules, particularly DNA molecules, are useful as probes for gene mapping, by in situ hybridization with chromosomes, and for detecting expression of the corresponding gene(s) in human tissue, for instance, by Northern blot analysis. The present invention is further directed to nucleic acid molecules encoding portions of the nucleotide sequences described herein as-well as to fragments of the isolated nucleic acid molecules described herein. By a "fragment" of an isolated nucleic acid molecule is intended fragments at least about 15 nt, and more preferably at least about 20 nt, still more preferably at least about 30 nt, and even more preferably, at least about 40 nt in length that are useful as diagnostic probes and primers. Of course, larger fragments 50-500 nt in length are also useful according to the present invention as are fragments corresponding to most, if not all, of the nucleic acid molecules encoding isoform 3.1. By a fragment "at least 20 nt in length," for example, is intended fragments that include 20 or more contiguous bases from the nucleic acid molecules encoding isoform 3.1. Some nucleic acid fragments of the present invention include the 1.1 Kb 5' untranslated region unique to isoform 3.1.

In another aspect, the invention provides an isolated nucleic acid molecule comprising a polynucleotide that hybridizes under stringent hybridization conditions to a portion of a nucleic acid molecule of the invention described above. By "stringent hybridization conditions" is intended overnight incubation at 42° C. in a solution comprising: 50% formamide, 5×SSC (750 mM NaCl, 75 mM trisodium citrate), 50 mM sodium phosphate (pH 7.6), 5×Denhardt's solution, 10% dextran sulfate, and 20 µg/ml denatured, sheared salmon sperm DNA, followed by washing the filters in 0.1× SSC at about 650 C.

By a polynucleotide that hybridizes to a "portion" of a polynucleotide is intended a polynucleotide (either DNA or RNA) hybridizing to at least about 15 nucleotides (nt), and more preferably at least about 20 nt, still more preferably at least about 30 nt, and even more preferably about 30-70 (e.g., 50) nt, or 50-500 nts in length or fragments corresponding to most, if not all, of the reference polynucleotide.

By a portion of a polynucleotide of "at least 20 nt in length," for example, is intended 20 or more contiguous nucleotides from the nucleotide sequence of the reference polynucleotide. Of course, a polynucleotide that hybridizes only to a poly A sequence (such as any 3' terminal poly(A) tract of a cDNA), or to a complementary stretch of T (or U)

residues, would not be included in a polynucleotide of the invention used to hybridize to a portion of a nucleic acid of the invention, since such a polynucleotide would hybridize to any nucleic acid molecule containing a poly (A) stretch or the complement thereof (e.g., practically any double-stranded cDNA clone).

Also encoded by nucleic acids of the invention are the amino acid sequences of the invention together with additional, non-coding sequences, including for example, but not limited to introns and non-coding 5' and 3' sequences, such as the transcribed, non-translated sequences that play a role in transcription, mRNA processing, including splicing and polyadenylation signals, for example—ribosome binding and stability of mRNA; and additional coding sequence that codes for additional amino acids, such as those that provide additional functionalities. Thus, the sequence encoding the polypeptide may be fused to a marker sequence, such as a sequence encoding a peptide that facilitates purification of the fused polypeptide. In certain preferred embodiments of this aspect of the invention, the marker amino acid sequence is a hexa-histidine peptide, such as the tag provided in a pQE vector (QIAGEN Inc., 28159 Avenue Stanford, Valencia, Calif. 91355), among others, many of which are commercially available. As described in Gentz et al. 1989 Proc Natl Acad USA 86:821-824, for instance, hexa-histidine provides for convenient purification of the fusion protein. The "HA" tag is another peptide useful for purification that corresponds to an epitope derived from the influenza hemagglutinin protein, which has been described by Wilson et al. 1984 Cell 37:767-778.

Variant and Mutant Polynucleotides

The present invention further relates to variants of the nucleic acid molecules of the i 0 present invention, which encode portions, analogs or derivatives of the isoform. Variants may occur naturally, such as a natural allelic variant. By an "allelic variant" is intended one of several alternate forms of a gene occupying a given locus on a chromosome of an organism. Genes II, Lewin, B., ed., John Wiley & Sons, New York (1985). Non-naturally occurring variants may be produced using art-known mutagenesis techniques.

Such variants include those produced by nucleotide substitutions, deletions or additions. The substitutions, deletions or additions may involve one or more nucleotides. The variants may be altered in coding regions, non-coding regions, or both. Alterations in the coding regions may produce conservative or non-conservative amino acid substitutions, deletions or additions. Especially preferred among these are silent substitutions, additions and deletions, which do not alter the properties and activities of the channel protein or portions thereof. Also especially preferred in this regard are conservative substitutions.

Most highly preferred are nucleic acid molecules encoding isoform 3.1 having the amino acid sequence of SEQ ID NO: 5 and the nucleotide sequence of the cDNA having SEQ ID NO: 3. Further embodiments include an isolated nucleic acid molecule comprising a polynucleotide having a nucleotide sequence at least 85% identical, more preferably at least 90% identical, and most preferably at least 95%, 96%, 97%, 98% or 99% identical to a polynucleotide of the invention, or a polynucleotide that hybridizes under stringent hybridization conditions to such a polynucleotide. This polynucleotide that hybridizes does not hybridize under stringent hybridization conditions to a polynucleotide 0 having a nucleotide sequence consisting of only A residues or of only T residues. An additional nucleic acid embodiment of the invention relates to an isolated nucleic acid molecule comprising a polynucleotide that includes the 1.1 Kb 5' untranslated region unique to isoform 3.1.

By a polynucleotide having a nucleotide sequence at least, for example, 95% "identical" to a reference nucleotide sequence is intended that the nucleotide sequence of the polynucleotide is identical to the reference sequence except that the polynucleotide sequence may include up to five point mutations per each 100 nucleotides of the reference nucleotide sequence encoding the reference polypeptide. In other words, to obtain a polynucleotide having a nucleotide sequence at least 95% identical to a reference nucleotide sequence, up to 5% of the nucleotides in the reference sequence may be deleted or substituted with another nucleotide, or a number of nucleotides up to 5% of the total nucleotides in the reference sequence may be inserted into the reference sequence. These mutations of the reference sequence may occur at the 5' or 3' terminal positions of the reference nucleotide sequence or anywhere between those terminal positions, interspersed either individually among nucleotides in the reference sequence or in one or more contiguous groups within the reference sequence.

As a practical matter, whether any particular nucleic acid molecule is at least 85%, 90%, 95%, 96%, 97%, 98% or 99% identical to, for instance, the nucleotide sequence encoding isoform 3.1 having the amino acid sequence of SEQ ID NO: 5 and the nucleotide sequence of the cDNA having SEQ ID NO: 3 can be determined conventionally using known computer programs such as the Bestfit program (Wisconsin Sequence Analysis Package, Version 8 for Unix, Genetics Computer Group, University Research Park, 575 Science Drive, Madison, Wis. 53711). Bestfit uses the local homology algorithm of Smith and Waterman 1981 Advances in Applied Mathematics 2:482-489, to find the best segment of homology between two sequences. When using Bestfit or any other sequence alignment program to determine whether a particular sequence is, for instance, 95% identical to a reference sequence according to the present invention, the parameters are set, of course, such that the percentage of identity is calculated over the full length of the reference nucleotide sequence and that gaps in homology of up to 5% of the total number of nucleotides in the reference sequence are allowed.

Vectors, Host Cells and Protein Production

The present invention also relates to vectors that include the isolated DNA molecules of the present invention, host cells that are genetically engineered with the recombinant vectors, and the production of polypeptides or fragments thereof by recombinant techniques. The vector may be, for example, a phage, plasmid, viral or retroviral vector. Retroviral vectors may be replication competent or replication defective. In the latter case, viral propagation generally will occur only in complementing host cells.

The polynucleotides may be joined to a vector containing a selectable marker for propagation in a host. Generally, a plasmid vector is introduced in a precipitate, such as a calcium phosphate precipitate, or in a complex with a charged lipid. If the vector is a virus, it may be packaged in vitro using an appropriate packaging cell line and then transduced into host cells.

The DNA insert should be operatively linked to an appropriate promoter, such as the phage lambda PL promoter, the *E. coli* lac, tip, phoA and tac promoters, the SV40 early and late promoters and promoters of retroviral LTRs, to name a few. Other suitable promoters will be known to the skilled artisan. The expression constructs will further contain sites for transcription initiation, termination and, in the transcribed region, a ribosome binding site for translation. The coding portion of the transcripts expressed by the constructs will preferably include a translation initiating codon at the beginning and a termination codon (UAA, UGA or UAG) appropriately positioned at the end of the polypeptide to be translated.

As indicated, the expression vectors will preferably include at least one selectable marker. Such markers include dihydrofolate reductase, G418 or neomycin resistance for eukaryotic cell culture and tetracycline, kanamycin or ampicillin resistance genes for culturing in *E. coli* and other bacteria. Representative examples of appropriate hosts include, but are not limited to, bacterial cells, such as *E. coli, Streptomyces* and *Salmonella typhimurium* cells; fungal cells, such as yeast cells; insect cells such as *Drosophila* S2 and *Spodoptera* Sf9 cells; animal cells such as CHO, COS, and 293 cells; and plant cells. Appropriate culture mediums and conditions for the above-described host cells are known in the art.

Among vectors available for use in bacteria include pQE70, pQE60 and pQE-9, available from QIAGEN, Inc., supra; pBluescript vectors, Phagescript vectors, pNH8A, pNH16a, pNH18A, pNH46A, available from Stratagene Cloning Systems, Inc.; and ptrc99a, pKK223-3, pKK233-3, pDR540, pRIT5 available from Pharmacia Biotech, Inc. Among suitable eukaryotic vectors are pWLNEO, pSV2CAT, pOG44, pXT1 and pSG available from Stratagene; and pSVK3, pBPV, pMSG and pSVL available from Pharmacia. Other suitable vectors will be readily apparent to the skilled artisan.

Introduction of the construct into the host cell can be effected by calcium phosphate transfection, DEAE-dextran mediated transfection, cationic lipid-mediated transfection, electroporation, transduction, infection or other methods. Such methods are described in many standard laboratory manuals, such as Davis et al., Basic Methods In Molecular Biology (1986).

The polypeptide may be expressed in a modified form, such as a fusion protein, and may include not only secretion signals, but also additional heterologous functional regions. For instance, a region of additional amino acids, particularly charged amino acids, may be added to the N-terminus of the polypeptide to improve stability and persistence in the host cell, during purification, or during subsequent handling and storage. Also, peptide moieties may be added to the polypeptide to facilitate purification. Such regions may be removed prior to final preparation of the polypeptide. The addition of peptide moieties to polypeptides to engender secretion or excretion, to improve stability and to facilitate purification, among others, are familiar and routine techniques in the art. A representative fusion protein comprises a heterologous region from immunoglobulin that is useful to stabilize and purify proteins.

A protein of this invention can be recovered and purified from recombinant cell cultures by well-known methods including ammonium sulfate or ethanol precipitation, acid extraction, anion or cation exchange chromatography, phosphocellulose chromatography, hydrophobic interaction chromatography, affinity chromatography, hydroxylapatite chromatography and lectin chromatography. Most preferably, high performance liquid chromatography ("HPLC") is employed for purification. Polypeptides of the present invention include: products purified from natural sources, including bodily fluids, tissues and cells, whether directly isolated or cultured; products of chemical synthetic procedures; and products produced by recombinant techniques from a prokaryotic or eukaryotic host, including, for example, bacterial, yeast, higher plant, insect and mammalian cells. Depending upon the host employed in a recombinant production procedure, the polypeptides of the present invention may be glycosylated or may be non-glycosylated. In addition, polypeptides of the invention may also include an initial modified methionine residue, in some cases as a result of host-mediated processes. Thus, it is well known in the art that the N-terminal methionine encoded by the translation initiation codon generally is removed with high efficiency from any protein after translation in all eukaryotic cells. While the N-terminal methionine on most proteins also is efficiently removed in most prokaryotes, for some proteins this prokaryotic removal process is inefficient, depending on the nature of the amino acid to which the N-terminal methionine is covalently linked Polypeptides and Fragments The invention further provides isolated polypeptides having an amino acid sequence encoded by isoform 3.1 nucleic acid molecules, or a peptide or polypeptide comprising a portion of the above polypeptides. At the simplest level, the amino acid sequence can be synthesized using commercially available peptide synthesizers. This is particularly useful in producing small peptides and fragments of larger polypeptides. Such fragments are useful, for example, in generating antibodies against the native polypeptide.

Variant and Mutant Polypeptides

To improve or alter the characteristics of the polypeptides of the invention, protein engineering may be employed. Recombinant DNA technology known to those skilled in the art can be used to create novel mutant proteins or "muteins" including single or multiple amino acid substitutions, deletions, additions or fusion proteins. Such modified polypeptides can show, e.g., enhanced activity or increased stability. In addition, they may be purified in higher yields and show better solubility than the corresponding natural polypeptide, at least under certain purification and storage conditions.

In addition, it also will be recognized by one of ordinary skill in the art that some amino acid sequences of a polypeptide can be varied without significant effect on the structure or function of the protein. If such differences in sequence are contemplated, it should be remembered that there will be critical areas on the protein that determine activity.

Thus, the invention further includes variants of a polypeptide that show substantial biological activity or that include regions of the protein such as the portions discussed below. Such mutants include deletions, insertions, inversions, repeats, and type substitutions selected according to general rules known in the art so as have little effect on activity. For example, guidance concerning how to make phenotypically silent amino acid substitutions is provided in Bowie, J. U. et al., 1990 Science 247:1306-1310, wherein the authors indicate that there are two main approaches for studying the tolerance of an amino acid sequence to change. The first method relies on the process of evolution, in which mutations are either accepted or rejected by natural selection. The second approach uses genetic engineering to introduce amino acid changes at specific positions of a cloned gene and selections or screens to identify sequences that maintain functionality.

As the authors state, these studies have revealed that proteins are surprisingly tolerant of amino acid substitutions. The authors further indicate which amino acid changes are likely to be permissive at a certain position of the protein. For example, most buried amino acid residues require nonpolar side chains, whereas few features of surface side chains are generally conserved. Other such phenotypically silent substitutions are described in Bowie, J. U. et al., supra, and the references cited therein. Typically seen as conservative substitutions are the replacements, one for another, among the aliphatic amino acids Ala, Val, Leu and Ile; interchange of the hydroxyl residues Ser and Thr, exchange of the acidic residues Asp and Glu, substitution between the amide residues Asn and Gln, exchange of the basic residues Lys and Arg and replacements among the aromatic residues Phe, Tyr.

Thus, the fragment, derivative or analog of a polypeptide of the invention may be (i) one in which one or more of the amino acid residues are substituted with a conserved or non-conserved amino acid residue (preferably a conserved amino acid residue) and such substituted amino acid residue may or may not be one encoded by the genetic code, or (ii) one in which one or more of the amino acid residues includes a substituent group, or (iii) one in which the mature polypeptide is fused with another compound, such as a compound to increase the half-life of the polypeptide (for example, polyethylene glycol), or (iv) one in which the additional amino acids are fused to the above form of the polypeptide, such as an IgG Fc fusion region peptide or leader or secretory sequence or a sequence that is employed for purification of the above form of the polypeptide or a proprotein sequence. Such fragments, derivatives and analogs are deemed to be within the scope of those skilled in the art from the teachings herein.

Thus, the polypeptides of the present invention may include one or more amino acid substitutions, deletions or additions, either from natural mutations or human manipulation. As indicated, changes are preferably of a minor nature, such as conservative amino acid substitutions that do not significantly affect the folding or activity of the protein (refer to Table 1).

TABLE 1

Conservative Amino Acid Substitutions

| | |
|---|---|
| Aromatic | Phenylalanine |
| | Tryptophan |
| | Tyrosine |
| Hydrophobic | Leucine |
| | Isoleucine |
| | Valine |
| Polar | Glutamine |
| | Asparagine |
| Basic | Arginine |
| | Lysine |
| | Histidine |
| Acidic | Aspartic Acid |
| | Glutamic Acid |
| Small | Alanine |
| | Serine |
| | Threonine |
| | Methionine |
| | Glycine |

Amino acids in the protein of the present invention that are essential for function can be identified by methods known in the art, such as site-directed mutagenesis or alanine-scanning mutagenesis (Cunningham and Wells 1989 Science 244: 1081-1085). The latter procedure introduces single alanine mutations at every residue in the molecule. The resulting mutant molecules are then tested for biological activity such as binding characteristics or in vitro or in vivo channel activity.

The polypeptides of the present invention are preferably provided in an isolated form. A recombinantly produced version of a polypeptide of the invention can be substantially purified by the one-step method described in Smith and Johnson, 1988 Gene 67:31-40. Polypeptides of the invention also can be purified from natural or recombinant sources using antibodies of the invention raised against the protein in methods that are well known in the art of protein purification.

Further polypeptides of the present invention include polypeptides that have at least 90% similarity, more preferably at least 95% similarity, and still more preferably at least 96%, 97%, 98% or 99% similarity to those described above. The polypeptides of the invention also comprise those that are at least 85% identical, more preferably at least 90% or 95% identical, still more preferably at least 96%, 97%, 98% or 99% identical to the polypeptide encoded by isoform 3.1 nucleic acid molecules, and also include portions of such polypeptides with at least 30 amino acids and more preferably at least 50 amino acids.

By "% similarity" for two polypeptides is intended a similarity score produced by comparing the amino acid sequences of the two polypeptides using the Bestfit program (Wisconsin Sequence Analysis Package, Version 8 for Unix, Genetics Computer Group, University Research Park, 575 Science Drive, Madison, Wis. 53711) and the default settings for determining similarity. Bestfit uses the local homology algorithm of Smith and Waterman 1981 Advances in Applied Mathematics 2:482-489, to find the best segment of similarity between two sequences.

By a polypeptide having an amino acid sequence at least, for example, 95% "identical" to a reference amino acid sequence of a polypeptide described herein is intended that the amino acid sequence of the polypeptide is identical to the reference sequence except that the polypeptide sequence may include up to five amino acid alterations per each 100 amino acids of the reference amino acid of the polypeptide of the invention. In other words, to obtain a polypeptide having an amino acid sequence at least 95% identical to a reference amino acid sequence, up to 5% of the amino acid residues in the reference sequence may be deleted or substituted with another amino acid, or a number of amino acids up to 5% of the total amino acid residues in the reference sequence may be inserted into the reference sequence. These alterations of the reference sequence may occur at the amino or carboxy terminal positions of the reference amino acid sequence or anywhere between those terminal positions, interspersed either individually among residues in the reference sequence or in one or more contiguous groups within the reference sequence.

As a practical matter, whether any particular polypeptide is at least 90%, 95%, 96%, 97%, 98% or 99% identical to, for instance, an amino acid sequence encoded by the isoform 3.1 nucleic acid molecules can be determined conventionally using known computer programs such the Bestfit program (Wisconsin Sequence Analysis Package, Version 8 for Unix, Genetics Computer Group, University Research Park, 575 Science Drive, Madison, Wis. 53711). When using Bestfit or any other sequence alignment program to determine whether a particular sequence is, for instance, 95% identical to a reference sequence according to the present invention, the parameters are set, of course, such that the percentage of identity is calculated over the full length of the reference amino acid sequence and that gaps in homology of up to 5% of the total number of amino acid residues in the reference sequence are allowed.

Antibodies

"Antibody" as used herein includes intact immunoglobulin molecules, as well as fragments thereof, such as Fab, F(ab')2, and Fv, which are capable of binding an epitope of isoform 3.1. Typically, at least 6, 8, 10, or 12 contiguous amino acids are required to form an epitope. However, epitopes that involve non-contiguous amino acids may require more, e.g., at least 15, 25, or 50 amino acid. An antibody that specifically binds to an epitope of isoform 3.1 can be used therapeutically, as well as in immunochemical assays, such as Western blots, ELISAs, radio immunoassays, immunohistochemical assays, immunoprecipitations, or other immunochemical assays known in the art. Various immunoassays can be used to identify antibodies having the desired specificity. Numerous protocols for competitive binding or immunoradiometric assays are well known in the art. Such immunoassays typically involve the measurement of complex formation between an immunogen and an antibody that specifically binds to the isoform 3.1 immunogen.

Typically, an antibody that specifically binds to isoform 3.1 provides a detection signal at least 5-, 10-, or 20-fold higher than a detection signal provided with other proteins when used in an immunochemical assay. Preferably, antibodies that specifically bind to isoform 3.1 do not detect other proteins, especially KCNH2, in immunochemical assays and can immunoprecipitate isoform 3.1 from solution.

Isoform 3.1 can be used to immunize a mammal, such as a mouse, rat or rabbit to produce polyclonal antibodies. If desired, isoform 3.1 can be conjugated to a carrier protein, such as bovine serum albumin, thyroglobulin, and keyhole limpet hemocyanin. Depending on the host species, various adjuvants can be used to increase the immunological response. Such adjuvants include, but are not limited to, Freund's adjuvant, mineral gels (e.g., aluminum hydroxide), and surface active substances (e.g., lysolecithin, pluronic polyols, polyanions, peptides, oil emulsions, keyhole limpet hemocyanin, and dinitrophenol). Among adjuvants used in humans, BCG (bacilli Calmette-Guerin) and *Corynebacterium parvum* are especially useful.

Monoclonal antibodies that specifically bind to isoform 3.1 can be prepared using any technique that provides for the production of antibody molecules by continuous cell lines in culture. These techniques include, but are not limited to, the hybridoma technique, the human B-cell hybridoma technique, and the EBV-hybridoma technique.

In addition, techniques developed for the production of "chimeric antibodies", the splicing of mouse antibody genes to human antibody genes to obtain a molecule with appropriate antigen specificity and biological activity, can be used. Monoclonal and other antibodies also can be "humanized" to prevent a patient from mounting an immune response against the antibody when it is used therapeutically. Such antibodies may be sufficiently similar in sequence to human antibodies to be used directly in therapy or may require alteration of a few key residues. Sequence differences between rodent antibodies and human sequences can be minimized by replacing residues that differ from those in the human sequences by site directed mutagenesis of individual residues or by grafting of entire complementarily determining regions. Antibodies that specifically bind to isoform 3.1 can contain antigen binding sites that are either partially or fully humanized.

Alternatively, techniques described for the production of single chain antibodies can be adapted using methods known in the art to produce single chain antibodies that specifically bind to isoform 3.1. Antibodies with related specificity, but of distinct idiotypic composition, can be generated by chain shuffling from random combinatorial immunoglobin libraries. Single-chain antibodies also can be constructed using a DNA amplification method, such as PCR, using hybridoma cDNA as a template. Single-chain antibodies can be mono- or bispecific, and can be bivalent or tetravalent. Construction of tetravalent, bispecific single-chain antibodies is taught. A nucleotide sequence encoding a single-chain antibody can be constructed using manual or automated nucleotide synthesis, cloned into an expression construct using standard recombinant DNA methods, and introduced into a cell to express the coding sequence. Alternatively, single-chain antibodies can be produced directly using, for example, filamentous phage technology.

Antibodies that specifically bind to isoform 3.1 also can be produced by inducing in vivo production in the lymphocyte population or by screening immunoglobulin libraries or panels of highly specific binding reagents. Other types of antibodies can be constructed and used therapeutically in methods of the invention. Binding proteins that are derived from immunoglobulins and that are multivalent and multispecific, such as the "diabodies" described in WO 94/13804, also can be prepared.

Antibodies according to the invention can be purified by methods well known in the art. For example, antibodies can be affinity purified by passage over a column to which isoform 3.1 is bound. The bound antibodies can then be eluted from the column using a buffer with a high salt concentration.

Antisense Oligonucleotides

Antisense oligonucleotides are nucleotide sequences that are complementary to a specific DNA or RNA sequence. Once introduced into a cell, the complementary nucleotides combine with natural sequences produced by the cell to form complexes and block either transcription or translation. Preferably, an antisense oligonucleotide is at least 11 nucleotides in length, but can be at least 12, 15, 20, 25, 30, 35, 40, 45, or 50 or more nucleotides long. Longer sequences also can be used. Antisense oligonucleotide molecules can be provided in a DNA construct and introduced into a cell as described above to decrease the level of isoform 3.1 gene products in the cell.

Antisense oligonucleotides can be deoxyribonucleotides, ribonucleotides, or a combination of both. Oligonucleotides can be synthesized manually or by an automated synthesizer, by covalently linking the 5' end of one nucleotide with the 3' end of another nucleotide with non-phosphodiester internucleotide linkages such alkylphosphonates, phosphorothioates, phosphorodithioates, alkylphosphonothioates, alkylphosphonates, phosphoramidates, phosphate esters, carbamates, acetamidate, carboxymethyl esters, carbonates, and phosphate triesters.

Modifications of isoform 3.1 gene expression can be obtained by designing antisense oligonucleotides that will form duplexes to the control, 5', or regulatory regions of the isoform 3.1 gene. Oligonucleotides derived from the transcription initiation site, e.g., between positions −10 and +10 from the start site, are preferred. Similarly, inhibition can be achieved using "triple helix" base-pairing methodology. Triple helix pairing is useful because it causes inhibition of the ability of the double helix to open sufficiently for the binding of polymerases, transcription factors, or chaperons. Therapeutic advances using triplex DNA have been described in the literature. An antisense oligonucleotide also can be designed to block translation of mRNA by preventing the transcript from binding to ribosomes.

Precise complementarity is not required for successful complex formation between an antisense oligonucleotide and the complementary sequence of an isoform 3.1 polynucleotide. Antisense oligo nucleotides that comprise, for example, 2, 3, 4, or 5 or more stretches of contiguous nucleotides that are precisely complementary to an isoform 3.1 polynucleotide, each separated by a stretch of contiguous nucleotides that are not complementary to adjacent isoform 3.1 nucleotides, can provide sufficient targeting specificity for isoform 3.1 mRNA. Preferably, each stretch of complementary contiguous nucleotides is at least 4, 5, 6, 7, or 8 or more nucleotides in length. Non-complementary intervening sequences are preferably 1, 2, 3, or 4 nucleotides in length. One skilled in the art can easily use the calculated melting point of an antisense-sense pair to determine the degree of mismatching that will be tolerated between a particular antisense oligonucleotide and a particular isoform 3.1 polynucleotide sequence. Antisense oligonucleotides can be modified without affecting their ability to hybridize to an isoform 3.1 polynucleotide. These modifications can be internal or at one or both ends of the antisense molecule. For example, internucleoside phosphate linkages can be modified by adding cholesteryl or diamine moieties with varying numbers of carbon residues between the amino groups and terminal ribose. Modified bases and/or sugars, such as arabinose instead of ribose, or a 3',5'-substituted oligonucleotide in which the 3' hydroxyl group or the 5' phosphate group are substituted, also can be employed in a modified antisense oligonucleotide. These modified oligonucleotides can be prepared by methods well known in the art.

Ribozymes

Ribozymes are RNA molecules with catalytic activity. Ribozymes can be used to inhibit gene function by cleaving an RNA sequence, as is known in the art. The mechanism of ribozyme action involves sequence-specific hybridization of the ribozyme molecule to complementary target RNA, followed by endonucleolytic cleavage. Examples include engineered hammerhead motif ribozyme molecules that can specifically and efficiently catalyze endonucleolytic cleavage of specific nucleotide sequences. The coding sequence of an isoform 3.1 polynucleotide can be used to generate ribozymes that will specifically bind to mRNA transcribed from an isoform 3.1 polynucleotide. Methods of designing and constructing ribozymes that can cleave other RNA molecules in trans in a highly sequence specific manner have been developed and described in the art. For example, the cleavage activity of ribozymes can be targeted to specific RNAs by engineering a discrete "hybridization" region into the ribozyme. The hybridization region contains a sequence complementary to the target RNA and thus specifically hybridizes with the target RNA.

Specific ribozyme cleavage sites within an isoform 3.1 RNA target can be identified by scanning the target molecule for ribozyme cleavage sites that include the following sequences: GUA, GUU, and GUC. Once identified, short RNA sequences of between 15 and 20 ribonucleotides corresponding to the region of the target RNA containing the cleavage site can be evaluated for secondary structural features that may render the target inoperable. Suitability of candidate isoform 3.1 RNA targets also can be evaluated by testing accessibility to hybridization with complementary oligonucleotides using ribonuclease protection assays. The nucleotide sequences shown in SEQ ID NO: 3 and its complement provide sources of suitable hybridization region sequences. Longer complementary sequences can be used to increase the affinity of the hybridization sequence for the target. The hybridizing and cleavage regions of the ribozyme can be integrally related such that upon hybridizing to the target RNA through the complementary regions, the catalytic region of the ribozyme can cleave the target.

Ribozymes can be introduced into cells as part of a DNA construct. Mechanical methods, such as microinjection, liposome-mediated transfection, electroporation, or calcium phosphate precipitation, can be used to introduce a ribozyme-containing DNA construct into cells in which it is desired to decrease isoform 3.1 expression. Alternatively, if it is desired that the cells stably retain the DNA construct, the construct can be supplied on a plasmid and maintained as a separate element or integrated into the genome of the cells, as is known in the art. A ribozyme-encoding DNA construct can include transcriptional regulatory elements, such as a promoter element, an enhancer or UAS element, and a transcriptional terminator signal, for controlling transcription of ribozymes in the cells. Ribozymes also can be engineered to provide an additional level of regulation, so that destruction of mRNA occurs only when both a ribozyme and a target gene are induced in the cells.

Screening/Screening Assays

Regulators

Regulators as used herein, refer to compounds that affect the functional activity of an isoform 3.1 in vitro and/or in vivo. Regulators can be agonists and antagonists of an isoform 3.1 polypeptide and can be compounds that exert their effect on the isoform 3.1 activity via the expression, via post-translational modifications, by direct interaction with the channel protein or by other means. Agonists of isoform 3.1 are molecules that, when bound to isoform 3.1, increase or prolong the functional activity of isoform 3.1. Agonists of isoform 3.1 include proteins, nucleic acids, carbohydrates, small molecules, or any other molecule that activate isoform 3.1. Antagonists of isoform 3.1 are molecules that, when bound to isoform 3.1, decrease the amount or the duration of the functional activity of isoform 3.1. Antagonists include proteins, nucleic acids, carbohydrates, antibodies, small molecules, or any other molecule that decrease the activity of isoform 3.1.

The term "modulate", as it appears herein, refers to a change in the activity of isoform 3.1 polypeptide. For example, modulation may cause an increase or a decrease in functional activity, binding characteristics, or any other biological, functional, or immunological properties of isoform 3.1.

As used herein, the terms "specific binding" or "specifically binding" refer to that interaction between a protein or peptide and an agonist, an antibody, or an antagonist. The interaction is dependent upon the presence of a particular structure of the protein recognized by the binding molecule (i.e., the antigenic determinant or epitope). For example, if an antibody is specific for epitope "A" the presence of a polypeptide containing the epitope A, or the presence of free unlabeled A, in a reaction containing free labeled A and the antibody will reduce the amount of labeled A that binds to the antibody.

The invention provides methods (also referred to herein as "screening assays") for identifying compounds that can be used for the treatment of neurological diseases, e.g., schizophrenia. The methods entail the identification of candidate or test compounds or agents (e.g., peptides, peptidomimetics, small molecules or other molecules) that bind to isoform 3.1 and/or have a stimulatory or inhibitory effect on the biological functional activity of isoform 3.1 or its expression and then determining which of these compounds have an effect on symptoms or diseases regarding neurological diseases, e.g., schizophrenia, in an in vivo assay.

Candidate or test compounds or agents that bind to isoform 3.1 and/or have a stimulatory or inhibitory effect on the functional activity or the expression of isoform 3.1 are identified either in assays that employ cells that express isoform 3.1 on the cell surface (cell-based assays) or in assays with isolated isoform 3.1 (cell-free assays). The various assays can employ a variety of variants of isoform 3.1 (e.g., full-length isoform 3.1, a biologically active fragment of isoform 3.1, or a fusion protein that includes all or a portion of isoform 3.1). Moreover, isoform 3.1 can be derived from any suitable mammalian species (e.g., human or monkey isoform 3.1). The assay can be a binding assay entailing direct or indirect measurement of the binding of a test compound or a known isoform 3.1 ligand to isoform 3.1. The assay can also be an activity assay entailing direct or indirect measurement of the activity of isoform 3.1. The assay can also be an expression assay entailing direct or indirect measurement of the expression of isoform 3.1 mRNA or isoform 3.1 protein. The various screening assays are combined with an in vivo assay entailing measuring the effect of the test compound on the symptoms of neurological diseases, e.g., schizophrenia.

In one embodiment, the invention provides assays for screening candidate or test compounds that bind to or modulate the functional activity of a membrane-bound (cell surface expressed) form of isoform 3.1. Such assays can employ full-length isoform 3.1, a biologically active fragment of isoform 3.1, or a fusion protein that includes all or a portion of isoform 3.1. As described in greater detail below, the test compound can be obtained by any suitable means, e.g., from conventional compound libraries. Determining the ability of the test compound to bind to a membrane-bound form of isoform 3.1 can be accomplished, for example, by coupling the test compound with a radioisotope or enzymatic label such that binding of the test compound to the isoform 3.1-expressing cell can be measured by detecting the labeled compound in a complex. For example, the test compound can be labelled with $^{125}I$, $^{35}S$, $^{14}C$, or $^{3}H$, either directly or indirectly, and the radioisotope detected by direct counting of radioemmission or by scintillation counting. Alternatively, the test compound can be enzymatically labelled with, for example, horseradish peroxidase, alkaline phosphatase, or luciferase, and the enzymatic label detected by determination of conversion of an appropriate substrate to product.

In a competitive binding format, the assay comprises contacting an isoform 3.1 expressing cell with a known compound that carries a detectable label and that binds to isoform 3.1 to form an assay mixture, contacting the assay mixture with a test compound, and determining the ability of the test compound to interact with the isoform 3.1 expressing cell, wherein determining the ability of the test compound to interact with the isoform 3.1 expressing cell comprises determining the ability of the test compound to preferentially bind the isoform 3.1 expressing cell as compared to the known compound.

In another embodiment, the assay is a cell-based assay comprising contacting a cell expressing a membrane-bound form of isoform 3.1 (e.g., full-length isoform 3.1, a biologically active fragment of isoform 3.1, or a fusion protein that includes all or a portion of isoform 3.1) expressed on the cell surface with a test compound and determining the ability of the test compound to modulate (e.g., stimulate or inhibit) the functional activity of the membrane-bound form of isoform 3.1. Determining the ability of the test compound to modulate the functional activity of the membrane-bound form of isoform 3.1 can be accomplished by any method suitable for measuring the functional activity of isoform 3.1, e.g., any method suitable for measuring the activity of any ion channel or other electrogenic target protein (described in greater detail below). The activity of an electrogenic target can be measured in a number of ways, not all of which are suitable for any given target protein. Among the measures of activity are: alteration in ion concentrations, measuring alterations in microphysiometric conditions, measuring alterations in voltage or measuring alterations in currents.

The present invention also includes cell-free assays. Such assays involve contacting a form of isoform 3.1 (e.g., full-length isoform 3.1, a biologically active fragment of isoform 3.1, or a fusion protein comprising all or a portion of isoform 3.1) with a test compound and determining the ability of the test compound to bind to isoform 3.1. Binding of the test compound to isoform 3.1 can be determined either directly or indirectly as described above. In one embodiment, the assay includes contacting isoform 3.1 with a known compound that carries a detectable label and that binds isoform 3.1 to form an assay mixture, contacting the assay mixture with a test compound, and determining the ability of the test compound to interact with isoform 3.1, wherein determining the ability of the test compound to interact with isoform 3.1 comprises determining the ability of the test compound to preferentially bind to isoform 3.1 as compared to the known compound.

The cell-free assays of the present invention are amenable to use of either a membrane-bound form of isoform 3.1 or a soluble fragment thereof. In the case of cell-free assays comprising the membrane bound form of the polypeptide, it may be desirable to utilize a solubilizing agent such that the membrane-bound form of the polypeptide is maintained in solution. Examples of such solubilizing agents include but are not limited to non-ionic detergents such as n-octylglucoside, n-dodecylglucoside, n-dodecylmaltoside, octanoyl-N-methylglucamide, decanoyl-N-methyl-glucamide, Triton X-100, Triton X-114, Thesit, Isotridecypoly(ethylene glycol ether)n, 3-[(3-cholamidopropyl)dimethylamminio]-1-propane sulfonate (CHAPS), 3-[(3-cholamidopropyl)dimethylamminio]-2-hydroxy-1-propane sulfonate (CHAPSO), or N-dodecyl=N,N-dimethyl-3 ammonio-1-propane sulfonate.

In various embodiments of the above assay methods of the present invention, it may be desirable to immobilize isoform 3.1 (or an isoform 3.1 target molecule) to facilitate separation of complexed from uncomplexed forms of one or both of the proteins, as well as to accommodate automation of the assay. Binding of a test compound to isoform 3.1, or interaction of isoform 3.1 with a target molecule in the presence and absence of a candidate compound, can be accomplished in any vessel suitable for containing the reactants.

Examples of such vessels include microtiter plates, test tubes, and micro-centrifuge tubes. In one embodiment, a fusion protein can be provided that adds a domain that allows one or both of the proteins to be bound to a matrix. For example, glutathione-S-transferase (GST) fusion proteins can be adsorbed onto glutathione sepharose beads (Sigma Chemical; St. Louis, Mo.) or glutathione derivatized microtiter plates, which are then combined with the test compound or the test compound and either the non-adsorbed target protein or isoform 3.1, and the mixture incubated under conditions conducive to complex formation (e.g., at physiological conditions for salt and pH). Following incubation, the beads or microtitre plate wells are washed to remove any unbound components and complex formation is measured either directly or indirectly, for example, as described above. Alternatively, the complexes can be dissociated from the matrix, and the level of binding or activity of isoform 3.1 can be determined using standard techniques.

Other techniques for immobilizing proteins on matrices can also be used in the screening assays of the invention. For example, either isoform 3.1 or its target molecule can be immobilized utilizing conjugation of biotin and streptavidin. Biotinylated polypeptide of the invention or target molecules can be prepared from biotin-NHS (N-hydroxy-succinimide) using techniques well known in the art (e.g., biotinylation kit, Pierce Chemicals; Rockford, IU.), and immobilized in the wells of streptavidin-coated plates (Pierce Chemical). Alternatively, antibodies reactive with isoform 3.1 or target molecules but that do not interfere with binding of the polypeptide of the invention to its target molecule can be derivatized to the wells of the plate, and unbound target or polypeptide of the invention trapped in the wells by antibody conjugation. Methods for detecting such complexes, in addition to those described above for the GST-immobilized complexes, include immunodetection of complexes using antibodies reactive with isoform 3.1 or target molecule, as well as enzyme-linked assays that rely on detecting an enzymatic activity associated with isoform 3.1 or target molecule.

The screening assay can also involve monitoring the expression of isoform 3.1. For example, regulators of expression of isoform 3.1 can be identified in a method in which a cell is contacted with a candidate compound and the expression of isoform 3.1 protein or mRNA in the cell is determined. The level of expression of isoform 3.1 protein or mRNA the presence of the candidate compound is compared to the level of expression of isoform 3.1 protein or mRNA in the absence of the candidate compound. The candidate compound can then be identified as a regulator of expression of isoform 3.1 based on this comparison.

For example, when expression of isoform 3.1 protein or mRNA protein is greater (statistically significantly greater) in the presence of the candidate compound than in its absence, the candidate compound is identified as a stimulator of isoform 3.1 protein or mRNA expression. Alternatively, when expression of isoform 3.1 protein or mRNA is less (statistically significantly less) in the presence of the candidate compound than in its absence, the candidate compound is identified as an inhibitor of isoform 3.1 protein or mRNA expression. The level of isoform 3.1 protein or mRNA expression in the cells can be determined by methods described below.

Binding Assays

For binding assays, the test compound is preferably a small molecule that potentially binds to a regulatory channel site or nearby the channel pore of isoform 3.1, thereby competing with physiological modulators for said regulatory site, blocking the channel pore, or holding it in its open or closed state such that normal biological activity is prevented, enhanced or otherwise modified. Examples of such small molecules include, but are not limited to, small peptides or peptide-like molecules as well as small compounds.

Potential ligands that bind to a polypeptide of the invention include, but are not limited to, the natural ligands of known isoform 3.1 ion channels and analogues or derivatives thereof. In binding assays, either the test compound or the isoform 3.1 polypeptide can comprise a detectable label, such as a fluorescent, radioisotopic, chemiluminescent, or enzymatic label, such as horseradish peroxidase, alkaline phosphatase, or luciferase. Detection of a test compound that is bound to isoform 3.1 polypeptide can then be accomplished, for example, by direct counting of radioemmission, by scintillation counting, or by determining conversion of an appropriate substrate to a detectable product. Alternatively, binding of a test compound to an isoform 3.1 polypeptide can be determined without labeling either of the interactants. For example, a microphysiometer can be used to detect binding of a test compound with a isoform 3.1 polypeptide. A microphysio-meter (e.g., Cytosensor™) is an analytical instrument that measures the rate at which a cell acidifies its environment using a light-addressable potentiometric sensor (LAPS). Changes in this acidification rate can be used as an indicator of the interaction between a test compound and isoform 3.1.

Determining the ability of a test compound to bind to isoform 3.1 also can be accomplished using a technology such as real-time Biomolecular Interaction Analysis (BIA). BIA is a technology for studying biospecific interactions in real time, without labeling any of the interactants (e.g., BIA-core™). Changes in the optical phenomenon surface plasmon resonance (SPR) can be used as an indication of real-time reactions between biological molecules. In a competitive binding format, the assay includes contacting isoform 3.1 with a known compound that carries a detectable label and that is coupled to a detectable label and that binds isoform 3.1 to form an assay mixture, contacting the assay mixture with a test compound, and determining the ability of the test compound to interact with isoform 3.1, wherein determining the ability of the test compound to interact with isoform 3.1 comprises determining the ability of the test compound to preferentially bind to isoform 3.1 as compared to the known compound. In yet another aspect of the invention, an isoform 3.1-like polypeptide can be used as a "bait protein" in a two-hybrid assay or three-hybrid assay to identify other proteins that bind to or interact with isoform 3.1 and modulate its activity.

The two-hybrid system is based on the modular nature of most transcription factors, which consist of separable DNA-binding and activation domains Briefly, the assay utilizes two different DNA constructs. For example, in one construct, polynucleotide encoding isoform 3.1 can be fused to a polynucleotide encoding the DNA binding domain of a known transcription factor (e.g., GAL-4). In the other construct a DNA sequence that encodes an unidentified protein ("prey" or "sample") can be fused to a polynucleotide that codes for the activation domain of the known transcription factor. If the "bait" and the "prey" proteins are able to interact in vivo to form a protein-dependent complex, the DNA-binding and activation domains of the transcription factor are brought into close proximity. This proximity allows transcription of a reporter gene (e.g., LacZ), which is operably linked to a transcriptional regulatory site responsive to the transcription factor. Expression of the reporter gene can be detected, and cell colonies containing the functional transcription factor can be isolated and used to obtain the DNA sequence encoding the protein that interacts with isoform 3.1.

It may be desirable to immobilize either the isoform 3.1 (or polynucleotide) or the test compound to facilitate separation of the bound form from unbound forms of one or both of the interactants, as well as to accommodate automation of the assay. Thus, either the isoform 3.1-like polypeptide (or polynucleotide) or the test compound can be bound to a solid support. Suitable solid supports include, but are not limited to, glass or plastic slides, tissue culture plates, microtiter wells, tubes, silicon chips, or particles such as beads (including, but not limited to, latex, polystyrene, or glass beads). Any method known in the art can be used to attach isoform 3.1-like polypeptide (or polynucleotide) or test compound to a solid support, including use of covalent and non-covalent linkages, passive absorption, or pairs of binding moieties attached respectively to the polypeptide (or polynucleotide) or test compound and the solid support. Test compounds are preferably bound to the solid support in an array, so that the location of individual test compounds can be tracked. Binding of a test compound to isoform 3.1 (or a polynucleotide encoding for isoform 3.1) can be accomplished in any vessel suitable for containing the reactants. Examples of such vessels include microtiter plates, test tubes, and microcentrifuge tubes.

In one embodiment, isoform 3.1 is a fusion protein comprising a domain that allows binding of isoform 3.1 to a solid support. For example, glutathione-S-transferase fusion proteins can be adsorbed onto glutathione sepharose beads (Sigma Chemical, St. Louis, Mo.) or glutathione derivatized microtiter plates, which are then combined with the test compound or the test compound and the non-adsorbed isoform 3.1; the mixture is then incubated under conditions conducive to complex formation (e.g., at physiological conditions for salt and pH). Following incubation, the beads or microtiter plate wells are washed to remove any unbound components.

Binding of the interactants can be determined either directly or indirectly, as described above. Alternatively, the complexes can be dissociated from the solid support before binding is determined.

Other techniques for immobilizing proteins or polynucleotides on a solid support also can be used in the screening assays of the invention. For example, either isoform 3.1 (or a polynucleotide encoding isoform 3.1) or a test compound can be immobilized utilizing conjugation of biotin and streptavidin. Biotinylated isoform 3.1 (or a polynucleotide encoding biotinylated isoform 3.1) or test compounds can be prepared from biotin-NHS (N-hydroxysuccinimide) using techniques well known in the art (e.g., biotinylation kit, Pierce Chemicals, Rockford, Ill.) and immobilized in the wells of streptavidin-coated plates (Pierce Chemical). Alternatively, antibodies that specifically bind to isoform 3.1, polynucleotide, or a test compound, but that do not interfere with a desired binding site, such as the active site of isoform 3.1, can be derivatized to the wells of the plate. Unbound target or protein can be trapped in the wells by antibody conjugation.

Methods for detecting such complexes, in addition to those described above for the GST-immobilized complexes, include immuno detection of complexes using antibodies that specifically bind to isoform 3.1 polypeptide or test compound, enzyme-linked assays that rely on detecting an activity of isoform 3.1 polypeptide, and SDS gel electrophoresis under non-reducing conditions.

Screening for test compounds that bind to an isoform 3.1 polypeptide or polynucleotide also can be carried out in an intact cell. Any cell that comprises an isoform 3.1 polypeptide or polynucleotide can be used in a cell-based assay system. An isoform 3.1 polynucleotide can be naturally occurring in the cell or can be introduced using techniques such as those described above. Binding of the test compound to isoform 3.1 or a polynucleotide encoding isoform 3.1 is determined as described above.

Functional Assays

Test compounds can be tested for the ability to increase or decrease isoform 3.1 functional activity of an isoform 3.1 polypeptide. The isoform 3.1 activity can be measured, for example, using methods described in the specific examples, below. Isoform 3.1 functional activity can be measured after contacting an intact cell having functional ion channel activity with a test compound. A test compound that decreases isoform 3.1 activity by at least about 10, preferably about 50, more preferably about 75, 90, or 100% is identified as a potential agent for decreasing isoform 3.1 activity. A test compound that increases isoform 3.1 activity by at least about 10, preferably about 50, more preferably about 75, 90, or 100% is identified as a potential agent for increasing isoform 3.1 activity.

Other screening techniques include the use of cells that express isoform 3.1 (for example, transfected CHO cells) in a system that measures extracellular pH changes caused by channel activation. For example, compounds may be contacted with a cell that expresses the channel polypeptide of the present invention and a second messenger response, e.g., signal transduction or pH changes, can be measured to determine whether the potential compound activates or inhibits the channel. Another such screening technique involves introducing RNA or DNA encoding isoform 3.1 into *Xenopus* oocytes to transiently express the channel. The receptor oocytes can then be contacted with the channel ligand or activated otherwise and a compound to be screened, followed by detection of modulation of the observed control signal. Other screening techniques include the use of cells that express isoform 3.1 (for example, transfected CHO cells) in a system that measures voltage changes caused by channel activation. For example, compounds may be contacted with a cell that expresses the channel polypeptide of the present invention and voltage changes can be measured to determine whether the potential compound activates or inhibits the channel.

Another screening technique involves expressing isoform 3.1 in cells in which the channel is linked to a phospholipase C or D. Such cells include endothelial cells, smooth muscle cells, embryonic kidney cells, etc. The screening may be accomplished as described above by quantifying the degree of activation of the channel from changes in the phospholipase activity.

Gene Expression

In another embodiment, test compounds that increase or decrease isoform 3.1 gene expression are identified. As used herein, the term "correlates with expression of a polynucleotide" indicates that the detection of the presence of nucleic acids, the same or related to a nucleic acid sequence encoding isoform 3.1, by northern analysis or real-time PCR is indicative of the presence of nucleic acids encoding isoform 3.1 in a sample, and thereby correlates with expression of the transcript from the polynucleotide encoding isoform 3.1. The term "microarray", as used herein, refers to an array of distinct polynucleotides or oligonucleotides arrayed on a substrate, such as paper, nylon or any other type of membrane, filter, chip, glass slide, or any other suitable solid support. An isoform 3.1 polynucleotide is contacted with a test compound, and the expression of an RNA or polypeptide product of isoform 3.1 polynucleotide is determined. The level of expression of appropriate mRNA or polypeptide in the presence of the test compound is compared to the level of expression of mRNA or polypeptide in the absence of the test compound. The test compound can then be identified as a regulator of expression based on this comparison. For example, when expression of mRNA or polypeptide is greater in the presence of the test compound than in its absence, the test compound is identified as a stimulator or enhancer of the mRNA or polypeptide expression. Alternatively, when expression of the mRNA or polypeptide is less in the presence of the test compound than in its absence, the test compound is identified as an inhibitor of the mRNA or polypeptide expression.

The level of isoform 3.1 mRNA or polypeptide expression in the cells can be determined by methods well known in the art for detecting mRNA or polypeptide. Either qualitative or quantitative methods can be used. The presence of polypeptide products of isoform 3.1 polynucleotide can be determined, for example, using a variety of techniques known in the art, including immuno chemical methods such as radioimmunoassay, Western blotting, and immunohistochemistry. Alternatively, polypeptide synthesis can be determined in vivo, in a cell culture, or in an in vitro translation system by detecting incorporation of labelled amino acids into isoform 3.1.

Such screening can be carried out either in a cell-free assay system or in an intact cell. Any cell that expresses isoform 3.1 polynucleotide can be used in a cell-based assay system. The isoform 3.1 polynucleotide can be naturally occurring in the cell or can be introduced using techniques such as those described above. Either a primary culture or an established cell line can be used.

Test Compounds

Suitable test compounds for use in the screening assays of the invention can be obtained from any suitable source, e.g., conventional compound libraries. The test compounds can also be obtained using any of the numerous approaches in combinatorial library methods known in the art, including: biological libraries; spatially addressable parallel solid phase or solution phase libraries; synthetic library methods requiring deconvolution; the "one-bead one-compound" library method; and synthetic library methods using affinity chromatography selection. The biological library approach is limited to peptide libraries, while the other four approaches are applicable to peptide, non-peptide oligomer or small molecule libraries of compounds. Examples of methods for the synthesis of molecular libraries can be found in the art. Libraries of compounds may be presented in solution or on beads, bacteria, spores, plasmids or phage.

Modeling of Regulators

Computer modeling and searching technologies permit identification of compounds, or the improvement of already identified compounds, that can modulate isoform 3.1 expression or activity. Having identified such a compound or composition, the active sites or regions are identified. Such active sites might typically be ligand binding sites, such as the interaction domain of the ligand with isoform 3.1. The active site can be identified using methods known in the art including, for example, from the amino acid sequences of peptides, from the nucleotide sequences of nucleic acids, or from study of complexes of the relevant compound or composition with its natural ligand. In the latter case, chemical or X-ray crystallographic methods can be used to find the active site by finding where on the factor the complexed ligand is found.

Next, the three dimensional geometric structure of the active site is determined. This can be done by known methods, including X-ray crystallography, which can determine a complete molecular structure. On the other hand, solid or liquid phase NMR can be used to determine certain intramolecular distances. Any other experimental method of structure determination can be used to obtain partial or complete geometric structures. The geometric structures may be measured with a complexed ligand, natural or artificial, which may increase the accuracy of the active site structure determined.

If an incomplete or insufficiently accurate structure is determined, the methods of computer based numerical modeling can be used to complete the structure or improve its accuracy. Any recognized modeling method may be used, including parameterized models specific to particular biopolymers such as proteins or nucleic acids, molecular dynamics models based on computing molecular motions, statistical mechanics models based on thermal ensembles, or combined models.

For most types of models, standard molecular force fields, representing the forces between constituent atoms and groups, are necessary, and can be selected from force fields known in physical chemistry. The incomplete or less accurate experimental structures can serve as constraints on the complete and more accurate structures computed by these modeling methods.

Finally, having determined the structure of the active site, either experimentally, by modeling, or by a combination, candidate modulating compounds can be identified by searching databases containing compounds along with information on their molecular structure. Such a search seeks compounds having structures that match the determined active site structure and that interact with the groups defining the active site. Such a search can be manual, but is preferably computer-assisted. These compounds found from this search are potential isoform 3.1 modulating compounds.

Alternatively, these methods can be used to identify improved modulating compounds from an already known modulating compound or ligand. The composition of the known compound can be modified and the structural effects of modification can be determined using the experimental and computer modeling methods described above applied to the new composition. The altered structure is then compared to the active site structure of the compound to determine if an improved fit or interaction results. In this manner systematic variations in composition, such as by varying side groups, can be quickly evaluated to obtain modified modulating compounds or ligands of improved specificity or activity.

Applications

The present invention provides for both prophylactic and therapeutic methods for neurological diseases, e.g., schizophrenia.

The regulatory method of the invention involves contacting a cell with an agent that modulates one or more of the activities of isoform 3.1. An agent that modulates activity can be an agent as described herein, such as a nucleic acid or a protein, a naturally-occurring cognate ligand of the polypeptide, a peptide, a peptidomimetic, or any small molecule. In one embodiment, the agent stimulates one or more of the biological activities of isoform 3.1. In another embodiment, the agent inhibits one or more of the biological activities of isoform 3.1. As such, the present invention provides methods of treating an individual afflicted with a disease or disorder characterized by unwanted expression or activity of isoform 3.1 or a protein in the isoform 3.1 signaling pathway. In one embodiment, the method involves administering an agent like any agent identified or being identifiable by a screening assay as described herein, or combination of such agents that may upregulate or downregulate the expression or activity of isoform 3.1 or of any protein in the isoform 3.1 signaling pathway. In another embodiment, the method involves administering a regulator of isoform 3.1 as therapy to compensate for increased or undesirably high expression or activity, or, alternatively, reduced or undesirably low expression or activity of isoform 3.1 or a protein in the isoform 3.1 signaling pathway.

Stimulation of activity or expression of isoform 3.1 is desirable in situations in which activity or expression is abnormally low and in which increased activity is likely to have a beneficial effect. Conversely, inhibition of activity or expression of isoform 3.1 is desirable in situations in which activity or expression of isoform 3.1 is abnormally high and in which decreasing its activity is likely to have a beneficial effect.

Pharmaceutical Compositions

This invention further pertains to novel agents identified by the above-described screening assays and uses thereof for treatments as described herein.

The active agents (also referred to herein as "active compounds") of the invention can be incorporated into pharmaceutical compositions suitable for administration. Such compositions typically comprise the active agents and a pharmaceutically acceptable carrier. As used herein the language "pharmaceutically acceptable carrier" is intended to include any and all solvents, dispersion media, coatings, antibacterial and antifungal agents, isotonic and absorption delaying agents, and the like, compatible with pharmaceutical administration. The use of such media and agents for pharmaceutically active substances is well known in the art. Except insofar as any conventional media or agent is incompatible with the active compound, use thereof in the compositions is contemplated. Supplementary active compounds can also be incorporated into the compositions.

The invention includes pharmaceutical compositions comprising a regulator of isoform 3.1 expression or activity (and/or a regulator of the activity or expression of a protein in the isoform 3.1 signaling pathway) as well as methods for preparing such compositions by combining one or more such regulators and a pharmaceutically acceptable carrier. Also within the invention are pharmaceutical compositions comprising a regulator identified using the screening assays of the invention packaged with instructions for use. For regulators that are antagonists of isoform 3.1 activity or that reduce isoform 3.1 expression, the instructions would specify use of the pharmaceutical composition for treatment of neurological diseases, e.g., schizophrenia. For regulators that are agonists of isoform 3.1 activity or increase isoform 3.1 expression, the instructions would specify use of the pharmaceutical composition for treatment of other neurological diseases.

An antagonist of isoform 3.1 may be produced using methods that are generally known in the art. In particular, purified isoform 3.1 may be used to produce antibodies or to screen libraries of pharmaceutical agents to identify those that specifically bind isoform 3.1. Antibodies to isoform 3.1 may also be generated using methods that are well known in the art. Such antibodies may include, but are not limited to, polyclonal, monoclonal, chimeric, single chain antibodies, Fab fragments, and fragments produced by a Fab expression library.

In another embodiment of the invention, the polynucleotides encoding isoform 3.1, or any fragment or complement thereof, may be used for therapeutic purposes. In one aspect, the complement of the polynucleotide encoding isoform 3.1 may be used in situations in which it would be desirable to block the transcription of the mRNA. In particular, cells may be transformed with sequences complementary to polynucleotides encoding isoform 3.1. Thus, complementary molecules or fragments may be used to modulate isoform 3.1 activity, or to achieve regulation of gene function. Such technology is now well known in the art, and sense or antisense oligonucleotides or larger fragments can be designed from various locations along the coding or control regions of sequences encoding isoform 3.1.

Expression vectors derived from lentiviruses, may be used for delivery of nucleotide sequences to the targeted organ, tissue, or cell population. Methods that are well known to those skilled in the art can be used to construct vectors that will express nucleic acid sequence complementary to the polynucleotides of the gene encoding isoform 3.1. These techniques are described, for example, in the scientific literature.

Any of the therapeutic methods described above may be applied to any subject in need of such therapy, including, preferably, humans.

An additional embodiment of the invention relates to the administration of a pharmaceutical composition containing isoform 3.1 in conjunction with a pharmaceutically acceptable carrier, for any of the therapeutic effects discussed above. Such pharmaceutical compositions may constitute isoform 3.1, antibodies to isoform 3.1, and mimetics, agonists, antagonists, or inhibitors of isoform 3.1. The compositions may be administered alone or in combination with at least one other agent, such as a stabilizing compound, which may be administered in any sterile, biocompatible pharmaceutical carrier including, but not limited to, saline, buffered saline, dextrose, and water. The compositions may be administered to a patient alone, or in combination with other agents, drugs or hormones.

A pharmaceutical composition of the invention is formulated to be compatible with its intended route of administration. Examples of routes of administration include parenteral, e.g., intravenous, intradermal, subcutaneous, oral (e.g., inhalation), transdermal (topical), transmucosal, and rectal administration. Solutions or suspensions used for parenteral, intradermal, or subcutaneous application can include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose. pH can be adjusted with acids or bases, such as hydrochloric acid or sodium hydroxide. The parenteral preparation can be enclosed in ampoules, disposable syringes or multiple dose vials made of glass or plastic.

Pharmaceutical compositions suitable for injectable use include sterile aqueous solutions (where water soluble) or dispersions and sterile powders for the extemporaneous preparation of sterile injectable solutions or dispersions. For intravenous administration, suitable carriers include physiological saline, bacteriostatic water or phosphate buffered saline (PBS). In all cases, the composition must be sterile and should be fluid to the extent that easy syringability exists. It must be stable under the conditions of manufacture and storage and must be preserved against the contaminating action of microorganisms such as bacteria and fungi. The carrier can be a solvent or dispersion medium containing, for example, water, ethanol, a pharmaceutically acceptable polyol like glycerol, propylene glycol, liquid polyetheylene glycol, and suitable mixtures thereof. The proper fluidity can be maintained, for example, by the use of a coating such as lecithin, by the maintenance of the required particle size in the case of dispersion and by the use of surfactants. Prevention of the action of microorganisms can be achieved by various antibacterial and antifungal agents, for example, parabens, chlorobutanol, phenol, ascorbic acid, thimerosal, and the like. In many cases, it will be preferable to include isotonic agents, for example, sugars, polyalcohols such as mannitol, sorbitol, and sodium chloride in the composition. Prolonged absorption of the injectable compositions can be brought about by including in the composition an agent that delays absorption, for example, aluminum monostearate and gelatin. Sterile injectable solutions can be prepared by incorporating the active compound in the required amount in an appropriate solvent with one or a combination of ingredients enumerated above, as required, followed by filtered sterilization. Generally, dispersions are prepared by incorporating the active compound into a sterile vehicle that contains a basic dispersion medium and the required other ingredients from those enumerated above. In the case of sterile powders for the preparation of sterile injectable solutions, the preferred methods of preparation are vacuum drying and freeze-drying, which yields a powder of the active ingredient plus any additional desired ingredient from a previously sterile-filtered solution thereof.

Oral compositions generally include an inert diluent or an edible carrier. They can be enclosed in gelatin capsules or compressed into tablets. For the purpose of oral therapeutic administration, the active compound can be incorporated with excipients and used in the form of tablets, troches, or capsules. Oral compositions can also be prepared using a fluid carrier for use as a mouthwash, wherein the compound in the fluid carrier is applied orally and swished and expectorated or swallowed.

Pharmaceutically compatible binding agents, and/or adjuvant materials can be included as part of the composition. The tablets, pills, capsules, troches and the like can contain any of the following ingredients, or compounds of a similar nature: a binder such as microcrystalline cellulose, gum tragacanth or gelatin; an excipient such as starch or lactose, a disintegrating agent such as alginic acid, Primogel, or corn starch; a lubricant such as magnesium stearate or sterotes; a glidant such as colloidal silicon dioxide; a sweetening agent such as sucrose or saccharin; or a flavoring agent such as peppermint, methyl salicylate, or orange flavoring.

For administration by inhalation, the compounds are delivered in the form of an aerosol spray from a pressurized container or dispenser that contains a suitable propellant, e.g., a gas such as carbon dioxide, or a nebulizer.

Systemic administration can also be by transmucosal or transdermal means. For transmucosal or transdermal administration, penetrants appropriate to the barrier to be permeated are used in the formulation. Such penetrants are generally known in the art, and include, for example, for transmucosal administration, detergents, bile salts, and fusidic acid derivatives. Transmucosal administration can be accomplished through the use of nasal sprays or suppositories. For transdermal administration, the active compounds are formulated into ointments, salves, gels, or creams as generally known in the art.

The compounds can also be prepared in the form of suppositories (e.g., with conventional suppository bases such as cocoa butter and other glycerides) or retention enemas for rectal delivery.

In one embodiment, the active compounds are prepared with carriers that will protect the compound against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid.

It is especially advantageous to formulate oral or parenteral compositions in dosage unit form for ease of administration and uniformity of dosage. Dosage unit form as used herein refers to physically discrete units suited as unitary dosages for the subject to be treated; each unit containing a predetermined quantity of active compound calculated to produce the desired therapeutic effect in association with the required pharmaceutical carrier. The specification for the dosage unit forms of the invention are dictated by and directly dependent on the unique characteristics of the active compound and the particular therapeutic effect to be achieved, and the limitations inherent in the art of compounding such an active compound for the treatment of individuals.

The pharmaceutical compositions can be included in a container, pack, or dispenser together with instructions for administration. For pharmaceutical compositions that include an antagonist of isoform 3.1 activity, a compound that reduces expression or activity of isoform 3.1, or a compound that reduces expression or activity of a protein in the isoform 3.1 signaling pathway or any combination thereof, the instructions for administration will specify use of the composition for neurological diseases, e.g., schizophrenia. For pharmaceutical compositions that include an agonist of isoform 3.1 activity, a compound that increases expression of isoform 3.1, or a compound that increases expression or activity of a protein in the isoform 3.1 signaling pathway or any combination thereof, the instructions for administration will specify use of the composition for other neurological diseases.

Determination of a Therapeutically Effective Dose

The determination of a therapeutically effective dose is well within the capability of those skilled in the art. A therapeutically effective dose refers to that amount of active ingredient that increases or decreases isoform 3.1 activity relative to isoform 3.1 activity that occurs in the absence of the therapeutically effective dose. For any compound, the therapeutically effective dose can be estimated initially either in cell culture assays or in animal models, usually mice, rats, rabbits, or monkeys. The animal model also can be used to determine the appropriate concentration range and route of administration. Such information can then be used to determine useful doses and routes for administration in humans.

Therapeutic efficacy and toxicity, e.g., $ED_{50}$ (the dose therapeutically effective in 50% of the population) and $LD_{50}$ (the dose lethal to 50% of the population), can be determined by standard pharmaceutical procedures in cell cultures or experimental animals. The dose ratio of toxic to therapeutic effects is the therapeutic index, and it can be expressed as the ratio, $LD_{50}/ED_{50}$. Pharmaceutical compositions that exhibit large therapeutic indices are preferred. The data obtained from cell culture assays and animal studies is used in formulating a range of dosage for human use. The dosage contained in such compositions is preferably within a range of circulating concentrations that include the $ED_{50}$ with little or no toxicity. The dosage varies within this range depending upon the dosage form employed, sensitivity of the patient, and the route of administration. The exact dosage will be determined by the practitioner, in light of factors related to the subject that requires treatment. Dosage and administration are adjusted to provide sufficient levels of the active ingredient or to maintain the desired effect. Factors that can be taken into account include the severity of the disease state, general health of the subject, age, weight, and gender of the subject, diet, time and frequency of administration, drug combination(s), reaction sensitivities, and tolerance/response to therapy. Long-acting pharmaceutical compositions can be administered every 3 to 4 days, every week, or once every two weeks depending on the half-life and clearance rate of the particular formulation. Normal dosage amounts can vary from 0.1 micrograms to 100,000 micrograms, up to a total dose of about 1 gram, depending upon the route of administration. Guidance as to particular dosages and methods of delivery is provided in the literature and generally available to practitioners in the art.

Those skilled in the art will employ different formulations for nucleotides than for proteins or their inhibitors. Similarly, delivery of polynucleotides or polypeptides will be specific to particular cells, conditions, locations, etc. If the reagent is a single-chain antibody, polynucleotides encoding the antibody can be constructed and introduced into a cell either ex vivo or in vivo using well-established techniques including, but not limited to, transferrin-polycation-mediated DNA transfer, transfection with naked or encapsulated nucleic acids, liposome-mediated cellular fusion, intracellular transportation of DNA-coated latex beads, protoplast fusion, viral infection, electroporation, "gene gun", and DEAE- or calcium phosphate-mediated transfection.

If the expression product is mRNA, the reagent is preferably an antisense oligonucleotide or a ribozyme. Polynucleotides that express antisense oligonucleotides or ribozymes can be introduced into cells by a variety of methods, as described above. Preferably, a reagent reduces expression of isoform 3.1 gene or the activity of isoform 3.1 by at least about 10, preferably about 50, more preferably about 75, 90, or 100% relative to the absence of the reagent. The effectiveness of the mechanism chosen to decrease the level of expression of isoform 3.1 gene or the activity of isoform 3.1 can be assessed using methods well known in the art, such as hybridization of nucleotide probes to isoform 3.1-specific mRNA, quantitative RT-PCR, immunologic detection of isoform 3.1, or measurement of isoform 3.1 activity.

In any of the embodiments described above, any of the pharmaceutical compositions of the invention can be administered in combination with other appropriate therapeutic agents. Selection of the appropriate agents for use in combination therapy can be made by one of ordinary skill in the art, according to conventional pharmaceutical principles. The combination of therapeutic agents can act synergistically to effect the treatment or prevention of the various disorders described above. Using this approach, one may be able to achieve therapeutic efficacy with lower dosages of each agent, thus reducing the potential for adverse side effects. Any of the therapeutic methods described above can be applied to any subject in need of such therapy, including, for example, humans.

Diagnostics

One embodiment of the invention relates to a method for predicting the likelihood that an individual will have a neuropsychiatric disorder, e.g., schizophrenia, or for aiding in the diagnosis of a neuropsychiatric disorder, e.g., schizophrenia, or a greater likelihood of having reduced symptomology associated with a neuropsychiatric disorder, e.g., schizophrenia, comprising the steps of obtaining a DNA sample from an individual to be assessed and determining the nucleotide present at a single nucleotide polymorphism (SNP) of the KCNH2 gene. The presence of a nucleotide from the protective allele at the SNP indicates that the individual has a lower likelihood of having a neuropsychiatric disorder, or a greater likelihood of having reduced symptomology associated with a neuropsychiatric disorder, than if that individual had a nucleotide from the risk allele at that SNP. Conversely, the presence of a nucleotide from the risk allele at the SNP indicates that the individual has a greater likelihood of having a neuropsychiatric disorder, or a likelihood of having increased symptomology associated with a neuropsychiatric disorder, than if that individual had a nucleotide from the protective allele at that SNP. In a preferred embodiment, the neuropsychiatric disorder is schizophrenia. In a particular embodiment, the individual is an individual at risk for development of schizophrenia.

In another embodiment the individual exhibits clinical symptomatology associated with schizophrenia. In one embodiment, the individual has been clinically diagnosed as having schizophrenia.

The SNP is selected from Marker M1, M2, M3, M4, M5, M6, M7, M8, M9, M10, M11, M12, M13, M14, M15, M16, M17, M18, M19, M20, M21, M22, M23, M24, M25, M26, M27, M28, M29, M30, M31, M32, M33, M34, M35, M36, M37, M38, M39, M40, M41, M42, or M43.

| MARKER | ALLELES | RISK | RISK | PROTECTIVE |
| --- | --- | --- | --- | --- |
| M1 | C/T | Allele 1 | C | T |
| M2 | G/A | Allele 2 | A | G |
| M3 | A/C | Allele 1 | A | C |
| M4 | G/A | Allele 2 | A | G |
| M5 | InsT | Allele 1 | — | InsT |
| M6 | T/C | Allele 1 | T | C |
| M7 | G/A | Allele 1 | G | A |
| M8 | T/G | Allele 1 | T | G |
| M9 | A/G | Allele 1 | A | G |
| M10 | G/A | Allele 1 | G | A |
| M11 | T/C | Allele 1 | T | C |
| M12 | G/A | Allele 1 | G | A |
| M13 | G/A | Allele 2 | G | A |
| M14 | T/C | Allele 1 | C | T |
| M15 | T/C | Allele 1 | T | C |
| M16 | G/A | Allele 2 | A | G |
| M17 | A/C | Allele 2 | C | A |
| M18 | C/T | Allele 1 | C | T |
| M19 | C/T | Allele 2 | T | C |
| M20 | C/T | Allele 1 | C | T |
| M21 | C/T | Allele 2 | T | C |
| M22 | G/C | Allele 1 | G | C |
| M23 | G/C | Allele 1 | G | C |
| M24 | G/C | Allele 1 | G | C |
| M25 | C/T | Allele 2 | T | C |
| M26 | C/T | Allele 1 | C | T |
| M27 | T/G | Allele 1 | T | G |
| M28 | C/T | Allele 1 | C | T |
| M29 | C/T | Allele 1 | C | T |
| M30 | G/T | Allele 2 | T | G |
| M31 | A/G | Allele 2 | G | A |
| M32 | C/T | Allele 1 | C | T |
| M33 | G/A | Allele 2 | A | G |
| M34 | G/A | Allele 1 | G | A |
| M35 | A/G | Allele 1 | A | G |
| M36 | G/T | Allele 1 | G | T |
| M37 | A/G | Allele 1 | A | G |
| M38 | T/A | Allele 1 | T | A |
| M39 | A/G | Allele 2 | G | A |
| M40 | C/G | Allele 1 | C | G |
| M41 | A/G | Allele 2 | G | A |
| M42 | G/A | Allele 2 | A | G |
| M43 | C/G | Allele 2 | G | C |

The genetic material to be assessed can be obtained from any nucleated cell from the individual. For assay of genomic DNA, virtually any biological sample (other than pure red blood cells) is suitable. For example, convenient tissue samples include whole blood, semen, saliva, tears, urine, fecal material, sweat, skin and hair. For assay of cDNA or mRNA, the tissue sample must be obtained from an organ in which the target nucleic acid is expressed. For example, cells from the central nervous system (such as cells of the hippocampus), neural crest-derived cells, skin, heart, lung and skeletal muscle are suitable sources for obtaining cDNA for the KCNH2 gene. Neural crest-derived cells include, for example, melanocytes and keratinocytes.

Many of the methods described herein require amplification of DNA from target samples. This can be accomplished by e.g., PCR. See generally: PCR Technology: Principles and Applications for DNA Amplification ed. H. A. Erlich, Freeman Press, NY, N.Y., 1992. Other suitable amplification methods include the ligase chain reaction (LCR), transcription amplification, self-sustained sequence replication and nucleic acid based sequence amplification (NASBA). The latter two amplification methods involve isothermal reactions based on isothermal transcription, which produce both single stranded RNA (ssRNA) and double stranded DNA (dsDNA) as the amplification products in a ratio of about 30 or 100 to 1, respectively. The nucleotide that occupies the polymorphic site of interest can be identified by a variety of methods, such as Southern analysis of genomic DNA; direct mutation analysis by restriction enzyme digestion; Northern analysis of RNA; denaturing high pressure liquid chromatography (DHPLC); gene isolation and sequencing; hybridization of an allele-specific oligonucleotide with amplified gene products; single base extension (SBE); or analysis of the KCNH2 protein. A sampling of suitable procedures are discussed below in turn.

Allele-Specific Probes

The design and use of allele-specific probes for analyzing polymorphisms is described by e.g., Saiki et al. 1986 Nature 324:163-166. Allele-specific probes can be designed that hybridize to a segment of target DNA from one individual but do not hybridize to the corresponding segment from another individual due to the presence of different polymorphic forms in the respective segments from the two individuals. Hybridization conditions should be sufficiently stringent that there is a significant difference in hybridization intensity between alleles, and preferably an essentially binary response, whereby a probe hybridizes to only one of the alleles. Hybridizations are usually performed under stringent conditions, for example, at a salt concentration of no more than 1M and a temperature of at least 25° C. For example, conditions of 5× SSPE (750 mM NaCl, 50 mM NaPhosphate, 5 mM EDTA, pH 7.4) and a temperature of 25-30° C., or equivalent conditions, are suitable for allele-specific probe hybridizations. Equivalent conditions can be determined by varying one or more of the parameters given as an example, as known in the art, while maintaining a similar degree of identity or similarity between the target nucleotide sequence and the primer or probe used.

Some probes are designed to hybridize to a segment of target DNA such that the polymorphic site aligns with a central position (e.g., in a 15-mer at the 7 position; in a 16-mer, at either the 8 or 9 position) of the probe. This design of probe achieves good discrimination in hybridization between different allelic forms.

Allele-specific probes are often used in pairs, one member of a pair showing a perfect match to a reference form of a target sequence and the other member showing a perfect match to a variant form. Several pairs of probes can then be immobilized on the same support for simultaneous analysis of multiple polymorphisms within the same target sequence.

Tiling Arrays

The polymorphisms can also be identified by hybridization to nucleic acid arrays, some examples of which are described in WO 95/11995. WO 95/11995 also describes subarrays that are optimized for detection of a variant form of a precharacterized polymorphism. Such a subarray contains probes designed to be complementary to a second reference sequence, which is an allelic variant of the first reference sequence. The second group of probes is designed by the same principles, except that the probes exhibit complementarity to the second reference sequence. The inclusion of a second group (or further groups) can be particularly useful for analyzing short subsequences of the primary reference sequence in which multiple mutations are expected to occur within a short distance commensurate with the length of the probes (e.g., two or more mutations within 9 to 21 bases).

Allele-Specific Primers

An allele-specific primer hybridizes to a site on target DNA overlapping a polymorphism and only primes amplification of an allelic form to which the primer exhibits perfect complementarity. See, Gibbs 1989 Nucleic Acid Res 17:2427-2448. This primer is used in conjunction with a second primer that hybridizes at a distal site. Amplification proceeds from the two primers, resulting in a detectable product that indicates the particular allelic form is present. A control is usually performed with a second pair of primers, one of which shows a single base mismatch at the polymorphic site and the other of which exhibits perfect complementarity to a distal site. The single-base mismatch prevents amplification and no detectable product is formed. The method works best when the mismatch is included in the 3'-most position of the oligonucleotide aligned with the polymorphism because this position is most destabilizing to elongation from the primer.

Direct-Sequencing

The direct analysis of the sequence of polymorphisms of the present invention can be accomplished using either the dideoxy chain termination method or the Maxam Gilbert method (see Molecular Cloning: a Laboratory Manual, 3rd edition, Sambrook et al. 2001 Cold Spring Harbor Laboratory Press, New York).

Denaturing Gradient Gel Electrophoresis

Amplification products generated using the polymerase chain reaction can be analyzed by the use of denaturing gradient gel electrophoresis. Different alleles can be identified based on the different sequence-dependent melting properties and electrophoretic migration of DNA in solution (Erlich, ed. 1992 PCR Technology, Principles and Applications for DNA Amplification, W.H. Freeman and Co, New York, Chapter 7).

Single-Strand Conformation Polymorphism Analysis

Alleles of target sequences can be differentiated using single-strand conformation polymorphism analysis, which identifies base differences by alteration in electrophoretic migration of single stranded PCR products, as described in Orita et al. 1989 PNAS USA 86:2766-2770. Amplified PCR products can be generated as described above, and heated or otherwise denatured, to form single-stranded amplification products. Single-stranded nucleic acids may refold or form secondary structures that are partially dependent on the base sequence. The different electrophoretic mobilities of single-stranded amplification products can be related to base-sequence differences between alleles of target sequences.

The polypeptide and polynucleotide markers of the isoform 3.1 of KCNH2 gene of the invention are useful in methods for diagnosing schizophrenia, determining the extent and/or severity of the disease, monitoring progression and neurological symptoms of the disease and/or response to therapy, and predicting the response of patients to therapy, including antipsychotic medications. The markers are also useful in methods for treating schizophrenia and for evaluating the efficacy of treatment for the disease. The markers may also be used to screen candidate drugs for treatment of schizophrenia. Such methods can be performed in human and non-human primate subjects.

The polypeptide markers of the isoform 3.1 of KCNH2 may be isolated by any suitable method known in the art. Native polypeptide markers can be purified from natural sources by standard methods known in the art (e.g., chromatography, centrifugation, differential solubility, immunoassay). In one embodiment, polypeptide markers may be isolated from a serum sample using the chromatographic methods disclosed herein. In another embodiment, polypeptide markers may be isolated from a sample by contacting the sample with substrate-bound antibodies or aptamers that specifically bind to the marker.

The present invention also includes polynucleotide markers of isoform 3.1 of KCNH2 related to the polypeptide markers of the present invention. In one aspect, the invention provides polynucleotides that encode the polypeptides of the invention. The polynucleotide may be genomic DNA, cDNA, or mRNA transcripts that encode the polypeptides of the invention. In one embodiment, the invention provides polynucleotide markers that are closely associated with expression of isoform 3.1 of KCNH2, including single nucleotide polymorphisms (SNPs).

In one embodiment, the invention includes polynucleotide markers of isoform 3.1 of KCNH2 that encode a polypeptide that is a fragment, precursor, successor or modified version of the isoform 3.1 of KCNH2.

In another embodiment, the invention includes polynucleotides that have substantial sequence similarity to a polynucleotide that encodes an isoform of a KCNH2 polypeptide or a fragment, precursor, successor or modified version of such polynucleotide, or a molecule that comprises such polypeptide. Two polynucleotides have "substantial sequence identity" when there is at least about 70% sequence identity, at least about 80% sequence identity, at least about 90% sequence identity, at least about 95% sequence identity or at least 99% sequence identity between their amino acid sequences or when the polynucleotides are capable of forming a stable duplex with each other under stringent hybridization conditions. Such conditions are described elsewhere herein. As described above with respect to polypeptides, the invention includes polynucleotides that are allelic variants, the result of SNPs, or that in alternative codons to those present in the native materials as inherent in the degeneracy of the genetic code.

In some embodiments, the polynucleotides described may be used as surrogate markers of schizophrenia. Thus, for example, if the level of a polypeptide marker is increased in schizophrenic patients, an increase in the mRNA that encodes the polypeptide marker may be interrogated rather than the polypeptide marker (e.g., to diagnose schizophrenia in a subject).

The present invention also provides methods of detecting the markers of isoform 3.1 of KCNH2 of the present invention. The practice of the present invention employs, unless otherwise indicated, conventional methods of analytical biochemistry, microbiology, molecular biology and recombinant DNA techniques within the skill of the art. Such techniques are explained fully in the literature. (See, e.g., Sambrook, J. et al. Molecular Cloning: A Laboratory Manual. 3rd, ed., Cold Spring Harbor Laboratory, Cold Spring Harbor Laboratory Press, Cold Spring Harbor, N.Y., 2000; DNA Cloning: A Practical Approach, Vol. I & II (D. Glover, ed.); Oligonucleotide Synthesis (N. Gait, ed., Current Edition); Nucleic Acid Hybridization (B. Hames & S. Higgins, eds., Current Edition); Transcription and Translation (B. Hames & S. Higgins, eds., Current Edition); CRC Handbook of Parvoviruses, Vol. I & II (P. Tijessen, ed.); Fundamental Virology, 2nd Edition, Vol. I & II (B. N. Fields and D. M. Knipe, eds.)).

The markers of the invention may be detected by any method known to those of skill in the art, including without limitation LC-MS, GC-MS, immunoassays, hybridization and enzyme assays. The detection may be quantitative or qualitative. A wide variety of conventional techniques are available, including mass spectrometry, chromatographic separations, 2-D gel separations, binding assays (e.g., immunoassays), competitive inhibition assays, and so on. Any effective method in the art for measuring the presence/absence, level or activity of a polypeptide or polynucleotide is included in the invention. It is within the ability of one of ordinary skill in the art to determine which method would be most appropriate for measuring a specific marker. Thus, for example, an ELISA assay may be best suited for use in a physician's office while a measurement requiring more sophisticated instrumentation may be best suited for use in a clinical laboratory. Regardless of the method selected, it is important that the measurements be reproducible.

The markers of the invention can be measured by mass spectrometry, which allows direct measurements of analytes with high sensitivity and reproducibility. A number of mass spectrometric methods are available. Electrospray ionization (ESI), for example, allows quantification of differences in relative concentration of various species in one sample against another; absolute quantification is possible by normalization techniques (e.g., using an internal standard). Matrix-assisted laser desorption ionization (MALDI) or the related SELDI® technology (Ciphergen, Inc.) also could be used to make a determination of whether a marker was present, and the relative or absolute level of the marker. Mass spectrometers that allow time-of-flight (TOF) measurements have high accuracy and resolution and are able to measure low abundant species, even in complex matrices like serum or CSF.

For protein markers, quantification can be based on derivatization in combination with isotopic labeling, referred to as isotope coded affinity tags ("ICAT"). In this and other related methods, a specific amino acid in two samples is differentially and isotopically labeled and subsequently separated from peptide background by solid phase capture, wash and release. The intensities of the molecules from the two sources with different isotopic labels can then be accurately quantified with respect to one another. Quantification can also be based on the isotope dilution method by spiking in an isotopically labeled peptide or protein analogous to those being measured. Furthermore, quantification can also be determined without isotopic standards using the direct intensity of the analyte comparing with another measurement of a standard in a similar matrix.

In addition, one- and two-dimensional gels have been used to separate proteins and quantify gels spots by silver staining, fluorescence or radioactive labeling. These differently stained spots have been detected using mass spectrometry, and identified by tandem mass spectrometry techniques.

In one embodiment, the markers are measured using mass spectrometry in connection with a separation technology, such as liquid chromatography-mass spectrometry or gas chromatography-mass spectrometry. In particular, coupling reverse-phase liquid chromatography to high resolution, high mass accuracy ESI time-of-flight (TOF) mass spectroscopy allows spectral intensity measurement of a large number of biomolecules from a relatively small amount of any complex biological material. Analyzing a sample in this manner allows the marker (characterized by a specific RT and m/z) to be determined and quantified.

As will be appreciated by one of skill in the art, many other separation technologies may be used in connection with mass spectrometry. For example, a wide selection of separation columns is commercially available. In addition, separations may be performed using custom chromatographic surfaces (e.g., a bead on which a marker specific reagent has been immobilized). Molecules retained on the media subsequently may be eluted for analysis by mass spectrometry.

Analysis by liquid chromatography-mass spectrometry produces a mass intensity spectrum, the peaks of which represent various components of the sample, each component having a characteristic mass-to-charge ratio (m/z) and retention time (RT). The presence of a peak with the m/z and RT of a marker indicates that the marker is present. The peak representing a marker may be compared to a corresponding peak from another spectrum (e.g., from a control sample) to obtain a relative measurement. Any normalization technique in the art (e.g., an internal standard) may be used when a quantitative measurement is desired. "Deconvoluting" software is available to separate overlapping peaks. The retention time depends to some degree on the conditions employed in performing the liquid chromatography separation. The preferred conditions, those used to obtain the retention times that appear in the Tables, are set forth in the Example. The mass spectrometer preferably provides high mass accuracy and high mass resolution. The mass accuracy of a well-calibrated Micromass TOF instrument, for example, is reported to be approximately 5 mDa, with resolution m/$\Delta$m exceeding 5000.

In other preferred embodiments, the level of the markers may be determined using a standard immunoassay, such as sandwiched ELISA using matched antibody pairs and chemi-luminescent detection. Commercially available or custom monoclonal or polyclonal antibodies are typically used. However, the assay can be adapted for use with other reagents that specifically bind to the marker. Standard protocols and data analysis are used to determine the marker concentrations from the assay data.

A number of the assays discussed above employ a reagent that specifically binds to the marker. Any molecule that is capable of specifically binding to a marker is included within the invention. In some embodiments, the binding molecules are antibodies or antibody fragments that specifically recognize the isoform 3.1 of KCNH2 or a fragment thereof. In other embodiments, the binding molecules are non-antibody species, such as aptamers that specifically recognize the isoform 3.1 of KCNH2 or a fragment thereof. Thus, for example, the binding molecule may be an enzyme for which the marker is a substrate. The binding molecules may recognize any epitope of the targeted markers.

As described above, the binding molecules may be identified and produced by any method accepted in the art. Methods for identifying and producing antibodies and antibody fragments specific for an analyte are well known. Examples of other methods used to identify the binding molecules include binding assays with random peptide libraries (e.g., phage display) and design methods based on an analysis of the structure of the marker.

The markers of the invention also may be detected or measured using a number of chemical derivatization or reaction techniques known in the art. Reagents for use in such techniques are known in the art, and are commercially available for certain classes of target molecules.

Finally, the chromatographic separation techniques described above also may be coupled to an analytical technique other than mass spectrometry such as fluorescence detection of tagged molecules, NMR, capillary UV, evaporative light scattering or electrochemical detection.

Measurement of the relative amount of an RNA or protein marker of the invention may be by any method known in the art (see, e.g., Sambrook, J., Fritsh, E. F., and Maniatis, T. Molecular Cloning: A Laboratory Manual. 2nd, ed., Cold Spring Harbor Laboratory, Cold Spring Harbor Laboratory Press, Cold Spring Harbor, N.Y., 1989; and Current Protocols in Molecular Biology, eds. Ausubel et al. John Wiley & Sons: 1992). Typical methodologies for RNA detection include RNA extraction from a cell or tissue sample, followed by hybridization of a labeled probe (e.g., a complementary polynucleotide) specific for the target RNA to the extracted RNA, and detection of the probe (e.g., Northern blotting). Typical methodologies for protein detection include protein extraction from a cell or tissue sample, followed by hybridization of a labeled probe (e.g., an antibody) specific for the target protein to the protein sample, and detection of the probe. The label group can be a radioisotope, a fluorescent compound, an enzyme, or an enzyme co-factor. Detection of specific protein and polynucleotides may also be assessed by gel electrophoresis, column chromatography, direct sequencing, or quantitative PCR (in the case of polynucleotides) among many other techniques well known to those skilled in the art.

Detection of the presence or number of copies of all or a part of a marker of the isoform 3.1 of KCNH2 gene of the invention may be performed using any method known in the art. Typically, it is convenient to assess the presence and/or quantity of a DNA or cDNA by Southern analysis, in which total DNA from a cell or tissue sample is extracted, is hybridized with a labeled probe (e.g., a complementary DNA molecule), and the probe is detected. The label group can be a radioisotope, a fluorescent compound, an enzyme, or an enzyme co-factor. Other useful methods of DNA detection and/or quantification include direct sequencing, gel electrophoresis, column chromatography, and quantitative PCR, as is known by one skilled in the art.

Polynucleotide similarity can be evaluated by hybridization between single stranded nucleic acids with complementary or partially complementary sequences. Such experiments are well known in the art. High stringency hybridization and washing conditions, as referred to herein, refer to conditions which permit isolation of nucleic acid molecules having at least about 80% nucleic acid sequence identity with the nucleic acid molecule being used to probe in the hybridization reaction (i.e., conditions permitting about 20% or less mismatch of nucleotides). Very high stringency hybridization and washing conditions, as referred to herein, refer to conditions which permit isolation of nucleic acid molecules having at least about 90% nucleic acid sequence identity with the nucleic acid molecule being used to probe in the hybridization reaction (i.e., conditions permitting about 10% or less mismatch of nucleotides). As discussed above, one of skill in the art can use the formulae in Meinkoth et al., ibid. to calculate the appropriate hybridization and wash conditions to achieve these particular levels of nucleotide mismatch. Such conditions will vary, depending on whether DNA:RNA or DNA:DNA hybrids are being formed. Calculated melting temperatures for DNA:DNA hybrids are 10° C. less than for DNA:RNA hybrids. In particular embodiments, stringent hybridization conditions for DNA:DNA hybrids include hybridization at an ionic strength of 6×SSC (0.9 M Na+) at a temperature of between about 20° C. and about 35° C. (lower stringency), more preferably, between about 28° C. and about 40° C. (more stringent), and even more preferably, between about 35° C. and about 45° C. (even more stringent), with appropriate wash conditions. In particular embodiments, stringent hybridization conditions for DNA:RNA hybrids include hybridization at an ionic strength of 6×SSC (0.9 M Na+) at a temperature of between about 30° C. and about 45° C., more preferably, between about 38° C. and about 50° C., and even more preferably, between about 45° C. and about 55° C., with similarly stringent wash conditions. These values are based on calculations of a melting temperature for molecules larger than about 100 nucleotides, 0% formamide and a G+C content of about 40%. Alternatively, Tm can be calculated empirically as set forth in Sambrook et al., supra, pages 9.31 to 9.62. In general, the wash conditions should be as stringent as possible, and should be appropriate for the chosen hybridization conditions. For example, hybridization conditions can include a combination of salt and temperature conditions that are approximately 20-25° C. below the calculated Tm of a particular hybrid, and wash conditions typically include a combination of salt and temperature conditions that are approximately 12-20° C. below the calculated Tm of the particular hybrid. One example of hybridization conditions suitable for use with DNA:DNA hybrids includes a 2-24 hour hybridization in 6×SSC (50% formamide) at about 42° C., followed by washing steps that include one or more washes at room temperature in about 2×SSC, followed by additional washes at higher temperatures and lower ionic strength (e.g., at least one wash as about 37° C. in about 0.1×-0.5×SSC, followed by at least one wash at about 68° C. in about 0.1×-0.5×SSC). Other hybridization conditions, and for example, those most useful with nucleic acid arrays, will be known to those of skill in the art.

The present invention also includes methods of diagnosing schizophrenia and related methods. In general, it is expected that the biomarkers described herein will be measured in combination with other signs, symptoms and clinical tests of schizophrenia, such as psychological evaluation, or schizophrenia biomarkers reported in the literature. Likewise, more than one of the biomarkers of the present invention may be measured in combination. Measurement of the biomarkers of the invention along with any other markers known in the art, including those not specifically listed herein, falls within the scope of the present invention. Markers appropriate for this embodiment include those that have been identified as increased or decreased in samples obtained from schizophrenia samples compared with samples from non-schizophrenia samples (e.g., any one of markers M1, M2, M3, M4, M5, M6, M7, M8, M9, M10, M11, M12, M13, M14, M15, M16, M17, M18, M19, M20, M21, M22, M23, M24, M25, M26, M27, M28, M29, M30, M31, M32, M33, M34, M35, M36, M37, M38, M39, M40, M41, M42, and M43). Other markers appropriate for this embodiment include fragments, precursors, successors and modified versions of such markers, polypeptides having substantial sequence identity to such markers, components having an m/z value and RT value of about the values set forth for these markers, and molecules comprising one of the foregoing. Other appropriate markers for this embodiment will be apparent to one of skill in the art in light of the disclosure herein.

In specific embodiments, the present invention provides methods for determining whether a subject has schizophrenia. In another aspect, the invention provides methods for diagnosing schizophrenia in a subject. In another aspect, the invention provides methods for determining the likelihood of developing schizophrenia in a subject. In another aspect, the invention provides methods for determining the likelihood that an individual will have increased symptomology associated with schizophrenia. These methods comprise obtaining a biological sample from a subject suspected of having schizophrenia, or at risk for developing schizophrenia, detecting the expression level or activity of one or more biomarkers of the 3.1 isoform of the KCNH2 gene in the sample, and comparing the result to the expression level or activity of the marker(s) in a sample obtained from a non-schizophrenia subject, or to a reference range or value established for non-schizophrenic individuals.

As used herein, the term "biological sample" includes a sample from any body fluid or tissue (e.g., serum, plasma, blood, cerebrospinal fluid, urine, brain tissue). Typically, the standard biomarker level or reference range is obtained by measuring the same marker or markers in a set of normal controls. Measurement of the standard biomarker level or reference range need not be made contemporaneously; it may be a historical measurement. Preferably the normal control is matched to the patient with respect to some attribute(s) (e.g., age). Depending upon the difference between the measured and standard level or reference range, the patient can be diagnosed as having schizophrenia or as not having schizophrenia. In some embodiments, schizophrenia is diagnosed in the patient if the expression level of the biomarker or biomarkers in the patient sample is statistically more similar to the expression level of the biomarker or biomarkers that has been associated with schizophrenia than the expression level of the biomarker or biomarkers that has been associated with the normal controls.

What is presently referred to as schizophrenia may turn out to be a number of related, but distinguishable conditions. Classifications may be made, and these types may be further distinguished into subtypes. Any and all of the various forms of schizophrenia are intended to be within the scope of the present invention. Indeed, by providing a method for subsetting patients based on biomarker measurement level, the compositions and methods of the present invention may be used to uncover and define various forms of the disease.

The methods of the present invention may be used to make the diagnosis of schizophrenia, independently from other information such as the patient's symptoms or the results of other clinical or paraclinical tests. However, the methods of the present invention may be used in conjunction with such other data points.

Because a diagnosis is rarely based exclusively on the results of a single test, the method may be used to determine whether a subject is more likely than not to have schizophrenia, or is more likely to have schizophrenia than to have another disease, based on the difference between the measured and standard level or reference range of the biomarkers of the 3.1 isoform of the KCNH2 gene. Thus, for example, a patient with a putative diagnosis of schizophrenia (e.g., suspected to be suffering from schizophrenia) may be diagnosed as being "more likely" or "less likely" to have schizophrenia in light of the information provided by a method of the present invention. If a plurality of biomarkers are measured, at least one and up to all of the measured biomarkers must differ, in the appropriate direction, for the subject to be diagnosed as having (or being more likely to have) schizophrenia. In some embodiments, such difference is statistically significant.

The biological sample may be of any tissue or fluid, including a serum or tissue sample, but other biological fluids or tissue may be used. Possible biological fluids include, but are not limited to, plasma, urine and brain tissue. In some embodiments, the level of a marker may be compared to the level of another marker or some other component in a different tissue, fluid or biological "compartment." Thus, a differential comparison may be made of a marker in brain tissue and serum. It is also within the scope of the invention to compare the level of a marker with the level of another marker or some other component within the same compartment.

As will be apparent to those of ordinary skill in the art, the above description is not limited to making an initial diagnosis of schizophrenia, but also is applicable to confirming a provisional diagnosis of schizophrenia or "ruling out" such a diagnosis. Furthermore, an increased or decreased level or activity of the marker(s) in a sample obtained from a subject suspected of having schizophrenia, or at risk for developing schizophrenia, is indicative that the subject has or is at risk for developing schizophrenia.

The invention also provides a method for determining a subject's risk of developing schizophrenia, the method comprising obtaining a biological sample from a subject, detecting the level or activity of a marker in the sample, and comparing the result to the level or activity of the marker in a sample obtained from a non-schizophrenic subject, or to a reference range or value wherein an increase or decrease of the marker is correlated with the risk of developing schizophrenia.

The assay system can also include a means for detecting a control marker that is characteristic of the cell type being sampled can generally be any type of reagent that can be used in a method of detecting the presence of a known marker (at the nucleic acid or protein level) in a sample, such as by a method for detecting the presence of a biomarker described previously herein. Specifically, the means is characterized in that it identifies a specific marker of the cell type being analyzed that positively identifies the cell type. For example, in a brain tissue assay, it is desirable to screen brain tissue for the level of the biomarker of the 3.1 isoform of the KCNH2 gene expression and/or protein activity. Therefore, the means for detecting a control marker identifies a marker that is characteristic of a brain cell, so that the cell is distinguished from other cell types, such as a connective tissue or inflammatory cell. Such a means increases the accuracy and specificity of the assay of the present invention. Such a means for detecting a control marker include, but are not limited to: a probe that hybridizes under stringent hybridization conditions to a nucleic acid molecule encoding a protein marker; PCR primers which amplify such a nucleic acid molecule; an aptamer that specifically binds to a conformationally-distinct site on the target molecule; and/or an antibody, antigen binding fragment thereof, or antigen binding peptide that selectively binds to the control marker in the sample. Nucleic acid and amino acid sequences for many cell markers are known in the art and can be used to produce such reagents for detection.

The assay systems and methods of the present invention can be used not only to identify patients that are predicted to be responsive to an antipsychotic medication, but also to identify treatments that can improve the responsiveness of schizophrenic patients to antipsychotic medications by identifying patients likely to discontinue a prescribed regimen of antipsychotic medications, and to develop adjuvant treatments that enhance the response of patients to antipsychotic medications.

The present inventors have demonstrated that patients heterozygous for mutations associated with the 3.1 isoform of the KCNH2 gene have schizophrenia or are likely to develop schizophrenia, and are likely to benefit from the administration of an antipsychotic medication, and are much less likely to discontinue a prescribed regimen of an antipsychotic medication. Taken together, these data provide the first evidence to indicate that the primate-specific isoform 3.1 of KCNH2 is strongly associated with schizophrenia and may play a causative roll in development and/or presentation of the clinical disease.

Therefore, one embodiment is a method for predicting the clinical response of a schizophrenic patient to an antipsychotic medication by detecting one or more markers of KCNH2 in a biological sample form a schizophrenia patient. The clinical response may include benefits to the schizophrenic patient, including a significant reduction in ratings of positive schizophrenic syndrome, significant improvement in general psychopathology, and significant decrease in thought disturbance.

Another embodiment is a method of identifying a patient at risk for developing schizophrenia by detecting the presence of mutations in KCNH2 in a biological sample of a subject having or suspected of having a schizophrenia.

Thus, another aspect of the present invention provides methods for predicting the clinical response of a patient having schizophrenia to an antipsychotic medication, including, for example one or more of olanzapine, perphenazine, quetiapine, risperidone, and ziprasidone. In one embodiment of this aspect of the invention the method of identifying patients that will respond to antipsychotic therapies includes obtaining a biological sample from a schizophrenia patient, and detecting in the sample for the presence of a maker of the invention which is a marker of the expression of the 3.1 isoform of the KCNH2 gene.

The presence of at least one mutation that is associated with the 3.1 isoform of the KCNH2 is indicative of whether or not the patient is likely to benefit from an antipsychotic medication. Alternatively, the absence of a biomarker of the invention that is associated with the 3.1 isoform of the KCNH2 protein or expression is indicative of an individual that is not likely to benefit from the administration of an antipsychotic medication. Any schizophrenic patient may be analyzed by these methods in order to assess the prognosis of the patient and assess the likely benefit of administering antipsychotic medications and therapies.

Another aspect of the present invention provides methods that can be used to identify individuals at risk for developing schizophrenia, and/or for predicting the prognosis of a patient having schizophrenia. This aspect of the invention relates to the discovery that the biomarkers of the invention that are associated with the 3.1 isoform of KCNH2 are associated with an increased risk and incidence of schizophrenia. Therefore, one embodiment of this aspect of the invention provides a method of diagnosing or assessing the risk of developing schizophrenia in an individual including obtaining a biological sample from an individual, analyzing the sample for the presence of at least one biomarker of the invention associated with the 3.1 isoform of KCNH2. Elevated gene expression and/or protein function of the 3.1 isoform of KCNH2 indicates that the individual is at risk for developing schizophrenia or is suffering from schizophrenia and is likely to benefit from the administration of an antipsychotic therapy, including an antipsychotic medication, and is unlikely to prematurely discontinue a prescribed regimen of antipsychotic medication. Alternatively, very low or absent gene expression and/or protein function of the 3.1 isoform of KCNH2 indicates that the individual is at low risk for developing schizophrenia or is unlikely to be suffering from schizophrenia and is unlikely to benefit from the administration of an antipsychotic therapy, including an antipsychotic medication, and is more likely to prematurely discontinue a regimen of an antipsychotic medication prescribed to that patient.

According to the present invention, the individual being tested can be a human or non-human primate. The individual may or may not be suspected of having schizophrenia. In one embodiment, the individual being tested has not been diagnosed as having schizophrenia. In another embodiment, the individual has been diagnosed as having a schizophrenia.

As used herein, a mutation refers to an alteration in a sequence of nucleotides in an KCNH2 nucleic acid molecule, such that the sequence of nucleotides is no longer identical to the sequence of nucleotides at the corresponding location in a wild-type KCNH2 gene. Such alterations can be nucleotide insertions, substitutions, deletions or modifications.

Any method suitable for detecting mutations in nucleic acid molecules can be used to practice the present invention. In one embodiment, at least a portion of the sequence of a KCNH2 nucleic acid molecule present in the sample is determined and compared to the corresponding sequence in the wild-type, KCNH2 gene. Any method that is capable of determining the sequence of a nucleic acid molecule can be used to determine the sequence of KCNH2 nucleic acid molecules in the sample. Such methods include, but are not limited to Sanger dideoxy sequencing, Pyrosequencing, RNA sequencing, next-generation sequencing technologies, single-strand conformation polymorphism, heteroduplex analysis, DNA microarray technology, denaturing gradient gel electrophoresis, allele-specific PCR, Scorpion Amplification Refractory Mutation System (SARMS) technology, SNaPshot analysis of PCR products, and mass spectrometry.

The inventors have disclosed specific mutations in KCNH2 genes that were obtained from brain tissue, indicating that the presence of at least one of these mutations in a KCNH2 nucleic acid molecule correlates with the presence of the 3.1 isoform of KCNH2 and/or schizophrenia of symptomatology of schizophrenia. Thus, in one embodiment, the step of analyzing comprises testing the nucleic acid molecules in the sample from a patient or individual for a mutation selected from the group consisting of Marker M1, M2, M3, M4, M5, M6, M7, M8, M9, M10, M11, M12, M13, M14, M15, M16, M17, M18, M19, M20, M21, M22, M23, M24, M25, M26, M27, M28, M29, M30, M31, M32, M33, M34, M35, M36, M37, M38, M39, M40, M41, M42, and M43. The In another embodiment, the step of analyzing comprises testing the nucleic acid molecules in the sample from a patient or individual for a mutation selected from the group consisting of at least one single nucleotide polymorphism in the KCNH2 gene selected from rs3900779, rs748693 and rs1036145.

It will be appreciated by those skilled in the art that such nomenclature (i.e., M10) refers to a specific position in the KCNH2 transcript. However, it is equally understood that such mutations correspond to mutations in the genomic DNA (e.g. rs1036145), and the mutations could also be referred to by nomenclature signifying their genomic location. Methods of detecting specific mutations in nucleic acid molecules are known in the art and can be utilized in the present invention. For example, as noted above, the full sequence of a KCNH2 nucleic acid molecule present in the sample could be determined and compared to the wild-type KCNH2 gene sequence.

In one embodiment, the polymerase chain reaction (PCR) is used to test for the presence of specific mutations. With regard to this embodiment, it is known that PCR relies on hybridization of nucleic acid primers to the nucleic acid molecule being amplified (i.e. the template nucleic acid molecule). It is also known in the art that mismatches in the hybridization between the nucleic acid primers and the template nucleic acid molecule can result in polymerase failing to extend the primers. In particular, if the 3' nucleotide in the primer does not pair with the nucleotide at the complementary position in the template, the polymerase fails to extend the primer and the template DNA is not amplified. Thus, in one embodiment of the present invention, the step of analyzing comprises performing PCR using primers specific for a KCNH2 nucleic acid template. In a further embodiment, the PCR is performed using primers in which the 3' nucleotide of at least one primer that does not pair with the nucleotide at the complementary position in the template. Other methods of detecting specific mutations can also be used to practice the present invention including, for example, single stranded conformation polymorphism analysis, loss/gain of restriction site analysis, heteroduplex analysis.

The 3.1 isoform of KCNH2 may also be determined by the expression and/or the activity level of the corresponding protein. Methods of measuring these activities are disclosed herein, and are known to those skilled in the art. For example, the 3.1 isoform of KCNH2 can be determined using protein-protein binding assays known to those skilled in the art. One example of such an assay is an immunoprecipitation assay. In such an assay, the proteins to be tested for binding are mixed together to allow binding, and then a precipitable capture molecule, such as a bead-bound antibody that binds to the 3.1 isoform of KCNH2, is added to the mixture. The capture molecule is then precipitated and the precipitate analyzed, for example using PAGE analysis and/or immunoblotting, to determine what proteins co-precipitate with the capture molecule. Such techniques are known to those skilled in the art.

Another useful assay for measuring protein-protein interactions is an enzyme-linked immunosorbent assay (ELISA). Such an assay comprises: a) contacting an ELISA plate, which is coated with a suitable amount of a first protein, with a solution containing a second protein being tested for its ability to bind the first protein; and b) determining if the first and second protein form a complex. The step of determining if a protein-protein complex is formed comprises assaying for the presence of a complex using an antibody to the second protein. The above description is a general description of an ELISA assay, and variations of such an assay are known to those skilled in the art.

Another embodiment of the invention relates to an assay kit for selecting a schizophrenic patient who is predicted to benefit or not to benefit from therapeutic administration of an antipsychotic medication. The assay kit includes: (a) a means for detecting in a biological sample obtained from the patient a level of a biomarker of the invention, which is a marker of the expression of the 3.1 isoform of KCNH2. The kit also includes: (b) a control selected from: (i) a control sample for detecting expression of the 3.1 isoform of KCNH2; (ii) a control sample for detecting low or absent expression of the 3.1 isoform of KCNH2; (iii) information containing a predetermined control level of the expression of the 3.1 isoform of KCNH2; and/or (iv) information containing a predetermined control level of a biomarker of the expression of the 3.1 isoform of KCNH2. In one aspect, the kit can further include at least one means for detecting at least one mutation in a KCNH2 polynucleotide.

A Novel, Primate-Specific Brain Isoform of KCNH2: Role in Cognition, Hippocampal Biology and Association with Schizophrenia Organized neuronal activity is critical for cortical information processing and is disrupted in schizophrenia. We have identified a primate-specific isoform (3.1) of the potassium channel KCNH2 that controls neuronal firing. Several SNPs in a 3 kb upstream region are associated with schizophrenia in four independent datasets. The risk-SNPs affect memory, IQ and speed of cognitive processing as well as hippocampal structure and physiology. Isoform 3.1 mRNA levels are comparable to KCNH2-1A in prefrontal cortex and hippocampus, but over 1000-fold lower in heart. Postmortem expression analysis shows a 2.5-fold increase in Isoform 3.1 relative to KCNH2-1A in schizophrenic hippocampus and association with risk SNPs. Structurally, Isoform 3.1 lacks most of the PAS domain critical for slow channel deactivation. Electrophysiological characterization in rodent cortical neurons reveals that overexpression of Isoform 3.1 results in a rapidly deactivating K+ current and a high-frequency, non-adapting firing pattern. These results reveal an unexpected role of a novel KCNH2 channel in cortical physiology, cognition, and psychosis and provide a potential new target for psychotherapeutic drugs.

Introduction

Using a combination of genetic, brain imaging, and behavioral analyses in the present study, we have identified a novel schizophrenia susceptibility gene—the KCNH2 potassium channel—in four independent clinical samples, and we have also found association with several intermediate phenotypes, including impaired cognition and imaging measures of HF structure and function in a sample of normal individuals who carry risk alleles. KCNH2 (also called hERG1), Genbank accession No. U04270, a member of the ether-a-go-go related family of voltage gated potassium channels (J. W. Warmke and B. Ganetzky 1994 Proc Natl Acad Sci USA 91:3438), is best known for its role in slow repolarization of the membrane potential during the myocardial action potential, thereby regulating the QT interval (M. C. Sanguinetti and M. Tristani-Firouzi 2006 Nature 440:463). Despite extensive characterization of KCNH2 in myocardial cells, surprisingly few studies have been carried out in neurons, let alone in human or non-human primate neurons. However, KCNH2 is expressed abundantly in many brain regions including hippocampus and frontal cortex (L. Guasti et al. 2005 J Comp Neurol 491:157; M. J. Saganich et al. 2001 J Neurosci 21:4609). Its distinct physiological features, namely slow activation, fast inactivation, and slow and voltage-dependent deactivation (J. W. Warmke and B. Ganetzky 1994 Proc Natl Acad Sci USA 91:3438, M. C. Trudeau et al. 1995 Science 269:92; P. L.

Smith et al. 1996 Nature 379:833; J. H. Morais Cabral et al. 1998 Cell 95:649), make KCNH2 an excellent candidate in controlling neuronal firing patterns and network oscillation in PFC and HF. Modeling work predicts that KCNH2 is critical for spike-frequency adaptation, or a gradual termination of a train of evoked action potentials, a common firing pattern seen in excitatory neurons in the brain (N. Chiesa et al. 1997 J Physiol 501:313). Several studies have shown that inhibition of KCNH2 converts low-frequency, adapting to high-frequency, non-adapting neuronal discharges (N. Chiesa et al. 1997 J Physiol 501:313; T. Sacco et al. 2003 J Neurophysiol 90:1817), a firing pattern necessary for sustained neuronal activity subserving numerous complex cognitive functions (Y. Wang et al. 2006 Nat Neurosci 9:534). To unravel the molecular mechanisms of our clinical associations with KCNH2, we have characterized the expression of KCNH2 mRNA in postmortem human brain. This led to the unexpected identification of a novel, primate brain specific isoform (Isoform 3.1) with its transcription start site near the risk sequence variants. Remarkably, the expression of Isoform 3.1 is increased in the hippocampus of schizophrenia patients and even in normal individuals who carry risk alleles of KCNH2. These results prompted us to introduce the gene into rodent cortical neurons, which do not express endogenous Isoform 3.1. Expression of Isoform 3.1 significantly alters hERG channel's deactivation rate, resulting in high-frequency, non-adapting firing patterns. Such changes in spike frequency could lead to desynchronization of neuronal assemblies thought to be a critical aspect of cortical dysfunction in schizophrenia (G. Winterer and D. R. Weinberger 2004 Trends Neurosci 27:683). Together, these convergent results implicate a role of a novel KCNH2 isoform in the etiology and pathophysiology of schizophrenia and make it a promising new target for antipsychotic therapy.

Identification of the NOS3/KCNH2 Region Associated with Schizophrenia

Figure 11:
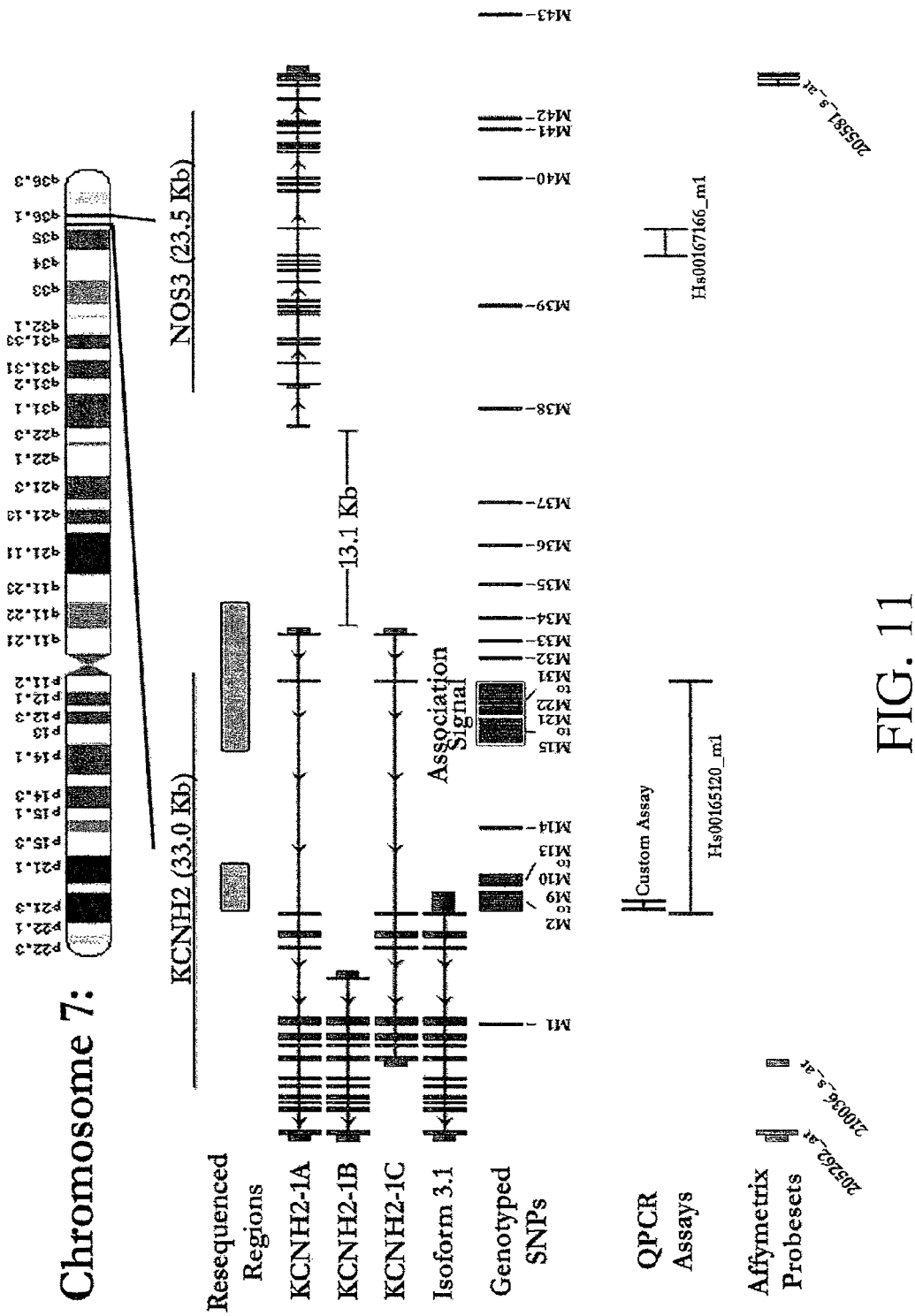
FIG. 11. Physical map of SNPs, transcripts, QPCR assays, PCR primers, and re-sequenced regions.

It has become increasingly apparent that genetic risk for schizophrenia and many other complex illnesses will not relate to major amino acid changes and highly detrimental protein mutations, though these may still occur in rare forms of the illness (R. E. Straub and D. R. Weinberger 2006 Biol Psychiatry 60:81). Instead, the molecular effects of susceptibility genes are more likely to be subtle, relating to the regulation and splicing of transcripts or proteins. Thus, the gene expression profiles of patient tissue may provide clues to the identification of candidate risk genes. Preliminary support for this possibility has emerged from the association of RGS4 (M. E. Talkowski et al. 2006 Schizophr Bull 32:203) and CNP (T. R. Peirce et al. 2006 Arch Gen Psychiatry 63:18) with schizophrenia, which were originally identified as candidate genes from microarray expression profile analyses in postmortem brain of patients with schizophrenia (K. Mimics et al. 2001 Mol Psychiatry 6:293). Consequently, we selected 10 genes recently reported as differentially expressed in a large number of schizophrenia patients as determined by microarray (S. Prabakaran et al. 2004 Mol Psychiatry 9:684) and genotyped haplotype tagging SNPs (htSNPs) taken from HapMap (release #15) in 170 Caucasian families with an offspring with schizophrenia. Family-based association analysis was performed (N. M. Laird et al. 2000 Genet Epidemiol 19 (Suppl 1) S36) and nominally significant signals were observed in 5 of the 10 genes (Table 2). In particular, SNPs located in the genomic region of NOS3 (7q36.1) demonstrated the highest linkage disequilibrium (LD) with the illness. The positive SNPs in this region, however, mapped upstream of NOS3, within a neighboring gene, KCNH2, which is transcribed in the opposite direction (FIG. 5; FIG. 11). A survey of comparative genomic databases indicates that the genomic contiguity and orientation of NOS3 and KCNH2 is highly conserved among mammalian species.

Figure 5:
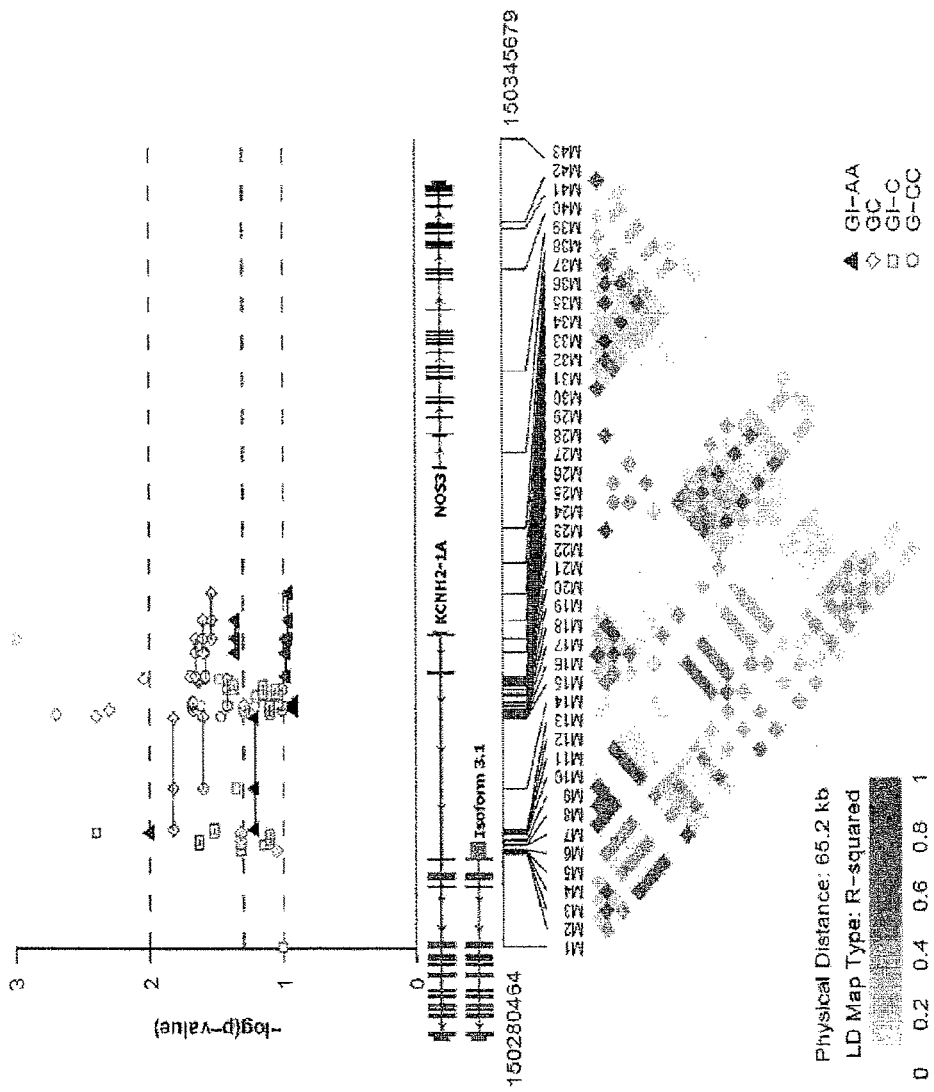
FIG. 5: Genetic association of 7q36.1 with risk for schizophrenia.

Referring to FIG. 5 (top) is shown the inverse log of the p-value from family-based association results for the CBDB Sibling Study (GC, diamonds), NIMHGI-C (GI-C, squares), NIMHGI-AA (GI-AA, triangles) and for the German case-control study (G, circles) for single SNPs and 3-SNP sliding window haplotypes. Only markers and haplotypes with p-values less than 0.1 are shown. A physical map of the region is given and depicts known genes within the region. Referring to FIG. 5 (bottom), the LD structure of the genotyped markers is given for 370 unrelated healthy control Caucasians and depicted as D'. Graphics were created using the R package snp.plotter available from nicodemusk@mail.nih.gov (A. Luna and K. K. Nicodemus 2007 Bioinformatics 23:774-776).

KCNH2 as a Risk Gene for Schizophrenia

A haplotype block indicative of minimal historical recombination (S. B. Gabriel et al. 2002 Science 296:2225) containing parts of NOS3 and KCNH2 was observed in persons of Western European ancestry genotyped by the International HapMap Project (The International HapMap Project 2003 Nature 426:789). The haplotype block begins 1.2 Kb downstream of the NO S 3 transcription start site (in the 5' UTR) and extends 21.3 Kb upstream of this gene (FIG. 11). The initial 13.1 Kb of this upstream region are non-coding and intergenic, but the remainder overlaps with 6.9 Kb of KCNH2. Of the 3 htSNPs required to tag this region (S. B. Gabriel et al. 2002 Science 296:2225), rs1036145 (M33) was over-transmitted (p=0.0032) to schizophrenia patients in a cohort of 295 Caucasian families (CBDB cohort) as was the entire haplotype block (global p=0.005).

Based on these data it was expected that M33 is in strong LD with causative SNP(s) and/or responsible for the association signal itself. Consequently, additional dbSNPs were genotyped across a region stretching from the 3'-end of KCNH2 to the 3'-end of NOS3, with highest coverage focused around M33. A 7.2 Kb region flanking M33 was re-sequenced in 48 schizophrenia patients to detect rare or unreported SNPs. We also re-sequenced exons 1-3 of KCNH2 and their intronic borders (total sequence 10.4 kb) and no coding polymorphisms were discovered. A total of 43 SNPs were genotyped in the CBDB cohort including 11 novel SNPs. Six SNPs were significantly associated with schizophrenia (5 with p<0.01) as were many of the 3-marker haplotypes containing them (FIG. 5; FIG. 12, Table 3). The majority of these significantly associated SNPs map to a small 3 kb segment of intron two of KCNH2.

Figure 12D:
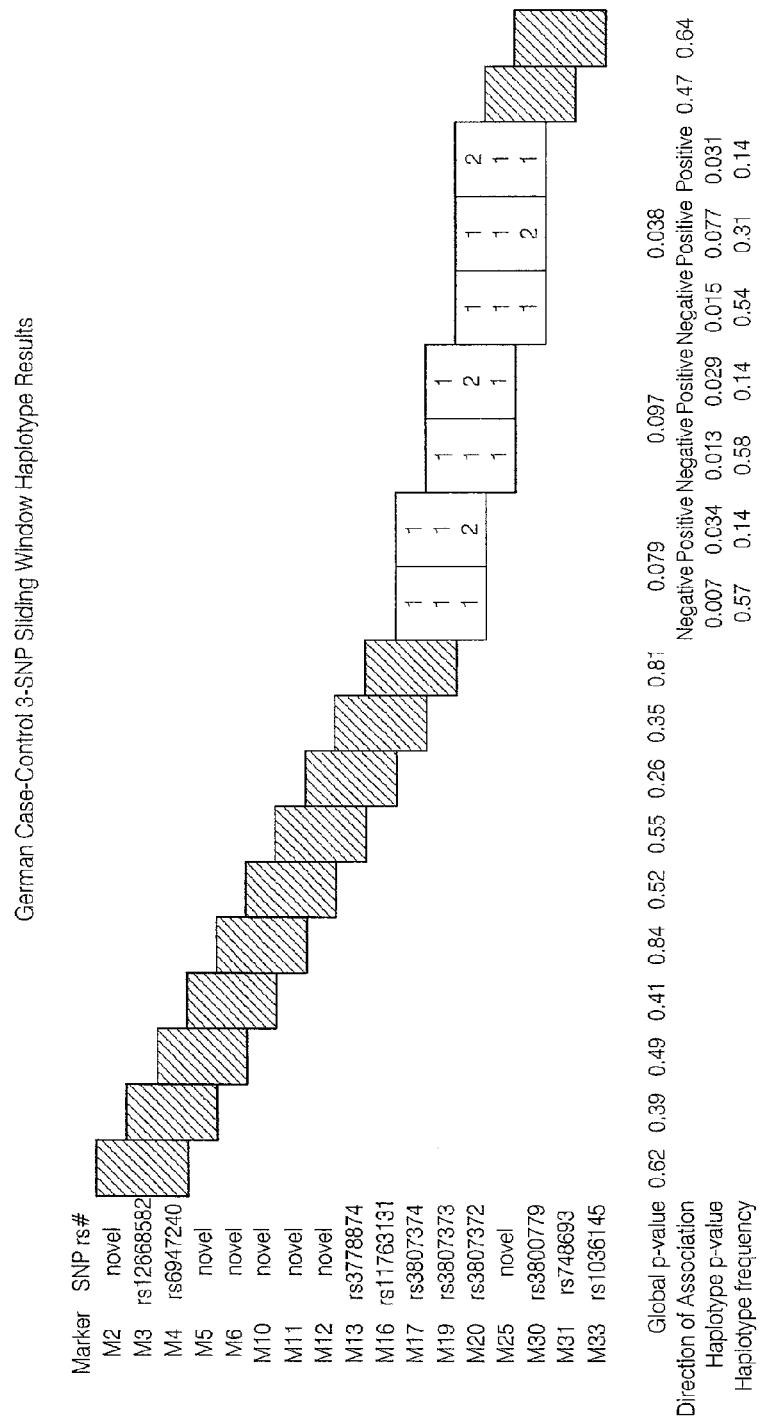
FIG. 12. Single-marker and 3-marker sliding-window results for (A) CBDB, (B) NIMHGI-C, (C) NIMHGI-AA, and (D) German DNA collections.

Referring to FIG. 12, single-marker and 3-marker sliding-window results are shown for CBDB, NIMHGI-C, NIMHGI-AA, and RU cohorts. SNPs denoted novel were identified by re-sequencing DNA from 48 schizophrenia patients (see Example 1). FIG. 12A depicts the FBAT three marker sliding windows in CBDB family sample (CBDB Sibling Study 3-SNP Sliding Window Haplotype Results (296 families). FIG. 12B depicts the FBAT three marker sliding windows in NIMH-C family sample (NIMHGI-C 3 SNP Sliding Window Haplotype Results (71 families). FIG. 12C depicts the FBAT three marker sliding windows in NIMH-AA family sample (NIMHGI-AA SNP Sliding Window Haplotype Results (51 families). FIG. 12D depicts the Haplo. stats three marker sliding windows in German case control sample (German Case-Control 3-SNP sliding window haplotype results).

Figure 13:
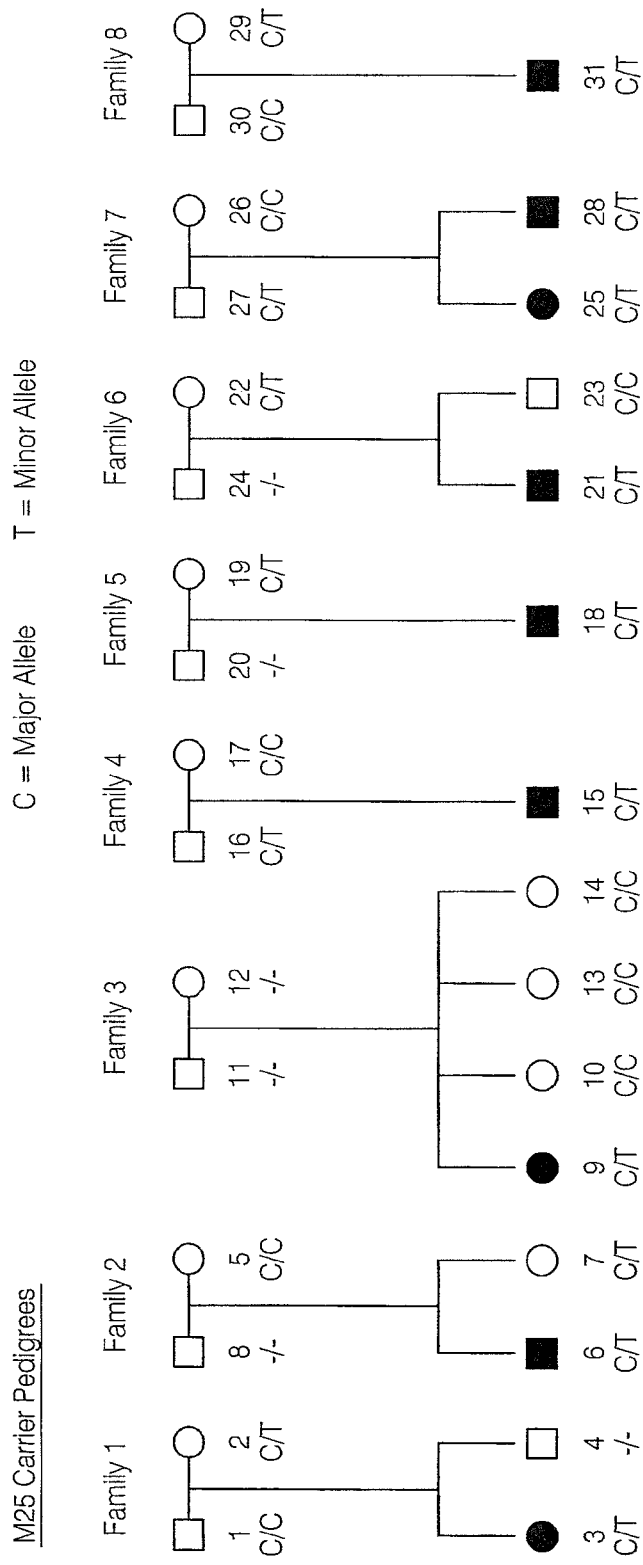
FIG. 13. Pedigrees of 8 families with rare SNP M25 and association tables excluding these families.

Forty of these markers were then genotyped in the two additional family-based cohorts derived from the NIMH Genetics Initiative project (C. R. Cloninger et al. 1998 Am J Med Genet 81:275), consisting of 71 Caucasian families (NIMHGI-C) and 51 African American families (NIMHGI-AA). Though substantially limited in power due to the small number of families, SNPs and/or haplotypes in the same small region were significantly associated with schizophrenia in both datasets (FIG. 5; FIG. 12, Table 3). In particular, in all 3 populations the association signal was localized to intron 2 of KCNH2, though significantly associated SNPs were not identical in all cohorts, as has been found in association with a number of other putative schizophrenia genes (R. E. Straub and D. R. Weinberger 2006 Biol Psychiatry 60:81). However, two common overlapping haplotypes containing A-G at M9 and M10 and C-G at M21 and M22 were associated with risk in both Caucasian family datasets: in the NIMHGI-C (M9-M10 global p=0.079, haplotype p=0.076; M21-M22 global p=0.092, haplotype p=0.082) and CDBD (M9-M10 global p=0.048, haplotype p=0.083; M21-M22 global p=0.098, haplotype p 0.10). Also, consistent with single SNP analyses, haplotypes containing M30 major allele G were negatively associated with schizophrenia in both the CBDB sample (global p=0.023, haplotype p=0.01) and NIMHGI-C (global p=0.10, haplotype p=0.028), even though no association between M30 and schizophrenia was observed in the single SNP analyses of NIMHGI-C. Haplotype C-A-G at M32-M33-M34 was significantly positively associated in both the CBDB and NIMH-GI AA samples (CBDB haplotype p=0.008; NIMHGI-AA haplotype p=0.044). Interestingly, one rare SNP (Caucasian MAF=0.007) was found in eight families across all study cohorts, and all of the nine affected offspring in these families inherited the same rare allele from a heterozygous parent (see FIG. 13). Referring to FIG. 13, all families found to contain at least one individual with the rare allele (T) are depicted. Plots follow standard pedigree methods (black=affected/schizophrenic, etc.). All individuals with "–/–" genotypes were unavailable for DNA collection. Note that all affected offspring inherit rare allele and all individuals were Caucasian.

Finally, given the positive family-based association signals, we tested for association in a fourth sample, a Caucasian case-control dataset collected in Germany consisting of 501 patients and 626 controls, typing the 6 significantly associated SNPs found in the CBDB cohort and also the novel SNPs that were found by resequencing. Using logistic regression for the single SNPs, significant association was observed in SNPs M20 and M30 corresponding to odds ratios of 2.99 (CI=1.26, 7.11) and 1.58 (CI=1.05, 2.38), respectively (FIG. 5; Table 3). Thus, in our two reasonably powered Caucasian samples, we confirm association for the same two SNPs and for the same alleles, and show evidence for association to varying haplotypes in two other small family samples, including one of AA origin. Taken together, these results identify the region of KCNH2 as a susceptibility locus for schizophrenia and suggest that KCNH2 is the gene responsible for this association.

Impact of KCNH2 SNPs on Cognition, Hippocampal Structure and Function

If inheriting variations of SNPs within this region increases risk for schizophrenia by altering brain function, then such genetic variations should be associated with schizophrenia intermediate brain phenotypes in individuals who carry risk alleles even if they do not manifest the entire diagnostic syndrome (A. Meyer-Lindenberg and D. R. Weinberger 2006 Nat Rev Neurosci 7:818). A variety of cognitive deficits, related to attention, memory, and IQ/processing speed have been prominently implicated as intermediate phenotypes related to schizophrenia and are associated with increased relative risk in unaffected relatives of patients (T. D. Cannon et al. 2000 Am J Hum Genet 67:369; M. F. Egan et al. 2000 Am J Psychiatry 157:1309; M. F. Egan et al. 2001 Biol Psychiatry 50:98; T. E. Goldberg et al. 2003 Arch Gen Psychiatry 60:889). Given the high expression of KCNH2 within the prefrontal cortex (PFC) and HF, two regions subserving these cognitive processes and consistently implicated in the neuropathology of schizophrenia (P. J. Harrison 1999 Brain 122:593, D. R. Weinberger et al. 2001 Biol Psychiatry 50:825), it is reasonable to expect that if risk SNPs impact on the biology of these brain regions, such cognitive deficits would also be associated with risk genotypes, regardless of disease status. Accordingly, the most significantly associated SNPs from the CBDB study (M30, M31, M33) were assessed for their effects on seven independent summary measures of cognitive function (Genderson, M. R. et al. Schiz Res (in press)) (Table 4) in an independent sample of healthy, unrelated controls who were screened to exclude individuals with a history of psychiatric disorders. Using linear regression adjusting for age in models assessing speed of processing (correlation coefficient p-value for test of processing speed and age=0.0062; t-test p-value for differences in means by sex=0.57) and no covariates in models assessing visual memory (t-test p-value for differences in means by sex=0.26; correlation coefficient for visual memory by age=0.75), significant association was observed between risk genotypes and performance on IQ/processing speed and visual memory tasks (FIG. 6A; Table 4). Thus, even in healthy controls, individuals carrying the same alleles observed more frequently in schizophrenia patients performed significantly worse on tasks measuring IQ, visual reasoning and memory, and timed sequencing than subjects without risk alleles.

The genetic associations with cognition suggest that variation in KCNH2 impacts on the biology of the neural systems that subserve these functions. Declarative memory is strongly dependent on hippocampal function, where at least in rodents, KCNH2 is most abundantly expressed (M. J. Saganich et al. 2001 J Neurosci 21:4609). Thus, these associations could reflect genetic modulation of the physiology of memory processing within the HF, and they might also represent more fundamental changes at the level of structural development of the hippocampus. Therefore, we hypothesized that the same SNPs significantly associated with schizophrenia in the CBDB family sample and the case control sample from Germany would relate to changes in hippocampal structure and physiology, and again, if such changes are manifestations of the biology of gene effects in brain, then healthy controls carrying risk alleles would be predicted to show evidence of such changes. We have argued for the use of healthy controls for genetic associations at the level of brain morphometry and information processing in order to avoid potential confounders related to chronic illness and medical treatment (A. R. Hariri and D. R. Weinberger 2003 Br Med Bull 65:259). Voxel-based morphometry (VBM) was used to assess regional brain volumes, focusing on the HF, of a sample of healthy control subjects.

Figures 6A, 6B:
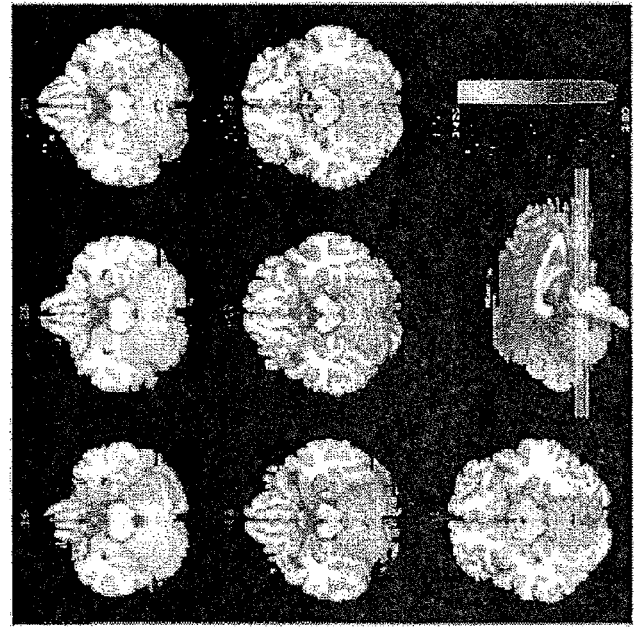
FIG. 6: Association of risk SNPs with (A) cognitive measures, (B) brain structure volumes, and (C) regional brain activity during memory-based tasks.

Following FDR correction ($\alpha$=0.05), significant volume decreases in hippocampal structures were observed in individuals carrying the minor alleles (risk alleles) of SNPs M30, M31, and M33 using both whole brain and region of interest (ROI) analyses, and additive allele load effects were observed (FIG. 6B; FIGS. 14-18; Tables 5-8). Control analyses based on non-risk SNPs were consistently negative for association with VBM changes (FIGS. 14-18, Tables 5-8).

Because abnormal cognitive function reflects physiologic dysfunction, we predicted that the same SNPs would impact on the physiology of memory processing subserved by the HF, again in healthy control risk allele carriers. In order to control for the effects of task performance on the fMRI response and thus to isolate the effect of genotype on the physiology of information processing, genotype groups were matched for performance on cognitive tasks (accuracy and reaction time). This matching strategy allowed a test of the effect of genotype on how cognitive information is handled physiologically at the neural system level, independent of how well subjects perform on the task. fMRI was used to assess regional activation during incidental encoding of a temporal lobe memory task (A. R. Hariri et al. 2003 J Neurosci 23:6690), again within healthy control subjects. We observed significantly greater activation (FWE correction $\alpha=0.05$) of the HF within normal risk carriers (FIG. 6C; FIGS. 14-18, Tables 5-8). This pattern of inefficient (i.e., excessive activity for a fixed level of performance) processing of memory information suggests that the tuning of the cortical microcircuits subserving memory processing in the HF is relatively disordered in individuals with risk genotypes. Similar patterns of inefficient processing of memory in HF have been reported for other genes impacting on episodic memory (e.g., S. Y. Bookheimer et al. 2000 N Engl J Med 343:450 and G. Egan et al. 2003 Proc Natl Acad Sci USA 100:15241).

Figure 6C:
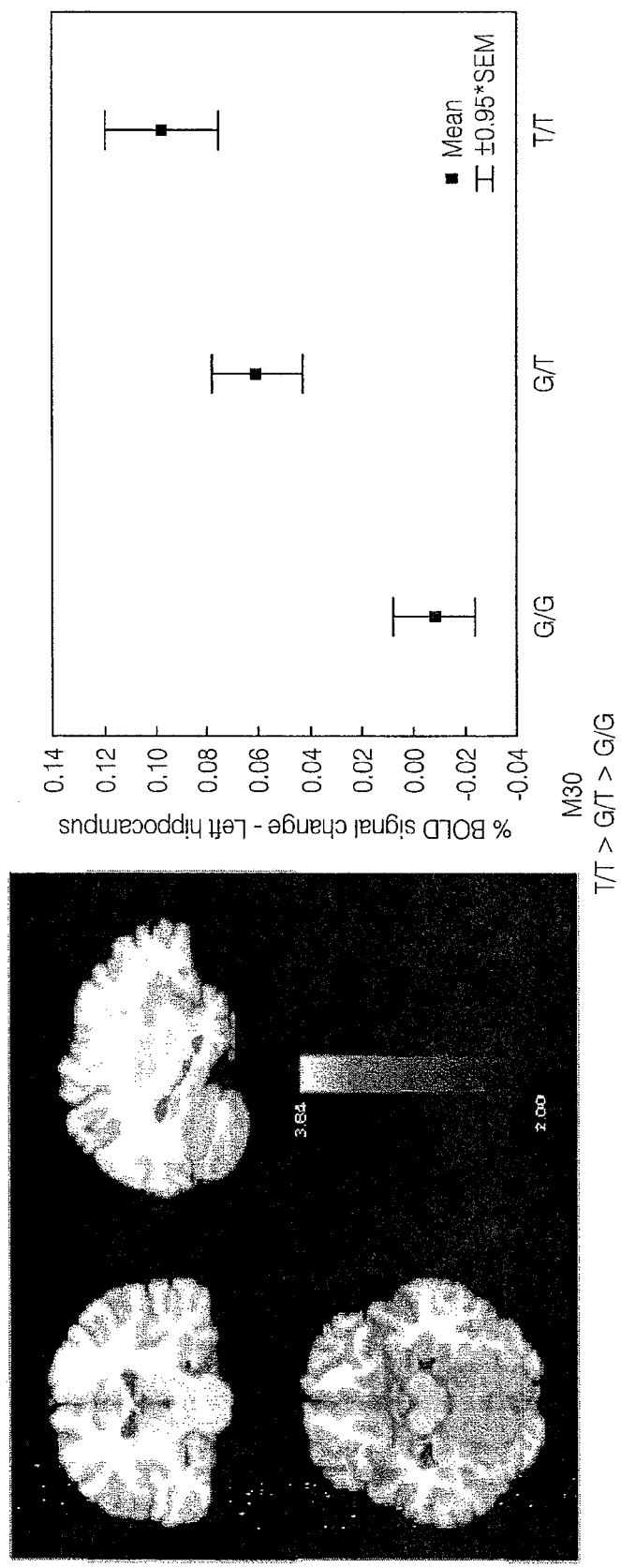

Referring to FIG. 6A, genotype effects of most significant family-based markers on cognitive performance measures are shown. P-values for the regression model are based on two-degree of freedom F-tests. Linear regression was used to assess differences between cognitive measures and heterozygote (G/A) and homozygote (A/A) carriers with respect to G/G non-risk carriers. P-values for each genotype comparison are shown followed by β-coefficients for genotypes indicated. Significant main effects (p<0.05) are shown in bold. Referring to FIG. 6B, optimized voxel based morphometry analysis (VBM) of a different cohort of healthy control carriers was performed using an analysis of covariance model with gray matter volume (GM), age, and gender as covariates of no interest. Thresholded (p=0.05 FDR corrected) statistical maps show a relative linear decrease in HF GM from subjects homozygous for the risk allele (n=17) to heterozygote carriers (n=59) to non carriers (n=63). Referring to FIG. 6C, thresholded (p<0.05 FWE corrected) statistical t-maps and mean (±1 SEM) percent blood oxygen level-dependent (BOLD) signal change during the encoding conditions of a declarative memory task in the left posterior hippocampus (MNI coordinates of peak cluster: −34 −25 −15 mm) showing a significant linear increase of activation in homozygote carriers (n=14) relative to heterozygote carriers (n=37), and to non carriers (n=28) of the risk allele of the M30 SNP.

Figure 14A:
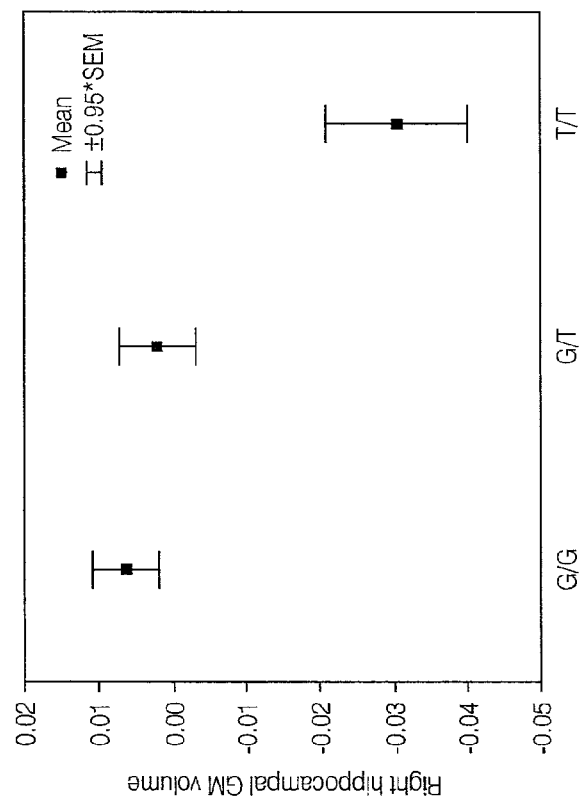
FIG. 14. Genotype based differences in right hippocampal gray matter volume (MNI coordinates: 26, −12, −22 mm) for SNP M30, derived using optimized VBM. A) Plot of gray matter volumes, B) Thresholded statistical t-maps.
Figure 14B:
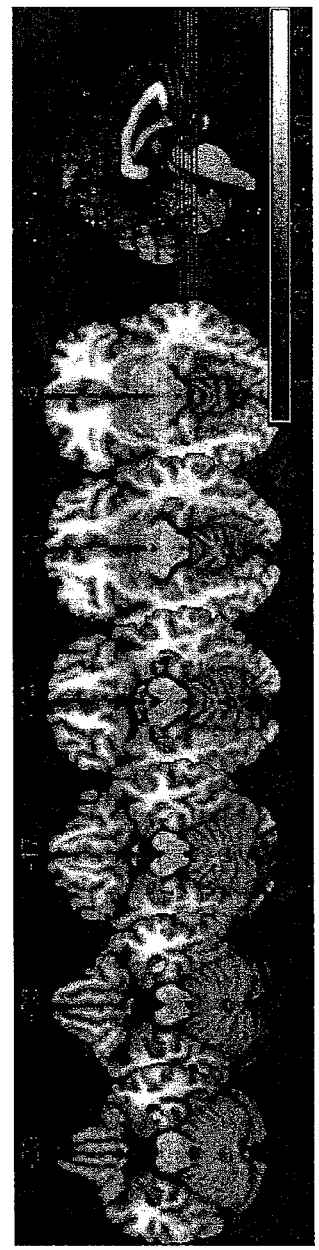

Referring to FIG. 14, genotype based differences in right hippocampal gray matter volume (MNI coordinates: 26, −12, −22 mm) for SNP M30 were derived using optimized VBM. This plot (FIG. 14A) and the thresholded (p=0.05 FDR corrected) statistical t-maps (FIG. 14B) show a linear decrease in gray matter volume from homozygotes (n=17) for the risk allele, to heterozygote carriers (n=59) to non carriers (n=63). For illustrative purposes, the measures for hippocampal gray matter volume were mean centered and extracted from the most significant right anterior hippocampal cluster on ANCOVA analysis in SPM 2 using age, gender, and total gray matter volume as covariates of no interest.

Figure 15A:
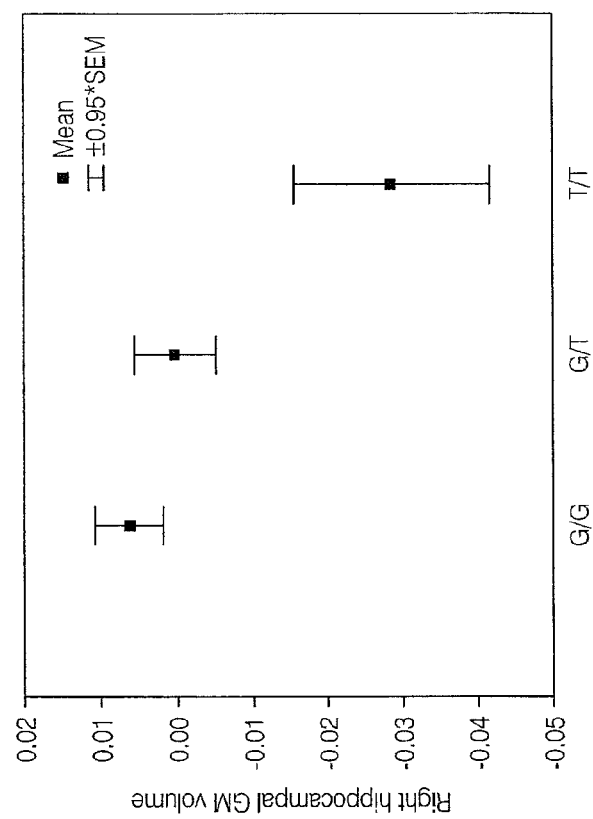
FIG. 15. Genotype based differences in right hippocampal gray matter volume (MNI coordinates: 26, −9, −24 mm) for SNP M31, derived using optimized VBM. A) Plot of gray matter volumes, B) Thresholded statistical t-maps.
Figure 15B:
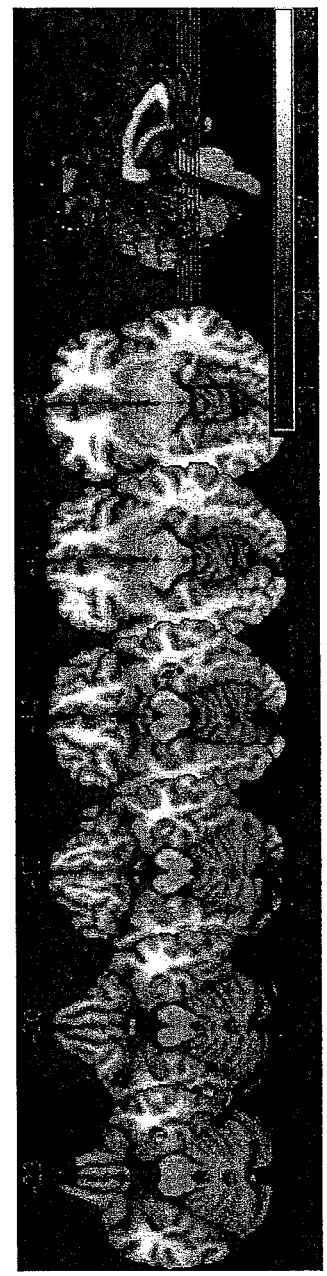

Referring to FIG. 15, genotype based differences in right hippocampal gray matter volume (MNI coordinates: 26, −9, −24 mm) for SNP M31 were derived using optimized VBM. This plot (FIG. 15A) and the thresholded (p=0.05 FDR corrected) statistical t-maps (FIG. 15B) show a linear decrease in gray matter volume from homozygotes (n=16) for the risk allele, to heterozygote carriers (n=59) to non carriers (n=66). For illustrative purposes, the measures for hippocampal gray matter volume were mean centered and extracted from the most significant right anterior hippocampal cluster on ANCOVA analysis in SPM 2 using age, gender, and total gray matter volume as covariates of no interest.

Figure 16A:
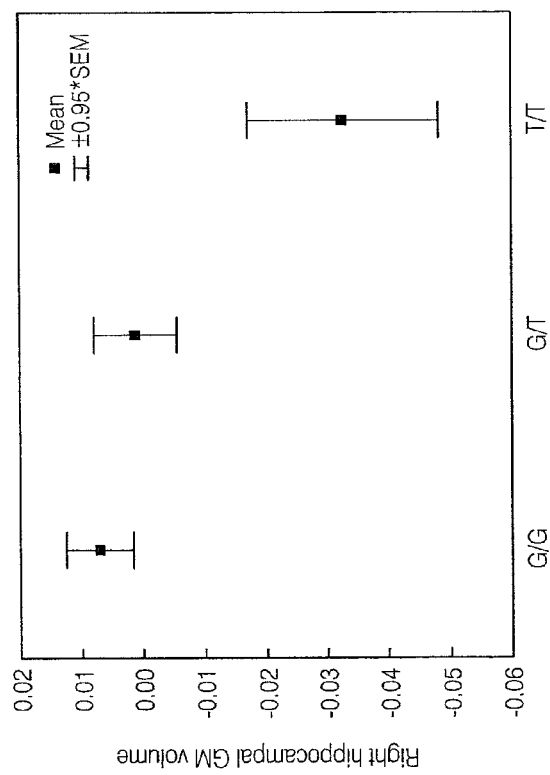
FIG. 16. Genotype based differences in right hippocampal gray matter volume (MNI coordinates: 26, −9, −24 mm) for SNP M33, derived using optimized VBM. A) Plot of gray matter volumes, B) Thresholded statistical t-maps.
Figure 16B:
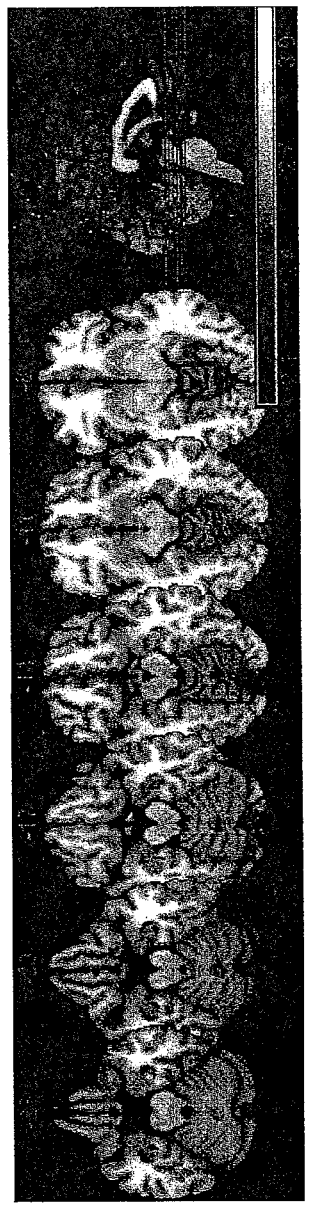

Referring to FIG. 16, genotype based differences in right hippocampal gray matter volume (MNI coordinates: 26, −9, −24 mm) for SNP M33 were derived using optimized VBM. This plot (FIG. 16A) and the (p=0.07 FDR corrected) statistical t-maps (FIG. 16B) show a linear decrease in gray matter volume from homozygotes (n=16) for the risk allele, to heterozygote carriers (n=61), to non carriers (n=64). For illustrative purposes, the measures for hippocampal gray matter volume were mean centered and extracted from the most significant right anterior hippocampal cluster on ANCOVA analysis in SPM 2 using age, gender, and total gray matter volume as covariates of no interest.

Referring to FIG. 17, genotype based differences in hippocampal engagement during a declarative memory task for SNP M31 are shown. FIG. 17A depicts mean (±1 SEM) percent BOLD signal change during the encoding condition of the task in the left posterior hippocampus (MNI coordinates of peak cluster: −34 −22 −15 mm) showing a significant linear increase of activation in homozygote carriers (n=12) relative to heterozygote carriers (n=35) and non carriers (n=30) of the risk allele. Thresholded (p<0.05 FWE corrected) statistical t-maps are shown in FIG. 17B.

Figure 18B:
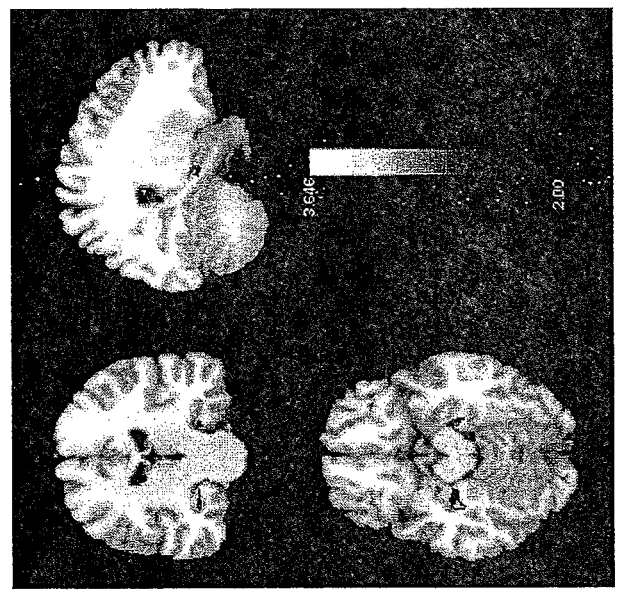
FIG. 18. Genotype based differences in hippocampal engagement during a declarative memory task for SNP M33. A) Percent blood oxygen level-dependent (BOLD) signal change during the encoding condition of the task in the left posterior hippocampus. B) Thresholded statistical t-maps.
Figure 18A:
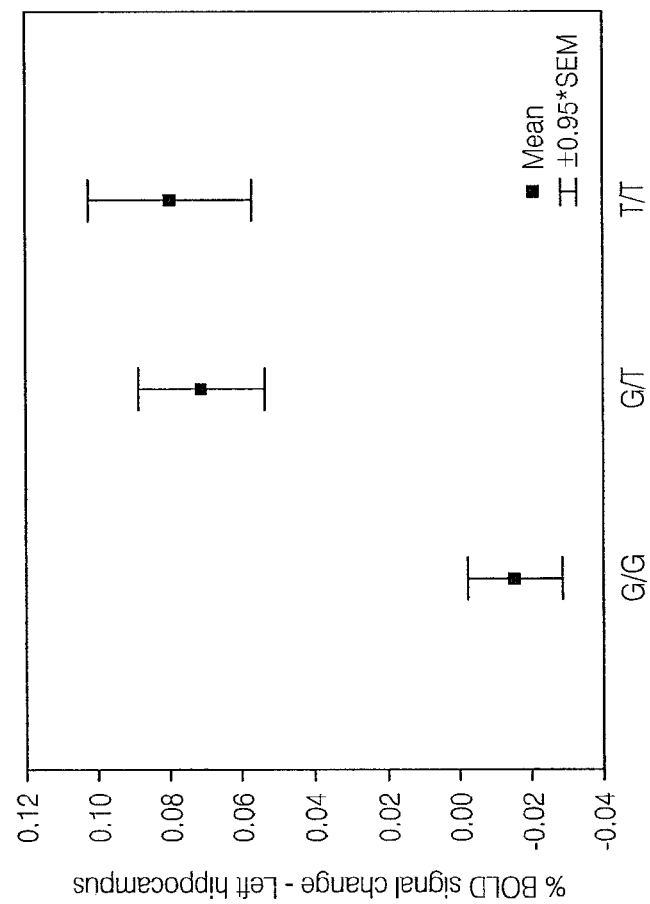

Referring to FIG. 18, genotype based differences in hippocampal engagement during a declarative memory task for SNP M33 are shown. FIG. 18A depicts mean (±1 SEM) percent BOLD signal change during the encoding condition of the task in the left posterior hippocampus (MM coordinates of peak cluster: −34 −22 −15 mm) showing a significant linear increase of activation in homozygote carriers (n=11) relative to heterozygote carriers (n=37) and non carriers (n=27) of the risk allele. Thresholded (p<0.05 FWE corrected) statistical t-maps are shown in FIG. 18B.

Effects of Schizophrenia and Risk Genotypes on KCNH2 mRNA Expression

Figure 7A:
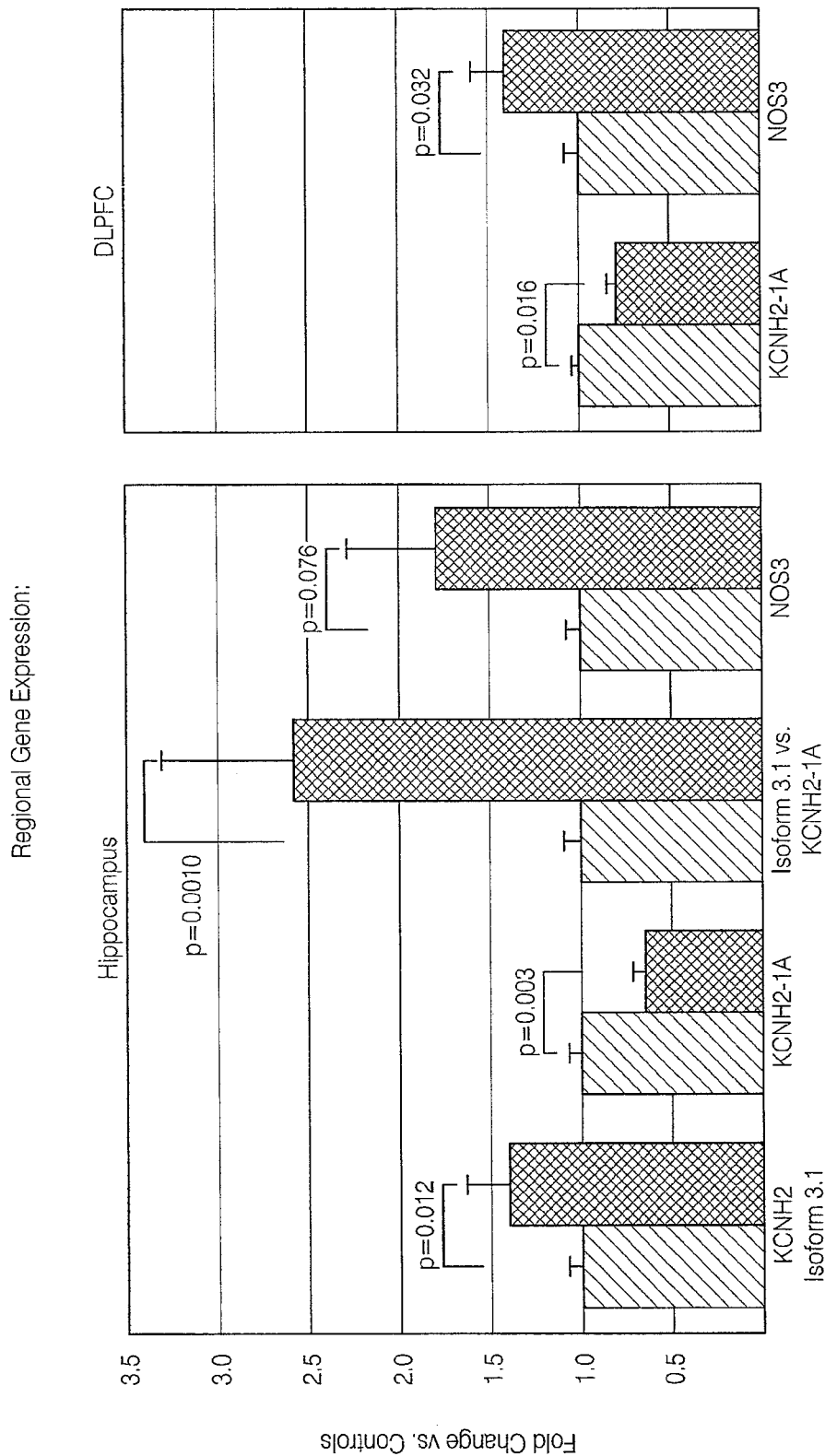
FIG. 7: (A) Regional gene expression and (B) association with risk genotype.

The association of genetic markers with schizophrenia and with related brain phenotypes in 5 independent data sets including samples of European and non-European ancestry and in healthy controls screened for psychiatric disorders lends strong support to the involvement of this genomic region in manifestations of the illness, including its neural system biology. However, these findings do not identify the underlying molecular mechanisms of risk. To begin addressing this issue, we investigated gene expression in human brain and its relationship to our evidence of genetic association. Indeed, using quantitative RT-PCR in a sample of postmortem brains from 31 schizophrenia and 69 healthy control subjects, we found KCNH2-1A expression levels to be significantly lower in the DLPFC of schizophrenia patients (p=0.008; FIG. 7A). We also replicated the increase in NOS3 expression (p=0.019; FIG. 6A) in DLPFC reported earlier in another set of postmortem schizophrenic brains (S. Prabakaran et al. 2004 Mol Psychiatry 9:684) (Table 9). Furthermore, given the enrichment of both genes within the HF, we also measured their expression in this region in a largely overlapping cohort of 29 schizophrenia and 59 healthy control subjects. KCNH2-1A was again significantly reduced in schizophrenia patients (p=0.005; FIG. 7A).

Figure 19:
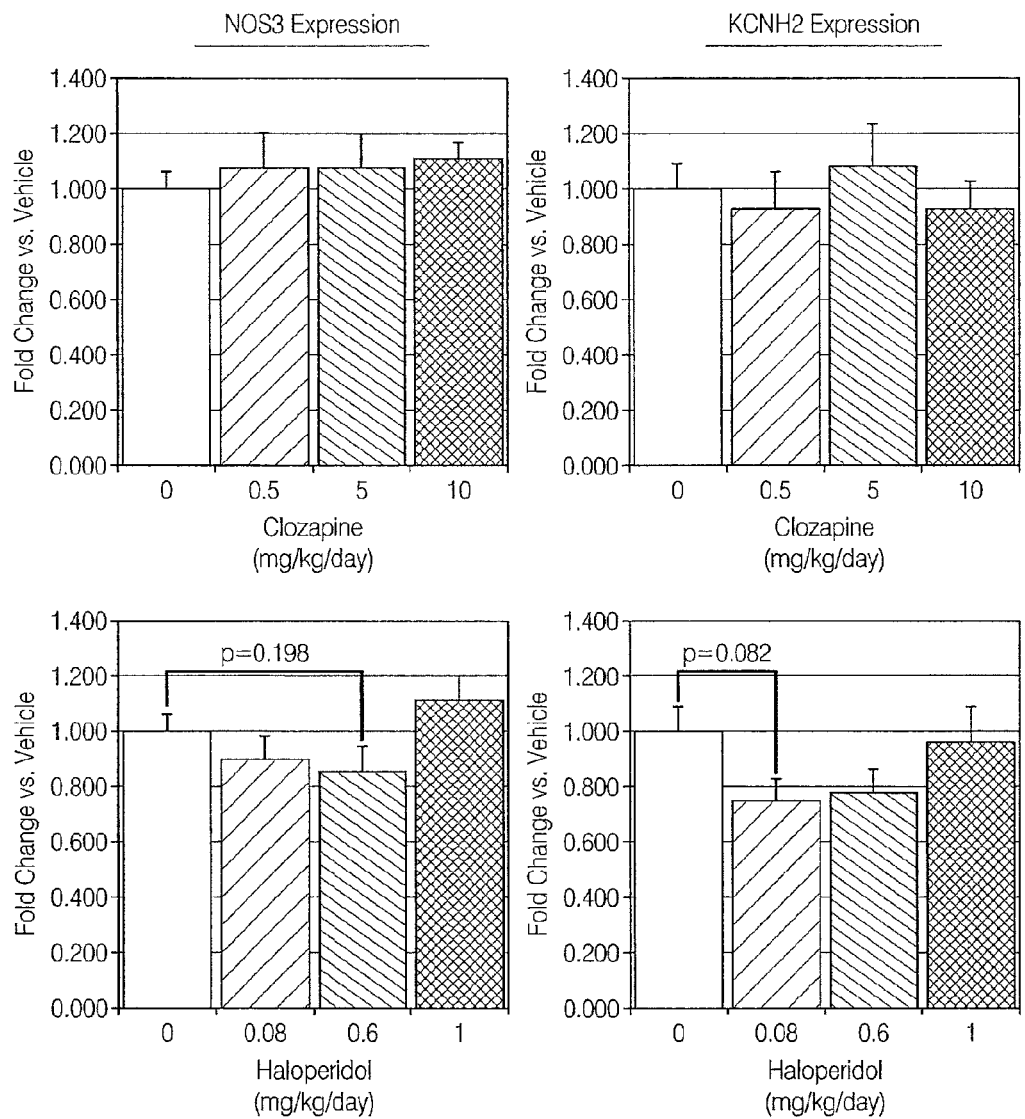
FIG. 19. NOS3 and KCNH2-1A expression in frontal cortex of neuroleptic treated rats.

Most patients with schizophrenia receive antipsychotic drugs, which may bind to KCNH2 and affect its expression (S. Kongsamut et al. 2002 Eur J Pharmacol 450:37). In order to assess the possibility that the observed changes in either gene might be a consequence of antipsychotic medication, 63 rats (8-10 per treatment group) were administered one of three doses of clozapine or haloperidol for 28 days. Neither clozapine nor haloperidol showed significant effects on the expression of either gene measured within the frontal cortex (FIG. 19). However, a slight decrease in KCNH2-1 A was observed in rats treated with 0.08 and 0.6 mg/kg/day of haloperidol though this did not reach significance (p=0.082 and 0.119, respectively). Thus, the effects of medication on the observed decrease in KCNH2-1 A cannot be excluded.

Referring to FIG. 7A, differences in mRNA expression within the hippocampus of 30 schizophrenia patients/62 healthy control subjects, and within the DLPFC of a largely overlapping set of 31 schizophrenia patients/69 healthy control subjects are shown. All expression values were normalized to the geometric mean of three housekeeping genes (B2M, GUSB, and PBGD) (J. Vandesompele et al. 2002 Genome Biol 3:RESEARCH0034) and are expressed as fold difference versus the mean of healthy controls. Data were tested for main effects using backwards stepwise linear regression using age, pH, RIN, and diagnosis as independent variables, p-values represent main effect of diagnosis in the final regression model.

Figure 7B:
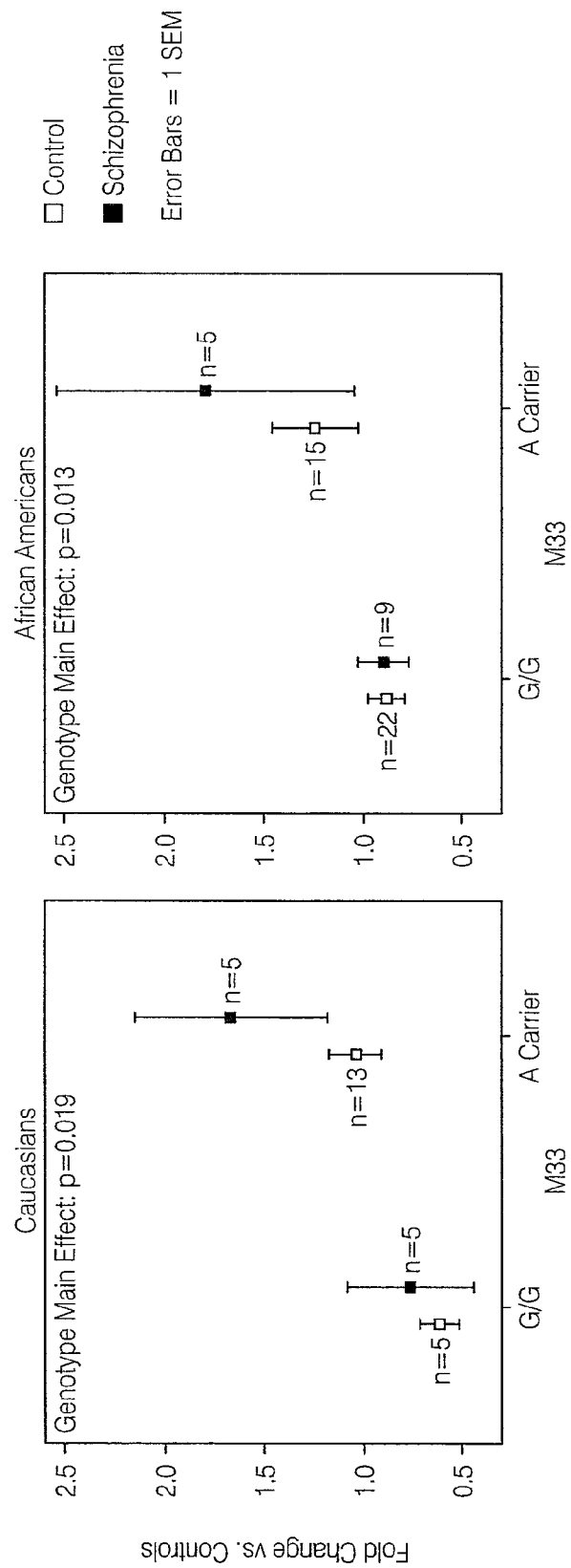

FIG. 7B depicts the association of marker 33 (M33) risk genotype (A carriers) with Isoform 3.1 expression within the hippocampus (data from A) with respect to rave and diagnosis. Main effect of genotype was determined following the same linear regression modeling as in A but within Caucasian and African American subsets separately and including M33 as a variable in the model. M33 A/G individuals were pooled due to the small number of A/A individuals. No significant differences were observed between A/G and G/G carriers as determined by multinomial logistic regression. All error bars represent one standard error of the mean.

Referring to FIG. 19, 8-10 rats per treatment group were treated with one of three doses of either Haloperidol (0.08, 0.6, and 1 mg/kg) or Clozapine (0.5, 5, 10 mg/kg) for 28 days (as compared to rats treated with vehicle alone). Frontal cortex expression levels of NOS3 (ABI assay Rn02132634_sl) and KCNH2-1A (ABI assay Rn01442523_ml) were normalized to the geometric mean of two housekeeping genes (GAPDH, B2M). Effects of antipsychotic treatment on gene expression were tested by linear regression with gene expression as the dependent variable. Differences between vehicle alone and the two therapeutic range equivalent dosages (0.08 and 0.6 mg/kg/day of Haloperidol; 0.5 and 5 mg/kg/day of Clozapine) were tested using post-hoc LSD. No significant differences were observed between any neuroleptic treatment group and vehicle only treated rats, p-values for the treatment with the greatest difference as compared to vehicle alone are shown for Haloperidol.

Given the physical proximity of KCNH2-1A to the genetic association signals in the clinical samples and its differential expression in schizophrenia patients, it seemed plausible that the molecular mechanism of association might involve transcriptional regulation. By the same logic applied to the cognition and imaging analyses, if genetic risk affects the transcription of KCNH2-1A, then individuals with risk alleles, even if normal controls, should have expression profiles of these genes similar to those of schizophrenia patients (i.e., reduced levels). Accordingly, we tested for differences in the expression of KCNH2-1A between healthy controls who were carriers of risk alleles versus those who were not. No significant effect of risk genotype was observed (KCNH2-1A: p=0.52; Table 10). NOS3 expression also showed no association with risk SNPs (Table 10). It is important to note that differential expression of KCNH2 was not detected in the original microarray study though an increase in NOS3 was (Prabakaran, S. et al. 2004 MoI Psychiatry 9:684-697; Huffaker, A et al. 2006 Proc Natl Acad Sci USA 103:10098-10103). Though this may reflect the overall greater average PMI of the sample set used in the microarray study, it more likely relates to the regions of KCNH2 probed by the microarrays. The 2 probe sets for KCNH2 included on the HG-UI 33 A (Affymetrix) microarrays are located in the 3'-UTR of the gene (FIG. 11). These probe sets would therefore be unable to distinguish the different isoforms particularly given the highly conserved 3'-UTR structure in KCNH2-1A and Isoform 3.1. Moreover, here, using isoform specific RT-QPCR, we report significant reductions in the expression of KCNH2-IA with concomitant increases in the expression of Isoform 3.1. Thus, the combined detection of both isoforms might result in little to no 'net' difference. While this may indicate the presence of allelic heterogeneity (i.e., different SNPs confer risk to the illness in different populations), it may also suggest that the molecular effects of genetic risk do not impact on the expression of KCNH2-1 A, or they may relate to more complex aspects of gene processing, such as the splicing of transcripts or the expression of other isoforms.

Identification of a Novel KCNH2 Isoform in Human Brain

Figure 20:
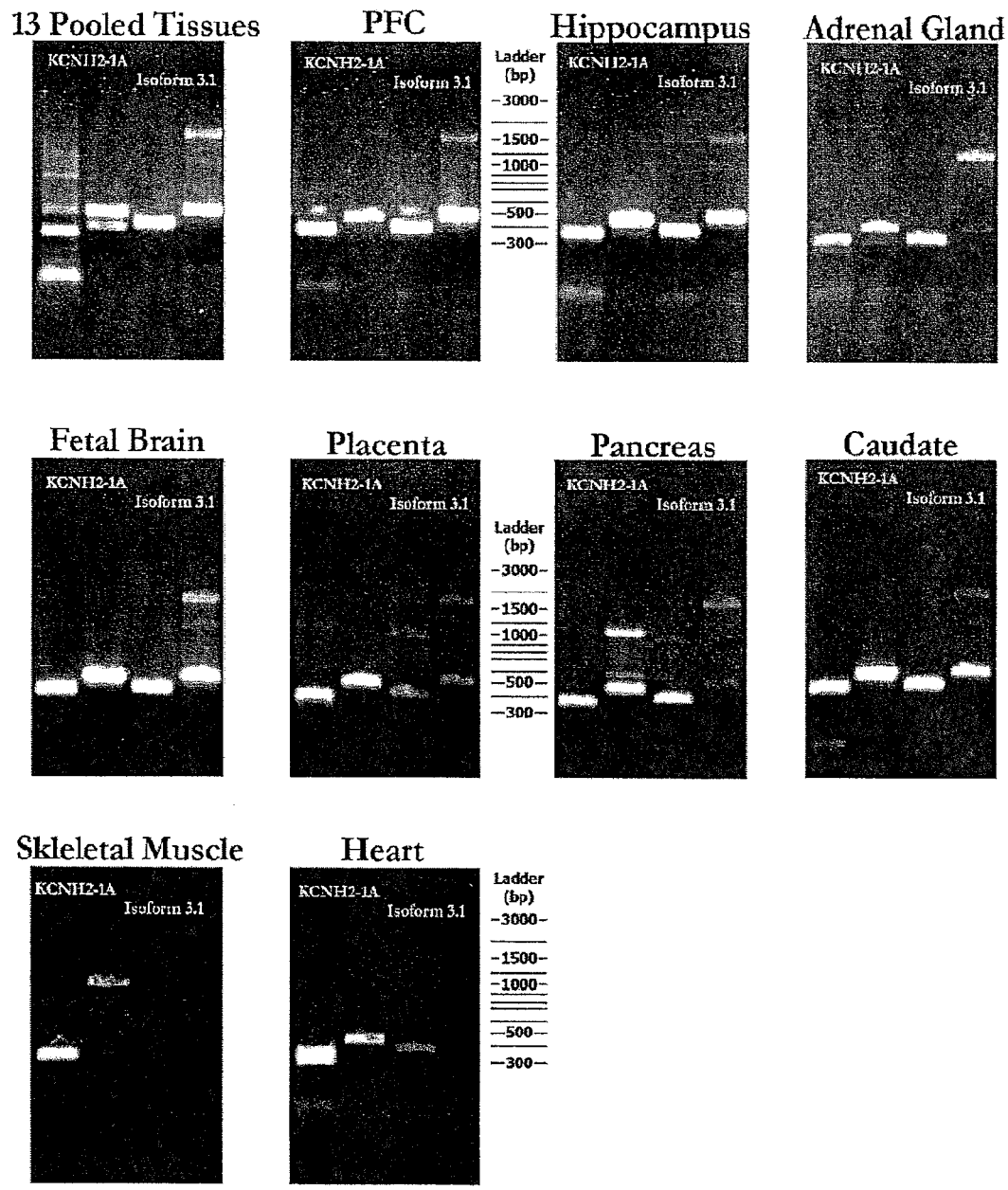
FIG. 20. Tissue differences in Isoform 3.1 and KCNH2-1A using PCR and QPCR.

Due to the large size of KCNH2 intron 2 and the presence of several regions highly conserved across species (genome.ucsc.edu), the effects of the risk SNPs may relate to the splicing of an, as yet, unidentified exon or the expression of a novel isoform in this intronic region. Using 5'-RACE on total RNA pooled from the DLPFC of 10 schizophrenia patients and beginning from exon 4 of the full-length KCNH2 transcript (KCNH2-1A; NM_00023) we identified a novel 5' extension of exon 3 producing an isoform that originates 1.1 Kb upstream of the known start of exon3 (FIG. 5; FIG. 11). Further cloning from a human cDNA library (Stratagene) found that the isoform is expressed endogenously and contains all of the downstream exons of the full-length form of the gene (through exon 15 of KCNH2-1A; FIG. 20, Table 11). In silico prediction (on the world-wide-web at ncbi.nlm.nih.gov) of the longest ORF of the novel isoform (referred to as Isoform 3.1) revealed that the majority of the 1.1 Kb 5' extension of exon 3 would be untranslated and that the first methionine is in frame with the full-length protein. As such, Isoform 3.1 is expected to be missing the first 102 amino acids of the full-length KCNH2-1A, replacing them with 6 amino acids unique to the isoform. Interestingly, the 102 amino acids encoded for by exons 1 and 2 of hERG1a comprise a large portion of the PAS domain, a motif that slows the rate of channel deactivation (J. H. Morais Cabral et al. 1998 Cell 95:649). The translation of Isoform 3.1 and the predicted difference in protein size was confirmed using western blot in transfected HEK cells (FIG. 8C). Western blot in human hippocampus and frontal cortex following immunoprecipitation revealed a protein band of similar molecular weight to that in transfected HEK cells (FIG. 8C). Furthermore, neuroblastoma cells transfected with constructs encoding either or both KCNH2-1A or Isoform 3.1 show overlapping expression of the protein isoforms on the plasma membrane (FIG. 8D).

To address the possibility that Isoform 3.1 is expressed primarily in brain, we measured the quantity of KCNH2-1A and Isoform 3.1 across several tissues, including heart and three different brain regions, using quantitative RT-PCR. Furthermore, since known isoforms of KCNH2 and its homologues can co-assemble to create heteromeric potassium channels with unique electrophysiological properties (L. Guasti et al. 2005 J Comp Neurol 491:157) further modified by the ratio and arrangement of subunits (S. Wimmers et al. 2002 Pflugers Arch 445:423), we measured the ratio of Isoform 3.1 to KCNH2-1A and found the two forms comparable in expression within several brain regions (FIG. 8B; FIG. 20, Table 11). However, Isoform 3.1 was over 1000-fold less abundant than KCNH2-1A within the heart, suggesting that the role of Isoform 3.1 may reside largely within the brain.

Referring to FIG. 8A, PCR products were generated for KCNH2-1A and Isoform 3.1 using forward primers in exon 1 of KCNH2-1A (ExI) and in the 5'-UTR of Isoform 3.1 (Iso1), respectively, and the same reverse primers in exons 3 (Ex3) and 4 (Ex4) of KCNH2—IA (see Example 1). PCR was performed using cDNA prepared from commercially available total RNA (Ambion) isolated from human heart, hippocampus, and fetal brain. PCR products for KCNH2-1A were expected at 373 and 463 bps, respectively, and for Isoform 3.1 at 388 and 478 bp, respectively. The band ~1.5 kb in Iso1-Ex4 lanes corresponds to small amounts of unspliced RNA or genomic DNA present in the samples. Referring to FIG. 8B, Quantitative PCR was performed using TaqMan assays (ABI) to measure relative mRNA expression of Isoform 3.1 (custom TaqMan assay designed to the 5'-UTR of Isoform 3.1) versus KCNH2-1A (HsOO1 65120 ml)±standard error of mean. Expression values were measured in cDNA made from DNAse treated (Invitrogen) commercially available total RNA (Ambion) from human hippocampus, prefrontal cortex, heart, and skeletal muscle. Referring to FIG. 8C, Western blots were prepared using protein extracted from post-mortem human hippocampus and frontal cortex. As positive controls, HEK cells were transfected with vectors encoding KCNH2-1A or Isoform 3.1 under the control of a CMV promoter. Westerns were probed with an antibody raised against the pore portions of KCNH2 (Santa Cruz, N-20) and thus predicted to detect isoform 3.1 and KCNH2-1 A. Proteins extracted from human brain regions showed two distinct bands, one at the same size as Isoform 3.1 transfected HEK cells. However, the larger, more dominant band in human brain was not observed at the size of KCNH2-1A transfected HEK proteins. Instead, the larger band occurs at ~160 kDa, which is the reported size of KCNH2-1A from in vivo protein extracts suggesting post-translational modifications (E. M. Jones et al. 2004 J Biol Chem 279:44690). Referring to FIG. 8D, Primary rat neurons transfected with KCNH2-1A or Isoform 3.1 containing vectors.

Referring to FIG. 20, PCR of KCNH2-1A (full-length) and Isoform 3.1 was performed using 10 different tissue extractions of total RNA. Full-length PCR products were generated using ExI-F forward primer to Ex3-R and Ex4-R reverse primers (see Example 1). Isoform 3.1 PCR products were generated using Ex3.1-F forward primer and the same Ex3-R and Ex4-R reverse primers. Expected product sizes: 373, 463, 388, 478 bps respectively. Cloning and sequencing of the band at 1547 bps in PCR of Ex-3.1-F to Ex4-R of some samples corresponded to sequences without intron 3 spliced out suggesting that this represents DNA contamination in these samples.

In Table 11, quantitative RT-PCR was used to measure the relative quantity of Isoform 3.1 as compared to KCNH2-1A expression in 8 total RNA isolates. All samples were DNase treated prior to cDNA synthesis to prevent the effects of DNA contamination on the samples. All Ct values were determined at the same threshold value and all sample expression values were measured in triplicate.

Finally, as ERG family genes are moderately conserved in sequence across several species (J. W. Warmke and B. Ganetzky 1994 Proc Natl Acad Sci USA 91:3438), we expected Isoform 3.1 to be present within other mammals. However, again using 5'-RACE, we were unable to detect Isoform 3.1 homologues in mouse brain. Moreover, in silico analysis revealed that the 1.1 Kb region unique to Isoform 3.1 was highly degenerate outside of primates (FIG. 21). In particular, in mouse, rat, canine, and zebrafish, no promoter-like sequences were observed within 3 Kb upstream of exon 3 and the longest ORF in frame with exon 3 lacks a starting methionine (FIG. 21).

Referring to FIG. 21A, a multiple alignment is shown of the 250 bp region upstream of KCNH2-1A (hERG-1A) exon 3 splice site and 180 bps of exon 3 in human, rhesus, mouse, and rat. Genome sequences were obtained from UCSC and aligned using Clustal W (on the world-wide-web at ebi.ac.uk/clustalw). Exon 3 splice site (CAG) is boxed by a fine dashed line followed by exon 3 (heavy dashed-line box), both of which are highly conserved across species. In-frame start codons (ATG) are shown with a closed box for human and rhesus sequences and equivalent ATG in mouse and rat are frameshifted (in frame codon is shown with a closed box). FIG. 21B shows multiple alignments of the predicted ORF of this region in frame with exon 3 and the remainder of the KCNH2 coding sequence. Again, human and rhesus sequences show starting methionines while mouse and rat sequences are devoid of upstream, in-frame methionines prior to stop codons.

Higher Expression of Isoform 3.1 in Schizophrenia and in Subjects with Risk Genotype Primate-specific, brain enriched expression, and the location of risk SNPs in the 5' upstream of Isoform 3.1's first exon led us to hypothesize that the mechanism of genetic risk for schizophrenia would involve differential expression of the Isoform 3.1. Using quantitative RT-PCR we found Isoform 3.1 expression significantly increased within the HF of patients versus healthy control subjects ($p=0.012$, FIG. 7A). The ratio of Isoform 3.1 to KCNH2-1A showed a dramatic, 2.5 fold increase in the patients ($p=0.003$). Additionally, higher expression levels of Isoform 3.1 were significantly associated with risk alleles even within healthy control subjects (FIG. 7B). This trend was observed irrespective of race or diagnosis eliminating the potential confounders of medication or genetic background stratification. These results converge on the conclusions that the genetic mechanism of association with schizophrenia involves regulation of Isoform 3.1 transcription and that overexpression of this isoform and its potential physiologic effects are related to the pathogenesis of the disorder.

Functional Role of Isoform 3.1 Revealed by Electrophysiology

Figure 9B:
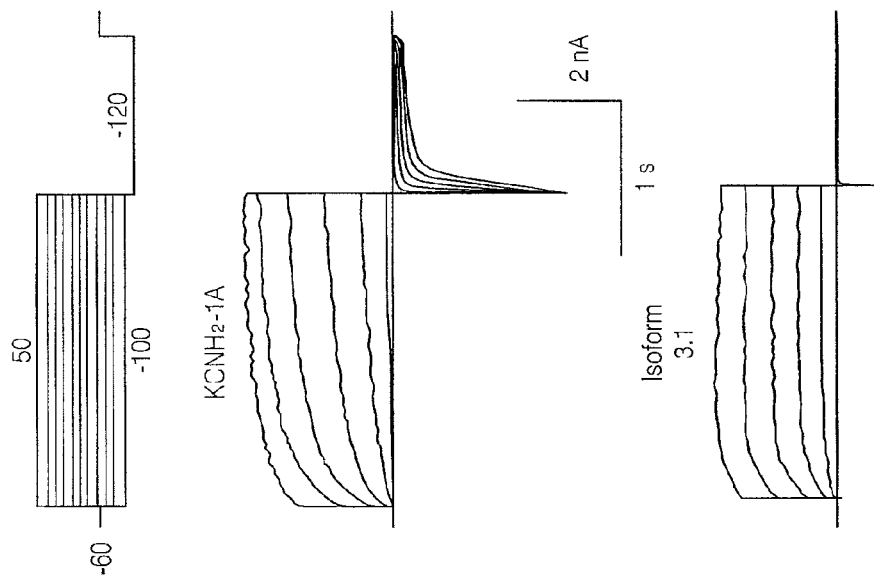
FIG. 9. Characterization of KCNH2 currents in HEK293T cells expressing KCNH2-1A and Isoform 3.1. (A) Diagram of domain structures; (B) Currents evoked by voltage steps; (C) Effects on tail currents; (D) Activation curves; (E) Tail currents evoked by voltage steps; and F) Deactivation time constants.
Figure 9A:
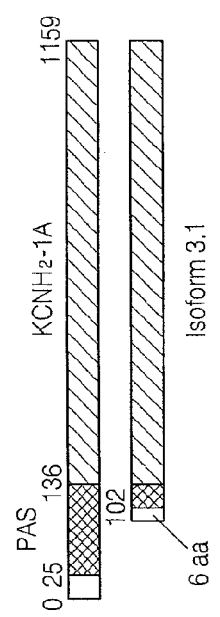
Figure 9D:
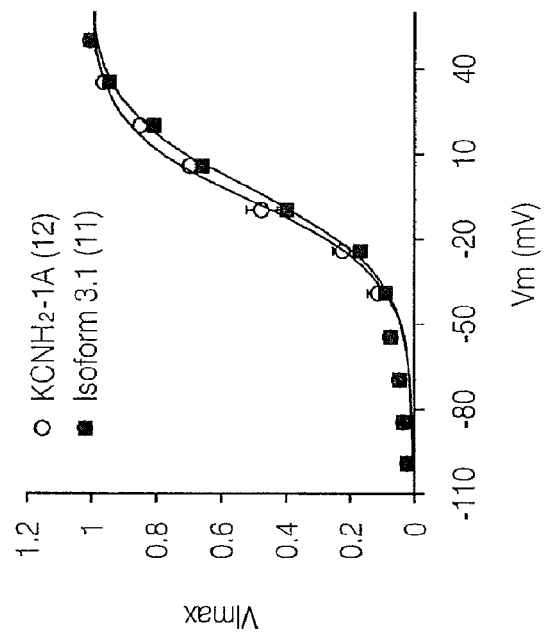
Figure 9C:
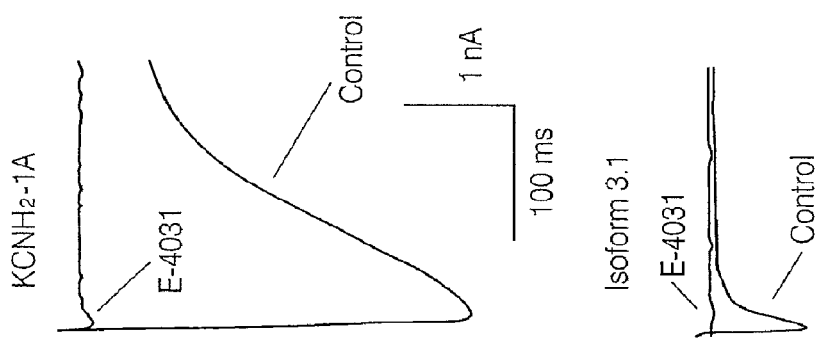

Structural analysis of Isoform 3.1 revealed some interesting properties that suggest potentially unique physiological effects. The PAS domain (aa 25-136) in the N-terminus ensures a slow deactivation of the KCNH2 channel, a unique feature of hERG (M. C. Sanguinetti and M. Tristani-Firouzi 2006 Nature 440:463). In contrast, a few amino acids (aa 7-12) in the N-terminal of hERG channels facilitate the channel deactivation (H. Terlau et al. 1997 J Physiol 502:537). Compared with KCNH2-1A, the Isoform 3.1 substitutes the first 102 amino acids at the N-terminus with 6 new amino acids (FIG. 9A), removing all the facilitating signals and deleting the majority of the PAS domain. To determine the biophysical properties of this new channel isoform, we performed whole-cell recording on HEK cells transfected with either KCNH2-1A or Isoform 3.1. Holding at −60 mV, the channels were activated by various depolarizing steps (FIG. 9B, top). As reported previously, KCNH2-1A exhibited a typical slow activation (FIG. 9B, middle). Isoform 3.1 was also activated slowly (FIG. 9B, bottom). Quantitative analysis revealed no difference in the activation kinetics of KCNH2-1A and Isoform 3.1 (FIG. 9D). When the membrane potential was hyperpolarized to −120 mV, the channel quickly recovered from the inactive state, resulting in a big "tail current" that deactivated slowly (FIG. 9C, top). Treatment of the cells with the hERG channel inhibitor E-4031 completely blocked the current (FIG. 9C, top), suggesting that this current is solely mediated by the hERG channel. In contrast, the cells transfected with Isoform 3.1 exhibited a dramatically reduced tail current (FIG. 9C, bottom).

Figure 9F:
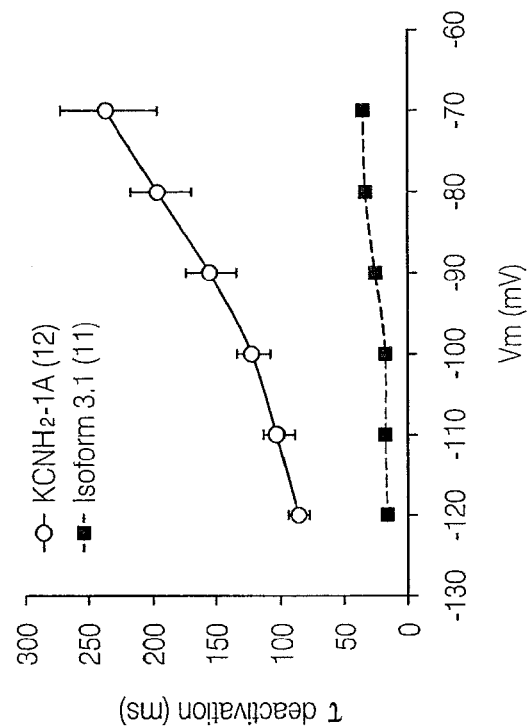
Figure 9E:
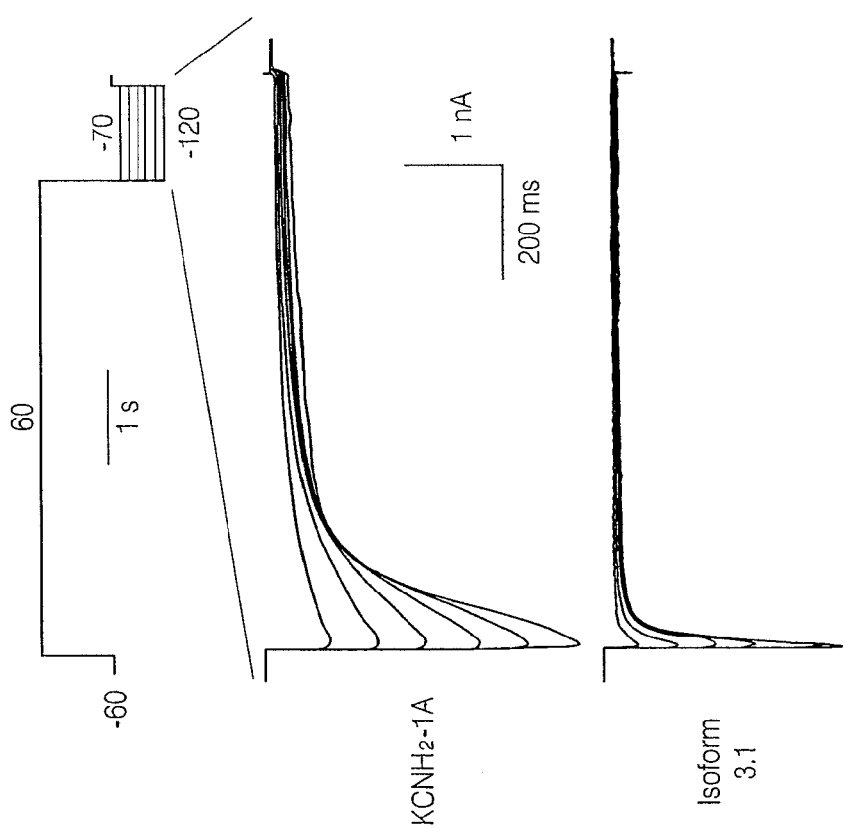

Treatment with E-4031 also blocked the current, confirming the nature of the channel. To better compare the deactivation kinetics of the two isoforms, membrane potential was first depolarized to +60 mV for 1 sec, followed by hyperpolarizing steps at various potentials (FIG. 9E, top). The large inward currents mediated by Isoform 3.1 decayed towards baseline much faster than those by KCNH2-1A (FIG. 9E, middle and bottom). The deactivation phase of the currents was fitted by a single exponential curve, generating a deactivation constant ($\tau$) that is voltage-dependent (FIG. 9F). In all voltage steps tested (−70 mV –120 mV), $\tau$ is greatly reduced in Isoform 3.1, as compared to that of KCNH2-1A. Taken together, Isoform 3.1 mediates an inward rectified K+ current with dramatically faster deactivation kinetics.

Referring to FIG. 9 A, schematic diagrams of the domain structures of KCNH2-1A and Isoform 3.1 depict initial leader sequences, the PAS domain (or partial PAS domain in the case of Isoform 3.1), and amino acid sequences identical between KCNH2-1A and Isoform 3.1. The numbers above the bars are positions of amino acids. FIG. 9B depicts currents evoked by voltage steps (2 sec) from VH of −60 mV to potentials from −100 to +80 mV in 10-mV increments, followed by a voltage pulse to −120 mV. Upper panel: voltage protocol. Middle and lower panels: traces obtained from cells transfected with KCNH2-1A and Isoform 3.1 cDNAs, respectively. These traces are corrected for leak currents. FIG. 9C shows the effects of E-4031 on tail currents evoked by a test pulse to −120 from holding potential of +80 mV, using the same protocol as in A. Traces recorded from the same cells before and after treatment with 10 µM E-4031 were superimposed. Upper and lower panels show KCNH2 currents recorded from cells transfected with KCNH2-1A and Isoform 3.1 cDNAs, respectively. FIG. 9D illustrates activation curves of KCNH2-1A and Isoform 3.1. FIG. 9E illustrates tail currents evoked by voltage steps from +60 mV to potentials between −120 mV and −70 mV in 10 mV increments. Traces in upper and lower panels represent tail currents of KCNH2-1A and Isoform 3.1, respectively. FIG. 9F illustrates deactivation time constants of KCNH2 currents at different re-polarizing voltages. Between −120 to −70 mV the decay phase of KCNH2 currents was fitted by a single-exponential function to calculate the deactivation constant. The data are presented as mean±SE. The numbers of cells recorded are indicated in the parentheses.

Figures 10A, 10B:
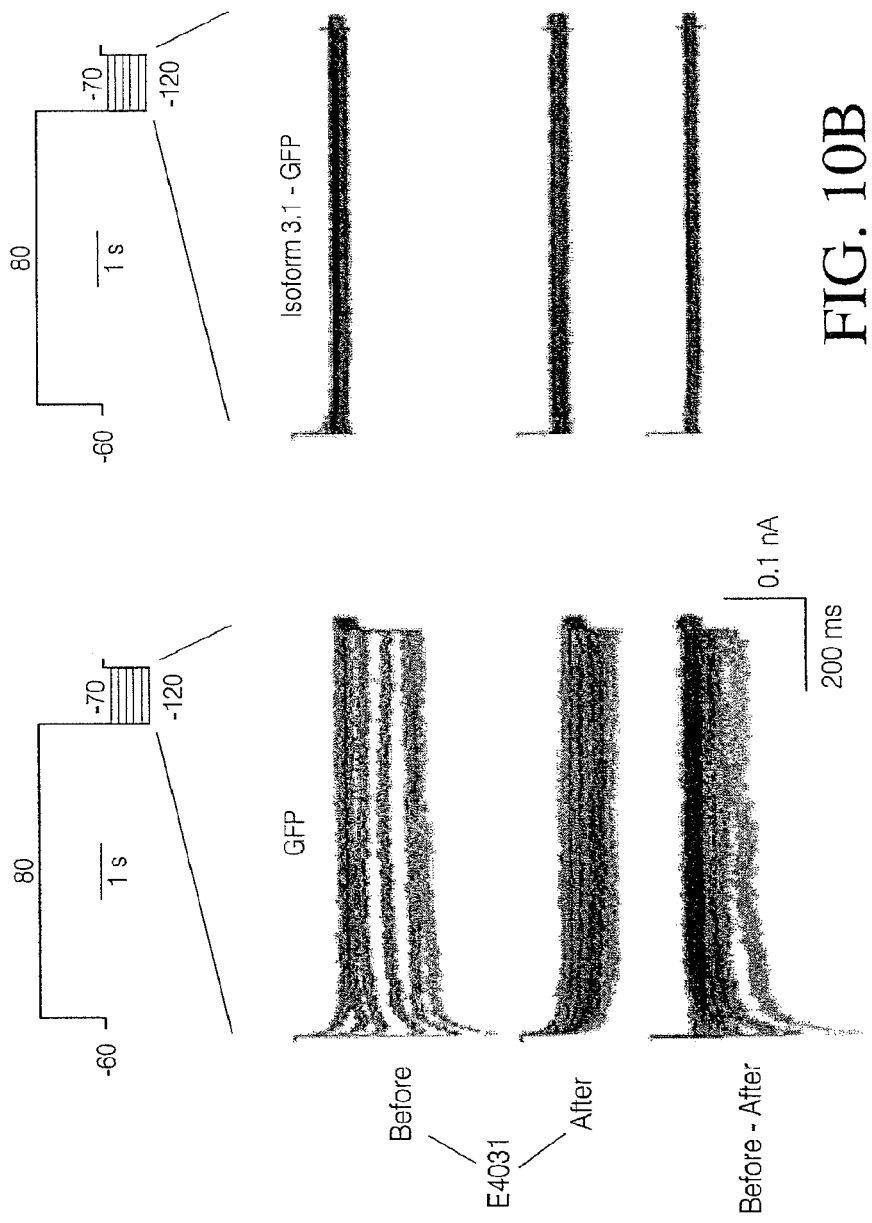
FIG. 10. Effect of Isoform 3.1 on KCNH2 currents and firing patterns in cortical neurons. (A) Tail currents in GFP-transfected neurons; (B) Tail currents in Isoform 3.1-transfected neurons; (C) Deactivation time constants; (D) Action potential discharge; (E) Spike frequencies; and F) Effect of Isoform 3.1 on spike frequency adaptation.
Figure 10D:
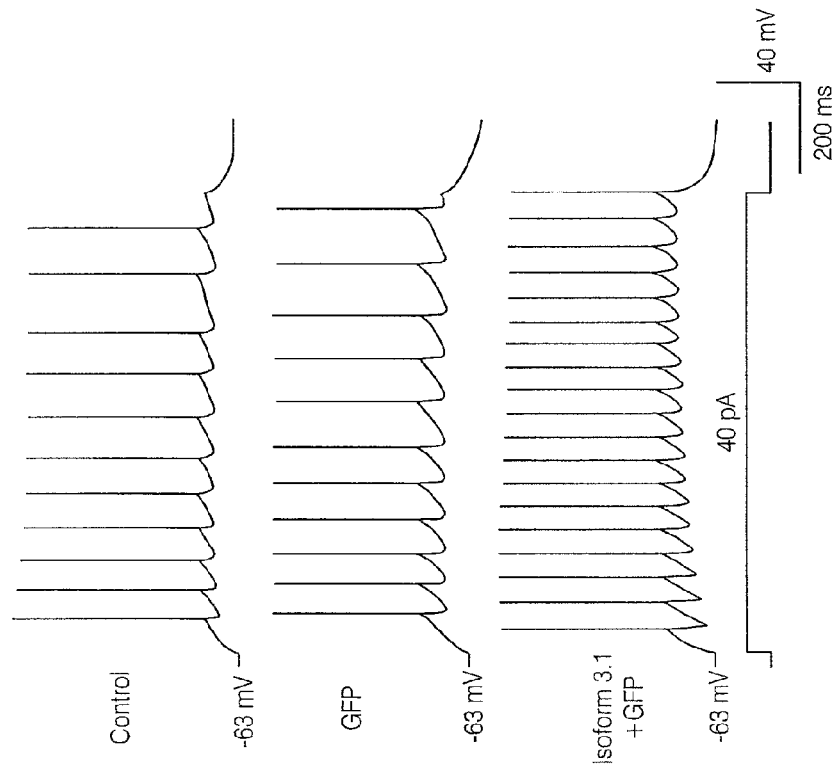
Figure 10C:
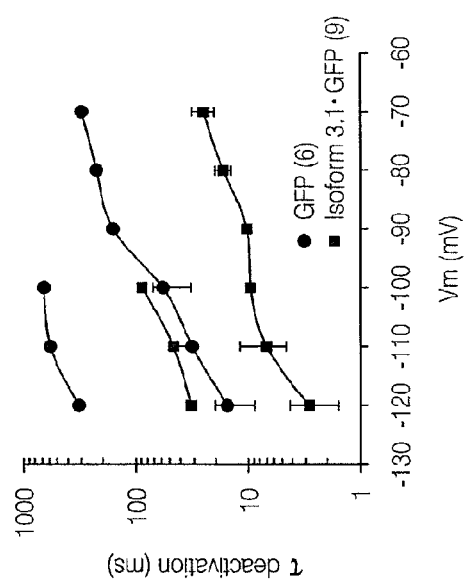
Figure 10F:
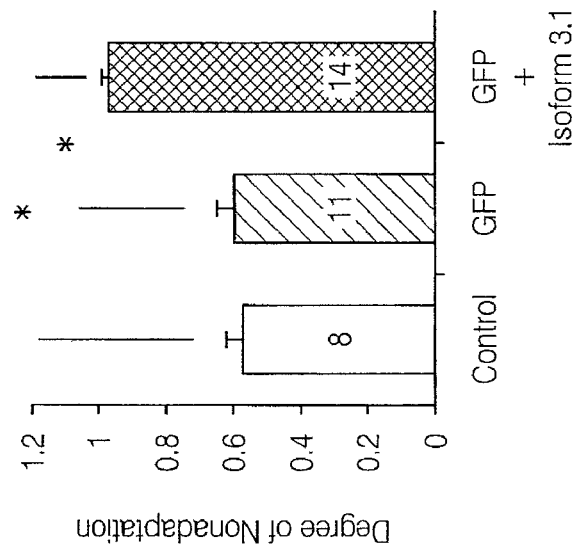
Figure 10E:
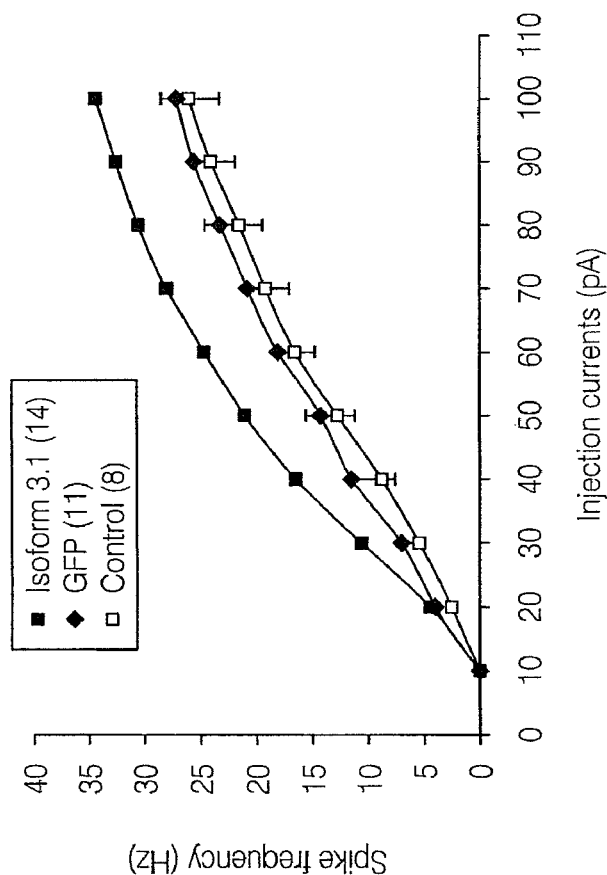

We next examined the functional role of Isoform 3.1 in cortical neurons. Given that rodent CNS neurons express KCNH2-1A, but not Isoform 3.1, Isoform 3.1 introduced into these neurons would presumably complex with the endogenous KCNH2-1A, thereby markedly changing the deactivation kinetics of the K+ current. Isoform 3.1 was transfected with or without GFP into the cultured cortical neurons on the day of plating, and whole-cell, voltage-clamp recording was performed on neurons cultured for 10 days following perfusion with a cocktail of inhibitors to block Na+ and Ca2+ currents. In neurons transfected with GFP alone, application of a voltage protocol similar to that in FIG. 9E elicited a series of tail currents that were blocked by E-4031 (FIG. 10A). Subtraction of the currents after E-4031 treatment (middle) from control currents (upper) generated pure "KCNH2-1A-mediated" current (lower) that exhibited a typical, slow deactivation kinetics (FIG. 10A). In contrast, application of the same protocol to neurons transfected with Isoform 3.1 elicited a dramatically reduced tail current with much faster deactivation (FIG. 10B). Quantitative analysis indicated that $\tau$ reduced by 5.88 (fast component) and 7.43 (slow component) folds at −100 mV of command potential, respectively (FIG. 10C). These results suggest that by complexing with the endogenous KCNH2-1A, Isoform 3.1 may alter the membrane repolarization kinetics, leading to an increase in neuronal excitability. To test this possibility, we examined action potentials induced by a step depolarization under the current-clamp conditions. In control neurons (non-transfected) as well as neurons transfected with GFP, a 1-sec depolarization elicited about 11 action potentials (FIG. 10D, upper and middle). In neurons transfected with Isoform 3.1, the same depolarization step induced significantly more spikes compared with control and GFP-transfected neurons (FIG. 10D, lower). On average, the spike frequencies induced by a 40-pA depolarizing step were 8.9±1.3 Hz in control and 16.6±0.5 Hz in Isoform 3.1-transfected neurons, respectively (FIG. 10E). Further examination of the inter-spike intervals (ISIs) also revealed that expression of Isoform 3.1 converted an adapting (FIG. 10D, upper) to a non-adapting (FIG. 10D, lower) firing pattern. Indeed, the ratio of 1st and last ISIs increased from 0.57±0.05 in control neurons to 0.96±0.02 in isoform 3.1-transfected neurons (FIG. 10F). This result is interesting, since the non-adapting discharge pattern has been implicated in persistent firing of neurons in PFC during working memory tasks (Y. Wang et al. 2006 Nat Neurosci 9:534). Taken together, these results suggest that expression of Isoform 3.1 in human PFC significantly increases neuronal excitability and offers a potential mechanism for persistent neuronal activity.

Referring to FIG. 10, cortical neurons were transfected with either GFP alone or GFP and Isoform 3.1, and cultured for 10 days. In FIGS. 10A and 10B, KCNH2-mediated tail currents in GFP- and Isoform 3.1-transfected neurons are shown, respectively. Tail currents evoked by voltage pulses (1 sec) from VH of +80 mV to potentials between −70 and −120 mV, in 10-mV increments. E-4031-sensitive currents are obtained by subtracting currents recorded after E-4031 application from those from before E-4031 application. FIG. 10C illustrates a semilogarithmic plot of deactivation time constants of E-4031-sensitive currents at different re-polarizing voltages. Between −120 and −100 mV decay of E-4031-sensitive currents was fitted by double-exponential functions, whereas between −90 and −70 mV time course followed single-exponential functions. Deactivation constants in the neurons transfected with isoform 3.1 are consistently smaller than those in control neurons at different re-polarizing voltages. FIG. 10D illustrates the effect of over-expression of Isoform 3.1 on action potential discharge of cultured cortical neurons. Repetitive firing was evoked by long depolarizing pulse (40 pA, 1 sec). Strong spike frequency adaptation is seen in control neurons and those transfected with GFP, whereas neurons transfected with Isoform 3.1 exhibit non-adaptation discharge behavior. FIG. 10E illustrates spike frequencies induced by injecting different depolarizing currents. Spike frequency is defined as the number of spikes per 1 sec. Neurons expressing Isoform 3.1 consistently exhibit significantly higher spike frequencies starting from 30 pA of current injection. FIG. 10F illustrates the effect of Isoform 3.1 on spike frequency adaptation. The degree of non-adaptation, measured by the ratio of first to last interspike intervals evoked by a 40-pA depolarizing pulse, was significantly higher in neurons expressing Isoform 3.1 than that in control or GFP-expressing neurons. The data are presented as mean±SE. The numbers of cells recorded are indicated in the parentheses (D) or columns (E) and asterisk indicates a significant difference (ANOVA, $p<0.01$).

TABLE 2

Microarray Candidate Gene Screen

| Gene | SNP rs# | Location | MAF | Alleles | Z-score | Empirical p-val | Global p-val | | Most Significant Haplotype | |
|---|---|---|---|---|---|---|---|---|---|---|
| TIMM17A (1q32.1) | rs2819370 | 198646712 | 0.45 | C/T | 1.90 | 0.0700 | 0.125 | 1 | 0.17 | Frequency |
| | rs2819376 | 198662876 | 0.17 | A/C | 0.19 | 0.8586 | | 1 | 0.05 | p-value |
| | rs7513 | 198670652 | 0.49 | G/A | 0.08 | 0.9270 | | 2 | −1.94 | Z-score |
| MDH1 (2p13.3) | rs1878505 | 63578241 | 0.28 | A/G | −1.20 | 0.2215 | 0.707 | 1 | 0.44 | Frequency |
| | rs11689644 | 63621359 | 0.12 | T/G | −0.41 | 0.6494 | | 1 | 0.45 | p-value |
| | rs262534 | 63818026 | 0.28 | T/A | −0.14 | 0.8973 | | 1 | 0.75 | Z-score |
| SLC25A12 (2q24) | rs2138349 | 172368904 | 0.32 | T/C | −0.94 | 0.3676 | 0.939 | 3 | 0.33 | Frequency |
| | rs6757773 | 172375137 | 0.31 | A/T | 1.00 | 0.3466 | | 1 | 0.38 | p-value |
| | rs312917 | 172396665 | 0.07 | A/G | 0.24 | 0.8249 | | 1 | −0.87 | Z-score |
| | rs10165126 | 172645822 | 0.30 | C/T | 0.29 | 0.8706 | | 1 | | |
| CFLAR (2q33-q34) | rs10931929 | 201673392 | 0.29 | C/G | −2.56 | 0.0180 | 0.521 | 1 | 0.04 | Frequency |
| | rs2041765 | 201848666 | 0.47 | C/T | −0.51 | 0.6250 | | 2 | 0.16 | p-value |
| | rs3900115 | 201876183 | 0.47 | A/G | −0.67 | 0.5141 | | 1 | 1.29 | Z-score |
| NOS3 (7q36.1) | rs1036145 | 150112078 | 0.30 | G/A | 3.24 | 0.0032 | 0.005 | 3 | 0.33 | Frequency |
| | rs2373885 | 150115728 | 0.26 | A/G | 2.03 | 0.0430 | | 1 | 0.00 | p-value |
| | | | | | | | | | 3.01 | Z-score |
| OAZIN (8q22.3) | rs2513910 | 103886282 | 0.43 | A/G | −1.73 | 0.0590 | 0.433 | 1 | 0.34 | Frequency |
| | rs2436854 | 103895213 | 0.28 | C/T | −0.52 | 0.5747 | | 1 | 0.16 | p-value |
| | rs2513921 | 103899571 | 0.42 | T/C | −1.76 | 0.0720 | | 1 | 1.43 | Z-score |
| | rs2916558 | 103916575 | 0.38 | C/A | 0.98 | 0.2747 | | 2 | | |
| | rs1055376 | 103946610 | 0.33 | C/T | −1.09 | 0.3136 | | | | |
| COX6A1 (12q24.2) | rs2076022 | 119338510 | 0.45 | C/T | −1.37 | 0.1730 | 0.266 | 1 | 0.29 | Frequency |
| | rs968474 | 119341250 | 0.34 | C/T | 0.28 | 0.7540 | | 2 | 0.02 | p-value |
| | rs2235218 | 119351339 | 0.30 | A/C | −1.92 | 0.0370 | | 1 | 2.21 | Z-score |
| | rs606443 | 119373350 | 0.36 | T/G | 0.47 | 0.6569 | | 2 | | |
| | rs7964008 | 119381117 | 0.15 | C/T | −1.46 | 0.2075 | | 1 | | |
| | rs7963543 | 119386668 | 0.15 | A/C | −0.13 | 0.8992 | | 1 | | |
| GOT2 (16q21) | rs6993 | 57298868 | 0.38 | C/T | 1.47 | 0.1030 | 0.643 | 2 | 0.05 | Frequency |
| | rs30842 | 57300955 | 0.25 | G/T | 1.00 | 0.3252 | | 1 | 0.30 | p-value |
| | rs30838 | 57302918 | 0.35 | G/A | 2.08 | 0.0260 | | 1 | 0.92 | Z-score |
| | rs7204324 | 57308370 | 0.09 | A/T | −1.25 | 0.1990 | | | | |
| ACOX1 (17q25.1) | rs1046446 | 71407894 | 0.22 | G/A | −0.49 | 0.6547 | 0.670 | 1 | 0.17 | Frequency |
| | rs1137582 | 71461135 | 0.47 | G/C | −0.61 | 0.5698 | | 2 | 0.28 | p-value |
| | | | | | | | | | −1.09 | Z-score |
| NDUFV2 (18p11.31-p11.2) | rs11081459 | 9097815 | 0.10 | T/C | −1.64 | 0.1180 | 0.455 | 1 | 0.76 | Frequency |
| | rs1785560 | 9106080 | 0.13 | T/C | −0.42 | 0.7564 | | 1 | 0.14 | p-value |
| | rs906807 | 9107867 | 0.23 | G/A | −0.22 | 0.8680 | | 1 | 1.36 | Z-score |
| | rs874250 | 9109156 | 0.14 | G/A | −1.07 | 0.3279 | | 1 | | |
| | rs11081463 | 9142875 | 0.10 | T/A | −1.18 | 0.2769 | | 1 | | |
| | rs11876821 | 9176684 | 0.08 | G/T | −0.41 | 0.7041 | | | | |

Shown is summary information for htSNPs genotyped in the regions of 10 candidate genes. Summary information includes: minor allele frequency (MAF) in the CBDB Cohort, chromosomal location, and SNP alleles (major/minor). Observed z-scores for transmission of the minor allele to affected offspring in 175 Caucasian families are reported for individual markers and the most significant combined haplotype as determined by FBAT (see Example 1). Reported p-values are simulated from the experimental data using 1000 iterations and reported for individual SNPs, the global haplotypes, and the most significant haplotype. Haplotypes are reported as 1 (major allele) and 2 (minor allele) at each included SNP and significantly associated (p <0.05) SNPs or haplotypes are shown in bold.

TABLE 3

SNPs Genotyped in Four Clinical Samples and FBAT Statistical Results

| Marker | SNP rs# | Chr. 7 position | Alleles | MAF | CBDB Sibling Study (296 Families) | | | NIMHGI-C (71 families) | | | NIMHGI-AA (51 families) | | | German Case-Control Study (501 cases/626 controls) | | |
|---|---|---|---|---|---|---|---|---|---|---|---|---|---|---|---|---|
| | | | | | Minor Allele Direction of Association | empirical p-value | MAF | Minor Allele Direction of Association | empirical p-value | MAF | Minor Allele Direction of Association | empirical p-value | Control MAF | Genotype | OR (95% CI) | p-value |
| M1 | rs1805120 | 150280464 | C/T | 0.26 | Negative | 0.33 | 0.18 | Negative | 0.09 | 0.19 | Negative | 0.39 | —*** | —*** | —*** | —*** |
| M2 | novel | 150288028 | G/A | 0.23 | Positive | 0.5 | 0.19 | Positive | 0.32 | 0.069 | Negative | 0.38 | 0.24 | 2/2 | 0.68 (0.39, 1.18) | 0.17 |
| M3 | rs12668582 | 150288134 | A/C | 0.35 | Negative | 0.26 | 0.3 | Negative | 0.76 | 0.48 | Negative | 0.1 | 0.31 | 2/2 | 1.23 (0.82, 1.83) | 0.31 |
| M4 | rs6947240 | 150288142 | G/A | 0.23 | Positive | 0.42 | 0.2 | Positive | 0.4 | 0.1 | Negative | 0.57 | 0.25 | 2/2 | 0.67 (0.38, 1.15) | 0.15 |
| M5 | novel | 150288178 | InsT | 0.35 | Negative | 0.26 | 0.3 | Negative | 0.53 | 0.47 | Negative | 0.1 | 0.32 | 2/2 | 1.21 (0.81, 1.79) | 0.35 |
| M6 | novel | 150288335 | T/C | 0.03 | Negative | 0.11 | 0.058 | Negative | 0.75 | 0.16 | Null** | 0.87 | 0.034 | 2 carrier | 0.89 (0.53, 1.48) | 0.65 |
| M7 | novel | 150288741 | G/A | 0.26 | Negative | 0.22 | 0.2 | Negative | 0.076 | 0.2 | Negative | 0.17 | —*** | —*** | —*** | —*** |
| M8 | rs3823587 | 150288823 | T/G | 0.26 | Negative | 0.42 | 0.19 | Negative | 0.13 | 0.2 | Negative | 0.15 | —*** | —*** | —*** | —*** |
| M9 | rs3807376 | 150289132 | A/G | 0.26 | Negative | 0.15 | 0.2 | Negative | 0.21 | 0.21 | Negative | 0.3 | —*** | —*** | —*** | —*** |
| M10 | novel | 150289611 | G/A | 0.26 | Negative | 0.34 | 0.2 | Negative | 0.12 | 0.25 | Negative | 0.45 | 0.21 | 2/2 | 0.93 (0.51, 1.67) | 0.8 |
| M11 | novel | 150289715 | T/C | 0.02 | Negative | 0.42 | 0.009 | —* | —* | 0 | —* | —* | 0.01 | 2 carrier | 1.39 (0.62, 3.11) | 0.43 |
| M12 | novel | 150289729 | G/A | 0.04 | Negative | 0.43 | 0.019 | Null** | 0.82 | 0.008 | Positive | *0.01* | 0.038 | 2 carrier | 1.30 (0.84, 2.01) | 0.24 |
| M13 | rs3778874 | 150289984 | G/A | 0.26 | Negative | 0.19 | 0.2 | Negative | *0.042* | 0.26 | Negative | 0.23 | 0.2 | 2/2 | 1.08 (0.58, 2.01) | 0.81 |
| M14 | rs2968857 | 150293263 | T/C | 0.38 | Positive | 0.68 | 0.42 | Positive | 0.65 | 0.14 | Null** | 0.88 | —*** | —*** | —*** | —*** |
| M15 | rs10236214 | 150299003 | T/C | 0.33 | Negative | 0.37 | 0.33 | Positive | 0.59 | 0.16 | Positive | 0.77 | —*** | —*** | —*** | —*** |
| M16 | rs11763131 | 150299115 | G/A | 0.31 | Positive | *0.004* | 0.31 | Positive | 0.38 | 0.11 | Null** | 0.82 | 0.27 | 2/2 | 1.72 (1.06, 2.80) | *0.029* |
| M17 | rs3807374 | 150299279 | A/C | 0.3 | Positive | *0.001* | 0.31 | Positive | 0.65 | 0.18 | Positive | 0.21 | 0.54 | 2/2 | 1.50 (0.94, 2.34) | *0.093* |
| M18 | rs4725984 | 150299447 | C/T | 0.32 | Negative | 0.28 | 0.3 | Positive | 0.72 | 0.17 | Positive | 0.75 | —*** | —*** | —*** | —*** |

TABLE 3-continued

SNPs Genotyped in Four Clinical Samples and FBAT Statistical Results

| Marker | SNP rs# | Chr. 7 position | Alleles | MAF | CBDB Sibling Study (296 Families) | | | NIMHGI-C (71 families) | | | NIMHGI-AA (51 families) | | | German Case-Control Study (501 cases/626 controls) | | | |
|---|---|---|---|---|---|---|---|---|---|---|---|---|---|---|---|---|---|
| | | | | | Minor Allele Direction of Association | empirical p-value | MAF | Minor Allele Direction of Association | empirical p-value | MAF | Minor Allele Direction of Association | empirical p-value | Control MAF | Genotype | OR (95% CI) | p-value |
| M19 | rs3807373 | 150299654 | C/T | 0.3 | Positive | 0.0065 | 0.29 | Positive | 0.47 | 0.1 | Null** | 0.88 | 0.27 | 2/2 | 1.49 (0.94, 2.38) | *0.091* |
| M20 | rs3807372 | 150299990 | C/T | 0.14 | Negative | 0.057 | 0.17 | Positive | 0.5 | 0.32 | Negative | 0.16 | 0.13 | 2/2 | 2.99 (1.26, 7.11) | *0.013* |
| M21 | novel | 150300253 | C/T | 0.02 | Positive | 0.56 | 0.02 | Negative | *0.062* | 0.017 | Negative | 0.24 | —*** | —*** | —*** | —*** |
| M22 | rs3778873 | 150300800 | G/C | 0.21 | Negative | 0.61 | 0.14 | Negative | *0.068* | 0.25 | Negative | 0.67 | —*** | —*** | —*** | —*** |
| M23 | novel | 150300839 | G/C | 0.03 | Negative | 0.34 | 0.057 | Negative | 0.75 | 0.066 | Positive | 0.43 | —*** | —*** | —*** | —*** |
| M24 | rs3778872 | 150300909 | G/C | 0.21 | Negative | 0.17 | 0.13 | Negative | *0.065* | 0.26 | Negative | 0.66 | —*** | —*** | —*** | —*** |
| M25 | novel | 150301321 | C/T | 0.01 | Positive | 0.26 | 0.014 | Positive | 0.24 | 0 | —* | —* | 0.013 | 2 carrier | 0.99 (0.45, 2.18) | 0.98 |
| M26 | novel | 150301660 | C/T | 0.02 | Negative | 0.11 | 0.057 | Negative | 0.5 | 0.008 | —* | —* | —*** | —*** | —*** | —*** |
| M27 | rs3778871 | 150301705 | T/G | 0.15 | Negative | 0.36 | 0.089 | Negative | *0.033* | 0.32 | Null** | 0.91 | —*** | —*** | —*** | —*** |
| M28 | rs3778870 | 150301925 | G/C | 0.05 | Negative | 0.94 | —*** | —*** | —*** | —*** | —*** | —*** | —*** | —*** | —*** | —*** |
| M29 | rs3778869 | 150302031 | C/T | 0.14 | Negative | 0.26 | —*** | —*** | —*** | —*** | —*** | —*** | —*** | —*** | —*** | —*** |
| M30 | rs3800779 | 150302147 | G/T | 0.35 | Positive | 0.0075 | 0.33 | Null | 0.93 | 0.17 | Negative | 0.73 | 0.31 | 2/2 | 1.58 (1.05, 2.38) | 0.03** |
| M31 | rs748693 | 150302370 | A/G | 0.35 | Positive | *0.019* | 0.33 | Null** | 0.93 | 0.17 | Positive | 0.72 | 0.36 | 2/2 | 1.26 (0.85, 1.87) | 0.25 |
| M32 | rs3807370 | 150304247 | C/T | 0.34 | Negative | 0.58 | 0.34 | Positive | 0.48 | 0.073 | Negative | 0.74 | —*** | —*** | —*** | —*** |
| M33 | rs1036145 | 150305363 | G/A | 0.35 | Positive | 0.0035 | 0.32 | Positive | 0.87 | 0.17 | Positive | *0.17* | 0.32 | 2/2 | 1.34 (0.90, 2.01) | 0.15 |
| M34 | rs11771808 | 150306801 | G/A | 0.34 | Negative | 0.7 | 0.36 | Positive | 0.59 | 0.15 | Negative | 0.82 | —*** | —*** | —*** | —*** |
| M35 | rs2373885 | 150309013 | A/G | 0.27 | Negative | 0.37 | 0.34 | Negative | 0.37 | 0.47 | Negative | 0.58 | —*** | —*** | —*** | —*** |
| M36 | rs4496877 | 150311439 | G/T | 0.34 | Negative | 0.49 | 0.37 | Positive | 0.3 | 0.063 | Null** | 0.87 | —*** | —*** | —*** | —*** |
| M37 | rs10277327 | 150314277 | A/G | 0.26 | Negative | 0.27 | 0.25 | Positive | 0.3 | 0.44 | Negative | 0.84 | —*** | —*** | —*** | —*** |
| M38 | rs1800783 | 150320330 | T/A | 0.35 | Negative | 0.48 | 0.4 | Positive | 0.22 | 0.46 | Negative | 0.81 | —*** | —*** | —*** | —*** |
| M39 | rs1007311 | 150326941 | A/G | 0.48 | Positive | 0.36 | 0.45 | Null | 0.95 | 0.52 | Negative | 0.5 | —*** | —*** | —*** | —*** |
| M40 | rs2566514 | 150335183 | C/G | 0.24 | Negative | 0.33 | 0.28 | Negative | 0.65 | 0.46 | Negative | 0.77 | —*** | —*** | —*** | —*** |

TABLE 3-continued

SNPs Genotyped in Four Clinical Samples and FBAT Statistical Results

| Marker | SNP rs# | Chr. 7 position | Alleles | MAF | CBDB Sibling Study (296 Families) | | | NMHGI-C (71 families) | | | NMHGI-AA (51 families) | | | German Case-Control Study (501 cases/626 controls) | | | |
|---|---|---|---|---|---|---|---|---|---|---|---|---|---|---|---|---|---|
| | | | | | Minor Allele Direction of Association | empirical p-value | MAF | Minor Allele Direction of Association | empirical p-value | MAF | Minor Allele Direction of Association | empirical p-value | Control MAF | Genotype | OR (95% CI) | p-value |
| M41 | rs743507 | 150338421 | A/G | 0.26 | Positive | 0.96 | 0.26 | Positive | 0.68 | 0.22 | Negative | 0.52 | —*** | —*** | —*** | —*** |
| M42 | rs891512 | 150339022 | G/A | 0.22 | Positive | 0.96 | 0.21 | Positive | 0.72 | 0.034 | Negative | 0.25 | —*** | —*** | —*** | —*** |
| M43 | rs1077872 | 150345679 | C/G | 0.34 | Positive | 0.68 | —*** | —*** | —*** | —*** | —*** | —*** | —*** | —*** | —*** | —*** |

*no transmissions were observed
**observed transmission exactly equal to expected value
***not genotyped SNPs denoted novel were identified by resequencing DNA from 48 schizophrenia patients (see Example 1). The type of SNP (major allele listed first) and MAF (minor allele frequency) is given for each cohort. For SNPs genotyped in the family-based cohorts, the Z-score of transmission for the minor allele to affected offspring is given followed by the simulated p-value (Max = 100,000 iterations). For SNPs genotyped in the German cohort, the odds ratio for the minor allele in cases vs. controls as well as the corresponding Chi-square p-value is given followed by the multinomial linear regression coefficient (β) for case vs. control 2/2 individuals and its simulated p-value (1000 iterations).
$p < 0.15$ are italicized;
$p < 0.05$ are bold.

TABLE 4

COGNITIVE PERFORMANCE FACTOR SUMMARY TABLE

| Factor | Included Tests |
|---|---|
| Factor 1: Verbal Memory | WMS-R Logical Memory—I and II |
|  | WMS-R Verbal Paired Associates—I Hard and II Total; |
|  | California Verbal Learning Tests 1-5 |
| Factor 2: Nback | Nback 1, 2, and 3 |
| Factor 3: Visual Memory | WMS-R Visual Reproduction I and II; |
|  | Benton Line Orientation |
| Factor 4: Processing Speed | WAIS IQ; |
|  | Trailmaking Test Parts A and B; |
|  | Letter Fluency; |
|  | Category Fluency |
| Factor 5: Card Sorting | Wisconsin Card Sorting Test—Preservative Error and Categories Completed |
| Factor 6: Attention | Nback 0; |
|  | Gordon Distractibility; |
|  | Gordon Vigilance |
| Factor 7: Digit Span | WMSR Digit Span—Forward and Backward |

TABLE 5

Demographic and Genetic Data of Normal Volunteers Included in VBM Analysis

|  | M30 | M31 | M33 | M40 |
|---|---|---|---|---|
| n | 139 | 141 | 141 | 140 |
| Gender (M:F) | 67:72 | 68:73 | 69:72 | 68:72 |
| Age (M ± SD, ys) | 31.9 ± 9.1 | 32.4 ± 9.4 | 32.4 ± 9.4 | 32.1 ± 9.4 |
| IQ | 107.1 ± 8.7 | 107.6 ± 9.1 | 107.6 ± 9.0 | 107.6 ± 9.0 |
| # copies of risk allele (HNR > H > HR) | 63/59/17 | 66/59/16 | 64/61/16 | 71/59/10 |

HNR = Homozygous for the Non-Risk Allele; H = Heterozygous for the Risk Allele; HR = Homozygous for the Risk Allele

TABLE 6

Demographic and Genetic Data of Normal Volunteers Included in fMRI

|  | M30 | M31 | M33 | M40 |
|---|---|---|---|---|
| n | 79 | 77 | 75 | 76 |
| Gender (M:F) | 34:45 | 34:43 | 31:44 | 34:42 |
| Age (M ± SD, ys) | 30.9 ± 9.7 | 31.0 ± 9.7 | 30.9 ± 9.6 | 30.8 ± 9.5 |
| IQ | 107.7 ± 9.7 | 107.8 ± 19.8 | 107.6 ± 9.9 | 107.7 ± 9.8 |
| # copies of risk allele (HNR > H > HR) | 28/37/14 | 30/35/12 | 27/37/11 | 39/35/2 |

HNR = Homozygous for the Non-Risk Allele; H = Heterozygous for the Risk Allele; HR = Homozygous for the Risk Allele

TABLE 7

Optimized voxel based morphometry (VBM) data for the KCNH2 SNPs.

|  | Z | x | y | z |
|---|---|---|---|---|
| M30 (n = 63, 59, 17) | 3.34*,† | 26 | −12 | −22 |
|  | 3.02* | −27 | −21 | −17 |
|  | 2.84* | 33 | −26 | −15 |
|  | 2.79* | −23 | −10 | −24 |
| M31 (n = 66, 59, 16) | 3.16*,† | 26 | −9 | −24 |
|  | 2.68* | 28 | −37 | −2 |
| M33 (n = 64, 61, 16) | 3.08§ | 26 | −9 | −24 |

Brain hippocampal areas that show a significant linear decrease in grey matter volume (GM) from subjects homozygous for the risk allele (HR) to heterozygote carriers (H) to non carriers (HNR). VBM analysis was performed using an analysis of covariance model with GM, age, and gender as covariates of no interest.
All the results are thresholded with a p < 0.005 and small-volume corrected for the hippocampus;
*significant with a threshold of pFDR = 0.05;
§pFDR = 0.07 and pFWE = 0.06;
†significant with a threshold of pFWE = 0.05.
Peak cluster coordinates are expressed in mm in MNI system.
n = sample size of HNR, H, HR, respectively.

TABLE 8

Genotyped based differential engagement of the hippocampus during incidental encoding of declarative memory task for the KCNH2 SNPs.

|  | Z | x | y | z |
|---|---|---|---|---|
| M30 (n = 28, 37, 14) | 3.48* | −34 | −25 | −15 |
| M31 (n = 30, 35, 12) | 3.11† | −34 | −22 | −15 |
| M33 (n = 27, 37, 11) | 3.24* | −34 | −22 | −15 |

This data shows a linear increase of activation in homozygous for the risk allele (HR) relative to heterozygote carriers (H) and non carriers (HNR).
All the results are thresholded with a p < 0.001 and small-volume corrected for the hippocampus;
*significant with a threshold of pFWE = 0.05;
†pFWE = 0.06.
Peak cluster coordinates are expressed in mm in MNI system.
n = sample size of HNR, H, HR, respectively.

TABLE 9

Demographic and Sample Details of Brain Collection Chart

A

|  | Control (n = 69) | Schizophrenia (n = 31) | p-value |
|---|---|---|---|
| Age | 40.6 ± 15.27 | 45.1 ± 14.89 | 0.175* |
| Gender (M/F) | 50/19 | 20/11 | 0.482@ |
| Race (C/AA) | 22/47 | 14/17 | 0.261@ |
| PMI (hours) | 31.2 ± 13.75 | 35.8 ± 14.94 | 0.134* |
| Brain pH | 6.62 ± 0.24 | 6.49 ± 0.22 | 0.011* |

B

|  | Control (n = 59) | Schizophrenia (n = 29) | p-value |
|---|---|---|---|
| Age | 41.7 ± 14.9 | 46.4 ± 15.5 | 0.178* |
| Gender (M/F) | 44/15 | 19/10 | 0.453@ |
| Race (C/AA) | 19/40 | 11/18 | 0.637@ |
| PMI | 31.5 ± 15.0 | 36.7 ± 15.1 | 0.129* |
| RIN_HIP | 5.8 ± 1.08 | 5.3 ± 0.94 | 0.038* |
| pH | 6.63 ± 0.25 | 6.48 ± 0.33 | 0.023* |

(A) Demographic information for real-time q-PCR analysis of post-mortem human DLPFC.
(B) Demographic information of samples used for real-time q-PCR analysis of human Hippocampus. Summary statistics of critical demographic variables are shown (±1 SD) by patient group. Differences between groups were assessed using either ANOVA followed by Least-Significant Difference post-hoc analysis (p-values denoted with '*') or using Fisher's Exact test (p-values denoted with '@').
*ANOVA Tested
@Fisher's exact test

TABLE 10

NOS3 and KCNH2 mRNA Expression Statistics in Human Brain

A - Case Control Expression Differences

| Gene | Reverse Stepwise Linear Regression | | | ANCOVA Model | |
|---|---|---|---|---|---|
| | Coefficient | β | p-value | Covariate | p-value |
| Hippocampus | | | | | |
| KCNH2-1A | PMI | −0.298 | 0.052 | | 0.102 |
| | | | | Dx | 0.003 |
| NOS3 | pH | −0.439 | 0.041 | | 0.061 |
| | | | | Dx | 0.076 |
| Isoform 3.1 | None | — | — | | — |
| | | | | Dx | 0.012 |
| DLPFC | | | | | |
| KCNH2-1A | Age | −0.843 | 0.001 | Age | 0.001 |
| | Agonal State | 0.346 | 0.041 | Agonal State | 0.725 |
| | | | | Dx | 0.016 |
| NOS3 | pH | −0.598 | 0.004 | | 0.154 |
| | | | | Dx | 0.032 |

B - Gene Expression vs. Genotype and Race

| | ANCOVA Model | |
|---|---|---|
| Gene | Coefficient | p-value |
| Hippocampus | | |
| KCNH2-1A | PMI | 0.366 |
| | Dx | 0.006 |
| | Race | 0.158 |
| | M33 | 0.516 |
| NOS3 | pH | 0.051 |
| | Dx | 0.084 |
| | Race | 0.009 |
| | M33 | 0.9 |
| Isoform 3.1 | Dx | 0.037 |
| | Race | 0.309 |
| | M33 | 0.007 |
| DLPFC | | |
| KCNH2-1A | Age | 0.001 |
| | Agonal State | 0.392 |
| | Dx | 0.009 |
| | Race | 0.533 |
| | M33 | 0.328 |
| NOS3 | pH | 0.199 |
| | Dx | 0.074 |
| | Race | 0.089 |
| | M33 | 0.557 |

(A) Expression within hippocampus and DLPFC of KCNH2-1A (ABI assay: Hs00165120_m1) and NOS3 (ABI assay: Hs_00167166_m1) was normalized to the geometric mean of 3 housekeeping genes (B2M, GUSB, PBGD) and then tested for potential effects of several demographic variables using backward stepwise linear regression. Tested variables included: RNA Integrity Number (RIN), agonal sate, post-mortem pH, post-mortem interval (PMI), and age. Isoform 3.1 (Custom ABI assay) was only measured in hippocampus due to the exhaustion of DLPFC total RNA.
Variables found to have significant main effects in the final regression model were included as covariates within an ANCOVA model testing for the main effect of diagnosis (Dx) on expression.
(B) After ANCOVA testing for case-control differences, the effects of race and M33 genotype were included into the ANCOVA model in order to test for the association between M33 and gene expression.
All analyses were performed using SPSS 12.0.

TABLE 11

Quantitative RT-PCR

| DNase Treated Sample | Detector | Average CT | CT Stdev | Fold difference vs. Full length (± SEM) |
|---|---|---|---|---|
| 13 Tissue Pool | KCNH2-1A | 26.10 | 0.02 | |
| | Isoform 3.1 | 31.85 | 0.13 | −53.6 ± 3.3 |
| Caudate Nucleus | KCNH2-full | 27.14 | 0.19 | |
| | KCNH2-3.1all | 29.76 | 0.11 | −6.14 ± 0.8 |
| Hippocampus | KCNH2-full | 24.46 | 0.09 | |
| | KCNH2-3.1all | 32.02 | 0.15 | −188.7 ± 19.7 |
| PFC | KCNH2-full | 27.83 | 0.44 | |
| | KCNH2-3.1all | 29.75 | 0.06 | −3.8 ± 0.9 |
| Skeletal Muscle | KCNH2-full | 31.69 | 0.20 | |
| | KCNH2-3.1all | — | — | — |
| Heart | KCNH2-full | 20.94 | 0.03 | |
| | KCNH2-3.1all | 31.28 | 0.14 | −1297.2 ± 91.6 |
| Placenta | KCNH2-full | 28.30 | 0.10 | |
| | KCNH2-3.1all | 35.09 | 0.36 | −110.05 ± 24.4 |
| Testicle | KCNH2-full | 21.93 | 0.07 | |
| | KCNH2-3.1all | 30.51 | 0.09 | −382.1 ± 25.1 |

Quantitative RT-PCR was used to measure the relative quantity of Isoform 3.1 as compared to KCNH2-1A expression in 8 total RNA isolates.
All samples were DNase treated prior to cDNA synthesis to prevent the effects of DNA contamination on the samples.
All Ct values were determined at the same threshold value and all sample expression values were measured in triplicate.

Discussion

The findings described here provide compelling evidence for a novel genetic association with risk for schizophrenia at 7q36.1, in the region of KCNH2, which was observed in four independent genetic cohorts of European and African American ancestry, including three family-based and one case-control dataset. Our results satisfy a proposed "3-cohort replication rule" for preliminary evidence that a gene conveys risk to a genetically complex illness (K. E. Lohmueller et al. 2003 Nat Genet 33:177). All samples showed association to SNPs within a small segment of intron 2 of KCNH2. Similar circumstances have been reported with other genes that appear to be compelling candidate susceptibility genes for schizophrenia (P. J. Harrison and D. R. Weinberger 2005 Mol Psychiatry 10:40; P. J. Harrison and A. J. Law 2006 Biol Psychiatry 60:132; D. J. Porteous et al. 2006 Biol Psychiatry 60:123; N. M. Williams et al. 2005 Schizophr Bull 31:800). Interestingly, the resequencing in 48 schizophrenia patients found a novel but rare (~1% MAF) SNP, M25. Investigation of these pedigrees found that every proband inherited the M25 minor allele from a heterozygote parent, which may indicate evidence for the contribution of a rare allele/rare variant hypothesis of genetic association at KCNH2. Though risk alleles may vary, affecting a variety of transcriptional and other regulatory domains, they appear to converge on similar downstream molecular changes.

All clinical samples showed association to a small region (<3 kb) and much of the genetic risk of the region appears to be sufficiently tagged by M30, M31, and M33. Accordingly, these markers also demonstrated the strongest independent associations with a priori predicted schizophrenia-associated intermediate phenotypes including cognitive impairments, brain volume reductions, brain activity changes, and also with increases in Isoform 3.1 expression, all in healthy unrelated individuals of various genetic backgrounds who carry the risk alleles yet have no history of mental illness. In sum, we show association of genetic variation in this small ~3 kb region with clinical phenomena strongly linked to schizophrenia and with selective expression of a specific novel transcript whose start site is only ~11 kb downstream of this risk region. We propose that these results identify a new schizophrenia susceptibility gene and that the mechanism of this association involves anomalous processing of a novel brain selective transcript of KCNH2 that leads to alterations in cortical development and function militating towards the clinical phenomenology of schizophrenia.

The control of membrane repolarization and spike frequency in neurons by KCNH2 isoforms has intriguing implications for cortical function and the pathophysiology of schizophrenia. Cortical information processing is critically dependent on organized neuronal oscillations within cortical circuits (R. T. Canolty et al. 2006 Science 313:1626). For example, neurons in the prefrontal cortex (PFC) exhibit sustained firing of high frequency activity during the delayed period that is thought to be critical for working memory (Y. Wang et al. 2006 Nat Neurosci 9:534). We found that expression of Isoform 3.1 in rat cultured cortical neurons results in a much faster deactivation of the hERG channels, leading to a marked increase in spike frequency and a conversion from adapting to non-adapting firing patterns. This "sustained" firing pattern might be important for cortical information processing underlying higher-order cognitive and memory tasks and suggests a role for Isoform 3.1 in normal human cognitive processing. However, the 2.5-fold increase in Isoform 3.1 relative to KCNH2-1A in schizophrenic brain might serve to abnormally increase neuronal excitability and disrupt normal oscillatory rhythms. "Dysrhythmia" of such tonic firing would be expected to result in anomalous modulation of microcircuits resulting in poor regulation of signal-to-noise (G. Winterer and D. R. Weinberger 2004 Trends Neurosci 27:683). Thus, the over-expression of Isoform 3.1 within the schizophrenia brain and its functional effects on neuronal firing is congruous with current hypotheses of a disease related alteration in cortical signal-to-noise processing within schizophrenia (G. Winterer and D. R. Weinberger 2004 Trends Neurosci 27:683).

The discovery of Isoform 3.1 has compelling therapeutic implications. The unique structure of isoform 3.1, its role in non-adaptive firing, its low expression in heart, and elevated expression in brains of schizophrenia patients and genetic risk carriers, lead to the conclusion that selective inhibition of Isoform 3.1 but not KCNH2 would correct the disorganized firing in schizophrenia brain without eliciting cardiac side effects. Thus, Isoform 3.1 is a promising novel therapeutic target for the treatment of schizophrenia.

In conclusion, we have identified and characterized a novel, primate specific brain potassium channel, localized a novel genetic association with risk for schizophrenia to within a small region of KCNH2 (7q36.1), and have confirmed this finding in four independent clinical-based samples. Three SNPs in particular (M30, M31, and M33) showed evidence of association in all tested populations. We report the observation that polymorphisms in a specific 3 Kb region of KCNH2 consistently occur with higher frequency within schizophrenia patients and that, regardless of allelic heterogeneity, that healthy control carriers of risk SNPs within this region demonstrate a schizophrenia-like shift in cognitive traits (processing speed and visual memory) and in hippocampal volume and physiologic engagement during memory processing. The mechanism of these associations appears to be related to genetic regulation of a novel Isoform 3.1 of KCNH2, which has unique electrophysiological properties, primate and brain specificity, and expressional dependence on risk genotypes. Our results represent a first step towards discovery of a novel therapeutic target for schizophrenia and related conditions.

Example 1

Genetic Association Cohorts

The CBDB Sibling Study consists of subjects collected as part of an ongoing investigation into neurobiological traits related to genetic risk for schizophrenia (M. F. Egan et al. 2000 Am J Psychiatry 157:1309). Participants were between the ages of 18 and 60 and only Caucasians of self-identified European decent were analyzed in this study to reduce genetic heterogeneity. DNA was available from 252 probands, 311 of their siblings (mostly unaffected), 268 parents, and 383 unrelated healthy controls. Further information about the collection, screening, and exclusion criteria has been previously described (M. F. Egan et al. 2000 Am J Psychiatry 157:1309). Two additional family-based cohorts were included from the National Institutes of Mental Health Genetics Initiative on schizophrenia (NIMHGI) (S. V. Faraone et al. 1998 Am J Med Genet 81:290). The cohorts consisted of 51 African American families (GI-AA) and 71 Caucasian families (GI-C). Only nuclear families were included with DNA available from at least one sibling with a diagnosis of schizophrenia or schizoaffective disorder, and at least one parent. A fourth cohort was collected from the Munich area in Germany consisting of 501 schizophrenia patients and 626 unrelated healthy controls (K. K. Nicodemus et al. 2007 Hum Genet 120:889-906). Further details regarding the collection, evaluation, and exclusion criteria of the German cohort have been described (K. K. Nicodemus et al. 2007 Hum Genet 120:889-906).

Candidate Gene Screening

Ten candidate genes were selected from those previously reported as differentially expressed between schizophrenia patients and healthy controls (S. Prabakaran et al. 2004 Mol Psychiatry 9:684). htSNPs tagging haplotype blocks overlapping with part or all of the gene of interest and which had predesigned TaqMan SNP assays (Applied Biosystems, Inc) were genotyped on a screening sample of 175 families (698 Caucasian subjects) of the CBDB Sibling Study. All SNPs were genotyped using 5'-exonuclease TaqMan SNP assays as previously described (K. J. Livak 1999 Genet Anal 14:143). Single marker and whole haplotype association testing was performed using family-based association test (FBAT) (S. Horvath et al. 2001 Eur J Hum Genet 9:301) and evaluated at $\alpha=0.05$.

KCNH2 Genotyping and Re-Sequencing

Genotypes were obtained for a total of 43 SNPs within a 65.2 Kb region of KCNH2 and NOS3 (chr7: 150280464-150345679). A total of 13.5 Kb were re-sequenced in 48 schizophrenia patients by Polymorphic Inc. (Alameda, Calif.) and also in house, including 10.4 Kb flanking rs 1036145 (chr7:150, 299,575-150,309,948) and 3.1 Kb upstream of exon 3 (chr7: 150,287,750-150,290) with high cross-species conservation in the UCSC genomes database (genome.ucsc.edu). Re-sequencing found 11 novel SNPs. SNPs were genotyped in all four cohorts using TaqMan SNP assays as before. Finally, SNP M33 was genotyped in 116 individuals (34 schizophrenia patients and 82 healthy controls) of the CBDB/NIMH Brain Collection (see below) for whom total RNA was also extracted from the DLPFC and hippocampus for QPCR (see below).

Cognitive Testing

Depending on the cognitive test, data were available for between 230 and 330 of the individuals included in the CBDB family-based cohort. The tests included tasks aimed at assessing a wide range of features shown to be significantly affected in patients with schizophrenia including IQ, visual and learning memory, attention span, etc. (M. F. Egan et al. 2001 Biol Psychiatry 50:98). Factor analysis of 24 performance scores from nine neuropsychological tests shown to be associated with increased genetic risk for schizophrenia (M. F. Egan et al. 2004 Proc Natl Acad Sci USA 101:12604; T. E. Goldberg et al. 2006 Neuropsychopharmacology 31:2022; J. H. Callicott et al. 2005 Proc Natl Acad Sci USA 102:8627) identified seven factors that explained 68% of the variance on these measures (Genderson, M. R. et al. Schiz Res (in press)). These 7 factors were used to assess genotype effects on cognitive task performance (see below) and are labeled as follows: Verbal Memory, Nback, Visual Memory, Processing Speed/IQ, Card Sorting, Attention, and Digit Span. Further information regarding the test measures included in each factor is provided in Table 4.

Statistical Genetics Analysis

Hardy-Weinberg Equilibrium (HWE) was tested using F-exact tests Analyses of single SNPs were conducted using the Family Based Association Test (FBAT) in nuclear families (S. Horvath et al. 2001 Eur J Hum Genet 9:301) and logistic regression in comparisons of unrelated cases and controls using STATA, version 8.2 (College Park, Tex., USA). Haplotype analysis was performed using FBAT for families and the R package haplo. stats (D. J. Schaid et al. 2002 Am J Hum Genet 70:425) in unrelated case-control tests. All tests were run with simulation and represent p-values following 1000 iterations. Cognitive intermediate phenotypes were tested in control subjects only using linear regression and were based on the seven normalized derived factor scores.

Quantitative Real-Time PCR (rt-PCR)

Human brain tissue was collected as part of the CBDB/NIMH Brain Collection. Details about the collection, screening, and dissection processes have been described (B. K. Lipska et al. 2006 Hum Mol Genet 15:1245). Predesigned TaqMan MGB Assays (Applied Biosystems, Inc.) for the major transcripts of NOS3 (Hs001 67166_ml) and KCNH2 (KCNH2-1A; Hs001 65120_ml) along with 3 housekeeping genes (GUSB, B2M, and PBGD) were used to measure expression in 100 ng of cDNA equivalents isolated from the DLPFC (69 controls; 31 schizophrenia) or the hippocampus (59 controls; 29 schizophrenia) of HBS subjects. A custom TaqMan MGB assay was designed for Isoform 3.1 targeting the 5'-UTR region of the gene (F-primer: 5'-CAT-GAGAAAAGAATTATATACATTATGTG-TATCACAACATC, SEQ ID NO: 18; R-Primer: 5'-GCCT-CATTTTTTCCATCTATAAAATGGGAA, SEQ ID NO: 19; Probe: 5'-ACTGTGTACCCCATAAATATGTA, SEQ ID NO: 20). A pool of cDNA from 16 individuals (randomly selected) was used to create an 8-point, 1A serial dilution standard curve. All QPCR reactions were performed in triplicate.

Expression levels of NOS3, KCNH2-1A, and Isoform 3.1 assays were normalized to the geometric mean of GUSB (Hs99999908 ml), B2M (Hs99999907 ml), and PBGD (Hs00609297_ml) (J. Vandesompele et al. 2002 Genome Biol 3:RESEARCH0034). Data was tested for normality using Shapiro-Wilk W test. NOS3 qPCR data were non-normally distributed and were consequently log2 transformed while KCNH2-1A and Isoform 3.1 qPCR data were normally distributed. All normalized expression values were tested for the main effects of various demographic and sample factors using reverse-stepwise linear regression. Tested factors included: RNA integrity number (RIN), postmortem brain pH, postmortem interval (PMI), age at death, agonal state, manner of death. Variables with significant regression model coefficients were included in the final ANCOVA model for diagnosis (evaluated at $\alpha=0.05$) (see Table 10). The effects of genotype and race were tested using a second ANCOVA model including race and M33.

Imaging Methods

Subjects: All the subjects who participated in the imaging aspects of this study were Caucasian (see Table 5 and 6 for demographics). They were cleared of neurological, psychiatric, or substance abuse problems and had no history of other medical problems or medical treatment relevant to cerebral metabolism and blood flow. There was no significant difference in age, sex, IQ score and education distribution across the genotype groups. All available scans of subjects with genotypes of interest were used in these analyses.

Structural image processing: Three-dimensional structural MRI scans were acquired on a 1.5-T GE scanner using a Tl-weighted SPGR sequence (TR/TE/NEX 24/5/1, flip angle 45°, matrix size 256×256, FOV 24×24 cm) with 124 sagittal slices (0.94×0.94×1.5 mm resolution) and pre-processed as previously described (L. Pezawas et al. 2004 J Neurosci 24:10099) followed by an optimized VBM protocol using customized templates (J. Ashburner and K. J. Friston 2000 Neuroimage 11:805; C. D. Good et al. 2001 Neuroimage 14:21). Resulting gray matter images were smoothed with a 12-mm Gaussian kernel prior to statistics. Analysis was performed on Linux workstations (RedHat) using MATLAB 7.02 (Math Works) within the General Linear Model in SPM2 (K. J. Friston et al. 1994 Hum Brain Mapp 2:189-210) (on the world-wide-web at fil.ion.ucl.ac.uk/spm). The specification of a design matrix identical to the one used in this study was described in detail elsewhere (L. Pezawas et al. 2004 J Neurosci 24:10099). Briefly, effects of the KCNH2 SNPs on gray matter volume were examined by using an analysis of covariance model including the following covariates of no interest: total gray matter volume, orthogonalized first- and second-order polynomials of age, and gender. A hypothesis-driven region of interest (ROI) approach was used to investigate genotype related alterations in structure within the hippocampal formation. Gray-matter volume changes were assessed statistically using one-tailed t-contrasts after small-volume correction for the hippocampus. False discovery rate estimations were used to correct for multiple comparisons, and a probability of 0.05 was considered to be significant. Anatomical hippocampal ROIs were created using the WFU Pick atlas (on the world-wide-web at fmri.wfubmc.edu) software. We used the volume of interest (VOI) SPM2 toolbox to extract the adjusted gray matter volumetric data from the peak of most significant hippocampal clusters.

Functional task: During fMRI scanning, subjects performed a declarative memory task previously described to robustly engage the hippocampal formation (A. R. Hariri et al. 2003 J Neurosci 23:6690). The paradigm consisted of the encoding and subsequent retrieval of novel, complex scenes. Four encoding blocks were followed by four retrieval blocks in an interleaved design with a passive cross-hair fixation rest condition, resulting in a total of 17 blocks. During encoding blocks, subjects viewed six images, presented serially for 3 sec each, and determined whether each image represented an "indoor" or "outdoor" scene. All scenes were of neutral emotional valence and were derived from a standardized set (P. Lang, B. M., B. Cuthbert, International Affective Picture System (IAPS): technical manual and affective ratings, (NIMH Center for the Study of Emotion and Attention, University of Florida, Gainesville, Fla., 1997)).

During subsequent retrieval blocks, subjects again viewed six images, presented serially for 3 sec each, and determined whether each scene was "new" or "old." In each retrieval block, half the scenes were "old" {i.e., presented during the encoding blocks) and half were "new" {i.e., not presented during the encoding blocks). The order of presentation of the images was counterbalanced across the subjects. During scanning, all subjects responded by button presses with their dominant hand, allowing for the determination of accuracy and reaction time.

Functional image processing: BOLD fMRI was performed on a GE Signa 3-T scanner using gradient echo EPI (24 axial slices, 4 mm thickness, 1 mm gap, TR/TE=2000/28 ms, FOV=24 cm, matrix=64×64). Images were processed as described previously (A. R. Hariri et al. 2003 J Neurosci 23:6690) using SPM99 (on the world-wide-web at fil.ion.u-cl.ac.uk/spm). Briefly, images were realigned to the first image of the scan run, spatially normalized into a standard stereotactic space (MNI template) using an affine and nonlinear (4×5×4 basis-functions) transformation, smoothed with a 8-mm FWHM Gaussian filter and ratio normalized to the whole-brain global mean. In the first level analyses, linear contrasts were computed producing t statistical parameter maps at each voxel for encoding, and retrieval assuming the rest condition as a baseline. These statistical images were entered in a second-level random effects model (ANOVA) to identify significant activations within and between genotype groups. A hypothesis-driven region of interest (ROI) approach was used to investigate genotype related alterations in functional activity within the hippocampal formation ($P<0.05$, corrected for the small volume and the multiple comparisons, FWE within the hippocampal VOI). Mean percent BOLD signal change was extracted with the MarsBar toolbox within SPM2 (M. Brett et al. in 8th International Conference on Functional Mapping of the Human Brain. (Neuroimage, 16, abstract 497, Sendai, Japan, 2002)) in significant clusters.

Behavioral results: There were no behavioral differences between the three groups in the accuracy and reaction times for each of the SNPs during either the encoding or the retrieval part of the task.

Isoform 3.1 Cloning and Expression

5'-RACE and Isoform 3.1 cloning: 5'-RACE was performed using a 5'-RACE System (v2.0) as recommended (Invitrogen). Template cDNA was made from commercially available total RNA from 10 human cell lines and tissues (Stratagene). Reverse primers in exon 5 (5'-TGTGGGT-TCGCTCCTTTATC) (SEQ ID NO: 21) were used as the first gene specific primer followed by primers in Exon 4 in the first PCR (5'-CATGGCCTCGATGTCGTC) (SEQ ID NO: 22). Nested PCR was performed using primers in Exon 3 (5'-ATGATGACAGCCCCATCCT) (SEQ ID NO: 23). 3 products were gel purified, cloned, and sequenced corresponding to hERG-1A (NM_000238), BCOO1 914, and Isoform 3.1. Products were reproduced using total RNA isolated and pooled from the prefrontal cortex of 10 schizophrenia control patients (B. K. Lipska et al. 2006 Hum Mol Genet 15:1245).

To determine the 3'-end of Isoform 3.1, forward primers in the unique region of Isoform 3.1 (5'-CATACGGGGAGGCA-GAAGT) (SEQ ID NO: 24) were used to produce PCR products spanning to exons 3 through 15. All products were confirmed by cloning and sequencing. Cloning and Transfection: Novel KCNH2 isoform3.1 cDNA was cloned by long PCR with specific primers (3.1F 5'-CATACGGGGAGGCA-GAAGT, SEQ ID NO: 25; ExI 5-R CTTCTTGGG-GAAGCTCTGG, SEQ ID NO: 26) and high fidelity DNA polymerase in the vector pZero-Blunt (Invitrogen), and then subcloned into the vector pcDNA3 (Invitrogen). Human KCNH2 cDNA in pcDNA3 is a gift from Dr. Gail A. Robertson. Isoform 3.1 cDNA, with deletion of exons 1 and 2 and addition of a Kozak consensus sequence, was generated by long PCR with high fidelity DNA polymerase Pfx (Invitrogen), and cloned into pcDNA3. HEK293 cells were transfected with the KCNH2, Isoform 3.1, and pcDNA3 vector, respectively. The transfected cells were lysed with 250 ul of T-PER protein extraction reagent (Pierce Chemical) with 1% proteinase inhibitor cocktail (Sigma) and phosphatase inhibitor (Sigma). Protein concentrations of homogenates were measured by the BCA protein assay reagent kit (Pierce Chemical, Rockford, Ill.). All samples were diluted with isolation solution to a specific concentration needed and denatured at 950 C for 5 min in protein sample loading buffer (Invitrogen).

Cortex protein extraction: Human dorsolateral prefrontal cortex and hippocampal tissues were homogenized with tissue lysis buffer (Pierce Chemical). Protein concentrations of homogenates were measured by the BCA protein assay reagent kit (Pierce Chemical, Rockford, Ill.).

Immunoprecipitation: Two µg of anti-HERG (N-20) antibody (Santa Cruz Biotechnology, Inc) was mixed with 500 µg of human cortical or hippocampal proteins, and incubated at 40 C on a rotator overnight. After the incubation, 20 µl of gamma protein G beads (Invitrogen) were added, and the mixture was incubated at 4° C. on a rotator for 1 hour. The antigen-antibody-protein G bead complex was precipitated by spinning at 10,000×g, 40 C for 30 seconds. The pellet was rinsed five times with washing buffer. 50 µl of IX sample buffer was added to the pellet and heated at 95° C. for 10 minutes to release the bound hERG proteins. The free hERG proteins were separated from the beads by spinning at 10,000×g for 5 minutes. The supernatant containing the hERG proteins was loaded to a 4-12% gradient polyacrylamide gel for Western blotting with the same antibody.

Western blot analysis: Protein samples were loaded to 4-12% gradient precast mini gel (Invitrogen) and run at 200V for 3 hours in the Tris NuPAGE running buffer. The proteins in the gel were transferred into nitrocellulose membrane in NuPAGE transfer buffer with 10% methanol at 100 V for 1.5 hours. The membrane was blocked with 5% dry milk in Tris-buffered saline (TBS) with 0.1% Tween-20 (TBS-T) and then was incubated with the polyclonal rabbit anti-herg1 antibody (1:1,000 dilution, Chemicon) at 4° C. overnight. The blot was rinsed in TBS-T, incubated in a peroxidase-conjugated goat anti-rabbit antibody (1:1,000 dilution, Santa Cruz) for 2 h in 5% normal goat serum in TBS-T and rinsed in TBS-T. The blot was developed in ECL Plus (Amersham) and was exposed to Kodak BioMax film. Films were digitized using a scanner, and the resulting images were analyzed using NIH image J.

Immunohistochemistry: Cortex was dissected from embryonic day 18 rats, dissociated in Ca and Mg free HBSS containing 0.125% tyrosine for 15 min, triturated in DMEM/10% FBS, then plated on poly-D-lysine coated 12-well plates at 5,000 per coverslip. Cells were grown at 37° C., 5% CO2 and 95% humidity, first in 10% FBS/DMEM, and 1 d later switched to serum-free medium Neurobasal plus B27. After 7 days, the cortical neurons were transfected with KCNH2, Isoform 3.1 in pcDNA3.0 vector or vector only. The transfected cells were then fixed with 4% paraformaldehyde. Slices were double labeled with anti-KCNH2 (hERG) rabbit antibody at 1:200 (Chemicon International). The primary antibodies were applied overnight (4° C.), and then tissues were rinsed in HSPBS. The secondary antibody used was Alexa-488 goat-anti-rabbit IgG applied 1 h at room temperature. Tissues were then rinsed again then mounted with anti-fad mounting medium. Confocal images were obtained using a Zeiss confocal microscope (LSM 510).

Electrophysiology

Cell culture and transient transfection: cDNA for KCNH2-1A and Isoform 3.1 were cloned and subcloned as described above. HEK293T cells were plated at 50% confluency in Dulbecco's Modified Eagle Medium (DMEM) supplemented with 10% fetal bovine serum (FBS). At the time of plating, HEK293T cells were transfected with the KCNH2-1A and Isoform 3.1 cDNA constructs, using Lipofectamine 2000 (Invitrogen), using manufacturer's protocols. pEGFP-Cl (Clontech) DNA was cotransfected for visualization of transfected cells. Cells transfected for 2-4 days were used for electrophysiology. Cortical neurons dissociated from embryonic day 18 (E18) rats were first nucleofected with Isoform 3.1 and EGFP cDNAs according to instruction provided by Amaxa. The cells were plated in DMEM containing 10% FBS at 1 million cells per 35 mm dish, and then transferred to Neurobasal medium supplemented with B27 (Invitrogen), glutamax I (Invitrogen) on the following day. Neurons grown for 11-15 days were used for electrophysiology.

Cell culture protein extraction: HEK293T cells were lysed 48 h after transfection with KCNH2-1A and Isoform 3.1 DNA constructs in RIPA buffer (50 mM Tris-HCl pH 7.4, 150 mM NaCl, 1% NP-40, 0.5% Sodium deoxycholate, 0.1% SDS) supplemented with a protease inhibitor cocktail (Sigma) and a phosphatase inhibitor cocktail (Calbiochem). Protein concentrations were determined by Bradford assay (Bio-Rad). Proteins were resolved by western blot as described above.

Electrophysiological recordings: Transfected HEK293T cells and cortical neurons on coverglass were transferred to a small cell bath mounted on the stage of an inverted microscope (Diaphot, Nikon), identified as GFP-positive under the fluorescence microscope, and superfused with extracellular saline solution containing (in mM): 137 Na-Isethionic acid, 4 K-gluconate, 1.8 $CaCl_2$, 1 $MgCl_2$, 10 HEPES, 10 glucose (pH 7.4 with NaOH). Standard whole-cell recordings were performed at room temperature. The recording pipette was filled with the internal pipette solution containing (in mM) 130 K-gluconate, 1 $MgCl_2$, 5 EGTA, 5 MgATP, 10 HEPES and 0.4 $Na_2GTP$ (pH 7.2 with KOH), and had a resistance of 2-4 MΩ. Data were collected by a patch clamp amplifier (Axopatch 200B) and analyzed by pClamp 9.0 software (Molecular Devices, Sunnyvale, Calif.). After the whole-cell configuration was achieved, series resistance were compensated by 80-90% and monitored periodically. Most cultured cortical neurons had series resistance around 7-8 MΩ (range, 4-13 MΩ). A small percentage of cortical neurons with a resting membrane potential of less than −50 mV, or gradual changes in membrane potential, input resistance or action potential amplitudes, were considered as unhealthy and discarded. Voltage protocols given by pClamp were delivered to the HEK293T cells under voltage-clamp conditions through the patch pipette. The decay of the "tail" currents in HEK cells, attributed to channel deactivation, was fitted by a mono-exponential equation $I_{(t)}=I_1[exp(-t/\tau)]+I_0$, where $I_{(t)}$ is the total current at time t, $I_1$ is the initial amplitude, $\tau$ is the deactivation time constant, and $I_0$ is the non-inactivating residual current. For cortical neurons, a double-exponential equation was used to generate τ1 and τ2. Current-clamp recordings were also performed. A depolarizing current step was injected to induce multiple action potentials. Both spike frequency (number of spikes/sec depolarization) and degree of adaptation (ratio of 1st to last interspike intervals) were calculated.

Example 2

Genetic Variation in KCNH2 Associated with Expression in Brain of a Unique hERG Isoform Modulates Treatment Response in Patients with Schizophrenia Context Antidopaminergic drugs, the only evidence based medical treatments for schizophrenia, bind to HERG1 potassium channels encoded by KCNH2, accounting for their side effect of QT interval prolongation. Recently, risk for schizophrenia has been associated with genetic variation in KCNH2, which also impacts on cognitive function, physiologic engagement of hippocampus and prefrontal cortex during memory, and increased expression of a novel, brain selective isoform KCNH2-3.1 with unique physiologic properties.

Objective

To assess the possibility that genetic variation associated with KCNH2 3.1 may impact the therapeutic effects of antipsychotic drugs.

Design, Setting, and Participants

We evaluated the therapeutic effects of antipsychotic drugs in a pharmacogenetic study of patients with schizophrenia in two independent studies: 1) an NIMH inpatient double blind, placebo-controlled, crossover trial (N=54), and 2) the multicenter, nationwide, outpatient CATIE study (N=364). KCNH2 genotype associated with increased expression of KNCH2 3.1 in brain was treated as a predictor variable.

Main Outcome Measure

Treatment associated changes in PANSS symptom ratings were evaluated in both groups. Time to discontinuation of olanzapine was also considered in the CATIE trial.

Results

In the first study, individuals who were homozygote for the KCNH2 3.1 expression-associated T allele of rs1036145 had highly significant improvement of positive symptoms, general psychopathology and thought disturbance, while patients with other genotypes showed little change. In the second larger study, analogous genotypic effects were observed for positive symptoms and total psychopathology ratings. Analysis of medication discontinuation in the CATIE study showed that individuals who are homozygote for the T allele at rs1036145 were 5-times less likely to discontinue medication.

Conclusion

These consistent findings in two markedly different studies of patients with schizophrenia support the hypothesis that hERG1 mediated effects of antipsychotics may not be limited to their potential cardiovascular side effects but also may involve therapeutic actions related to the brain-specific 3.1 isoform of KCNH2.

Schizophrenia is a complex and heterogeneous psychiatric illness with significant interplay between environmental and genetic components. Among the neurotransmitter systems implicated in this illness, dopamine (DA) has been at the forefront of research for almost fifty years. Both experimental and clinical studies support a role for this neurotransmitter in the pathophysiology of schizophrenia. (Snyder S H. Dopamine hypothesis of schizophrenia-Focus on dopamine receptor. Am. J. Psychiat. 1976; 133(2):197-202; Crow T J, Johnstone E C, Longden A J, Owen F. Dopaminergic mechanisms in schizophrenia-Antipsychotic effect and disease process. Life Sci. 1978; 23(6):563; Grace AA. Phasic versus tonic dopamine release and the modulation of dopamine system responsivity-A hypothesis for the etiology of schizophrenia. Neuroscience. 1991; 41(1):1-24.) In this context, initial studies on the relationship between the potency of antipsychotic medications to block DA receptors and their clinical efficacy represented a milestone in the formulation of the DA hypothesis of schizophrenia and its treatment. (Creese I, Burt D R, Snyder S H. Dopamine receptor-binding predicts clinical and pharmacological potencies of anti-schizophrenic drugs Science. 1976; 192(4238):481-483.) Over the last 60 years, the singular approach for the treatment of schizophrenia is the use of DA receptor (D2 subtype) inhibitors. (Bennett M R. Monoaminergic synapses and schizophrenia: 45 years of neuroleptics. J Psychopharmacol. 1998; 12(3):289-304; Delay J, Deniker P, Ropert R Four years of experience with chlorpromazine in therapy of psychoses. Presse Med. 1956; 64(22):

493-496; Kurland A A. Chlorpromazine in the treatment of schizophrenia; a study of 75 cases. J Nerv Ment Dis. 1955 121(4):321-329.) More recently, the development of so-called atypical antipsychotics with additional serotonin receptor (5-HT2 subtype) blocking properties provided modified therapeutic tools with less motor side effects but with more metabolic effects. (Costall B, Naylor, R J. Detection of the neuroleptic properties of clozapine, sulpiride and thioridazine. Psychopharmacologia. 1975; 43(1):69-74; Komossa K, C. Rummel-Kluge, et al. Risperidone versus other atypical antipsychotics for schizophrenia. Cochrane Database of Systematic Reviews. 2011; 1; Newcomer J W. Second-generation (atypical) antipsychotics and metabolic effects—A comprehensive literature review. CNS Drugs. 2005; 19:1-93.) While the newer drugs are better tolerated and effectively reduce positive symptoms, they rarely induce recovery. This unfortunate reality is not different from the older typical antipsychotics, indicating that neither the old nor the new antipsychotic medications are specific enough to address the complex pathophysiology of the disease.

One of the variable limitations of antipsychotic medications is prolongation of the QT interval (long QT syndrome [LQT]) and increased rates of sudden death, potentially related to this side effect. (Recanatini M, Poluzzi E, Masetti M, Cavalli A, De Ponti F. QT prolongation through hERG K+ channel blockade: Current knowledge and strategies for the early prediction during drug development. Med. Res. Rev. March 2005; 25(2):133-166.) The QT prolongation associated with antipsychotic drugs results from the blockade of the human ether-a-go-go-related potassium channel (hERG1) in the heart. (Kongsamut S, Kang J S, Chen X L, Roehr J, Rampe D. A comparison of the receptor binding and HERG channel affinities for a series of antipsychotic drugs. Eur J. Pharmacol. August 2002; 450(1):37-41; Shepard P D, Canavier C C, Levitan E S. Ether-a-go-go-Related gene potassium channels: What's all the buzz about? Schizophr. Bull. November 2007; 33(6):1263-1269.) hERG1, along with hERG2 and hERG3 (Gutman G, Chandy K G, Grissmer S, Lazdunski M, McKinnon D, Pardo L A, Robertson G A, Rudy B, Sanguinetti M C, Stühmer W, Wang X. International Union of Pharmacology. LIII. Nomenclature and molecular relationships of voltage-gated potassium channels. Pharmacol Rev. 2005 2005; 12(91):473-508), belong to a subfamily of voltage-gated K+ channels (Warmke J W, Ganetzky B. A family of potassium channel genes related to EAG in *drosophila* and mammals. P Natl Acad Sci USA. April 1994; 91(8):3438-3442) that plays a critical role in regulating excitability and repolarization in cardiac and smooth muscle, as well as in neurons. (Schwarz J R, Bauer C K. Functions of erg K+ channels in excitable cells. Journal of Cellular and Molecular Medicine. January-March 2004; 8(1):22-30.) The hERG1 channel is responsible for the delayed rectifier potassium current (IKr), a major component of cardiac repolarization. (Schwarz J R, Bauer C K. Functions of erg K+ channels in excitable cells. Journal of Cellular and Molecular Medicine. January-March 2004; 8(1):22-30; Wehrens X. Structural determinants of potassium channel blockade and drug-induced arrhythmias. Handb Exp Pharmacol. 2006; 171:123-157.) The hERG1 channel displays a tetrameric structure with one α-subunit with six transmembrane spanning domains and one auxiliary beta subunit with one transmembrane spanning domain (Phartiyal P, Jones E M C, Robertson G A. Heteromeric assembly of human ether-a-go-go-related gene (hERG) 1a/1b channels occurs cotranslationally via N-terminal interactions. J Biol Chem. March 2007; 282(13):9874-9882.) The assemblage of the different hERG channels gives rise to a supramolecular structure that serves as the voltage-gated K+ channel. (Perry M, Sachse F B, Sanguinetti M C. Structural basis of action for a human ether-a-go-go-related gene 1 potassium channel activator. P Natl Acad Sci USA. August 2007; 104(34):13827-13832.) The hERG1 protein is encoded by the KCNH2 gene which contains 15 exons on chromosome 7q36.1 and produces at least three distinct isoforms by alternative splicing. Studies have identified over 300 genetic variants in KCNH2 that can either cause a congenital form of LQT syndrome or predispose to acquired LQT syndromes. (Thomas D, Karle C A, Kiehn J. The cardiac hERG/IKr potassium channel as pharmacological target: structure, function, regulation, and clinical applications. Curr Pharm Des. 2006; 12(18):2271-2283; Witchel H. The hERG potassium channel as a therapeutic target. Expert Opin Ther Targets. 2007; 11(3):321-336.) Blockade of hERG1 channels by antipsychotics may represent the most frequent cause of the acquired LQT syndrome. (Perrin M, Subbiah R N, Vandenberg J I, Hill A P. Human ether-a-go-go related gene (hERG) K+ channels: function and dysfunction. Prog Biophys Mol Biol. 2008; 98(2-3):137-148.)

Using mRNA characterization techniques in human postmortem brain samples, Huffaker et al. identified a brain-selective and primate-specific isoform (3.1) of the KCNH2 gene that regulates neuronal firing patterns. When compared with the full-length KCNH2 (1A) isoform, KCNH2-3.1 messenger RNA levels are similar in the brain but 3-orders of magnitude lower in the heart. This novel isoform has a novel 5' exon extension and is lacking the PAS domain of the full length protein that is critical for slow channel deactivation and repolarization. Meta-analysis of five independent clinical data sets showed an association of single nucleotide polymorphisms (SNPs) in KCNH2 with schizophrenia and the risk associated alleles predicted lower intelligence quotient (IQ) scores and reduced speed of cognitive processing in living human subjects. (Huffaker S J, Chen J S, Nicodemus K K, et al. A primate-specific, brain isoform of KCNH2 affects cortical physiology, cognition, neuronal repolarization and risk of schizophrenia. Nat. Med. May 2009; 15(5):509-518.) The same risk-associated alleles also predicted increased KCNH2.3.1 mRNA expression in postmortem hippocampus of both patients and healthy subjects, implicating a molecular mechanism of the clinical associations. Moreover, in postmortem brain of patients with schizophrenia, the relative expression of the novel 3.1 isoform was increased 2.5 fold compared with normal brain, suggesting a potential pathophysiologic role of KCNH2 3.1 in the clinical state. This primate-specific isoform of KCNH2 was shown to have unique physiological properties in neuronal culture, mediating fast neuronal spiking. Two recent studies have further confirmed the association of the same SNPs in KCNH2 with schizophrenia. (Atalar F, Acuner T T, Cine N, et al. Two four-marker haplotypes on 7q36.1 region indicate that the potassium channel gene HERG1 (KCNH2, Kv1 1.1) is related to schizophrenia: a case control study. Behav. Brain Funct. May 2010; 6(27); Hashimoto R, Ohi K, Yasuda Y, et al. The KCNH2 gene is associated with neurocognition and the risk of schizophrenia. The World Journal of Biological Psychiatry. 2011; In Press.) While it is not known whether antipsychotic drugs affect the brain-specific KCNH2 3.1 channel as they do the full-length channel, the fact that antipsychotic drugs have hERG1 effects and KCNH2 3.1 is genetically associated with schizophrenia at both the clinical and molecular level, raises the possibility that the therapeutic effects of antipsychotic drugs may at least in part relate to changes in KCNH2 3.1 activity.

In this study we have evaluated the impact of genetic variation in KCNH2, which was previously associated with risk for schizophrenia and with increased expression of the 3.1 isoform in postmortem brain, in two independent clinical trials of antipsychotic medications in patients with schizophrenia: 1) a group of patients admitted to NIMH to participate in a double blind, placebo-controlled, crossover study, and b) a sample of patients with schizophrenia who participated in the NIMH sponsored multi-center CATIE trial. The hypothesis of this pharmacogenetic study is that KCNH2 genotype related to risk for schizophrenia and expression of the brain-selective and primate-specific isoform 3.1 of KCNH2 impacts treatment response to antipsychotic drugs. The results of both independent trials support this hypothesis.

Methods

Patients

Two independent cohorts of patients undergoing antipsychotic treatment trials were included in this study. The first cohort consisted of 54 partially treatment-resistant patients with schizophrenia admitted to the Clinical Brain Disorders Branch schizophrenia research inpatient unit at the NIMH Clinical Center between 1998 and 2010. All of these subjects were self-reported Caucasian of European ancestry and were diagnosed with chronic schizophrenia using DSM-IV criteria. (Task Force on DSM-IV. Diagnostic and Statistical Manual of Mental Disorders. Fourth ed. Washington, D.C.: American Psychiatric Association; 2005.) They volunteered to participate in a double-blind, placebo-controlled, crossover study with standard doses of atypical antipsychotics, including olanzapine, perphenazine, quetiapine, risperidone, or ziprasidone. All patients, and a family member if necessary, provided informed consent for participation in the study, which was approved by the NIH Institutional Review Board. The program typically enrolled patients who already had adequate trials of standard antipsychotic medication interventions but were only partially effective in decreasing their symptoms. Upon admission, all patients underwent medical, neurological, and psychiatric evaluation lasting four to twelve weeks. If it was then concluded that the patient had significant medical problems, a history of violence or suicidal behavior not identified during the pre-hospitalization screening, or if the patient decided to withdraw his/her consent, he/she could leave the hospital or participate in other protocols not involving placebo studies. The demographic characteristics of the patients are shown in Table 12.

All patients included in this study were on atypical antipsychotic medications prior to their admission. After the initial evaluation period, patients were maintained on a standard dose of one atypical antipsychotic and all other medications were discontinued. The decision about which antipsychotic medication would be used in the coded study was based on best prior response, patient preference, and side effect profile. The patients then remained on the single antipsychotic medication in an open-label fashion for several weeks before transitioning to coded medication and were tapered from their medication over a period of four to seven days. Subgroup 1 (N=35) received sequentially four weeks of coded placebo followed by four weeks of coded standard atypical antipsychotics. Subgroup 2 (N=19) received the inverse sequence, i.e. after a similar open medication and taper period they received standard antipsychotic treatment for four weeks followed by placebo for four weeks. Because of the highly supervised and structured nature of the NIMH inpatient environment, most patients tolerated the four weeks of placebo well. At the end of the coded double-blind protocol, the patients were restarted on an active medication for six or more weeks before starting another experimental protocol, or until they were well enough to be discharged.

Weekly rating on the 16-item Positive and Negative Syndrome Scale (PANSS) (Kay S R, Fiszbein A, Opler L A. The positive and negative syndrome scale (PANSS) for schizophrenia. Schizophr. Bull. 1987; 13(2):261-276) was performed independently by one of four trained research nurses. Two weeks prior to starting the double blind protocol and up to four weeks after completing the protocol, ratings were performed twice a week. The PANSS is a 7-point rating scale (1-7), with one indicating the absence of a symptom or behavior and seven indicating greatest severity of illness. The PANSS items comprise three different scales, which include Positive Syndrome, Negative Syndrome and General Psychopathology, and five different clusters comprised of Anergia, Thought Disturbance, Activation, Paranoid/Belligerence and Depression. Mean PANSS baseline ratings in the NIMH study before entering the placebo-controlled protocol were: Positive Syndrome: 14.25+4.09, Negative Syndrome: 15.69+4.6, General Psychopathology: 29.58+5.81, Anergia: 8.48+2.23, Thought Disturbance: 8.36+3.61, Activation: 5.08+1.31, Paranoid/Belligerence: 4.89+0.85 and Depression: 8.40+2.18.

The second cohort consisted of patients randomly assigned to five medications during the Phase 1/1A (first drug assigned) of the Clinical Antipsychotic Trials of Intervention Effectiveness (CATIE), (Stroup T S, McEvoy J P, Swartz M S, et al. The National Institute of Mental Health Clinical Antipsychotic Trials of Intervention Effectiveness (CATIE) project: Schizophrenia trial design and protocol development. Schizophr. Bull. 2003; 29(1):15-31) a clinical trial to compare the effectiveness of antipsychotic drugs. The demographic characteristics of the patients in the CATIE cohort are shown in Table 13. Patients were initially randomly assigned to receive olanzapine, perphenazine, quetiapine, risperidone or ziprasidone under double-blind conditions and followed up for 18 months or until treatment was discontinued or switched to another antipsychotic (i.e. Phase 2). Eligible patients were 18 to 65 years of age, had received a diagnosis of schizophrenia based on DSM-IV criteria 26 and were able to take oral antipsychotic medication. The primary outcome measure in the CATIE sample was time to medication discontinuation, most often due to lack of efficacy or side-effects. PANSS ratings were included as a secondary efficacy outcome. Details on the CATIE trial methods have been previously published. (Stroup T S, McEvoy J P, Swartz M S, et al. The National Institute of Mental Health Clinical Antipsychotic Trials of Intervention Effectiveness (CATIE) project: Schizophrenia trial design and protocol development. Schizophr. Bull. 2003; 29(1):15-31.) For consistency with the NIMH inpatient study and to reduce effects of genetic heterogeneity, only Caucasian subjects were included for analysis. Because of the outpatient and parallel design of this study, information about compliance based on drug clearance is an important factor determining symptom change during the CATIE trial. (Bigos K L, Pollock B G, Coley K C, et al. Sex, race, and smoking impact olanzapine exposure. Journal of Clinical Pharmacology. 2008; 48(2):157-165; Bigos K L, Bies R R, Pollock B G, Lowy J J, Zhang F, Weinberger D R.

Genetic Variation in CYP3A43 Explains Racial Difference in Olanzapine Clearance. Molecular Psychiatry. In Press.) Thus, we only analyzed treatment response from subjects on whom we had drug clearance data (N=364) (Bigos K L, Pollock B G, Coley K C, et al. Sex, race, and smoking impact olanzapine exposure. Journal of Clinical Pharmacology. 2008; 48(2): 157-165). Drug clearance was estimated using population pharmacokinetic modeling of drug concentrations and used in the statistical analysis of treatment response as previously described. (Bigos K L, Pollock B G, Coley K C, et al. Sex, race, and smoking impact olanzapine exposure. Journal of Clinical Pharmacology. 2008; 48(2):157-165. Bigos K L, Bies R R, Pollock B G, Lowy J J, Zhang F, Weinberger D R. Genetic Variation in CYP3A43 Explains Racial Difference in Olanzapine Clearance. Molecular Psychiatry. In Press.)

Genotyping

We genotyped three SNPs rs3900779, rs748693 and rs1036145 in KCNH2 which have been associated with schizophrenia and with expression of the novel KCNH2 3.1 isoform in human post-mortem brain. (Huffaker S J, Chen J S, Nicodemus K K, et al. A primate-specific, brain isoform of KCNH2 affects cortical physiology, cognition, neuronal repolarization and risk of schizophrenia. Nat. Med. May 2009; 15(5):509-518.) Genotypes were determined using the 5'-exonuclease fluorescent Taqman assay (assay by design or assay on demand) and the allelic discrimination was read on an ABI 7900 SDS system (Applied Biosystems, Foster City, Calif.). (Livak K J. Allelic discrimination using fluorogenic probes and the 5' nuclease assay. Genet. Anal.-Biomol. Eng. February 1999; 14(5-6):143-149.)

Statistical Analysis

Several statistical analyses were performed based on the specifics of study design and measurement of outcomes. In the NIMH inpatient study (cohort 1), which is a within-subject crossover design with repeated measures, with some discontinuation due to clinical decompensation, we employed a linear mixed-effect model to examine the effects of treatment, genotype, and their interaction on PANSS ratings. In the CATIE sample (cohort 2), a general linear model was used to examine the association of KCNH2 genotype with change (first-last evaluation) in PANSS ratings while controlling for covariates such as age, sex, drug clearance, medications, time from the first evaluation to the last evaluation. Because the mean and variations of drug clearance measure varied with drugs, we assigned an ordinal measure of 1 to 4 according to the quartile distribution of each drug clearance to make the measurement of clearance comparable between drugs.

We also attempted to examine time to discontinuation of medication, which was a primary outcome measure of the CATIE trial. Time to discontinuation in the CATIE trial, however, is a problematic measure in a pharmacogenetic analysis of treatment response, because it was confounded by many issues, including side effects, patient preference and other subjective individual considerations. Patients in the CATIE trial were allowed to stop medication for literally any reason at any time. An illustration of the uncertainties inherent in time to discontinuation is that it was not predicted by drug clearance rate, which did predict symptom change during treatment (Bigos K L, Pollock B G, Coley K C, et al. Sex, race, and smoking impact olanzapine exposure. Journal of Clinical Pharmacology. 2008; 48(2):157-165; Bigos K, Bies R R, Pollock B G, Lowy J J, Zhang F, Weinberger D R. Molecular Psychiatry. Genetic Variation in CYP3A43 Explains Racial Difference in Olanzapine Clearance. In Press. 2011). In addition, the various drug arms differed substantially in reasons for discontinuation and time to discontinuation for whatever reason. Nevertheless, we assessed genotype effect on time to discontinuation in the olanzapine response data. Olanzapine had the longest time to discontinuation in the study and the least number of discontinuations for reasons other than efficacy; thus, time to discontinuation of olanzapine may better reflect variable efficacy, per se. Furthermore, we had previously meticulously curated the olanzapine data to exclude noncompliant subjects and subjects receiving other medications as part of the clearance determinations. The Cox proportional hazard model was used to analyze the time to discontinuation data while controlling for age, sex, and drug clearance.

Results

Demographics of the NIMH sample are shown in Table 12 based on rs1036145 genotype, a SNP showing effects on treatment in this sample. Age at admission (p<0.032) and duration of illness (p<0.001) were statistically different by genotype groups.

TABLE 12

Demographics of patients in the NIMH cohort by KCNH2 genotype at rs1036145

| | CC | TC | TT | Genotype p value |
|---|---|---|---|---|
| N (M/F)# | 16 (15/1) | 28 (16/12) | 10 (9/1) | 0.014* |
| Age, years | 26.6 ± 5.45 | 26.6 ± 6.01 | 32.8 ± 9.07 | 0.032* |
| FSIQ | 88.1 ± 13.91 | 95.6 ± 13.45 | 89.5 ± 12.52 | 0.175 |
| Education, years | 13.75 ± 2.41 | 13.79 ± 1.71 | 13.60 ± 1.58 | 0.966 |
| Age of onset, years | 22.1 ± 4.95 | 20.7 ± 4.83 | 19.7 ± 2.54 | 0.390 |
| Duration of illness, years | 4.8 ± 3.54 | 6.5 ± 5.00 | 13.5 ± 9.16 | 0.001* |
| Smokers/Nonsmokers# | 8/8 | 12/16 | 7/3 | 0.051 |

Values represent the mean ± standard deviation.
Fisher extact test p value

The genotype groups differed slightly in gender proportions and in frequency of smokers. None of these effects can account for the genotype effects on outcome variables, as described below. No significant differences by genotype groups were observed for IQ, years of education and prestudy antipsychotic dose in CPZ equivalents. Demographics of the CATIE sample by KCNH2 genotype of rs1036145 are shown in Table 13. No significant differences were observed for mean CPZ equivalents, education, and age of onset or duration of illness. Smoking status did not differ by genotypes.

TABLE 13

Summary statistics in CATIE sample of European ancestry by genotype of rs1036145

| Variable | Total | | Missing | | | CC | | | TC | | | TT | | | p |
|---|---|---|---|---|---|---|---|---|---|---|---|---|---|---|---|
| | N | Mean | Std Dev | N | Mean | Std Dev | N | Mean | Std Dev | N | Mean | Std Dev | N | Mean | Std Dev | |
| Male % | 364 | 0.777 | | 6 | 7.550 | | 115 | 0.772 | | 123 | 0.783 | | 39 | 0.780 | | 0.955 |
| Smoking % | 364 | 0.360 | | 5 | 0.625 | | 94 | 0.631 | | 103 | 0.656 | | 31 | 0.580 | | 0.218 |
| Alcohol use % | 364 | 0.637 | | 4 | 0.500 | | 45 | 0.302 | | 62 | 0.395 | | 21 | 0.380 | | 0.992 |
| MEAN_CPZEQ | 364 | 478.20 | 168.21 | 8 | 410.61 | 109.3 | 149 | 479.2 | 169.3 | 157 | 487.0 | 158.7 | 50 | 458.40 | 199.44 | 0.492 |
| CPZEQ first dose | 361 | 378.53 | 160.06 | 8 | 330.00 | 91.8 | 146 | 371.9 | 163.6 | 157 | 391.3 | 147.0 | 50 | 365.50 | 194.42 | 0.511 |
| CPZEQ last dose | 356 | 520.90 | 190.46 | 8 | 448.75 | 132.5 | 146 | 522.4 | 189.2 | 154 | 532.3 | 185.5 | 48 | 491.67 | 216.04 | 0.418 |
| Education (years) | 363 | 12.34 | 2.20 | 8 | 11.75 | 1.3 | 148 | 12.2 | 2.2 | 157 | 12.5 | 2.2 | 50 | 12.26 | 2.32 | 0.599 |
| AOO (years) | 349 | 26.48 | 9.16 | 7 | 27.00 | 7.6 | 144 | 26.5 | 9.8 | 150 | 26.5 | 8.9 | 48 | 26.27 | 8.48 | 0.997 |
| Baseline PANSS rating | 363 | 72.68 | 17.53 | 8 | 70.88 | 16.1 | 149 | 71.6 | 17.2 | 157 | 73.8 | 18.2 | 49 | 72.63 | 16.76 | 0.544 |
| Age (years) | 364 | 41.55 | 11.42 | 8 | 36.13 | 9.3 | 149 | 42.0 | 11.4 | 157 | 41.3 | 11.6 | 50 | 41.94 | 11.13 | 0.531 |
| Age 1st treated for emotion/behavioral | 350 | 23.83 | 9.08 | 7 | 26.29 | 9.6 | 145 | 24.3 | 9.3 | 152 | 23.1 | 9.0 | 46 | 24.50 | 8.81 | 0.531 |

In the NIMH inpatient study, a significant effect of antipsychotic treatment on psychopathology ratings was observed in different scales and clusters of the PANSS (Table 14). Overall, medications had a significant impact on alleviation of positive symptoms (Beta=−1.356, p=0.0007) and general psychopathology (Beta=−2.285, p=0.0093), and a trend towards decreased negative symptoms was also observed (Beta=−1.084, p=0.0124) that did not survive correction for multiple testing. Analysis of the PANSS clusters also revealed significant changes in thought disturbance (Beta=−0.893, p=0.0004) and activation (Beta=−0.684, p=0.0018).

TABLE 14

Treatment Effect on Neuropsychiatric Symptoms from general linear mixed model (coded ARM1 and ARM2)

| Effect | Beta | SE | t | P | |
|---|---|---|---|---|---|
| Negative syndrome | −1.0836 | 0.4204 | −2.58 | 0.0124 | |
| Positive syndrome | −1.3565 | 0.3798 | −3.57 | 0.0007 | ** |
| Composite index | −0.2667 | 0.3806 | −0.7 | 0.4861 | |
| General Psychopathology | −2.2851 | 0.8507 | −2.69 | 0.0093 | ** |
| Anergia | −0.3037 | 0.2398 | −1.27 | 0.2102 | |
| Thought disturbance | −0.8928 | 0.2383 | −3.75 | 0.0004 | ** |
| Activation | −0.6841 | 0.21 | −3.26 | 0.0018 | ** |
| Paranoid belligerence | −0.268 | 0.1474 | −1.82 | 0.0742 | |
| Depression | −0.4189 | 0.3173 | −1.32 | 0.1918 | |

Note:
Beta: coefficient estimates; SE: standard error of coefficient estimate.

rs1036145 genotype showed a significant effect on treatment outcome (Table 15). Individuals with the TT genotype had a better response to antipsychotic treatment. Specifically, individuals who were homozygote of the risk and isoform 3.1 expression associated T allele (i.e. genotype TT) had a significant reduction in ratings of positive syndrome (Beta=−2.84, p=0.0078), general psychopathology (Beta=−6.23, p=0.022) and thought disturbance (Beta=−2.08, p=0.0041) when they were on medications; whereas individuals carrying other genotypes (CC+TC) had relatively little change in the same PANSS ratings (Table 15). The effect size of TT genotype on treatment was much larger than for genotypes CC+TC. The ratio of effect size for TT compared with TC+CC genotypes was 1.65 (0.42/0.25) for the positive syndrome, 1.88 (0.339/0.180) for general psychopathology and 1.84 (0.458/0/249). There were no significant effects of the other two SNPs (rs3900779 and rs748693) on the change in PANSS scores in the NIMH cohort.

TABLE 15

Mean differences in antipsychotic treatment response by genotypes of rs1036145

| Symptoms | Group 1 | | Group2 | | Beta | SE | P | | Effect size |
|---|---|---|---|---|---|---|---|---|---|
| | Treatment | Genotype | Treatment | Genotype | | | | | |
| Positive symptom | Medication | CC + TC | Placebo | CC + TC | −0.73 | 0.44 | 0.1042 | | 0.254 |
| | Medication | TT | Placebo | TT | −2.84 | 1.02 | 0.0078 | *** | 0.420 |
| General psychopathology | Medication | CC + TC | Placebo | CC + TC | −1.39 | 1.15 | 0.2336 | | 0.180 |
| | Medication | TT | Placebo | TT | −6.23 | 2.63 | 0.022 | ** | 0.339 |
| Thought disturbance | Medication | CC + TC | Placebo | CC + TC | −0.48 | 0.3 | 0.1117 | | 0.249 |
| | Medication | TT | Placebo | TT | −2.08 | 0.69 | 0.0041 | *** | 0.458 |

Note:
Beta is mean difference in PANSS ratings based on least-square estimation

Similar genotypic effects on PANSS ratings were also observed in the larger CATIE cohort for each of the genotyped SNPs (Table 16). The change in total PANSS score was associated with all three SNPs: rs390079 (p=0.0236), rs748693 (p=0.0213) and rs1036145 (p=0.012). Compared with homozygotes of the risk allele, the change in total PANSS score was less for genotype GT (Beta=−5,335, p=0.0173) and GG (Beta=−1.884, p=0.3908) at rs390079; for AG (Beta=−4.813, p=0.0286) and AA (Beta=−1.033, p=0.645) at rs748693; and for CT (Beta=−5,186, p=0.0192) and CC(Beta=−1.082, p=0.6266) at rs1036145 (Table 16). The change in PANSS positive symptoms also significantly varied with rs390079 (p=0.0327), rs748693 (p=0.0223) and rs1036145 (p=0.0046) genotypes; and similarly, the change in PANSS rating was greater for individuals homozygote for the risk associated alleles at all three SNPs compared with other genotypes. We did not observe significant associations of the change in negative symptoms with any SNP.

This study provides strong and consistent evidence of an association between variation in KCNH2 and short- and long-term clinical response to antipsychotic drugs in patients with schizophrenia. In fact, in two different treatment cohorts ascertained and examined with notably differing approaches, KCNH2 genotype previously associated with schizophrenia and with expression of a brain-selective isoform of this potassium channel modulated the therapeutic effects of antipsychotic drugs.

KCNH2 genotype (rs1036145) had a significant impact on the response to antipsychotic treatment in the NIMH cohort in two separate groups (i.e. those receiving placebo first, and those receiving active drug first). Interestingly, patients who were homozygous for the risk-associated allele (TT genotype) showed a greater change in positive symptoms, thought disturbance and general psychopathology when compared with carriers of the C allele. This strong effect of genotype, which remained significant after correction for multiple test-

TABLE 16

Effect of SNPs in KCNH2 on the change in PANSS rating in the CATIE trial

| | Positive symptom | | | | Negative symptom | | | | Total PANSS score | | | |
|---|---|---|---|---|---|---|---|---|---|---|---|---|
| | Beta | t | p | P* | Beta | t | p | P | Beta | t | P | P* |
| rs3900779 | | | | 0.03 | | | | 0.2365 | | | | 0.0236 |
| GG | −0.394 | −0.54 | 0.5901 | | −0.05 | −0.06 | 0.9495 | | −1.884 | −0.86 | 0.3908 | |
| GT | −1.59 | −2.13 | 0.0336 | | −0.92 | −1.19 | 0.2359 | | −5.335 | −2.39 | 0.0173 | |
| TT | 0 | — | — | | 0 | — | — | | 0 | — | — | |
| rs748693 | | | | 0.02 | | | | 0.3082 | | | | 0.0213 |
| AA | 0.053 | 0.07 | 0.9434 | | 0.08 | 0.1 | 0.9221 | | −1.033 | −0.46 | 0.6425 | |
| AG | −1.334 | −1.82 | 0.0696 | | −0.73 | −0.96 | 0.3382 | | −4.813 | −2.2 | 0.0286 | |
| GG | 0 | — | — | | 0 | — | — | | 0 | — | — | |
| rs1036145 | | | | 0 | | | | 0.1747 | | | | 0.012 |
| CC | 0.294 | 0.4 | 0.689 | | −0.05 | −0.07 | 0.9475 | | −1.082 | −0.49 | 0.6266 | |
| CT | −1.402 | −1.92 | 0.0559 | | −1.01 | −1.31 | 0.1916 | | −5.186 | −2.35 | 0.0192 | |
| TT | 0 | — | — | | 0 | — | — | | 0 | — | — | |

Note:
P* is p value from testing for association of genotype with change in PANSS rating;
Beta is estimate of genotype effect (0 for reference group)

Analysis of the time to discontinuation of olanzapine in the CATIE sample (n=89) also indicated that SNPs in KCNH2 affected this measure of response to antipsychotic treatment (Table 17). While we observed trends for genotypic variation in overall time to discontinuation of medication at rs748693 (p=0.0781) and rs1036145 (p=0.0633), compared with non-risk allele homozygote individuals, individuals with GG genotype at rs748693 were nearly 4 times (HR=0.254, p=0.031), and TT genotypes at rs1036145 were nearly 5 times (HR=0.208, p=0.033) less likely to have discontinued medication.

ing and covarying for age, sex and IQ, is remarkable considering the relatively small sample size of this cohort and the variation in the protocol sequence of the two groups.

The pharmacogenetic associations and their directionality were confirmed and further extended in the analysis of the larger CATIE trial cohort. Interestingly, the significant changes in positive symptoms and general psychopathology were observed in the homozygous risk associated alleles at all three SNPs: rs3900779-TT, rs748693-GG and rs1036145-TT, the latter showing the strongest statistical significance in line with the results obtained in the smaller NIMH cohort. The

TABLE 17

Hazard ratio estimates of three SNPs in KCNH2 from the COX proportional hazard model (Olanzapine; n = 89, event = 46)

| | Est | Se | Chi-square | p | | HR | DF | Chi-Square | P |
|---|---|---|---|---|---|---|---|---|---|
| rs3900779 | 0 | | | | | 1 | 2 | 2.4947 | 0.2873 |
| | −0.431 | 0.344 | 1.567 | 0.211 | | 0.65 | | | |
| | −0.688 | 0.536 | 1.646 | 0.2 | | 0.503 | | | |
| rs748693 | 0 | | | | | 1 | 2 | 5.0986 | 0.0781 |
| | −0.119 | 0.352 | 0.115 | 0.735 | | 0.888 | | | |
| | −1.371 | 0.634 | 4.683 | 0.031 | * | 0.254 | | | |
| rs1036145 | 0 | | | | | 1 | 2 | 5.5206 | 0.0633 |
| | −0.06 | 0.397 | 0.023 | 0.88 | | 0.942 | | | |
| | −1.569 | 0.736 | 4.546 | 0.033 | * | 0.208 | | | | impact of this replication in two independent cohorts is underscored by the fact that these trials were performed with two different clinical and experimental models, one that involved an outpatient, parallel cohort design while the other was a double blind, placebo-controlled, in-patient crossover, as well as different outcome measures. The effect size of the association also is noteworthy. In the placebo controlled NIMH inpatient study, individuals homozygote for the risk allele showed almost twice the effect size of response change compared with the other genotype groups. In the CATIE trial, individuals with the risk genotypes showed a four to five times lesser likelihood of discontinuing olanzapine, a primary outcome measure of the trial.

In both the NIMH and the CATIE samples, individuals with risk-associated genotypes, which predict increased expression of the novel, brain- and primate-specific isoform of KCNH2, responded better to antipsychotic drug therapy. In other words, the greater the putative expression of the novel isoform, the larger the therapeutic response. It is tempting to conclude that our pharmacogenetic results reflect the ability of typical and atypical antipsychotics to bind to this novel KNCH2 potassium channel and that their therapeutic effects are at least in part related to this effect. (Kongsamut S, Kang J S, Chen X L, Roehr J, Rampe D. A comparison of the receptor binding and HERG channel affinities for a series of antipsychotic drugs. Eur J Pharmacol. August 2002; 450(1): 37-41; Shepard P D, Canavier C C, Levitan E S. Ether-a-go-go-Related gene potassium channels: What's all the buzz about? Schizophr. Bull. November 2007; 33(6):1263-1269.) This conclusion, however, must be viewed with caution. Clearly, many drugs bind to hERG channels, and only few of them are antipsychotic. hERG channels are heterodimers of various hERG components and the combinations of full length and 3.1 isoform channels may be critical for understanding the action in brain of varying effects of KCNH2 active drugs. Moreover, if the antipsychotic effect of drugs is selectively related to their modulation of channels containing 3.1 isoforms, then drugs that impact only 3.1-lacking hERG channels might not be antipsychotic. It is also worth noting that the physiological effect of the 3.1 isoform as described in Huffaker et al (2009) suggests that the optimum therapeutic effect would not be channel blockade per se, but restoration of normal KCNH2 potassium conductance kinetics. Whether antipsychotic drugs act in part by this mechanism is also not known.

An alternative, indirect mechanism for the relationship of KCNH2 genotype and antipsychotic drug response might also be considered. Since hERG1 channels are expressed on DA neurons, it is conceivable that their relationship to antipsychotic drug action is via an indirect mechanism related to the firing characteristics of these neurons. If DA neurons are overactive in psychotic patients, as is implicated from in vivo imaging studies (Laruelle M, Abi-Dargham A, Gil R, Kegeles L, Innis R. Increased dopamine transmission in schizophrenia: Relationship to illness phases. Biological Psychiatry. July 1999; 46(1):56-72; Abi-Dargham A, Gil R, Krystal J, et al. Increased striatal dopamine transmission in schizophrenia: Confirmation in a second cohort. Am. J. Psychiat. June 1998; 155(6):761-767), increased KCNH2.3.1 expression may at least in part drive this over activity, which is compensated by postsynaptic blockade of D2 receptors. By either mechanism, our results raise intriguing questions for further work and for the potential of KCNH2 3.1 selective drugs to be novel antipsychotic therapies.

Each of the clinical trials in this report has limitations. The NIMH study involved a relatively small number of patients. However, it was a double-blind, placebo-controlled, crossover design in a stable, inpatient population with chronic, unremitting schizophrenia in which medication intake is strictly monitored by experienced nursing staff in a highly structured research environment. A limitation of the CATIE cohort is the relatively uncontrolled outpatient nature of the study in which no stringent control existed for medication compliance. This problem was addressed by determination of antipsychotic medication levels and only those individuals in whom drug level was sufficient to determine plasma clearance rates were included in this analysis.

One of the main concerns related to the pharmacological action of antipsychotic drugs has been the inconsistent therapeutic response observed between individuals. This may represent one of the reasons why some individuals discontinue medications earlier than others due to the limited efficacy of the drugs. (Lieberman J A, Stroup T S, McEvoy J P, et al. Effectiveness of antipsychotic drugs in patients with chronic schizophrenia. N. Engl. J. Med. September 2005; 353(12): 1209-1223.) While there are likely many factors relating to this variable treatment response, our data suggest that KCNH2 genotype is one important factor. Moreover, our findings support the hypothesis that KCNH2 activity of antipsychotics may be connected not only with their potential cardiovascular side effects 36 but also with their therapeutic actions involving the brain-selective 3.1 isoform of KCNH2. (Huffaker S J, Chen J S, Nicodemus K K, et al. A primate-specific, brain isoform of KCNH2 affects cortical physiology, cognition, neuronal repolarization and risk of schizophrenia. Nat. Med. May 2009; 15(5):509-518; Atalar F, Acuner T T, Cine N, et al. Two four-marker haplotypes on 7q36.1 region indicate that the potassium channel gene HERG1 (KCNH2, Kv11.1) is related to schizophrenia: a case control study. Behav. Brain Funct. May 2010; 6(27)).

While the present invention has been described in some detail for purposes of clarity and understanding, one skilled in the art will appreciate that various changes in form and detail can be made without departing from the true scope of the invention. All figures, tables, and appendices, as well as patents, applications, and publications, referred to above, are hereby incorporated by reference.

What is claimed is:

1. A method for predicting the clinical response of a human schizophrenic patient to an antipsychotic medication comprising:
    obtaining a biological sample from a patient diagnosed with schizophrenia, said sample comprising nucleic acids from the patient;
    detecting in said nucleic acids the presence of a T/T genotype at the rs1036145 single nucleotide polymorphism wherein said detecting is performed by contacting said nucleic acids with a fluorogenic DNA probe and a DNA polymerase having 5'-exonuclease activity using polymerase chain reaction (PCR); and
    correlating the presence of said T/T genotype with an increased likelihood for said patient to have a beneficial clinical response to an antipsychotic medication.

2. The method of claim 1, wherein the antipsychotic medication is an atypical antipsychotic medication selected from the group consisting of olanzapine, perphenazine, quetiapine, risperidone, and ziprasidone.

3. The method of claim 1, wherein the benefit is selected from a significant reduction in ratings of positive syndrome, significant improvement in general psychopathology, and significant decrease in thought disturbance.

4. The method of claim 1, wherein the biological sample is a sample of biological fluid or a tissue sample.

5. The methods of claim 4, wherein the sample is selected from the group consisting of blood, tears, urine, saliva, skin, muscle and lymph tissue.

* * * * *

SEQUENCE LISTING

<160> NUMBER OF SEQ ID NOS: 28

<210> SEQ ID NO 1
<211> LENGTH: 3897
<212> TYPE: DNA
<213> ORGANISM: Homo sapiens

<400> SEQUENCE: 1
ccatgggctc aggatgccgg tgcggagggg ccacgtcgcg ccgcagaaca ccttcctgga    60

```
caccatcatc cgcaagtttg agggccagag ccgtaagttc atcatcgcca acgctcgggt    120
ggagaactgc gccgtcatct actgcaacga cggcttctgc gagctgtgcg gctactcgcg    180
ggccgaggtg atgcagcgac cctgcacctg cgacttcctg cacgggccgc gcacgcagcg    240
ccgcgctgcc gcgcagatcg cgcaggcact gctgggcgcc gaggagcgca aagtggaaat    300
cgccttctac cggaaagatg ggagctgctt cctatgtctg gtggatgtgg tgcccgtgaa    360
gaacgaggat ggggctgtca tcatgttcat cctcaatttc gaggtggtga tggagaagga    420
catggtgggg tccccggctc atgacaccaa ccaccggggc cccccacca gctggctggc     480 cccaggccgc gccaagacct tccgcctgaa gctgcccgcg ctgctggcgc tgacggcccg    540
ggagtcgtcg gtgcggtcgg gcggcgcggg cggcgcgggc gccccggggg ccgtggtggt    600
ggacgtggac ctgacgcccg cggcacccag cagcgagtcg ctggccctgg acgaagtgac    660
agccatggac aaccacgtgg cagggctcgg gcccgcggag gagcggcgtg cgctggtggg    720
tcccggctct ccgccccgca gcgcgccccgg ccagctccca tcgccccggg cgcacagcct   780
caaccccgac gcctcgggct ccagctgcag cctggcccgg acgcgctccc gagaaagctg    840
cgccagcgtg cgccgcgcct cgtcggccga cgacatcgag gccatgcgcg ccggggtgct    900
gcccccgcca ccgcgccacg ccagcaccgg ggccatgcac ccactgcgca gcggcttgct    960
caactccacc tcggactccg acctcgtgcg ctaccgcacc attagcaaga ttccccaaat   1020
caccctcaac tttgtggacc tcaagggcga ccccttcttg gcttcgccca ccagtgaccg   1080
tgagatcata gcacctaaga taaaggagcg aacccacaat gtcactgaga aggtcaccca   1140
ggtcctgtcc ctgggcgccg acgtgctgcc tgagtacaag ctgcaggcac cgcgcatcca   1200
ccgctggacc atcctgcatt acagcccctt caaggccgtg tgggactggc tcatcctgct   1260
gctggtcatc tacacggctg tcttcacacc ctactcggct gccttcctgc tgaaggagac   1320
ggaagaaggc ccgcctgcta ccgagtgtgg ctacgcctgc cagccgctgg ctgtggtgga   1380
cctcatcgtg gacatcatgt tcattgtgga catcctcatc aacttccgca ccacctacgt   1440
caatgccaac gaggaggtgg tcagccaccc cggccgcatc gccgtccact acttcaaggg   1500
ctggttcctc atcgacatgg tggccgccat ccccttcgac ctgctcatct tcggctctgg   1560
ctctgaggag ctgatcgggc tgctgaagac tgcgcggctg ctgcggctgg tgcgcgtggc   1620
gcggaagctg gatcgctact cagagtacgg cgcggccgtg ctgttcttgc tcatgtgcac   1680 cttttgcgctc atcgcgcact ggctagcctg catctggtac gccatcggca acatggagca   1740
gccacacatg gactcacgca tcggctggct gcacaacctg ggcgaccaga taggcaaacc   1800
ctacaacagc agcggcctgg gcggcccctc catcaaggac aagtatgtga cggcgctcta   1860
cttcaccttc agcagcctca ccagtgtggg cttcggcaac gtctctccca caccaactc    1920 agagaagatc ttctccatct gcgtcatgct cattggctcc ctcatgtatg ctagcatctt   1980
cggcaacgtg tcgccatca tccagcggct gtactcgggc acagcccgct accacacaca    2040
gatgctgcgg gtgcgggagt tcatccgctt ccaccagatc cccaatcccc tgcgccagcg   2100
cctcgaggag tacttccagc acgcctggtc ctacaccaac ggcatcgaca tgaacgcggt   2160
gctgaagggc ttccctgagt gcctgcaggc tgacatctgc ctgcacctga accgctcact   2220
gctgcagcac tgcaaaccct tccgagggggc caccaagggc tgccttcggg ccctggccat   2280
gaagttcaag accacacatg caccgccagg ggacacactg gtgcatgctg ggacctgct    2340 caccgccctg tacttcatct cccggggctc catcgagatc ctgcggggcg acgtcgtcgt   2400
```

```
ggccatcctg gggaagaatg acatctttgg ggagcctctg aacctgtatg caaggcctgg    2460
caagtcgaac ggggatgtgc gggccctcac ctactgtgac ctacacaaga tccatcggga    2520
cgacctgctg gaggtgctgg acatgtaccc tgagttctcc gaccacttct ggtccagcct    2580
ggagatcacc ttcaacctgc gagataccaa catgatcccg ggctcccccg gcagtacgga    2640
gttagagggt ggcttcagtc ggcaacgcaa gcgcaagttg tccttccgca ggcgcacgga    2700
caaggacacg gagcagccag gggaggtgtc ggccttgggg ccgggccggg cggggggcagg   2760 gccgagtagc cggggccggc cggggggggcc gtgggggggag agcccgtcca gtggcccctc   2820
cagccctgag agcagtgagg atgagggccc aggccgcagc tccagccccc tccgcctggt    2880
gcccttctcc agccccaggc cccccggaga gccgccgggt ggggagcccc tgatggagga    2940
ctgcgagaag agcagcgaca cttgcaaccc cctgtcaggc gccttctcag gagtgtccaa    3000
cattttcagc ttctgggggg acagtcgggg ccgccagtac caggagctcc ctcgatgccc    3060
cgcccccacc cccagcctcc tcaacatccc cctctccagc ccgggtcggc ggccccgggg    3120
cgacgtggag agcaggctgg atgccctcca gcgccagctc aacaggctgg agacccggct    3180
gagtgcagac atggccactg tcctgcagct gctacagagg cagatgacgc tggtcccgcc    3240
cgcctacagt gctgtgacca ccccgggggcc tggccccact ccacatcccc cgctgttgcc    3300
cgtcagcccc ctccccaccc tcaccttgga ctcgctttct caggtttccc agttcatggc    3360
gtgtgaggag ctgcccccgg gggcccagga gcttccccaa gaaggcccca cacgacgcct    3420
ctccctaccg ggccagctgg gggccctcac ctcccagccc ctgcacagac acggctcgga    3480
cccgggcagt tagtggggct gcccagtgtg gacacgtggc tcacccaggg atcaaggcgc    3540
tgctgggccg ctccccttgg aggccctgct caggaggccc tgaccgtgga aggggagagg    3600
aactcgaaag cacagctcct cccccagccc ttgggaccat cttctcctgc agtcccctgg    3660
gccccagtga gaggggcagg ggcagggccg gcagtaggtg gggcctgtgg tcccccccact   3720 gccctgaggg cattagctgg tctaactgcc cggaggcacc cggccctggg ccttaggcac    3780
ctcaaggact tttctgctat ttactgctct tattgttaag gataataatt aaggatcata    3840
tgaataatta atgaagatgc tgatgactat gaataataaa taattatcct gaggaga       3897
```

<210> SEQ ID NO 2
<211> LENGTH: 1159
<212> TYPE: PRT
<213> ORGANISM: Homo sapiens

<400> SEQUENCE: 2

```
Met Pro Val Arg Arg Gly His Val Ala Pro Gln Asn Thr Phe Leu Asp
1               5                   10                  15

Thr Ile Ile Arg Lys Phe Glu Gly Gln Ser Arg Lys Phe Ile Ile Ala
            20                  25                  30

Asn Ala Arg Val Glu Asn Cys Ala Val Ile Tyr Cys Asn Asp Gly Phe
        35                  40                  45

Cys Glu Leu Cys Gly Tyr Ser Arg Ala Glu Val Met Gln Arg Pro Cys
    50                  55                  60

Thr Cys Asp Phe Leu His Gly Pro Arg Thr Gln Arg Arg Ala Ala Ala
65                  70                  75                  80

Gln Ile Ala Gln Ala Leu Leu Gly Ala Glu Glu Arg Lys Val Glu Ile
                85                  90                  95

Ala Phe Tyr Arg Lys Asp Gly Ser Cys Phe Leu Cys Leu Val Asp Val
            100                 105                 110
```

-continued

```
Val Pro Val Lys Asn Glu Asp Gly Ala Val Ile Met Phe Ile Leu Asn
            115                 120                 125

Phe Glu Val Val Met Glu Lys Asp Met Val Gly Ser Pro Ala His Asp
130                 135                 140

Thr Asn His Arg Gly Pro Pro Thr Ser Trp Leu Ala Pro Gly Arg Ala
145                 150                 155                 160

Lys Thr Phe Arg Leu Lys Leu Pro Ala Leu Leu Ala Leu Thr Ala Arg
                165                 170                 175

Glu Ser Ser Val Arg Ser Gly Gly Ala Gly Gly Ala Gly Ala Pro Gly
            180                 185                 190

Ala Val Val Asp Val Asp Leu Thr Pro Ala Ala Pro Ser Ser Glu
        195                 200                 205

Ser Leu Ala Leu Asp Glu Val Thr Ala Met Asp Asn His Val Ala Gly
    210                 215                 220

Leu Gly Pro Ala Glu Glu Arg Arg Ala Leu Val Gly Pro Gly Ser Pro
225                 230                 235                 240

Pro Arg Ser Ala Pro Gly Gln Leu Pro Ser Pro Arg Ala His Ser Leu
                245                 250                 255

Asn Pro Asp Ala Ser Gly Ser Ser Cys Ser Leu Ala Arg Thr Arg Ser
            260                 265                 270

Arg Glu Ser Cys Ala Ser Val Arg Arg Ala Ser Ser Ala Asp Asp Ile
        275                 280                 285

Glu Ala Met Arg Ala Gly Val Leu Pro Pro Pro Arg His Ala Ser
    290                 295                 300

Thr Gly Ala Met His Pro Leu Arg Ser Gly Leu Leu Asn Ser Thr Ser
305                 310                 315                 320

Asp Ser Asp Leu Val Arg Tyr Arg Thr Ile Ser Lys Ile Pro Gln Ile
                325                 330                 335

Thr Leu Asn Phe Val Asp Leu Lys Gly Asp Pro Phe Leu Ala Ser Pro
            340                 345                 350

Thr Ser Asp Arg Glu Ile Ile Ala Pro Lys Ile Lys Glu Arg Thr His
        355                 360                 365

Asn Val Thr Glu Lys Val Thr Gln Val Leu Ser Leu Gly Ala Asp Val
    370                 375                 380

Leu Pro Glu Tyr Lys Leu Gln Ala Pro Arg Ile His Arg Trp Thr Ile
385                 390                 395                 400

Leu His Tyr Ser Pro Phe Lys Ala Val Trp Asp Trp Leu Ile Leu Leu
                405                 410                 415

Leu Val Ile Tyr Thr Ala Val Phe Thr Pro Tyr Ser Ala Ala Phe Leu
            420                 425                 430

Leu Lys Glu Thr Glu Glu Gly Pro Pro Ala Thr Glu Cys Gly Tyr Ala
        435                 440                 445

Cys Gln Pro Leu Ala Val Val Asp Leu Ile Val Asp Ile Met Phe Ile
    450                 455                 460

Val Asp Ile Leu Ile Asn Phe Arg Thr Thr Tyr Val Asn Ala Asn Glu
465                 470                 475                 480

Glu Val Val Ser His Pro Gly Arg Ile Ala Val His Tyr Phe Lys Gly
                485                 490                 495

Trp Phe Leu Ile Asp Met Val Ala Ala Ile Pro Phe Asp Leu Leu Ile
            500                 505                 510

Phe Gly Ser Gly Ser Glu Glu Leu Ile Gly Leu Leu Lys Thr Ala Arg
        515                 520                 525

Leu Leu Arg Leu Val Arg Val Ala Arg Lys Leu Asp Arg Tyr Ser Glu
```

```
                530                535                540
Tyr Gly Ala Ala Val Leu Phe Leu Leu Met Cys Thr Phe Ala Leu Ile
545                550                555                560

Ala His Trp Leu Ala Cys Ile Trp Tyr Ala Ile Gly Asn Met Glu Gln
              565                570                575

Pro His Met Asp Ser Arg Ile Gly Trp Leu His Asn Leu Gly Asp Gln
              580                585                590

Ile Gly Lys Pro Tyr Asn Ser Ser Gly Leu Gly Gly Pro Ser Ile Lys
          595                600                605

Asp Lys Tyr Val Thr Ala Leu Tyr Phe Thr Phe Ser Ser Leu Thr Ser
          610                615                620

Val Gly Phe Gly Asn Val Ser Pro Asn Thr Asn Ser Glu Lys Ile Phe
625                630                635                640

Ser Ile Cys Val Met Leu Ile Gly Ser Leu Met Tyr Ala Ser Ile Phe
              645                650                655

Gly Asn Val Ser Ala Ile Ile Gln Arg Leu Tyr Ser Gly Thr Ala Arg
              660                665                670

Tyr His Thr Gln Met Leu Arg Val Arg Glu Phe Ile Arg Phe His Gln
          675                680                685

Ile Pro Asn Pro Leu Arg Gln Arg Leu Glu Glu Tyr Phe Gln His Ala
690                695                700

Trp Ser Tyr Thr Asn Gly Ile Asp Met Asn Ala Val Leu Lys Gly Phe
705                710                715                720

Pro Glu Cys Leu Gln Ala Asp Ile Cys Leu His Leu Asn Arg Ser Leu
              725                730                735

Leu Gln His Cys Lys Pro Phe Arg Gly Ala Thr Lys Gly Cys Leu Arg
              740                745                750

Ala Leu Ala Met Lys Phe Lys Thr Thr His Ala Pro Pro Gly Asp Thr
          755                760                765

Leu Val His Ala Gly Asp Leu Leu Thr Ala Leu Tyr Phe Ile Ser Arg
770                775                780

Gly Ser Ile Glu Ile Leu Arg Gly Asp Val Val Ala Ile Leu Gly
785                790                795                800

Lys Asn Asp Ile Phe Gly Glu Pro Leu Asn Leu Tyr Ala Arg Pro Gly
              805                810                815

Lys Ser Asn Gly Asp Val Arg Ala Leu Thr Tyr Cys Asp Leu His Lys
              820                825                830

Ile His Arg Asp Asp Leu Leu Glu Val Leu Asp Met Tyr Pro Glu Phe
          835                840                845

Ser Asp His Phe Trp Ser Ser Leu Glu Ile Thr Phe Asn Leu Arg Asp
850                855                860

Thr Asn Met Ile Pro Gly Ser Pro Gly Ser Thr Glu Leu Glu Gly Gly
865                870                875                880

Phe Ser Arg Gln Arg Lys Arg Lys Leu Ser Phe Arg Arg Thr Asp
              885                890                895

Lys Asp Thr Glu Gln Pro Gly Glu Val Ser Ala Leu Gly Pro Gly Arg
          900                905                910

Ala Gly Ala Gly Pro Ser Ser Arg Gly Arg Pro Gly Pro Trp Gly
              915                920                925

Glu Ser Pro Ser Ser Gly Pro Ser Ser Pro Glu Ser Ser Glu Asp Glu
          930                935                940

Gly Pro Gly Arg Ser Ser Ser Pro Leu Arg Leu Val Pro Phe Ser Ser
945                950                955                960
```

| | | | | | | | | | | |
|---|---|---|---|---|---|---|---|---|---|---|
|Pro|Arg|Pro|Pro|Gly|Glu|Pro|Gly|Gly|Glu|Pro|Leu|Met|Glu|Asp|
| | | |965| | | |970| | | |975| | | |

Cys Glu Lys Ser Ser Asp Thr Cys Asn Pro Leu Ser Gly Ala Phe Ser
           980                 985                 990

Gly Val Ser Asn Ile Phe Ser Phe Trp Gly Asp Ser Arg Gly Arg Gln
       995                1000                1005

Tyr Gln Glu Leu Pro Arg Cys Pro Ala Pro Thr Pro Ser Leu Leu
   1010             1015             1020

Asn Ile Pro Leu Ser Ser Pro Gly Arg Arg Pro Arg Gly Asp Val
   1025             1030             1035

Glu Ser Arg Leu Asp Ala Leu Gln Arg Gln Leu Asn Arg Leu Glu
   1040             1045             1050

Thr Arg Leu Ser Ala Asp Met Ala Thr Val Leu Gln Leu Leu Gln
   1055             1060             1065

Arg Gln Met Thr Leu Val Pro Pro Ala Tyr Ser Ala Val Thr Thr
   1070             1075             1080

Pro Gly Pro Gly Pro Thr Ser Thr Ser Pro Leu Leu Pro Val Ser
   1085             1090             1095

Pro Leu Pro Thr Leu Thr Leu Asp Ser Leu Ser Gln Val Ser Gln
   1100             1105             1110

Phe Met Ala Cys Glu Glu Leu Pro Pro Gly Ala Pro Glu Leu Pro
   1115             1120             1125

Gln Glu Gly Pro Thr Arg Arg Leu Ser Leu Pro Gly Gln Leu Gly
   1130             1135             1140

Ala Leu Thr Ser Gln Pro Leu His Arg His Gly Ser Asp Pro Gly
   1145             1150             1155

Ser

<210> SEQ ID NO 3
<211> LENGTH: 4717
<212> TYPE: DNA
<213> ORGANISM: Homo sapiens

<400> SEQUENCE: 3

```
ggggcggggg gcggtggggc agcaggggc ccatgtgctc aacagggagc tgagggagac    60
caggggtgct tggcttaggg gactgacctc atctggtaca gggcctttgg tggacagaga   120
gagactggaa aagaaaaagt caaggatcga ggggaacgcg aggcgaggtg aagatgaaag   180
atctagaagc agtgcttctt agactctttg gtgaaggatc agtgtttttt aatgctaata   240
tgttataggc tggtacatct gtgaaataca agagcacatg cgtggatttt gtggtgatgc   300
caaattgctg taaagttttt gaattcttg ctctcaacgt ctgtccttat cttgtgtgct   360
gacacaacgg ctggtgctaa tctagagaga acagagagac agatagtaac agctaaccgt   420
ctgtagtgtg cggcatacgc caggcattgc ctaagcgctc agcatgtgct gacttggtta   480
atctttataa ctcatgagaa aagaattata tacattatgt gtatcacaac atcactgtgt   540
acccataaa tatgtacaat tattgtgtca attaaaaagt taaaaatttt taaaaagaaa   600
aaattattat tcttcccatt ttatagatgg aaaaaatgag gcacaaggat gttaaataat   660
ttaggaaaaa agcataagtg attaagcagc agatccgggc tatgaaccca gagatcgtag   720
gcctaaagtc tgtgggctta agcactgtgc tacagcgcct cgcttgaggg aaaggcagag   780
gtgctgggag gatatgagga aatgagatag ggaggaaatg agatcaaaga tggcagaaga   840
aaggatcata gccagcgtga gaaaaagtgc agccgggaaa gagctagata aatcatatag   900
```

```
gcagagagag gggtagggga gcctggcagc aacaagctgg ggtagacaga ttgaggggag    960
ccataagggc ggcaggcaca tggccgggtg ggggatcagg acgggagatc ccggagagga   1020
agggccatac ggggaggcag aagtggacgg gcccacttgg gttccagggt ccatcctgcg   1080
tggctttctg ctctgcccac tgagtgggtg ccaaggggge tatgtcctcc cactctgcag   1140
ggagctgctt cctatgtctg gtggatgtgg tgcccgtgaa gaacgaggat ggggctgtca   1200
tcatgttcat cctcaatttc gaggtggtga tggagaagga catggtgggg tccccggctc   1260
atgacaccaa ccaccggggc ccccccacca gctggctggc cccaggccgc gccaagacct   1320
tccgcctgaa gctgcccgcg ctgctggcgc tgacggcccg ggagtcgtcg gtgcggtcgg   1380
gcggcgcggg cggcgcgggc gccccggggg ccgtggtggt ggacgtggac ctgacgcccg   1440
cggcacccag cagcgagtcg ctggcccctgg acgaagtgac agccatggac aaccacgtgg   1500
cagggctcgg gcccgcggag gagcggcgtg cgctggtggg tcccggctct ccgccccgca   1560
gcgcgcccgc ccagctccca tcgcccccggg cgcacagcct caaccccgac gcctcgggct   1620
ccagctgcag cctggcccgg acgcgctccc gagaaagctg cgccagcgtg cgccgcgcct   1680
cgtcggccga cgacatcgag gccatgcgcg ccggggtgct gccccccgcca ccgcgccacg   1740
ccagcaccgg ggccatgcac ccactgcgca gcggcttgct caactccacc tcggactccg   1800
acctcgtgcg ctaccgcacc attagcaaga ttccccaaat caccctcaac tttgtggacc   1860
tcaagggcga cccccttcttg gcttcgccca ccagtgaccg tgagatcata gcacctaaga   1920
taaaggagcg aacccacaat gtcactgaga aggtcaccca ggtcctgtcc ctgggcgccg   1980
acgtgctgcc tgagtacaag ctgcaggcac cgcgcatcca ccgctggacc atcctgcatt   2040
acagccccctt caaggccgtg tgggactggc tcatcctgct gctggtcatc tacacggctg   2100
tcttcacacc ctactcggct gccttcctgc tgaaggagac ggaagaaggc ccgcctgcta   2160
ccgagtgtgg ctacgcctgc cagccgctgg ctgtggtgga cctcatcgtg gacatcatgt   2220
tcattgtgga catcctcatc aacttccgca ccacctacgt caatgccaac gaggaggtgg   2280
tcagccaccc cggccgcatc gccgtccact acttcaaggg ctggttcctc atcgacatgg   2340
tggccgccat cccccttcgac ctgctcatct tcggctctgg ctctgaggag ctgatcgggc   2400
tgctgaagac tgcgcggctg ctgcggctgg tgcgcgtggc gcggaagctg atcgctact   2460
cagagtacgg cgcggccgtg ctgttcttgc tcatgtgcac ctttgcgctc atcgcgcact   2520
ggctagcctg catctggtac gccatcggca acatggagca gccacacatg gactcacgca   2580
tcggctggct gcacaacctg ggcgaccaga taggcaaacc ctacaacagc agcggcctgg   2640
gcggcccctc catcaaggac aagtatgtga cggcgctcta cttcaccttc agcagcctca   2700
ccagtgtggg cttcggcaac gtctctccca acaccaactc agagaagatc ttctccatct   2760
gcgtcatgct cattggctcc ctcatgtatg ctagcatctt cggcaacgtg tcggccatca   2820
tccagcggct gtactcgggc acagcccgct accacacaca gatgctgcgg gtgcgggagt   2880
tcatccgctt ccaccagatc cccaatcccc tgcgccagcg cctcgaggag tacttccagc   2940
acgcctggtc ctacaccaac ggcatcgaca tgaacgcggt gctgaagggc ttccctgagt   3000
gcctgcaggc tgacatctgc ctgcacctga accgctcact gctgcagcac tgcaaaccct   3060
tccgaggggc caccaagggc tgccttcggg ccctggccat gaagttcaag accacacatg   3120
caccgccagg ggacacactg gtgcatgctg gggacctgct caccgccctg tacttcatct   3180
cccggggctc catcgagatc ctgcggggcg acgtcgtcgt ggccatcctg gggaagaatg   3240
```

```
acatctttgg ggagcctctg aacctgtatg caaggcctgg caagtcgaac ggggatgtgc    3300
gggccctcac ctactgtgac ctacacaaga tccatcggga cgacctgctg gaggtgctgg    3360
acatgtaccc tgagttctcc gaccacttct ggtccagcct ggagatcacc ttcaacctgc    3420
gagataccaa catgatcccg ggctcccccg gcagtacgga gttagagggt ggcttcagtc    3480
ggcaacgcaa gcgcaagttg tccttccgca ggcgcacgga caaggacacg gagcagccag    3540
gggaggtgtc ggccttgggg ccgggccggg cggggcagg gccgagtagc cggggccggc    3600
cgggggggcc gtggggggag agcccgtcca gtggcccctc cagccctgag agcagtgagg    3660
atgagggccc aggccgcagc tccagccccc tccgcctggt gcccttctcc agccccaggc    3720 ccccggaga gccgccgggt ggggagcccc tgatggagga ctgcgagaag agcagcgaca    3780
cttgcaaccc cctgtcaggc gccttctcag gagtgtccaa cattttcagc ttctgggggg    3840
acagtcgggg ccgccagtac caggagctcc ctcgatgccc cgcccccacc cccagcctcc    3900
tcaacatccc cctctccagc ccgggtcggc ggccccgggg cgacgtggag agcaggctgg    3960
atgccctcca gcgccagctc aacaggctgg agacccggct gagtgcagac atggccactg    4020
tcctgcagct gctacagagg cagatgacgc tggtcccgcc cgcctacagt gctgtgacca    4080 ccccggggc tggcccccact tccacatccc cgctgttgcc cgtcagcccc ctccccaccc    4140
tcaccttgga ctcgctttct caggtttccc agttcatggc gtgtgaggag ctgccccgg    4200 gggcccaga gcttccccaa gaaggcccca cgacgcgcct ccctaccg gccagctgg    4260 gggccctcac ctcccagccc ctgcacagac acggctcgga cccgggcagt tagtggggct    4320
gcccagtgtg gacacgtggc tcacccaggg atcaaggcgc tgctgggccg ctccccttgg    4380
aggccctgct caggaggccc tgaccgtgga aggggagagg aactcgaaag cacagctcct    4440
cccccagccc ttgggaccat cttctcctgc agtccctgg gccccagtga gaggggcagg    4500
ggcagggccg gcagtaggtg gggcctgtgg tcccccccact gccctgaggg cattagctgg    4560
tctaactgcc cggaggcacc cggccctggg ccttaggcac ctcaaggact tttctgctat    4620
ttactgctct tattgttaag gataataatt aaggatcata tgaataatta atgaagatgc    4680
tgatgactat gaataataaa taattatcct gaggaga                            4717
```

<210> SEQ ID NO 4
<211> LENGTH: 1063
<212> TYPE: PRT
<213> ORGANISM: Homo sapiens

<400> SEQUENCE: 4

```
Met Ser Ser His Ser Ala Gly Ser Cys Phe Leu Cys Leu Val Asp Val
1               5                   10                  15

Val Pro Val Lys Asn Glu Asp Gly Ala Val Ile Met Phe Ile Leu Asn
                20                  25                  30

Phe Glu Val Val Met Glu Lys Asp Met Val Gly Ser Pro Ala His Asp
            35                  40                  45

Thr Asn His Arg Gly Pro Pro Thr Ser Trp Leu Ala Pro Gly Arg Ala
        50                  55                  60

Lys Thr Phe Arg Leu Lys Leu Pro Ala Leu Leu Ala Leu Thr Ala Arg
65                  70                  75                  80

Glu Ser Ser Val Arg Ser Gly Gly Ala Gly Gly Ala Gly Ala Pro Gly
                85                  90                  95

Ala Val Val Val Asp Val Asp Leu Thr Pro Ala Pro Ser Ser Glu
            100                 105                 110
```

-continued

```
Ser Leu Ala Leu Asp Glu Val Thr Ala Met Asp Asn His Val Ala Gly
            115                 120                 125
Leu Gly Pro Ala Glu Glu Arg Arg Ala Leu Val Gly Pro Gly Ser Pro
        130                 135                 140
Pro Arg Ser Ala Pro Gly Gln Leu Pro Ser Pro Arg Ala His Ser Leu
145                 150                 155                 160
Asn Pro Asp Ala Ser Gly Ser Cys Ser Leu Ala Arg Thr Arg Ser
                165                 170                 175
Arg Glu Ser Cys Ala Ser Val Arg Arg Ala Ser Ser Ala Asp Asp Ile
                180                 185                 190
Glu Ala Met Arg Ala Gly Val Leu Pro Pro Pro Arg His Ala Ser
        195                 200                 205
Thr Gly Ala Met His Pro Leu Arg Ser Gly Leu Leu Asn Ser Thr Ser
    210                 215                 220
Asp Ser Asp Leu Val Arg Tyr Arg Thr Ile Ser Lys Ile Pro Gln Ile
225                 230                 235                 240
Thr Leu Asn Phe Val Asp Leu Lys Gly Asp Pro Phe Leu Ala Ser Pro
                245                 250                 255
Thr Ser Asp Arg Glu Ile Ile Ala Pro Lys Ile Lys Glu Arg Thr His
                260                 265                 270
Asn Val Thr Glu Lys Val Thr Gln Val Leu Ser Leu Gly Ala Asp Val
        275                 280                 285
Leu Pro Glu Tyr Lys Leu Gln Ala Pro Arg Ile His Arg Trp Thr Ile
    290                 295                 300
Leu His Tyr Ser Pro Phe Lys Ala Val Trp Asp Trp Leu Ile Leu Leu
305                 310                 315                 320
Leu Val Ile Tyr Thr Ala Val Phe Thr Pro Tyr Ser Ala Ala Phe Leu
                325                 330                 335
Leu Lys Glu Thr Glu Glu Gly Pro Pro Ala Thr Glu Cys Gly Tyr Ala
                340                 345                 350
Cys Gln Pro Leu Ala Val Val Asp Leu Ile Val Asp Ile Met Phe Ile
        355                 360                 365
Val Asp Ile Leu Ile Asn Phe Arg Thr Thr Tyr Val Asn Ala Asn Glu
    370                 375                 380
Glu Val Val Ser His Pro Gly Arg Ile Ala Val His Tyr Phe Lys Gly
385                 390                 395                 400
Trp Phe Leu Ile Asp Met Val Ala Ala Ile Pro Phe Asp Leu Leu Ile
                405                 410                 415
Phe Gly Ser Gly Ser Glu Glu Leu Ile Gly Leu Leu Lys Thr Ala Arg
                420                 425                 430
Leu Leu Arg Leu Val Arg Val Ala Arg Lys Leu Asp Arg Tyr Ser Glu
        435                 440                 445
Tyr Gly Ala Ala Val Leu Phe Leu Leu Met Cys Thr Phe Ala Leu Ile
    450                 455                 460
Ala His Trp Leu Ala Cys Ile Trp Tyr Ala Ile Gly Asn Met Glu Gln
465                 470                 475                 480
Pro His Met Asp Ser Arg Ile Gly Trp Leu His Asn Leu Gly Asp Gln
                485                 490                 495
Ile Gly Lys Pro Tyr Asn Ser Ser Gly Leu Gly Gly Pro Ser Ile Lys
                500                 505                 510
Asp Lys Tyr Val Thr Ala Leu Tyr Phe Thr Phe Ser Ser Leu Thr Ser
        515                 520                 525
Val Gly Phe Gly Asn Val Ser Pro Asn Thr Asn Ser Glu Lys Ile Phe
```

```
            530                 535                 540
Ser Ile Cys Val Met Leu Ile Gly Ser Leu Met Tyr Ala Ser Ile Phe
545                 550                 555                 560

Gly Asn Val Ser Ala Ile Ile Gln Arg Leu Tyr Ser Gly Thr Ala Arg
                565                 570                 575

Tyr His Thr Gln Met Leu Arg Val Arg Glu Phe Ile Arg Phe His Gln
                    580                 585                 590

Ile Pro Asn Pro Leu Arg Gln Arg Leu Glu Glu Tyr Phe Gln His Ala
                595                 600                 605

Trp Ser Tyr Thr Asn Gly Ile Asp Met Asn Ala Val Leu Lys Gly Phe
610                 615                 620

Pro Glu Cys Leu Gln Ala Asp Ile Cys Leu His Leu Asn Arg Ser Leu
625                 630                 635                 640

Leu Gln His Cys Lys Pro Phe Arg Gly Ala Thr Lys Gly Cys Leu Arg
                    645                 650                 655

Ala Leu Ala Met Lys Phe Lys Thr Thr His Ala Pro Pro Gly Asp Thr
                660                 665                 670

Leu Val His Ala Gly Asp Leu Leu Thr Ala Leu Tyr Phe Ile Ser Arg
                675                 680                 685

Gly Ser Ile Glu Ile Leu Arg Gly Asp Val Val Ala Ile Leu Gly
                690                 695                 700

Lys Asn Asp Ile Phe Gly Glu Pro Leu Asn Leu Tyr Ala Arg Pro Gly
705                 710                 715                 720

Lys Ser Asn Gly Asp Val Arg Ala Leu Thr Tyr Cys Asp Leu His Lys
                    725                 730                 735

Ile His Arg Asp Asp Leu Leu Glu Val Leu Asp Met Tyr Pro Glu Phe
                740                 745                 750

Ser Asp His Phe Trp Ser Ser Leu Glu Ile Thr Phe Asn Leu Arg Asp
                755                 760                 765

Thr Asn Met Ile Pro Gly Ser Pro Gly Ser Thr Glu Leu Glu Gly Gly
770                 775                 780

Phe Ser Arg Gln Arg Lys Arg Lys Leu Ser Phe Arg Arg Thr Asp
785                 790                 795                 800

Lys Asp Thr Glu Gln Pro Gly Glu Val Ser Ala Leu Gly Pro Gly Arg
                    805                 810                 815

Ala Gly Ala Gly Pro Ser Ser Arg Gly Arg Pro Gly Gly Pro Trp Gly
                820                 825                 830

Glu Ser Pro Ser Ser Gly Pro Ser Ser Pro Glu Ser Ser Glu Asp Glu
                835                 840                 845

Gly Pro Gly Arg Ser Ser Ser Pro Leu Arg Leu Val Pro Phe Ser Ser
850                 855                 860

Pro Arg Pro Pro Gly Glu Pro Pro Gly Gly Glu Pro Leu Met Glu Asp
865                 870                 875                 880

Cys Glu Lys Ser Ser Asp Thr Cys Asn Pro Leu Ser Gly Ala Phe Ser
                    885                 890                 895

Gly Val Ser Asn Ile Phe Ser Phe Trp Gly Asp Ser Arg Gly Arg Gln
                900                 905                 910

Tyr Gln Glu Leu Pro Arg Cys Pro Ala Pro Thr Pro Ser Leu Leu Asn
                915                 920                 925

Ile Pro Leu Ser Ser Pro Gly Arg Arg Pro Arg Gly Asp Val Glu Ser
                930                 935                 940

Arg Leu Asp Ala Leu Gln Arg Gln Leu Asn Arg Leu Glu Thr Arg Leu
945                 950                 955                 960
```

```
Ser Ala Asp Met Ala Thr Val Leu Gln Leu Leu Gln Arg Gln Met Thr
                965                 970                 975

Leu Val Pro Pro Ala Tyr Ser Ala Val Thr Thr Pro Gly Pro Gly Pro
            980                 985                 990

Thr Ser Thr Ser Pro Leu Leu Pro Val Ser Pro Leu Pro Thr Leu Thr
        995                1000                1005

Leu Asp Ser Leu Ser Gln Val Ser Gln Phe Met Ala Cys Glu Glu
   1010                1015                1020

Leu Pro Pro Gly Ala Pro Glu Leu Pro Gln Glu Gly Pro Thr Arg
   1025                1030                1035

Arg Leu Ser Leu Pro Gly Gln Leu Gly Ala Leu Thr Ser Gln Pro
   1040                1045                1050

Leu His Arg His Gly Ser Asp Pro Gly Ser
   1055                1060
```

<210> SEQ ID NO 5
<211> LENGTH: 1058
<212> TYPE: PRT
<213> ORGANISM: Homo sapiens

<400> SEQUENCE: 5

```
Met Gly Ser Cys Phe Leu Cys Leu Val Asp Val Val Pro Val Lys Asn
1               5                   10                  15

Glu Asp Gly Ala Val Ile Met Phe Ile Leu Asn Phe Glu Val Val Met
                20                  25                  30

Glu Lys Asp Met Val Gly Ser Pro Ala His Thr Asn His Arg Gly
                35                  40                  45

Pro Pro Thr Ser Trp Leu Ala Pro Gly Arg Ala Lys Thr Phe Arg Leu
    50                  55                  60

Lys Leu Pro Ala Leu Leu Ala Leu Thr Ala Arg Glu Ser Ser Val Arg
65                  70                  75                  80

Ser Gly Gly Ala Gly Ala Gly Ala Pro Gly Ala Val Val Val Asp
                85                  90                  95

Val Asp Leu Thr Pro Ala Ala Pro Ser Ser Glu Ser Leu Ala Leu Asp
                100                 105                 110

Glu Val Thr Ala Met Asp Asn His Val Ala Gly Leu Gly Pro Ala Glu
            115                 120                 125

Glu Arg Arg Ala Leu Val Gly Pro Gly Ser Pro Pro Arg Ser Ala Pro
    130                 135                 140

Gly Gln Leu Pro Ser Pro Arg Ala His Ser Leu Asn Pro Asp Ala Ser
145                 150                 155                 160

Gly Ser Ser Cys Ser Leu Ala Arg Thr Arg Ser Arg Glu Ser Cys Ala
                165                 170                 175

Ser Val Arg Arg Ala Ser Ser Ala Asp Asp Ile Glu Ala Met Arg Ala
                180                 185                 190

Gly Val Leu Pro Pro Pro Arg His Ala Ser Thr Gly Ala Met His
            195                 200                 205

Pro Leu Arg Ser Gly Leu Leu Asn Ser Thr Ser Asp Ser Asp Leu Val
    210                 215                 220

Arg Tyr Arg Thr Ile Ser Lys Ile Pro Gln Ile Thr Leu Asn Phe Val
225                 230                 235                 240

Asp Leu Lys Gly Asp Pro Phe Leu Ala Ser Pro Thr Ser Asp Arg Glu
                245                 250                 255

Ile Ile Ala Pro Lys Ile Lys Glu Arg Thr His Asn Val Thr Glu Lys
```

```
                260                 265                 270
Val Thr Gln Val Leu Ser Leu Gly Ala Asp Val Leu Pro Glu Tyr Lys
                275                 280                 285
Leu Gln Ala Pro Arg Ile His Arg Trp Thr Ile Leu His Tyr Ser Pro
            290                 295                 300
Phe Lys Ala Val Trp Asp Trp Leu Ile Leu Leu Val Ile Tyr Thr
305                 310                 315                 320
Ala Val Phe Thr Pro Tyr Ser Ala Ala Phe Leu Leu Lys Glu Thr Glu
                325                 330                 335
Glu Gly Pro Pro Ala Thr Glu Cys Gly Tyr Ala Cys Gln Pro Leu Ala
                340                 345                 350
Val Val Asp Leu Ile Val Asp Ile Met Phe Ile Val Asp Ile Leu Ile
                355                 360                 365
Asn Phe Arg Thr Thr Tyr Val Asn Ala Asn Glu Glu Val Val Ser His
            370                 375                 380
Pro Gly Arg Ile Ala Val His Tyr Phe Lys Gly Trp Phe Leu Ile Asp
385                 390                 395                 400
Met Val Ala Ala Ile Pro Phe Asp Leu Leu Ile Phe Gly Ser Gly Ser
                405                 410                 415
Glu Glu Leu Ile Gly Leu Leu Lys Thr Ala Arg Leu Leu Arg Leu Val
                420                 425                 430
Arg Val Ala Arg Lys Leu Asp Arg Tyr Ser Glu Tyr Gly Ala Ala Val
                435                 440                 445
Leu Phe Leu Leu Met Cys Thr Phe Ala Leu Ile Ala His Trp Leu Ala
                450                 455                 460
Cys Ile Trp Tyr Ala Ile Gly Asn Met Glu Gln Pro His Met Asp Ser
465                 470                 475                 480
Arg Ile Gly Trp Leu His Asn Leu Gly Asp Gln Ile Gly Lys Pro Tyr
                485                 490                 495
Asn Ser Ser Gly Leu Gly Gly Pro Ser Ile Lys Asp Lys Tyr Val Thr
                500                 505                 510
Ala Leu Tyr Phe Thr Phe Ser Ser Leu Thr Ser Val Gly Phe Gly Asn
                515                 520                 525
Val Ser Pro Asn Thr Asn Ser Glu Lys Ile Phe Ser Ile Cys Val Met
                530                 535                 540
Leu Ile Gly Ser Leu Met Tyr Ala Ser Ile Phe Gly Asn Val Ser Ala
545                 550                 555                 560
Ile Ile Gln Arg Leu Tyr Ser Gly Thr Ala Arg Tyr His Thr Gln Met
                565                 570                 575
Leu Arg Val Arg Glu Phe Ile Arg Phe His Gln Ile Pro Asn Pro Leu
                580                 585                 590
Arg Gln Arg Leu Glu Glu Tyr Phe Gln His Ala Trp Ser Tyr Thr Asn
                595                 600                 605
Gly Ile Asp Met Asn Ala Val Leu Lys Gly Phe Pro Glu Cys Leu Gln
                610                 615                 620
Ala Asp Ile Cys Leu His Leu Asn Arg Ser Leu Leu Gln His Cys Lys
625                 630                 635                 640
Pro Phe Arg Gly Ala Thr Lys Gly Cys Leu Arg Ala Leu Ala Met Lys
                645                 650                 655
Phe Lys Thr Thr His Ala Pro Pro Gly Asp Thr Leu Val His Ala Gly
                660                 665                 670
Asp Leu Leu Thr Ala Leu Tyr Phe Ile Ser Arg Gly Ser Ile Glu Ile
                675                 680                 685
```

Leu Arg Gly Asp Val Val Ala Ile Leu Gly Lys Asn Asp Ile Phe
690                 695                 700

Gly Glu Pro Leu Asn Leu Tyr Ala Arg Pro Gly Lys Ser Asn Gly Asp
705                 710                 715                 720

Val Arg Ala Leu Thr Tyr Cys Asp Leu His Lys Ile His Arg Asp Asp
        725                 730                 735

Leu Leu Glu Val Leu Asp Met Tyr Pro Glu Phe Ser Asp His Phe Trp
            740                 745                 750

Ser Ser Leu Glu Ile Thr Phe Asn Leu Arg Asp Thr Asn Met Ile Pro
        755                 760                 765

Gly Ser Pro Gly Ser Thr Glu Leu Gly Gly Phe Ser Arg Gln Arg
    770                 775                 780

Lys Arg Lys Leu Ser Phe Arg Arg Thr Asp Lys Asp Thr Glu Gln
785                 790                 795                 800

Pro Gly Glu Val Ser Ala Leu Gly Pro Gly Arg Ala Gly Ala Gly Pro
                805                 810                 815

Ser Ser Arg Gly Arg Pro Gly Gly Pro Trp Gly Glu Ser Pro Ser Ser
            820                 825                 830

Gly Pro Ser Ser Pro Glu Ser Ser Glu Asp Glu Gly Pro Gly Arg Ser
                835                 840                 845

Ser Ser Pro Leu Arg Leu Val Pro Phe Ser Ser Pro Arg Pro Pro Gly
850                 855                 860

Glu Pro Pro Gly Gly Glu Pro Leu Met Glu Asp Cys Glu Lys Ser Ser
865                 870                 875                 880

Asp Thr Cys Asn Pro Leu Ser Gly Ala Phe Ser Gly Val Ser Asn Ile
                885                 890                 895

Phe Ser Phe Trp Gly Asp Ser Arg Gly Arg Gln Tyr Gln Glu Leu Pro
                900                 905                 910

Arg Cys Pro Ala Pro Thr Pro Ser Leu Leu Asn Ile Pro Leu Ser Ser
                915                 920                 925

Pro Gly Arg Arg Pro Arg Gly Asp Val Glu Ser Arg Leu Asp Ala Leu
930                 935                 940

Gln Arg Gln Leu Asn Arg Leu Glu Thr Arg Leu Ser Ala Asp Met Ala
945                 950                 955                 960

Thr Val Leu Gln Leu Leu Gln Arg Gln Met Thr Leu Val Pro Pro Ala
                965                 970                 975

Tyr Ser Ala Val Thr Thr Pro Gly Pro Gly Pro Thr Ser Thr Ser Pro
            980                 985                 990

Leu Leu Pro Val Ser Pro Leu Pro Thr Leu Thr Leu Asp Ser Leu Ser
            995                 1000                1005

Gln Val Ser Gln Phe Met Ala Cys Glu Glu Leu Pro Pro Gly Ala
    1010                1015                1020

Pro Glu Leu Pro Gln Glu Gly Pro Thr Arg Arg Leu Ser Leu Pro
    1025                1030                1035

Gly Gln Leu Gly Ala Leu Thr Ser Gln Pro Leu His Arg His Gly
    1040                1045                1050

Ser Asp Pro Gly Ser
    1055

<210> SEQ ID NO 6
<211> LENGTH: 135
<212> TYPE: PRT
<213> ORGANISM: Homo sapiens

<400> SEQUENCE: 6

Met Pro Val Arg Arg Gly His Val Ala Pro Gln Asn Thr Phe Leu Asp
1               5                   10                  15

Thr Ile Ile Arg Lys Phe Glu Gly Gln Ser Arg Lys Phe Ile Ile Ala
            20                  25                  30

Asn Ala Arg Val Glu Asn Cys Ala Val Ile Tyr Cys Asn Asp Gly Phe
        35                  40                  45

Cys Glu Leu Cys Gly Tyr Ser Arg Ala Glu Val Met Gln Arg Pro Cys
    50                  55                  60

Thr Cys Asp Phe Leu His Gly Pro Arg Thr Gln Arg Ala Ala Ala
65                  70                  75                  80

Gln Ile Ala Gln Ala Leu Leu Gly Ala Glu Glu Arg Lys Val Glu Ile
                85                  90                  95

Ala Phe Tyr Arg Lys Asp Gly Ser Cys Phe Leu Cys Leu Val Asp Val
            100                 105                 110

Val Pro Val Lys Asn Glu Asp Gly Ala Val Ile Met Phe Ile Leu Asn
            115                 120                 125

Phe Glu Val Val Met Glu Lys
        130                 135

<210> SEQ ID NO 7
<211> LENGTH: 125
<212> TYPE: PRT
<213> ORGANISM: Homo sapiens

<400> SEQUENCE: 7

Met Glu His Val Ala Phe Gly Ser Glu Asp Ile Glu Asn Thr Leu Ala
1               5                   10                  15

Lys Met Asp Asp Gly Gln Leu Asp Gly Leu Ala Phe Gly Ala Ile Gln
            20                  25                  30

Leu Asp Gly Asp Gly Asn Ile Leu Gln Tyr Asn Ala Ala Glu Gly Asp
        35                  40                  45

Ile Thr Gly Arg Asp Pro Lys Gln Val Ile Gly Lys Asn Phe Phe Lys
    50                  55                  60

Asp Val Ala Pro Cys Thr Asp Ser Pro Glu Phe Tyr Gly Lys Phe Lys
65                  70                  75                  80

Glu Gly Val Ala Ser Gly Asn Leu Asn Thr Met Phe Glu Tyr Thr Phe
                85                  90                  95

Asp Tyr Gln Met Thr Pro Thr Lys Val Lys Val His Met Lys Lys Ala
            100                 105                 110

Leu Ser Gly Asp Ser Tyr Trp Val Phe Val Lys Arg Val
            115                 120                 125

<210> SEQ ID NO 8
<211> LENGTH: 403
<212> TYPE: DNA
<213> ORGANISM: Homo sapiens

<400> SEQUENCE: 8
ggggagcctg gcagcaacaa gctggggtag acagattgag gggagccata agggcggcag      60
gcacatggcc gggtggggga tcaggacggg agatcccgga gaggaagggc catacgggga     120
ggcagaagtg gacgggccca cttgggttcc aggtccatc ctgcgtggct ttctgctctg     180
cccactgagt gggtgccaag ggggctatgt cctcccactc tgcagggagc tgcttcctat     240
gtctggtgga tgtggtgccc gtgaagaacg aggatggggc tgtcatcatg ttcatcctca     300

```
atttcgaggt ggtgatggag aaggacatgg tggggtcccc ggctcatgac accaaccacc    360 ggggccccc  caccagctgg ctggcccag  gtaagtgtac ttg                      403

<210> SEQ ID NO 9
<211> LENGTH: 377
<212> TYPE: DNA
<213> ORGANISM: Rhesus

<400> SEQUENCE: 9
tagcaacaag ctggggcaga cagattgagg ggagccataa gggtggcagg cacatggccg     60
ggtgggggat caggatggga gatcctggag aggaagggcc atatgggag  cagaagtgg    120 aagggtccgc ttgggctcca ggctttctgc tctgcccact gagagggtgc caaggggact   180
atgttctccc actccacagg gagctgcttc ctatgtctgg tggatgtggt gcccgtgaag   240
aacgaggatg gggctgtcat catgttcatc ctcaatttcg aggtggtgat ggagaaggac   300
atggtggggt ccccggctca tgacaccaat caccggggcc ccccaccag  ctggctggcc   360 tcaggtaagt gtacttg                                                  377

<210> SEQ ID NO 10
<211> LENGTH: 430
<212> TYPE: DNA
<213> ORGANISM: Mus musculus

<400> SEQUENCE: 10
caggagaaac agggaaagaa ggctgagaga tgagatgagc agtgagggag gaagtgtgga    60
ctggctggca gtctggcaca gccagctgca gggttagagc agggtcagga gttgcagatg   120
tgggctattg ggctgtggta gaggctgatg ggcccttttg ggtttagagg tccttcctgg   180
ccattttgtg tcatgcacac ttggggagga gaatctgggg tcaccatggc caatgccttt   240
cctactctgc agggagctgc ttcctgtgtc tggtggatgt ggtacccgtg aagaatgaag   300
atggggctgt gatcatgttc atcctcaact ttgaagtagt gatggagaag gacatggtag   360
ggtccccggc tcatgacacc aaccacaggg gcccctctac cagctggcta gcttctggta   420
agtgcagcca                                                          430

<210> SEQ ID NO 11
<211> LENGTH: 426
<212> TYPE: DNA
<213> ORGANISM: Rattus norvecicus

<400> SEQUENCE: 11
aggagaaact gggaaagaag gctgagggat gagatgggtg gtgagggagg aagtgtggac    60
tggctgcagt ctggcctagc caggtgcagg ggtcagagca gggctgggaa ttgtagatgt   120
gggctgttgg ggtgtggtag aagttgatgg gcccttctgg gttcagaggt ccttcctggt   180
cactttgtgt cctgcccact tggggagaag gatctggtgt caccatggcc catgcctttc   240
ccttgcaggg agctgcttcc tgtgtttggt ggatgtggtg cccgtgaaga atgaggatgg   300
ggctgtcatc atgtttatcc tcaactttga agtggtgatg gagaaggaca tggtagggtc   360
gccagctcat gacaccaatc acaggggcc  ctctaccagc tggctagctt ctggtaagtg   420
cagtca                                                              426

<210> SEQ ID NO 12
<211> LENGTH: 65
<212> TYPE: PRT
<213> ORGANISM: Homo sapiens
```

<400> SEQUENCE: 12

Met Ser Ser His Ser Ala Gly Ser Cys Phe Leu Cys Leu Val Asp Val
1               5                   10                  15

Val Pro Val Lys Asn Glu Asp Gly Ala Val Ile Met Phe Ile Leu Asn
            20                  25                  30

Phe Glu Val Val Met Glu Lys Asp Met Val Gly Ser Pro Ala His Asp
        35                  40                  45

Thr Asn His Arg Gly Pro Pro Thr Ser Trp Leu Ala Pro Gly Lys Cys
    50                  55                  60

Thr
65

<210> SEQ ID NO 13
<211> LENGTH: 65
<212> TYPE: PRT
<213> ORGANISM: Rhesus

<400> SEQUENCE: 13

Met Phe Ser His Ser Thr Gly Ser Cys Phe Leu Cys Leu Val Asp Val
1               5                   10                  15

Val Pro Val Lys Asn Glu Asp Gly Ala Val Ile Met Phe Ile Leu Asn
            20                  25                  30

Phe Glu Val Val Met Glu Lys Asp Met Val Gly Ser Pro Ala His Asp
        35                  40                  45

Thr Asn His Arg Gly Pro Pro Thr Ser Trp Leu Ala Ser Gly Lys Cys
    50                  55                  60

Thr
65

<210> SEQ ID NO 14
<211> LENGTH: 84
<212> TYPE: PRT
<213> ORGANISM: Mus musculus

<400> SEQUENCE: 14

Leu Ala Ile Leu Cys His Ala His Leu Gly Arg Arg Ile Trp Gly His
1               5                   10                  15

His Gly Gln Cys Leu Ser Tyr Ser Ala Gly Ser Cys Phe Leu Cys Leu
            20                  25                  30

Val Asp Val Val Pro Val Lys Asn Glu Asp Gly Ala Val Ile Met Phe
        35                  40                  45

Ile Leu Asn Phe Glu Val Val Met Glu Lys Asp Met Val Gly Ser Pro
    50                  55                  60

Ala His Asp Thr Asn His Arg Gly Pro Ser Thr Ser Trp Leu Ala Ser
65                  70                  75                  80

Gly Lys Cys Ser

<210> SEQ ID NO 15
<211> LENGTH: 107
<212> TYPE: PRT
<213> ORGANISM: Rattus norvegicus

<400> SEQUENCE: 15

Leu Gly Ile Val Asp Val Gly Cys Trp Gly Val Val Glu Val Asp Gly
1               5                   10                  15

Pro Phe Trp Val Gln Arg Ser Phe Leu Val Thr Leu Cys Pro Ala His
            20                  25                  30

```
Leu Gly Arg Arg Ile Trp Cys His His Gly Pro Cys Leu Ser Leu Ala
        35                  40                  45

Gly Ser Cys Phe Leu Cys Leu Val Asp Val Val Pro Val Lys Asn Glu
 50                  55                  60

Asp Gly Ala Val Ile Met Phe Ile Leu Asn Phe Glu Val Met Glu
65                   70                  75                  80

Lys Asp Met Val Gly Ser Pro Ala His Asp Thr Asn His Arg Gly Pro
                 85                  90                  95

Ser Thr Ser Trp Leu Ala Ser Gly Lys Cys Ser
                100                 105
```

<210> SEQ ID NO 16
<211> LENGTH: 6
<212> TYPE: PRT
<213> ORGANISM: Artificial Sequence
<220> FEATURE:
<223> OTHER INFORMATION: N-terminal peptide

<400> SEQUENCE: 16

```
Met Ser Ser His Ser Ala
1               5
```

<210> SEQ ID NO 17
<211> LENGTH: 6
<212> TYPE: PRT
<213> ORGANISM: Artificial sequence
<220> FEATURE:
<223> OTHER INFORMATION: N-terminal peptide

<400> SEQUENCE: 17

```
Met Phe Ser His Ser Thr
1               5
```

<210> SEQ ID NO 18
<211> LENGTH: 41
<212> TYPE: DNA
<213> ORGANISM: Artificial Sequence
<220> FEATURE:
<223> OTHER INFORMATION: synthetic oligonucleotide

<400> SEQUENCE: 18
catgagaaaa gaattatata cattatgtgt atcacaacat c                     41

<210> SEQ ID NO 19
<211> LENGTH: 30
<212> TYPE: DNA
<213> ORGANISM: Artificial sequence
<220> FEATURE:
<223> OTHER INFORMATION: synthetic oligonucleotide

<400> SEQUENCE: 19
gcctcatttt ttccatctat aaaatgggaa                                  30

<210> SEQ ID NO 20
<211> LENGTH: 23
<212> TYPE: DNA
<213> ORGANISM: Artificial sequence
<220> FEATURE:
<223> OTHER INFORMATION: synthetic oligonucleotide

<400> SEQUENCE: 20
actgtgtacc ccataaatat gta                                         23

```
<210> SEQ ID NO 21
<211> LENGTH: 20
<212> TYPE: DNA
<213> ORGANISM: Artificial sequence
<220> FEATURE:
<223> OTHER INFORMATION: synthetic oligonucleotide

<400> SEQUENCE: 21
tgtgggttcg ctcctttatc                                              20

<210> SEQ ID NO 22
<211> LENGTH: 18
<212> TYPE: DNA
<213> ORGANISM: Artificial sequence
<220> FEATURE:
<223> OTHER INFORMATION: synthetic oligonucleotide

<400> SEQUENCE: 22
catggcctcg atgtcgtc                                                18

<210> SEQ ID NO 23
<211> LENGTH: 19
<212> TYPE: DNA
<213> ORGANISM: Artificial sequence
<220> FEATURE:
<223> OTHER INFORMATION: synthetic oligonucleotide

<400> SEQUENCE: 23
atgatgacag ccccatcct                                               19

<210> SEQ ID NO 24
<211> LENGTH: 19
<212> TYPE: DNA
<213> ORGANISM: Artificial sequence
<220> FEATURE:
<223> OTHER INFORMATION: synthetic oligonucleotide

<400> SEQUENCE: 24
catacgggga ggcagaagt                                               19

<210> SEQ ID NO 25
<211> LENGTH: 19
<212> TYPE: DNA
<213> ORGANISM: Artificial sequence
<220> FEATURE:
<223> OTHER INFORMATION: synthetic oligonucleotide

<400> SEQUENCE: 25
catacgggga ggcagaagt                                               19

<210> SEQ ID NO 26
<211> LENGTH: 19
<212> TYPE: DNA
<213> ORGANISM: Artificial sequence
<220> FEATURE:
<223> OTHER INFORMATION: synthetic oligonucleotide

<400> SEQUENCE: 26
cttcttgggg aagctctgg                                               19

<210> SEQ ID NO 27
<211> LENGTH: 1063
<212> TYPE: PRT
<213> ORGANISM: Homo sapiens

<400> SEQUENCE: 27
```

```
Met Ser Ser His Ser Ala Gly Ser Cys Phe Leu Cys Leu Val Asp Val
1               5                   10                  15

Val Pro Val Lys Asn Glu Asp Gly Ala Val Ile Met Phe Ile Leu Asn
            20                  25                  30

Phe Glu Val Val Met Glu Lys Asp Met Val Gly Ser Pro Ala His Asp
        35                  40                  45

Thr Asn His Arg Gly Pro Pro Thr Ser Trp Leu Ala Pro Gly Arg Ala
    50                  55                  60

Lys Thr Phe Arg Leu Lys Leu Pro Ala Leu Leu Ala Leu Thr Ala Arg
65                  70                  75                  80

Glu Ser Ser Val Arg Ser Gly Ala Gly Gly Ala Gly Ala Pro Gly
                85                  90                  95

Ala Val Val Asp Val Asp Leu Thr Pro Ala Ala Pro Ser Ser Glu
                100                 105                 110

Ser Leu Ala Leu Asp Glu Val Thr Ala Met Asp Asn His Val Ala Gly
            115                 120                 125

Leu Gly Pro Ala Glu Glu Arg Arg Ala Leu Val Gly Pro Gly Ser Pro
    130                 135                 140

Pro Arg Ser Ala Pro Gly Gln Leu Pro Ser Pro Arg Ala His Ser Leu
145                 150                 155                 160

Asn Pro Asp Ala Ser Gly Ser Ser Cys Ser Leu Ala Arg Thr Arg Ser
                165                 170                 175

Arg Glu Ser Cys Ala Ser Val Arg Arg Ala Ser Ser Ala Asp Asp Ile
                180                 185                 190

Glu Ala Met Arg Ala Gly Val Leu Pro Pro Pro Arg His Ala Ser
                195                 200                 205

Thr Gly Ala Met His Pro Leu Arg Ser Gly Leu Leu Asn Ser Thr Ser
    210                 215                 220

Asp Ser Asp Leu Val Arg Tyr Arg Thr Ile Ser Lys Ile Pro Gln Ile
225                 230                 235                 240

Thr Leu Asn Phe Val Asp Leu Lys Gly Asp Pro Phe Leu Ala Ser Pro
                245                 250                 255

Thr Ser Asp Arg Glu Ile Ile Ala Pro Lys Ile Lys Glu Arg Thr His
                260                 265                 270

Asn Val Thr Glu Lys Val Thr Gln Val Leu Ser Leu Gly Ala Asp Val
            275                 280                 285

Leu Pro Glu Tyr Lys Leu Gln Ala Pro Arg Ile His Arg Trp Thr Ile
    290                 295                 300

Leu His Tyr Ser Pro Phe Lys Ala Val Trp Asp Trp Leu Ile Leu Leu
305                 310                 315                 320

Leu Val Ile Tyr Thr Ala Val Phe Thr Pro Tyr Ser Ala Ala Phe Leu
                325                 330                 335

Leu Lys Glu Thr Glu Glu Gly Pro Pro Ala Thr Glu Cys Gly Tyr Ala
            340                 345                 350

Cys Gln Pro Leu Ala Val Val Asp Leu Ile Val Asp Ile Met Phe Ile
                355                 360                 365

Val Asp Ile Leu Ile Asn Phe Arg Thr Thr Tyr Val Asn Ala Asn Glu
    370                 375                 380

Glu Val Val Ser His Pro Gly Arg Ile Ala Val His Tyr Phe Lys Gly
385                 390                 395                 400

Trp Phe Leu Ile Asp Met Val Ala Ala Ile Pro Phe Asp Leu Leu Ile
                405                 410                 415

Phe Gly Ser Gly Ser Glu Glu Leu Ile Gly Leu Leu Lys Thr Ala Arg
```

-continued

```
              420                 425                 430
Leu Leu Arg Leu Val Arg Val Ala Arg Lys Leu Asp Arg Tyr Ser Glu
            435                 440                 445
Tyr Gly Ala Ala Val Leu Phe Leu Leu Met Cys Thr Phe Ala Leu Ile
            450                 455                 460
Ala His Trp Leu Ala Cys Ile Trp Tyr Ala Ile Gly Asn Met Glu Gln
465                 470                 475                 480
Pro His Met Asp Ser Arg Ile Gly Trp Leu His Asn Leu Gly Asp Gln
                485                 490                 495
Ile Gly Lys Pro Tyr Asn Ser Ser Gly Leu Gly Gly Pro Ser Ile Lys
                500                 505                 510
Asp Lys Tyr Val Thr Ala Leu Tyr Phe Thr Phe Ser Ser Leu Thr Ser
                515                 520                 525
Val Gly Phe Gly Asn Val Ser Pro Asn Thr Asn Ser Glu Lys Ile Phe
            530                 535                 540
Ser Ile Cys Val Met Leu Ile Gly Ser Leu Met Tyr Ala Ser Ile Phe
545                 550                 555                 560
Gly Asn Val Ser Ala Ile Ile Gln Arg Leu Tyr Ser Gly Thr Ala Arg
                565                 570                 575
Tyr His Thr Gln Met Leu Arg Val Arg Glu Phe Ile Arg Phe His Gln
                580                 585                 590
Ile Pro Asn Pro Leu Arg Gln Arg Leu Glu Glu Tyr Phe Gln His Ala
            595                 600                 605
Trp Ser Tyr Thr Asn Gly Ile Asp Met Asn Ala Val Leu Lys Gly Phe
            610                 615                 620
Pro Glu Cys Leu Gln Ala Asp Ile Cys Leu His Leu Asn Arg Ser Leu
625                 630                 635                 640
Leu Gln His Cys Lys Pro Phe Arg Gly Ala Thr Lys Gly Cys Leu Arg
                645                 650                 655
Ala Leu Ala Met Lys Phe Lys Thr Thr His Ala Pro Pro Gly Asp Thr
                660                 665                 670
Leu Val His Ala Gly Asp Leu Leu Thr Ala Leu Tyr Phe Ile Ser Arg
            675                 680                 685
Gly Ser Ile Glu Ile Leu Arg Gly Asp Val Val Ala Ile Leu Gly
            690                 695                 700
Lys Asn Asp Ile Phe Gly Glu Pro Leu Asn Leu Tyr Ala Arg Pro Gly
705                 710                 715                 720
Lys Ser Asn Gly Asp Val Arg Ala Leu Thr Tyr Cys Asp Leu His Lys
                725                 730                 735
Ile His Arg Asp Asp Leu Leu Glu Val Leu Asp Met Tyr Pro Glu Phe
                740                 745                 750
Ser Asp His Phe Trp Ser Ser Leu Glu Ile Thr Phe Asn Leu Arg Asp
            755                 760                 765
Thr Asn Met Ile Pro Gly Ser Pro Gly Ser Thr Glu Leu Glu Gly Gly
            770                 775                 780
Phe Ser Arg Gln Arg Lys Arg Lys Leu Ser Phe Arg Arg Thr Asp
785                 790                 795                 800
Lys Asp Thr Glu Gln Pro Gly Glu Val Ser Ala Leu Gly Pro Gly Arg
                805                 810                 815
Ala Gly Ala Gly Pro Ser Ser Arg Gly Arg Pro Gly Gly Pro Trp Gly
                820                 825                 830
Glu Ser Pro Ser Ser Gly Pro Ser Ser Pro Glu Ser Ser Glu Asp Glu
            835                 840                 845
```

```
Gly Pro Gly Arg Ser Ser Pro Leu Arg Leu Val Pro Phe Ser Ser
        850                 855                 860

Pro Arg Pro Pro Gly Glu Pro Gly Gly Glu Pro Leu Met Glu Asp
865                 870                 875                 880

Cys Glu Lys Ser Ser Asp Thr Cys Asn Pro Leu Ser Gly Ala Phe Ser
                885                 890                 895

Gly Val Ser Asn Ile Phe Ser Phe Trp Gly Asp Ser Arg Gly Arg Gln
            900                 905                 910

Tyr Gln Glu Leu Pro Arg Cys Pro Ala Pro Thr Pro Ser Leu Leu Asn
        915                 920                 925

Ile Pro Leu Ser Ser Pro Gly Arg Arg Pro Arg Gly Asp Val Glu Ser
930                 935                 940

Arg Leu Asp Ala Leu Gln Arg Gln Leu Asn Arg Leu Glu Thr Arg Leu
945                 950                 955                 960

Ser Ala Asp Met Ala Thr Val Leu Gln Leu Leu Gln Arg Gln Met Thr
                965                 970                 975

Leu Val Pro Pro Ala Tyr Ser Ala Val Thr Thr Pro Gly Pro Gly Pro
            980                 985                 990

Thr Ser Thr Ser Pro Leu Leu Pro Val Ser Pro Leu Pro Thr Leu Thr
        995                 1000                1005

Leu Asp Ser Leu Ser Gln Val Ser Gln Phe Met Ala Cys Glu Glu
     1010                1015                1020

Leu Pro Pro Gly Ala Pro Glu Leu Pro Gln Glu Gly Pro Thr Arg
     1025                1030                1035

Arg Leu Ser Leu Pro Gly Gln Leu Gly Ala Leu Thr Ser Gln Pro
     1040                1045                1050

Leu His Arg His Gly Ser Asp Pro Gly Ser
     1055                1060

<210> SEQ ID NO 28
<211> LENGTH: 1063
<212> TYPE: PRT
<213> ORGANISM: Homo sapiens

<400> SEQUENCE: 28

Met Phe Ser His Ser Thr Gly Ser Cys Phe Leu Cys Leu Val Asp Val
1               5                   10                  15

Val Pro Val Lys Asn Glu Asp Gly Ala Val Ile Met Phe Ile Leu Asn
                20                  25                  30

Phe Glu Val Val Met Glu Lys Asp Met Val Gly Ser Pro Ala His Asp
            35                  40                  45

Thr Asn His Arg Gly Pro Pro Thr Ser Trp Leu Ala Pro Gly Arg Ala
        50                  55                  60

Lys Thr Phe Arg Leu Lys Leu Pro Ala Leu Leu Ala Leu Thr Ala Arg
65                  70                  75                  80

Glu Ser Ser Val Arg Ser Gly Ala Gly Ala Gly Ala Pro Gly
                85                  90                  95

Ala Val Val Val Asp Val Asp Leu Thr Pro Ala Ala Pro Ser Ser Glu
            100                 105                 110

Ser Leu Ala Leu Asp Glu Val Thr Ala Met Asp Asn His Val Ala Gly
        115                 120                 125

Leu Gly Pro Ala Glu Glu Arg Arg Ala Leu Val Gly Pro Gly Ser Pro
    130                 135                 140

Pro Arg Ser Ala Pro Gly Gln Leu Pro Ser Pro Arg Ala His Ser Leu
```

-continued

```
            145                 150                 155                 160
        Asn Pro Asp Ala Ser Gly Ser Ser Cys Ser Leu Ala Arg Thr Arg Ser
                            165                 170                 175

Arg Glu Ser Cys Ala Ser Val Arg Arg Ala Ser Ser Ala Asp Asp Ile
                            180                 185                 190

Glu Ala Met Arg Ala Gly Val Leu Pro Pro Pro Arg His Ala Ser
                    195                 200                 205

Thr Gly Ala Met His Pro Leu Arg Ser Gly Leu Leu Asn Ser Thr Ser
                    210                 215                 220

Asp Ser Asp Leu Val Arg Tyr Arg Thr Ile Ser Lys Ile Pro Gln Ile
        225                 230                 235                 240

Thr Leu Asn Phe Val Asp Leu Lys Gly Asp Pro Phe Leu Ala Ser Pro
                            245                 250                 255

Thr Ser Asp Arg Glu Ile Ile Ala Pro Lys Ile Lys Glu Arg Thr His
                            260                 265                 270

Asn Val Thr Glu Lys Val Thr Gln Val Leu Ser Leu Gly Ala Asp Val
                    275                 280                 285

Leu Pro Glu Tyr Lys Leu Gln Ala Pro Arg Ile His Arg Trp Thr Ile
                    290                 295                 300

Leu His Tyr Ser Pro Phe Lys Ala Val Trp Asp Trp Leu Ile Leu Leu
        305                 310                 315                 320

Leu Val Ile Tyr Thr Ala Val Phe Thr Pro Tyr Ser Ala Ala Phe Leu
                            325                 330                 335

Leu Lys Glu Thr Glu Glu Gly Pro Pro Ala Thr Glu Cys Gly Tyr Ala
                            340                 345                 350

Cys Gln Pro Leu Ala Val Val Asp Leu Ile Val Asp Ile Met Phe Ile
                    355                 360                 365

Val Asp Ile Leu Ile Asn Phe Arg Thr Thr Tyr Val Asn Ala Asn Glu
                    370                 375                 380

Glu Val Val Ser His Pro Gly Arg Ile Ala Val His Tyr Phe Lys Gly
        385                 390                 395                 400

Trp Phe Leu Ile Asp Met Val Ala Ala Ile Pro Phe Asp Leu Leu Ile
                            405                 410                 415

Phe Gly Ser Gly Ser Glu Glu Leu Ile Gly Leu Leu Lys Thr Ala Arg
                            420                 425                 430

Leu Leu Arg Leu Val Arg Val Ala Arg Lys Leu Asp Arg Tyr Ser Glu
                    435                 440                 445

Tyr Gly Ala Ala Val Leu Phe Leu Leu Met Cys Thr Phe Ala Leu Ile
        450                 455                 460

Ala His Trp Leu Ala Cys Ile Trp Tyr Ala Ile Gly Asn Met Glu Gln
        465                 470                 475                 480

Pro His Met Asp Ser Arg Ile Gly Trp Leu His Asn Leu Gly Asp Gln
                            485                 490                 495

Ile Gly Lys Pro Tyr Asn Ser Ser Gly Leu Gly Gly Pro Ser Ile Lys
                    500                 505                 510

Asp Lys Tyr Val Thr Ala Leu Tyr Phe Thr Phe Ser Ser Leu Thr Ser
                    515                 520                 525

Val Gly Phe Gly Asn Val Ser Pro Asn Thr Asn Ser Glu Lys Ile Phe
        530                 535                 540

Ser Ile Cys Val Met Leu Ile Gly Ser Leu Met Tyr Ala Ser Ile Phe
        545                 550                 555                 560

Gly Asn Val Ser Ala Ile Ile Gln Arg Leu Tyr Ser Gly Thr Ala Arg
                            565                 570                 575
```

```
Tyr His Thr Gln Met Leu Arg Val Arg Glu Phe Ile Arg Phe His Gln
            580                 585                 590

Ile Pro Asn Pro Leu Arg Gln Arg Leu Glu Glu Tyr Phe Gln His Ala
            595                 600                 605

Trp Ser Tyr Thr Asn Gly Ile Asp Met Asn Ala Val Leu Lys Gly Phe
610                 615                 620

Pro Glu Cys Leu Gln Ala Asp Ile Cys Leu His Leu Asn Arg Ser Leu
625                 630                 635                 640

Leu Gln His Cys Lys Pro Phe Arg Gly Ala Thr Lys Gly Cys Leu Arg
                645                 650                 655

Ala Leu Ala Met Lys Phe Lys Thr Thr His Ala Pro Pro Gly Asp Thr
            660                 665                 670

Leu Val His Ala Gly Asp Leu Leu Thr Ala Leu Tyr Phe Ile Ser Arg
            675                 680                 685

Gly Ser Ile Glu Ile Leu Arg Gly Asp Val Val Ala Ile Leu Gly
690                 695                 700

Lys Asn Asp Ile Phe Gly Glu Pro Leu Asn Leu Tyr Ala Arg Pro Gly
705                 710                 715                 720

Lys Ser Asn Gly Asp Val Arg Ala Leu Thr Tyr Cys Asp Leu His Lys
                725                 730                 735

Ile His Arg Asp Asp Leu Leu Glu Val Leu Asp Met Tyr Pro Glu Phe
            740                 745                 750

Ser Asp His Phe Trp Ser Ser Leu Glu Ile Thr Phe Asn Leu Arg Asp
            755                 760                 765

Thr Asn Met Ile Pro Gly Ser Pro Gly Ser Thr Glu Leu Glu Gly Gly
            770                 775                 780

Phe Ser Arg Gln Arg Lys Arg Lys Leu Ser Phe Arg Arg Thr Asp
785                 790                 795                 800

Lys Asp Thr Glu Gln Pro Gly Glu Val Ser Ala Leu Gly Pro Gly Arg
            805                 810                 815

Ala Gly Ala Gly Pro Ser Ser Arg Gly Arg Pro Gly Gly Pro Trp Gly
            820                 825                 830

Glu Ser Pro Ser Ser Gly Pro Ser Ser Pro Gly Ser Ser Glu Asp Glu
            835                 840                 845

Gly Pro Gly Arg Ser Ser Ser Pro Leu Arg Leu Val Pro Phe Ser Ser
850                 855                 860

Pro Arg Pro Pro Gly Glu Pro Pro Gly Gly Glu Pro Leu Met Glu Asp
865                 870                 875                 880

Cys Glu Lys Ser Ser Asp Thr Cys Asn Pro Leu Ser Gly Ala Phe Ser
                885                 890                 895

Gly Val Ser Asn Ile Phe Ser Phe Trp Gly Asp Ser Arg Gly Arg Gln
            900                 905                 910

Tyr Gln Glu Leu Pro Arg Cys Pro Ala Pro Thr Pro Ser Leu Leu Asn
            915                 920                 925

Ile Pro Leu Ser Ser Pro Gly Arg Arg Pro Arg Gly Asp Val Glu Ser
            930                 935                 940

Arg Leu Asp Ala Leu Gln Arg Gln Leu Asn Arg Leu Glu Thr Arg Leu
945                 950                 955                 960

Ser Ala Asp Met Ala Thr Val Leu Gln Leu Leu Gln Arg Gln Met Thr
                965                 970                 975

Leu Val Pro Pro Ala Tyr Ser Ala Val Thr Thr Pro Gly Pro Gly Pro
            980                 985                 990
```

```
-continued

Thr Ser Thr Ser Pro Leu Leu Pro Val Ser Pro Leu Pro Thr Leu Thr
            995                 1000                1005

Leu Asp Ser Leu Ser Gln Val Ser Gln Phe Met Ala Cys Glu Glu
    1010            1015                1020

Leu Pro Pro Gly Ala Pro Glu Leu Pro Gln Glu Gly Pro Thr Arg
    1025                1030                1035

Arg Leu Ser Leu Pro Gly Gln Leu Gly Ala Leu Thr Ser Gln Pro
    1040                1045                1050

Leu His Arg His Gly Ser Asp Pro Gly Ser
    1055                1060
```